US006350934B1

(12) United States Patent
Zwick et al.

(10) Patent No.: US 6,350,934 B1
(45) Date of Patent: Feb. 26, 2002

(54) NUCLEIC ACID ENCODING DELTA-9 DESATURASE

(75) Inventors: Michael G. Zwick, Loveland; Brent E. Edington; James A. McSwiggen, both of Boulder, all of CO (US); Patricia Ann Owens Merlo, Carmel, IN (US); Lining Guo, Brownsburg, IN (US); Thomas A. Skokut, Carmel, IN (US); Scott A. Young, Indianapolis, IN (US); Otto Folkerts; Donald J. Merlo, both of Carmel, IN (US)

(73) Assignees: Ribozyme Pharmaceuticals, Inc., Indianapolis, IN (US); DowElanco, Boulder, CO (US)

( * ) Notice: Subject to any disclaimer, the term of this patent is extended or adjusted under 35 U.S.C. 154(b) by 0 days.

(21) Appl. No.: 08/679,645

(22) Filed: Jul. 12, 1996

Related U.S. Application Data

(63) Continuation-in-part of application No. 08/300,726, filed on Sep. 2, 1994.
(60) Provisional application No. 60/001,135, filed on Jul. 13, 1995.

(51) Int. Cl.$^7$ .......................... C12N 5/04; C12N 15/29; C12N 15/82; A01H 5/00
(52) U.S. Cl. .................. 800/281; 800/278; 800/286; 800/287; 800/292; 800/293; 800/294; 800/300; 800/320.1; 435/412; 435/419; 435/320.1; 435/469; 435/470; 536/23.2; 536/23.6
(58) Field of Search ............................... 536/23.2, 23.6; 800/278, 281, 286, 292, 293, 294, 298, 287, 300, 320.1; 435/320.1, 469, 470, 412, 419

(56) References Cited

U.S. PATENT DOCUMENTS

| | | |
|---|---|---|
| 4,693,976 A | 9/1987 | Schilperoot |
| 4,762,785 A | 8/1988 | Calgene |
| 4,940,838 A | 7/1990 | Schilperoot |
| 4,945,050 A | 7/1990 | Cornell |
| 4,987,071 A | 1/1991 | Cech et al. |
| 5,004,863 A | 4/1991 | Agracetus |
| 5,104,310 A | 4/1992 | Saltin |
| 5,107,065 A | 4/1992 | Shewmaker et al. |
| 5,141,131 A | 8/1992 | Elmo |
| 5,149,645 A | 9/1992 | Schilperoot |
| 5,177,010 A | 1/1993 | Goldman |
| 5,231,019 A | 7/1993 | Geigy |
| 5,302,523 A | 4/1994 | Zeneca |
| 5,334,529 A | 8/1994 | Adams et al. |
| 5,384,523 A | 1/1995 | Dekalb |
| 5,453,566 A | 9/1995 | Shewmaker et al. |
| 5,463,174 A | 10/1995 | Calgene |
| 5,464,763 A | 11/1995 | Schilperoot |
| 5,464,765 A | 11/1995 | Zeneca |
| 5,469,976 A | 11/1995 | Schilperoot |
| 5,472,869 A | 12/1995 | Dekalb |

FOREIGN PATENT DOCUMENTS

| | | |
|---|---|---|
| EP | 0120516 | 10/1984 |
| EP | 0131624 | 1/1985 |
| EP | 0159148 | 10/1985 |
| EP | 0176112 | 4/1986 |
| EP | 0267159 | 5/1988 |
| EP | 0290799 | 11/1988 |
| EP | 0292435 | 11/1988 |
| EP | 0320500 | 6/1989 |
| EP | 0321201 | 6/1989 |
| EP | 0360257 | 3/1990 |
| EP | 0116718 | 5/1990 |
| EP | 0416572 | 9/1990 |
| EP | 0604662 | 7/1994 |
| EP | 0627752 | 12/1994 |
| WO | 8706614 | 11/1987 |
| WO | 9113972 | 9/1991 |
| WO | 9113994 | 9/1991 |
| WO | 9118985 | 12/1991 |
| WO | 9209696 | 6/1992 |
| WO | 9213090 | 8/1992 |
| WO | 9302197 | 2/1993 |
| WO | 9321335 | 10/1993 |
| WO | 9323569 | 11/1993 |
| WO | 9400012 | 1/1994 |
| WO | 9402595 | 2/1994 |
| WO | 9419476 | 9/1994 |
| WO | 9503404 | 2/1995 |
| WO | 9506128 | 4/1995 |

OTHER PUBLICATIONS

Atanassova et al., "Altered lignin composition in transgenic tobacco expressing O–methyltransferase sequences in sense and antisense orientation," *The Plant Journal* 8:465–477 (1995).

Atkins et al., "The expression of antisense and ribozyme genes targeting citrus exocortis viroid in transgenic plants," *J. Gen. Virol.* 76:1781–1790 (1995).

Bennett and Cullimore, "Selective cleavage of closely–related mRNAs by synthetic ribozymes," *Nucleic Acids Research* 20:831–837 (1992).

Bevan, "Binary Agrobacterium vectors for plant transformation," *Nucleic Acids Research* 12:8711–8721 (1984).

Bourque, "Antisense strategies for genetic manipulations in plants," *Plant Science* 105:125–149 (1995).

Cech, "Ribozymes and Their Medical Implications," *JAMA* 260:3030–3034 (1988).

(List continued on next page.)

*Primary Examiner*—David T. Fox
*Assistant Examiner*—Anne R. Kubelik
(74) *Attorney, Agent, or Firm*—McDonnell Boehnen Hulbert & Berghoff

(57) ABSTRACT

The present invention relates to nucleic acid molecules encoding delta 9 desaturase gene, and expression vectors, plant cells, and transgenic plants expressing delta 9 desaturase nucleic acid. The nucleic acid molecules of the present invention can be used, for example, to decrease delta 9 desaturase activity in plant cells, resulting in decreased unsaturated fatty acid production.

11 Claims, 44 Drawing Sheets

OTHER PUBLICATIONS

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chomcyzynski and Sacchi, "Single Step Method of RNA Isolation by Acid Guanidinum Thiocyanate–Phenol–Chloroform Extraction," *Analytical Biochem.* 162:156–159 (1987).

Chowrira and Burke, "Extensive Phosphorothioate Substitution Yields Highly Active and Nuclease–Resistant Hairpin Ribozymes," *Nucleic Acids Res.* 20:2835–2840 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Christoffersen and Marr, "Ribozymes as Human Therapeutic Agents," *J. Med. Chem.* 38:2023–2037 (1995).

Collins and Olive, "Reaction Conditions and Kinetics of Self–Cleavage of a Ribozyme Derived From Neurospora VS RNA," *Biochemistry* 32:2795–2799 (1993).

D'Halliun et al., "Transgenic Maize Plants by Tissue Electroporation," *The Plant Cell* 4:1495–1505 (1992).

Das et al., "A new allele of the duplicated 27kD zein locus of maize generated by homologous recombination," *Nucleic Acids Research* 19:3325–3330 (1991).

Dennis et al., "Molecular analysis of the alcohol dehydrogenase (Adhl) gene of maize," *Nucleic Acids Research* 12:3983–4000 (1984).

DePicker et al., "Nopaline Synthase: Transcript Mapping and DNA Sequence," *Journal of Molecular and Applied Genetics* 1:561–573 (1982).

van Doorsselaere et al., "A novel lignin in poplar trees with a reduced caffeic acid/5–hydroxyferulic acid O–methyltransferase activtiy," *The Plant Journal* 8:855–864 (1995).

Dreyfus, "Restriction Ribozymes?" *Einstein Quarterly J. Bio. Med.* 6:92–93 (1988).

Dropulic et al., "Functional Characterization of a U5 Ribozyme: Intracellular Suppression of Human Immunodeficiency Virus Type I Expression," *Journal of Virology* 66:1432–1441 (1992).

Dwivedi et al., "Modification of lignin biosynthesis in transgenic Nicotiana through expression of an antisense O–methyltransferase gene from Populus," *Plant Molecular Biology* 26:61–71 (1994).

Echt and Schwartz, "Evidence for the Inclusion of Controlling Elements Within the Structural Gene at the Waxy Locus in Maize," *Genetics* 99:275–284 (1981).

Edington and Nelson, "Utilization of Ribozymes in Plants: Plant Viral Resistance," in *Gene Regulation: Biology of antisense RNA and DNA*—vol. 1, Erickson and Izant editors, Raven Press, New York, pp. 209–221 (1992).

Egholm et al., "PNA hybridizes to complementary oligonucleotides obeying the Watson–Crick hydrogen–bonding rules," *Nature* 365:566–568 (1993).

Feldstein et al., "Two sequences participating in the autolytic processing of satellite tobacco ringspot virus complementary RNA," *Gene* 82:53–61 (1989).

de Feyter et al., "A ribozyme gene and an antisense gene are equally effective in conferring resistance to tobacco mosaic virus on transgenic tobacco," *Mol. Gen. Genet.* 250:329–338 (1996).

Finnegan and McElroy, "Transgene Inactivation: Plants Fight Back!" *BioTechnology* 12:883–888 (1994).

Fitch–Haumann, "Corn Oil: Production up as corn refining grows," *J. Am. Oil Chem. Soc.* 62:1524–1531 (1985).

Forster and Altman, "External Guide Sequences for an RNA Enzyme," *Science* 249:783–786 (1990).

Fox et al., "Stearoyl–acyl carrier protein $\Delta^9$ desaturase from *Ricinus communis* is a diiron–oxo protein," *Proc. Natl. Acad. Sci. USA* 90:2486–2490 (1993).

Franck et al., "Nucleotide Sequence of Cauliflower Mosaic Virus DNA," *Cell* 21:285–294 (1980).

Frentzen, "Ch. 6—Acyltransferases and Triacylglycerols," in *Lipid Metabolism in Plants*, T.S. Moore editor, CRC Press, Boca Raton, Florida, pp. 195–230 (1993).

Fromm et al., "Stable Transformation of Maize After Gene Transfer by Electroporation," *Nature* 319:791–793 (1986).

Gasser and Fraley, "Genetically Engineering Plants For Crop Improvement," *Science* 244:1293–1299 (1989).

Gasser and Fraley, "Transgenic Crops—Biotechnology Has Already Created Plants That Withstand Pests and Fruits That Resist Spoilage. Recent Advances Confirm Its Environmental Soundness And Commercial Viability," *Scientific American* Jun. 1992 pp. 62–69.

Gibson et al., "Use of transgenic plants and mutants to study the regulation and function of lipid composition," *Plant, Cell and Environment* 17:627–637 (1994).

Glover and Mertz, "Ch. 7—Corn," in *Nutritional Quality of Cereal Grains: Genetic and Agronomic Improvement*, Olson and Frey editors, Am. Soc. Agronomy, Inc., Madison, WI, pp. 183–336 (1987).

Gordon–Kamm et al., "Transformation of Maize Cells and Regeneration of Fertile Transgenic Plants," *The Plant Cell* 2:603–618 (1990).

Graef et al., "Inheritance of Three Stearic Acid Mutants of Soybean," *Crop Science* 25:1076–1079 (1985).

Gray et al., "Molecular biology of fruit ripening and its manipulation with antisense genes," *Plant Molecular Biology* 19:69–87 (1992).

Grayburn et al., "Fatty Acid Alteration by a $\Delta 9$ Desaturase in Transgenic Tobacco Tissue," *BioTechnology* 10:675–678 (1992).

Green et al., "The Role of Antisense RNA in Gene Regulation," *Ann. Rev. Biochem.* 55:569–597 (1986).

Griffin et al., "Group II intron ribozymes that cleave DNA and RNA linkages with similar efficiency, and lack contacts with substrate 2'–hydroxyl groups," *Chemistry & Biology* 2:761–770 (1995).

Gruber et al., "Ribozymes and Coat Protein Mediated CMV Resistance in Melon," *J. Cell. Biol.* Suppl. 18A:110 at abstract No. X1–406 (1994).

Guerrier–Takada et al., "The RNA Moiety of Ribonuclease P Is the Catalytic Subunit of the Enzyme," *Cell* 35:849–857 (1983).

Guo and Collins, "Efficient trans–cleavage of a stem–loop RNA substrate by a ribozyme derived from Neurospora VS RNA," *EMBO J.* 14:363–376 (1995).

Hammond and Fehr, "Improving the Fatty Acid Composition of Soybean Oil," *J. Amer. Oil Chem. Soc.* 61:1713–1716 (1984).

Hampel and Tritz, "RNA Catalytic Properties of the Minimum (–)sTRSV Sequence," *Biochemistry* 28:4929–4933 (1989).

Hampel et al., "'Hairpin' Catalytic RNA Model: Evidence for Helices and Sequence Requirement for Substrate RNA," *Nucleic Acids Research* 18:299–304 (1990).

Haseloff and Gerlach, "Simple RNA Enzymes with New and Highly Specific Endoribonuclease Activities," *Nature* 334:585–591 (1988).

Haseloff and Gerlach, "Sequences required for self–catalysed cleavage of the satellite RNA of tobacco ringspot virus," *Gene* 82:43–52 (1989).

Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159–10171 (1990).

Hertel et al., "Numbering System for the Hammerhead," *Nucleic Acids Res.* 20:3252 (1992).

Hovenkamp–Hermelink et al., "Isolation of an amylose–free starch mutant of the potato (*Solanum Tuberosum* L.)," *Theor. Appl. Genet.* 75:217–221 (1987).

Hovenkamp–Hermelink et al., "Rapid estimation of the amylose/amylopectin ratio in small amounts of tuber and leaf tissue of the potato," *Potato Research* 31:241–246 (1988).

Izant and Weintraub, "Inhibition of Thymidine Kinase Gene Expression by Anti–Sense RNA: A Molecular Approach to Genetic Analysis," *Cell* 36:1007–1015 (1984).

James et al., "Transgenes Display Stable Patterns of Expression in Apple Fruit and Mendelian Segregation in the Progeny," *Bio/Technology* 14:56–60 (1996).

Jefferson, "Assaying Chimeric Genes in Plants: The GUS Gene Fusion System," *Plant Molec. Biol. Reporter* 5:387–405 (1987).

Jeffries and Symons, "A Catalytic 13–mer Ribozyme," *Nucleic Acids Research* 17:1371–1377 (1989).

Jorgensen, "Cosuppression, Flower Color Patterns, and Metastable Gene Expression States," *Science* 268:686–691 (1995).

Kashani–Sabet et al., "Reversal of the Malignant Phenotype by an Anti–ras Ribozyme," *Antisense Research & Development* 2:3–15 (1992).

Kim and Cech, "Three–dimensional model of the active site of the self–splicing rRNA precursor of Tetrahymena," *Proc. Natl. Acad. Sci. USA* 84:8788–8792 (1987).

Kinney, "Genetic modification of the storage lipids of plants," *Current Opinion in Biotechnology* 5:144–151 (1994).

Knutzon et al., "Nucleotide Sequence of a Complementary DNA Clone Encoding Stearoyl–acyl Carrier Protein Desaturase from Castor Bean, *Ricinus communis*," *Plant Physiology* 96:344–345 (1991).

Knutzon et al., "Modification of Brassica seed oil by antisense expression of a stearoyl–acyl carrier protein desaturase gene," *Proc. Natl. Acad. Sci. USA* 89:2624–2728 (1992).

Kull et al., "Genetic engineering of potato starch composition: inhibition of amylose biosynthesis in tubers from transgenic potato lines by the expression of antisense sequences of the gene for granule–bound starch synthase," *J. Genet. & Breed.* 49:69–76 (1995).

Ladd and Knowles, Inheritance of Stearic Acid in the Seed Oil of Safflower (*Carthamus tinctorius* L.) *Crop Science* 10:525–527 (1970).

Laemmli, "Cleavage of Structural Proteins during the Assembly of the Head of Bacteriophage T4," *Nature* 227:680–686 (1970).

Lamb and Hay, "Ribozymes that cleave potato leafroll virus RNA within the coat protein and polymerase genes," *J. Gen. Virol.* 71:2257–2264 (1990).

Laursen et al., "Production of Fertile Transgenic Maize by Electroporation of Suspension Culture Cells," *Plant Molecular Biology* 24:51–61 (1994).

Leong et al., "A Specific Stain for the Detection of Nonheme Iron Proteins in Polyacrylamide Gels," *Anal. Biochem.* 207:317–320 (1992).

Li and Altman, "Cleavage by RNase P of gene N mRNA reduces bacteriophage λ burst size," *Nucleic Acids Research* 24:835–842 (1996).

MacDonald and Preiss, "Partial Purification and Characterization of Granule–Bound Starch Synthases from Normal and Waxy Maize," *Plant Physiol.* 78:849–852 (1985).

Mazzolini et al., "Assaying synthetic ribozymes in plants: high–level expression of a functional hammerhead structure fails to inhibit target gene activity in transiently transformed protoplasts," *Plant Molecular Biology* 20:715–731 (1992).

McCready and Hassid, "The Separation and Quantitative Estimation of Amylose and Amylopectin in Potato Starch," *The Journal of American Chemical Society* 65:1154–1157 (1943).

McElroy and Brettell, "Foreign Gene Expression in Transgenic Cereals," *TIBTECH* 12:62–68 (1994).

McKeon and Stumpf, "Purification and Characterization of the Stearoyl–acyl Carrier Protein Desaturase and the Acyl–acyl Carrier Protein Thioesterase from Maturing Seeds of Safflower," *J. Biol. Chem.* 257:12141–12147 (1982).

Messing, "New M13 Vectors for Cloning," *Methods in Enzymology* 101:20–78 (1983).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Milligan and Uhlenbeck, "Synthesis of Small RNAs Using T7 RNA Polymerase," *Methods Enzymol.* 180:51–62 (1989).

Miyamoto et al., *Plant Physiol.* 26:193–199 (1985).

Mullineaux et al., "The nucleotide sequence of maize streak virus DNA," *EMBO J.* 3:3063–3068 (1984).

Murphy and Cech, "Alteration of Substrate Specificity for the Endoribonucleolytic Cleavage of RNA by the Tetrahymena Ribozyme," *Proc. Natl. Acad. Sci. USA* 86:9218–9222 (1989).

Napoli et al., "Introduction of a Chimeric Chalcone Synthase Gene into Petunia Results in Reversible Co–Suppression of Homologous Genes in trans," *Plant Cell* 2:279–289 (1990).

Nelson et al., "Nucleoside Diphosphate Sugar–Starch Glucosyl Transferase Activity of wx Starch Granules," *Plant Physiol.* 62:383–386 (1978).

Norrander et al., "Construction of improved M13 vectors using oligodeoxynucleotide–directed mutagenesis," *Gene* 26:101–106 (1983).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ohlrogge, "Design of New Plant Products: Engineering of Fatty Acid Metabolism," *Plant Physiol.* 104:821–826 (1994).

Ojwang et al., "Inhibition of Human Immunodeficiency Virus Type 1 Expression by a Hairpin Ribozyme," *Proc. Natl. Acad. Sci. USA* 89:10802–10806 (1992).

Pazkowski et al., "Gene targeting in plants," *EMBO J.* 7:4021–4026 (1988).

Perriman et al., "Effective ribozyme delivery in plant cells," *Proc. Natl. Acad. Sci. USA* 92:6175–6179 (1995).

Perriman et al., "A Ribozyme That Enhances Gene Suppression in Tobacco Protoplasts," *Antisense Res. Dev.* 3:253–263 (1993).

Perrotta and Been, "Cleavage of Oligoribonucleotides by a Ribozyme Derived from the Hepatitis δ Virus RNA Sequence," *Biochemistry* 31:16–21 (1992).

Picton et al., "Altered fruit ripening and leaf senescence in tomatoes expressing an antisense ethylene–forming enzyme transgene," *The Plant J.* 3:469–481 (1993).

Polashock et al., "Expression of the yeast Δ–9 Fatty Acid Desaturase in *Nicotiana tabacum*," *Plant Physiol.* 100:894–901 (1992).

Potrykus, "Gene Transfer To Plants: Assessment of Published Approaches and Results," *Ann. Rev. Plant Physiol. Plant Mol. Biol.* 42:205–225 (1991).

Pouwels et al., *Cloning Vectors* and Supplements (1985).

Rhodes et al., "Genetically Transformed Maize Plants From Protoplasts," *Science* 240:204–207 (1988).

Rock and Cronan, "Solubilzation, Purification and Salt Activation of Acyl–Acyl Carrier Protein Synthetase from *Escherichia coli*," *J. Biol. Chem.* 254:7116–7122 (1979).

Ronchi et al., "The reduced expression of endogenous duplications (REED) in the maize R gene family is mediated by DNA methylation," *EMBO J.* 14:5318–5328 (1995).

Rossi et al., "Ribozymes as Anti–HIV–1 Therapeutic Agents: Principles, Applications, and Problems," *Aids Research and Human Retroviruses* 8:183–189 (1992).

Salehuzzaman et al., "Isolation and characterization of a cDNA encoding granule–bound starch synthase in cassava (*Manihot esculenta* Crantz) and its antisense expression in potato," *Plant Molecular Biology* 23:947–962 (1993).

Sano, "Differential regulation of waxy gene expression in rice endosperm," *Theor. Appl. Genet.* 68:467–473 (1984).

Sarver et al., "Ribozymes as Potential Anti–HIV–1 Therapeutic Agents" *Science* 247:1222–1225 (1990).

Sato et al., "Nucleotide Sequence of a Complementary DNA Clone Encoding Stearoyl–Acyl Carrier Protein Desaturase from *Simmondsia chinensis*," *Plant Physiol.* 99:362–363 (1992).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Shanklin and Somerville, "Stearoyl–acyl–carrier–protein desaturase from higher plants in structurally unrelated to the animal and fungal homologs," *Proc. Natl. Acad. Sci. USA* 88:2510–2514 (1991).

Shanklin et al., "Sequence of a Complementary DNA from *Cucumis sativus* L. Encoding the Stearoyl–Acyl–Carrier Protein Desaturase," *Plant Physiol.* 97:467–468 (1991).

Sheridan et al., "Black Mexican Sweet Corn: Its Use for Tissue Cultures," in *Maize for Biological Research,* W.F. Sheridan editor, University Press, University of South Dakota, Grand Forks, ND pp. 385–388 (1982).

Shure et al., "Molecular Identification and Isolation of the Waxy Locus in Maize," *Cell* 35:225–233 (1983).

Simons, "Naturally occurring antisense RNA control—a brief review," *Gene* 72:35–44 (1988).

Simons and Kleckner, "Translational Control of IS10 Transposition," *Cell* 34:683–691 (1983).

Slocombe et al., "Nucleotide sequence and temporal regulation of a seed–specific *Brassica napus* cDNA encoding a stearoly–acyl carrier protein (ACP) desaturase," *Plant Molecular Biology* 20:151–155 (1992).

Smith et al., "Antisense RNA inhibition of polygalacturonase gene expression in transgenic tomatoes," *Nature* 334:724–726 (1988).

Somerville and Browse, "Plant Lipids: Metabolism, Mutants and Membranes," *Science* 252:80–87 (1991).

Southern, "Detection of Specific Sequences Among DNA Fragments Separated by Gel Electrophoresis," *J. Mol. Biol.* 98:503–517 (1975).

Southern, "Gel Electrophoresis of Restriction Fragments," *Methods in Enzymology* 69:152–176 (1980).

Spencer et al., "Segregation of Transgenes in Maize," *Plant Molecular Biology* 18:201–210 (1992).

Stein and Cheng, "Antisense Oligonucleotides as Therapeutic Agents—Is the Bullet Really Magical?" *Science* 261:1004–1288 (1993).

Steinecke et al., "A stable hammerhead structure is not required for endonucleolytic activity of a ribozyme in vivo," *Gene* 149:47–54 (1994).

Steinecke et al., *EMBO J.* 11(4):1525–1530 (1992).

Strecker et al., "Corn Oil—Composition, Processing and Utlization," in *Edible Fats and Oils: Basic Principles and Modern Practices,* D.R. Erickson editor, American Oil Chemists' Society, Champaign, IL, pp. 309–323 (1990).

Sukhapinda et al., "Transformation of Maize (*Zea mays* L.) Protoplasts and Regeneration of Haploid Transgenic Plants," *Plant Cell Rep.* 13:63–68 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Taylor et al., "The Primary Structure of a cDNA Clone of the Stearoyl–Acyl Carrier Protein Desaturase Gene From Potato (*Solanum tuberosum* L.)," *Plant Physiol.* 100:533–534 (1992).

Thompson et al., "Primary Structures of the precursor and mature forms of stearoyl–acyl carrier protein desaturase from safflower embryos and requirement of ferredoxin for enzyme activity," *Proc. Natl. Acad. Sci. USA* 88:2578–2582 (1991).

Thompson et al., "Characterization of the herbicide–resistance gene bar from *Streptomyces hygroscopicus*," *EMBO J.* 6:2519–2523 (1987).

Tieman et al., "An Antisense Pectin Methylesterase Gene Alters Pectin Chemistry and Soluble Solids in Tomato Fruit," *Plant Cell* 4:667–669 (1992).

Towbin et al., "Electrophoretic transfer of proteins from polyaccrylamide gels to nitrocellulose sheets: Procedure and some applications," *Proc. Natl. Acad. Sci. USA* 76:4350–4354 (1979).

Uhlenbeck, "A Small Catalytic Oligoribonucleotide," *Nature* 328:596–600 (1987).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman and McSwiggen, "Ch. 30—Catalytic RNA (Ribozymes) as Drugs," *Annual Reports in Medicinal Chemistry* 30:285–294 (1995).

Vain et al., "Osmotic Treatment Chances Particle Bombardment–Mediated Transient and Stable Transformation of Maize," *Plant Cell. Rep.* 12:84–88 (1993).

van Bokland et al., "Transgene–mediated suppression of a chalcone synthase expression in *Petunia hybrida* results from an increase in RNA turnover," *Plant J.* 6:861–877 (1994).

van der Krol et al., "An anti–sense chaclone synthase gene in transgenic plants inhibits flower pigmentation," *Nature* 333:866–869 (1988).

van der Krol et al., "Inhibition of flower pigmentation by antisense CHS genes: promoter and minimal sequence requirements for the antisense effort," *Plant Molecular Biology* 14:457–466 (1990).

Ventura et al., "Activation of HIV–Specific Ribozyme Activity by Self–Cleavage," *Nucleic Acids Research* 21:3249–3255 (1993).

Visser et al., "Inhibition of the expression of the gene for granule–bound starch synthase in potato by antisense constructs," *Mol. Gen Genetics* 225:289–296 (1991).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1994).

Wegener et al., "Expression of a reporter gene is reduced by a ribozyme in transgenic plants," *Mol. Gen. Genet.* 245:465–470 (1994).

Weymann et al., "Isolation of Transgenic Progeny of Maize by Embryo Rescue Under Selective Conditions," *In Vitro Cell Dev. Biol.* 29P:33–37 (1993).

White et al., "A cassette containing the bar gene of *Streptomyces hygroscopicus*: a selectable marker for plant transformation," *Nucleic Acids Research* 18:1062 (1990).

Wincott et al., "Synthesis, deprotection, analysis and purification of RNA and ribozymes," *Nucleic Acids Research* 23:2677–2684 (1995).

Woolf et al., "Specificity of Antisense Oligonucleotides in vivo," *Proc. Natl. Acad. Sci. USA* 89:7305–7309 (1992).

Xu et al., "Cleavages of Transcripts of Tobacco Moasic Virus by Synthetic Ribozymes in vitro," *Science in China* (Ser. B) 35:1434–1443 (1992).

Zaug et al., "The Tetrahymena Ribozyme Acts Like an RNA Restriction Endonuclease," *Nature* 324:429–433 (1986).

Zuker, "On Finding All Suboptimal Foldings of an RNA Molecule," *Science* 244:48–52 (1989).

Kuipers et al., "Field evaluation of transgenic potato plants expressing an antisense granule–bound starch synthase gene: increase of the antisense effect during tuber growth," *Plant Molecular Biology* 26:1758–1773 (1994).

Doorsselaere et al., *The Plant J.* 8:855 (1995).

Feyter et al., *Mol. Gen. Genet.* 250:329–338 (1996).

Gibson et al., *Plant Cell Envir.* 17:627 (1994).

Grayburn et al., *BioTechnology* 10:675 (1992).

Griffin et al., *Chem. Biol.* 2:761 (1995).

Hammond and Fehr, *J. Amer. Oil Chem. Soc.* 61:1713–1716 (1984).

Kinney, *Curr. Opin. Cell Biol.* 5:144 (1994).

Michels and Pyle, *Biochemistry* 34:2965 (1995).

Picton et al., *The Plant J.* 3:469 (1993).

Polashock et al., *Plant Physiol.* 100:894 (1992).

Rock and Cronan, *J. Biol. Chem.* 254:7116–7122 (1981).

Sato et al., *Plant Physiol.* 99:362–363 (1992).

Southern, *J.Mol. Biol.* 98:503 (1975).

Southern, *Methods in Enzymology* 69:152 (1980).

Tieman et al., *Plant Cell* 4:667 (1992).

van der Krol et al., *Nature* 333:866 (1988).

Xu et al., *Science in China* (Ser. B) 35:1434–1433 (1992).

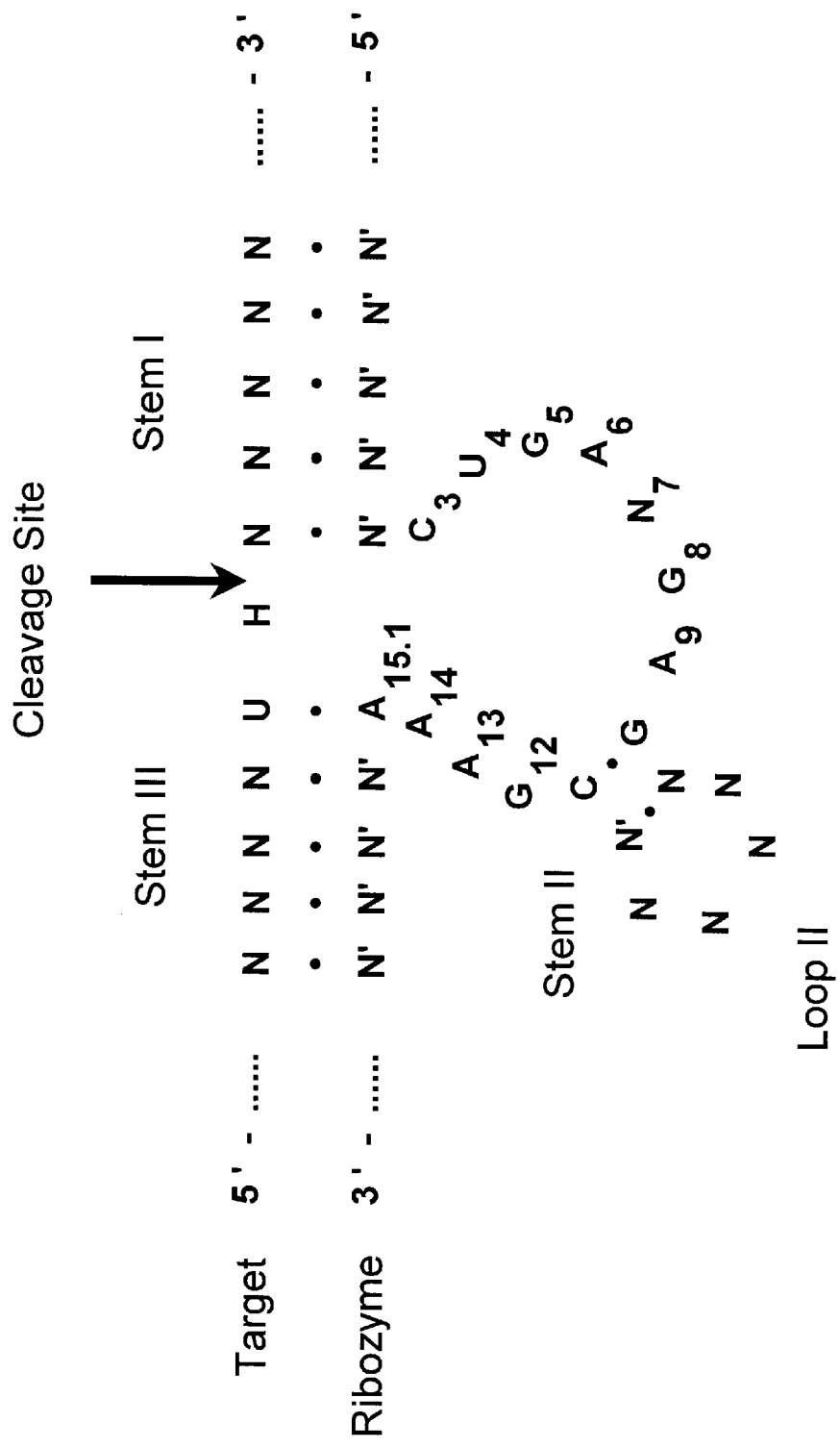
Figure 1: Hammerhead Ribozyme

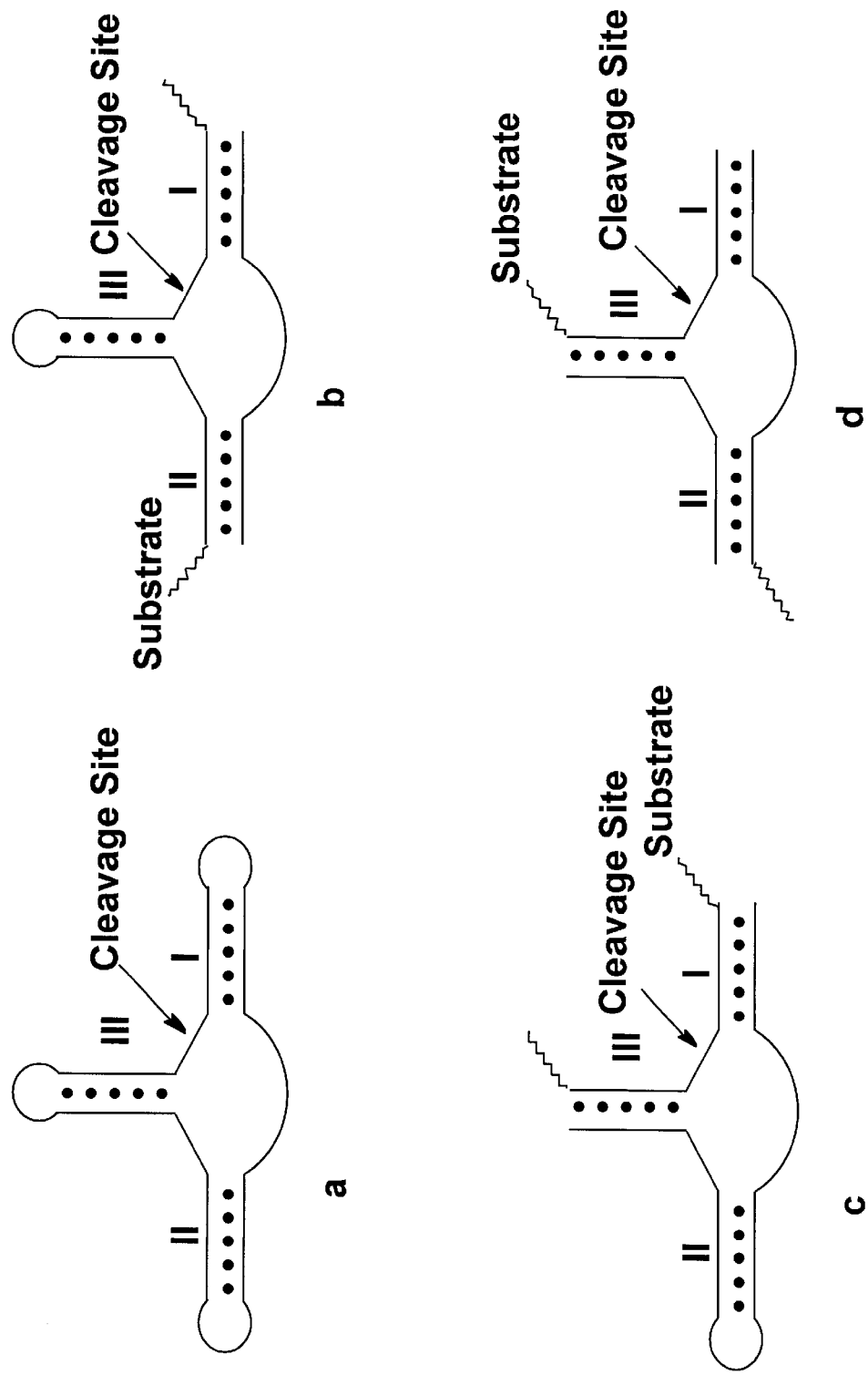

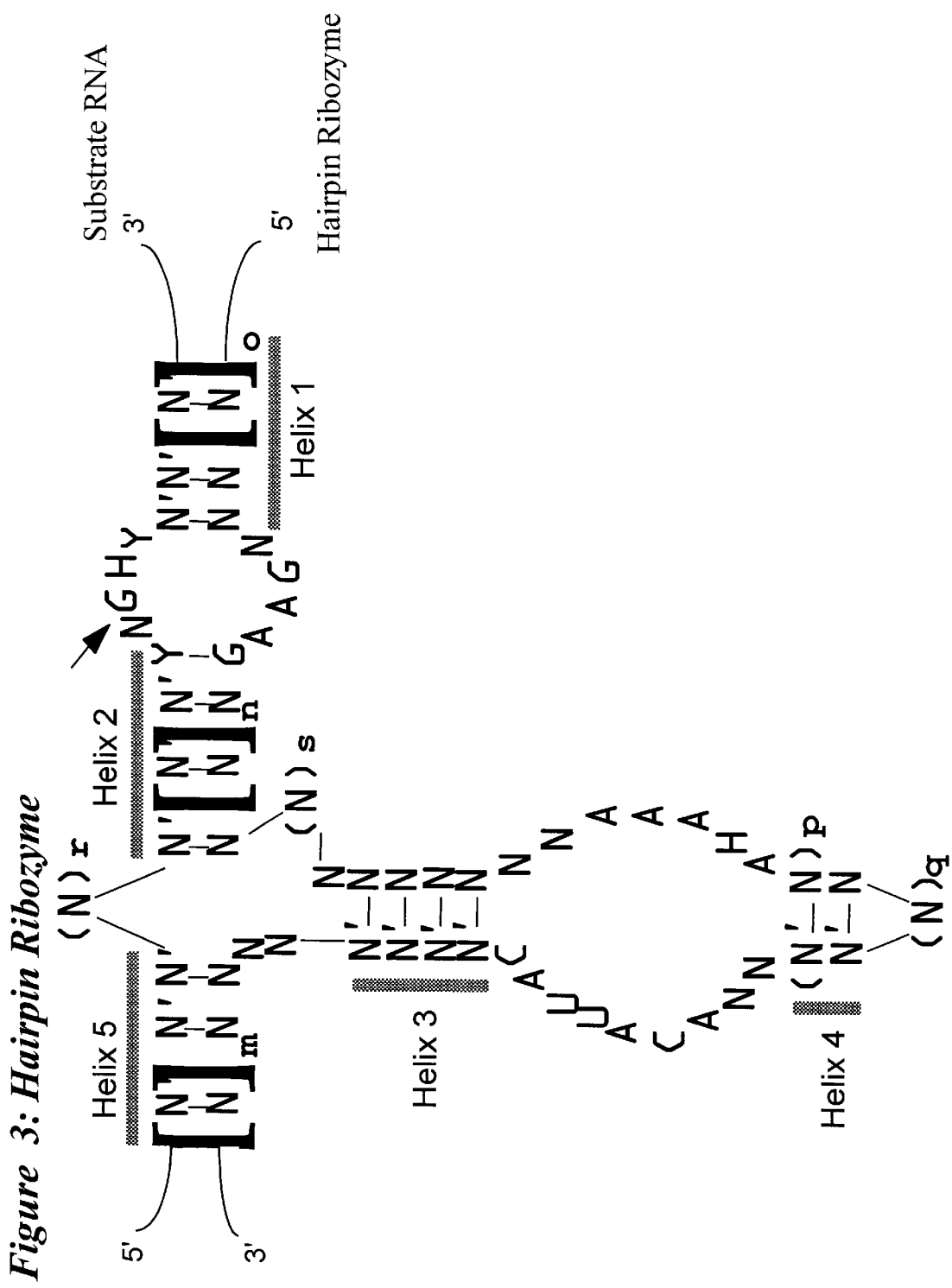
*Figure 3: Hairpin Ribozyme*

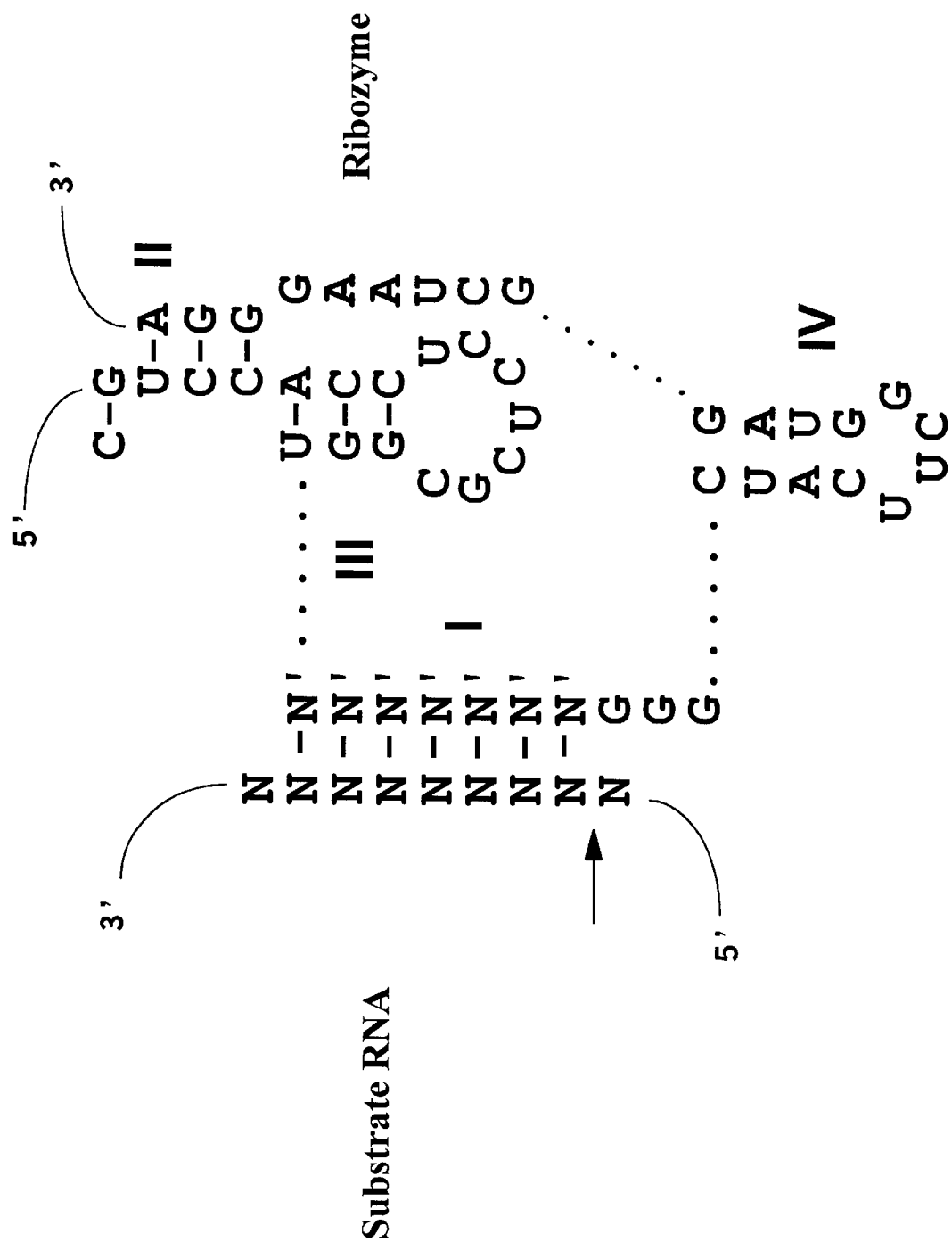
*Figure 4. Hepatitis Delta Virus (HDV) Ribozyme*

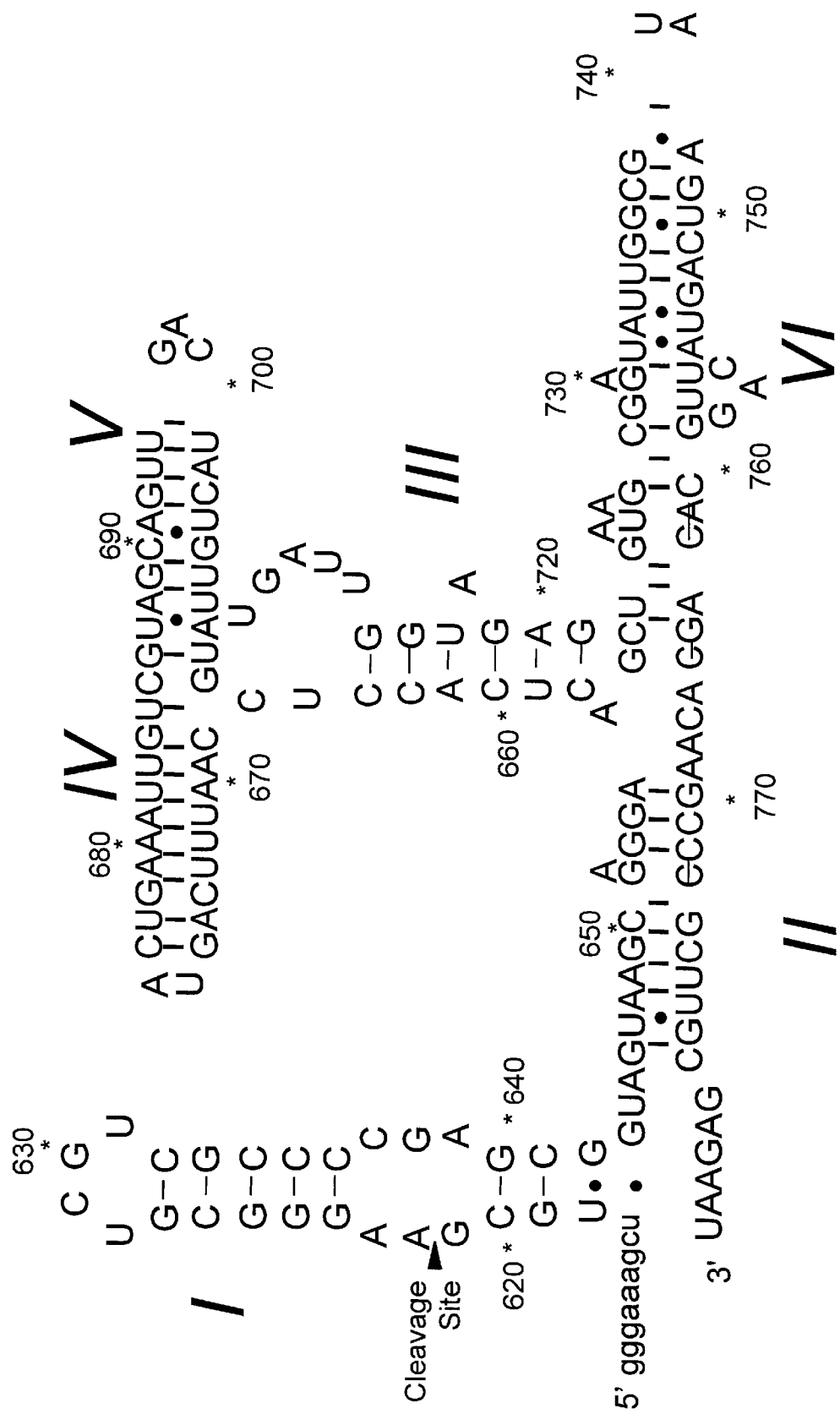
Figure 5. Neurospora vs Ribozyme

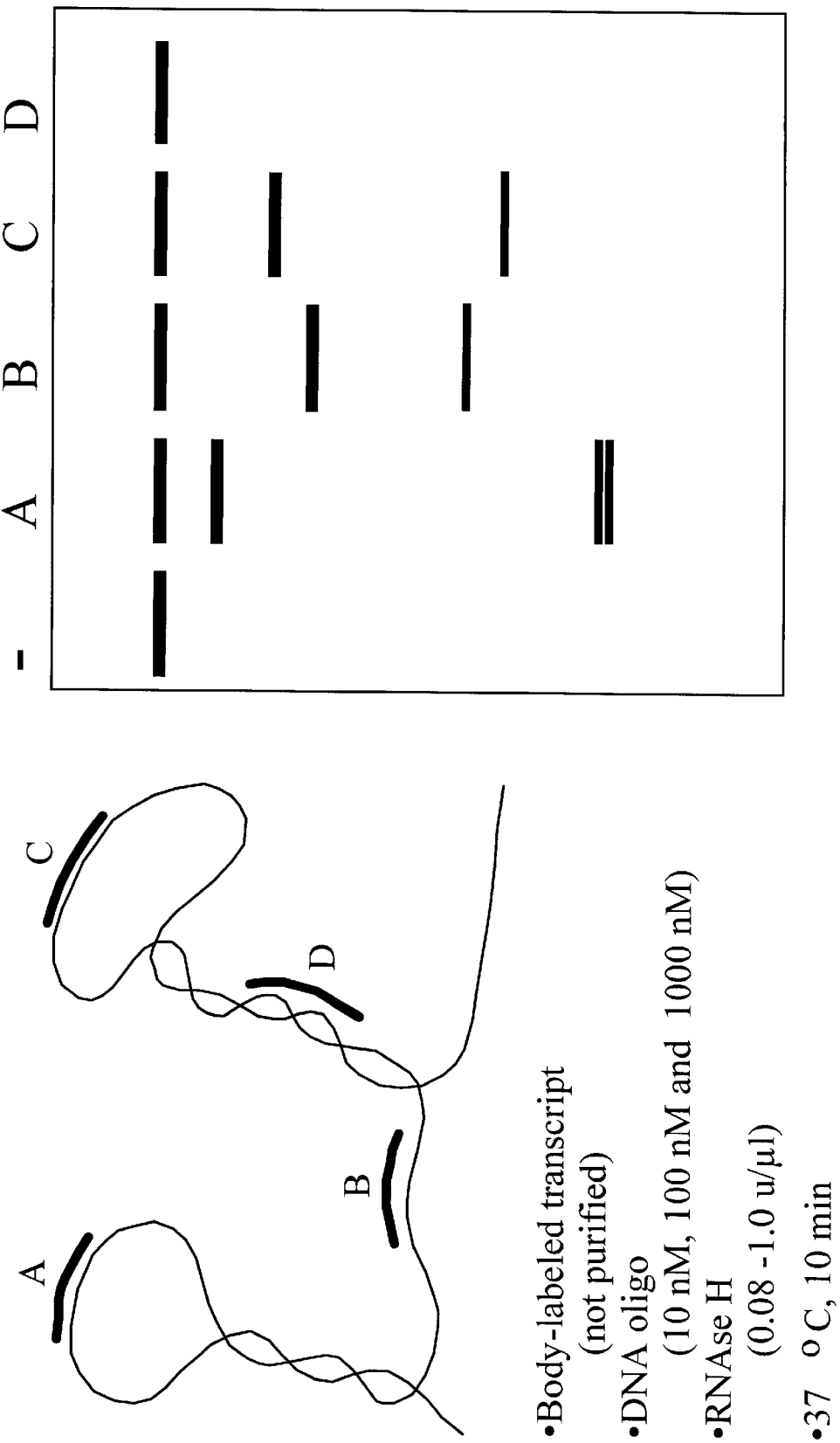

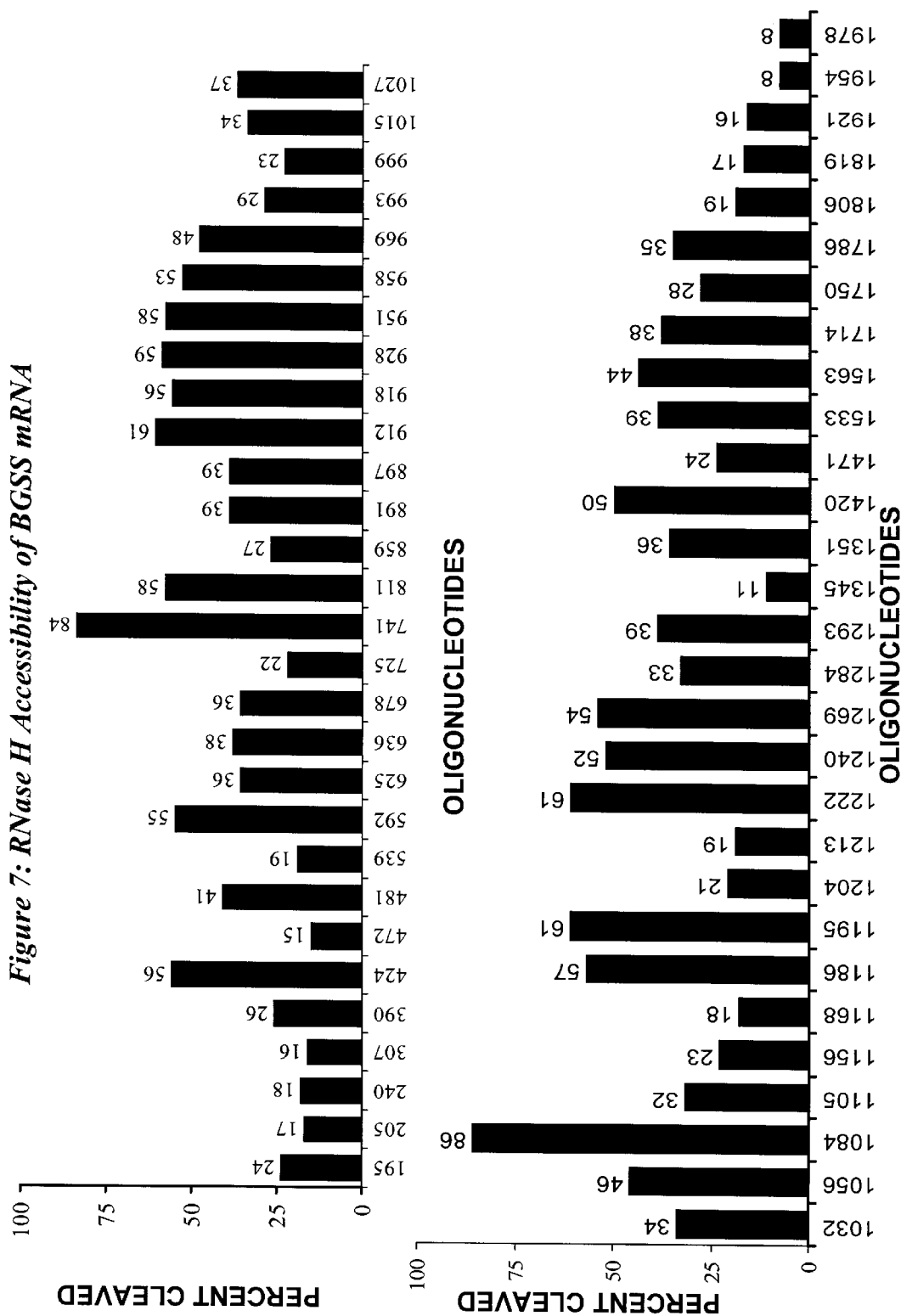

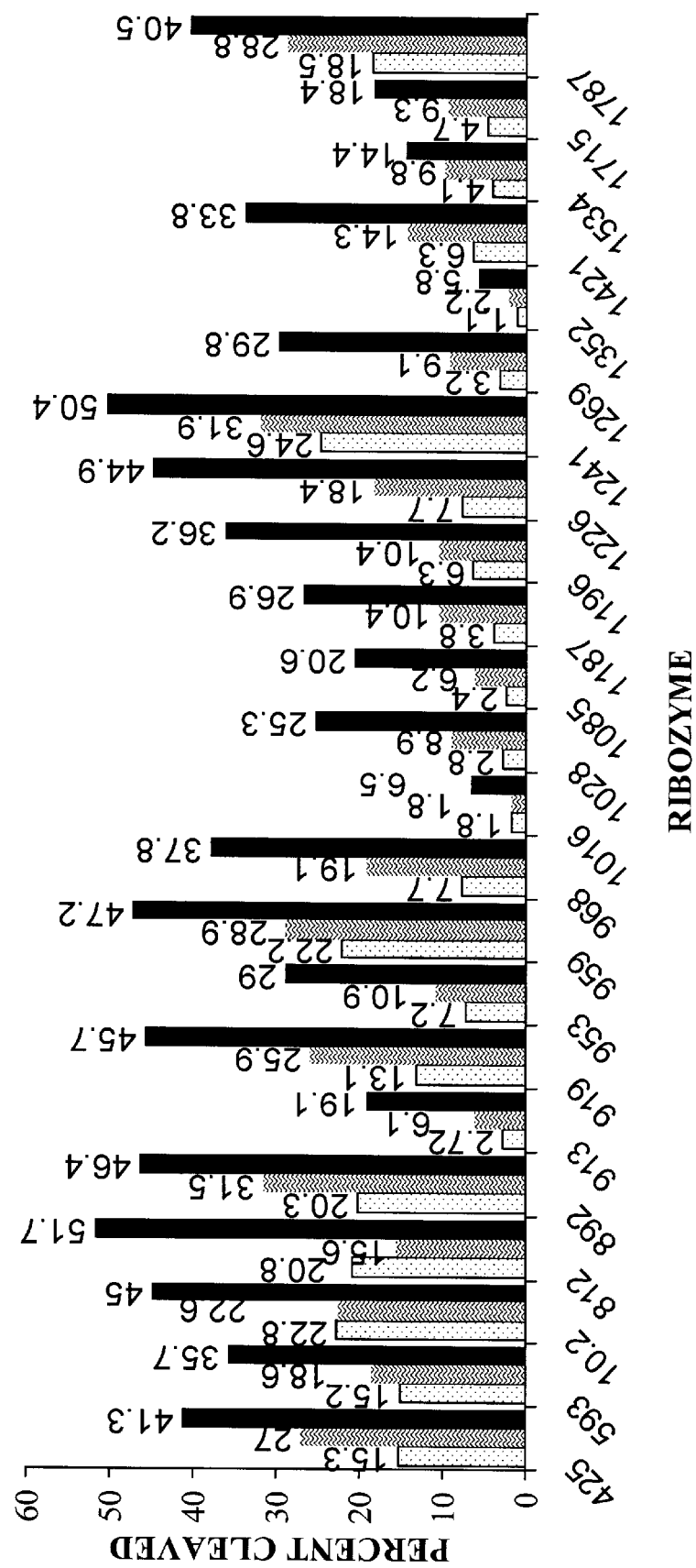
Figure 8: Cleavage of GBSS RNA by HH Ribozymes

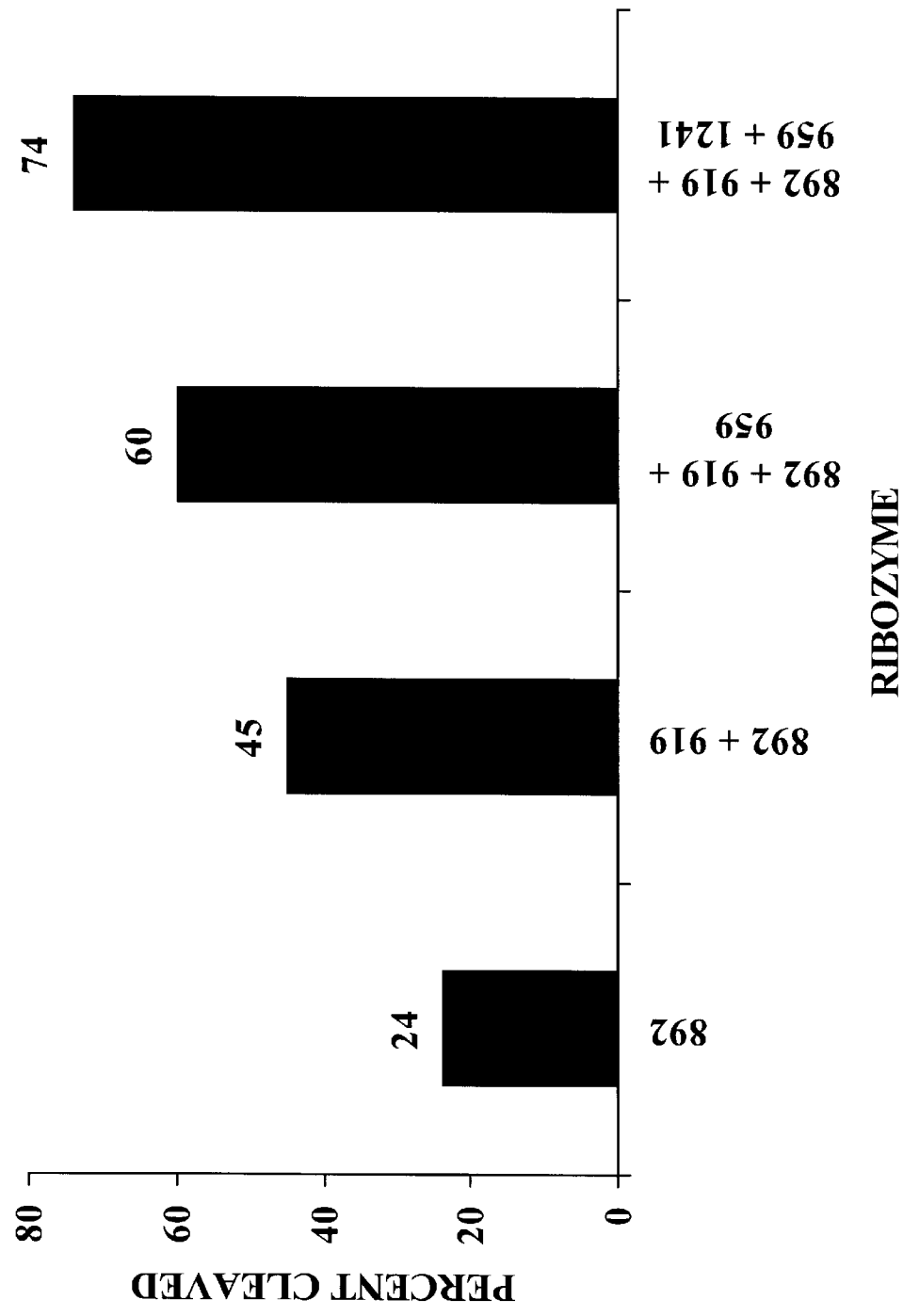
Figure 9: Cleavage of GBSS RNA by Multiple HH Ribozymes

```
       5         10          15    20          25    30          35    40          45    50          55    60
       *                     *                 *                 *                 *                 *
CGCACGCGCC  CTCTGCCGCT  TGTTCGTTCC  TCGCGCTCGC  CACCAGGCAC  CACCACACAC 65    70          75    80          85    90          95   100         105   110         115   120
             *                 *                 *                 *                 *                 *
ATCCCAATCT  CGCGAGGGCA  AGCAGCAGGG  TCTGCGGCGG  CGGCGGCGGC  CGCGCTTCCG 125  130         135  140         145        150    155         160        165         170
                 *              *                  *                  *                        *
GCTCCCCTTC  CCATTGGCCT      CCACG ATG GCG CTC CGC CTC AAC GAC GTC GCG
                                  MET ALA LEU ARG LEU ASN ASP VAL ALA>

175       180       185        190       195        200       205        210       215       220
              *                    *                    *                    *                   *
CTC TGC CTC TCC CCG CCG CTC GCC GCC CGC CGC CGC CGC CGC AGC AGC
LEU CYS LEU SER PRO PRO LEU ALA ALA ARG ARG ARG ARG ARG SER SER>

225       230   235        240       245        250       255        260   265
                    *                *                    *                    *
GGC AGG TTC GTC GCC GTC GCC TCC ATG ACG TCC GCC GTC TCC ACC AAG
GLY ARG PHE VAL ALA VAL ALA SER MET THR SER ALA VAL SER THR LYS>

270       275       280        285       290   295        300       305        310       315
    *                    *                    *                    *                   *
GTC GAG AAT AAG AAG CCA TTT GCT CCT CCA AGG GAG GTA CAT GTC CAG
VAL GLU ASN LYS LYS PRO PHE ALA PRO PRO ARG GLU VAL HIS VAL GLN>

320   325        330   335        340       345        350       355        360
                    *                *                    *                    *
GTT ACA CAT TCA ATG CCA CCT CAC AAG ATT GAA ATT TTC AAG TCG CTT
VAL THR HIS SER MET PRO PRO HIS LYS ILE GLU ILE PHE LYS SER LEU>

365       370       375        380       385        390       395        400       405       410
           *                    *                    *                    *                   *
GAT GAT TGG GCT AGA GAT AAT ATC TTG ACG CAT CTC AAG CCA GTC GAG
ASP ASP TRP ALA ARG ASP ASN ILE LEU THR HIS LEU LYS PRO VAL GLU>

415       420   425        430       435        440   445        450       455        460
                    *                    *                    *                    *
AAG TGT TGG CAG CCA CAG GAT TTC CTC CCG GAC CCA GCA TCT GAA GGA
LYS CYS TRP GLN PRO GLN ASP PHE LEU PRO ASP PRO ALA SER GLU GLY>

465       470   475        480       485        490       495   500         505
                    *                    *                    *                    *
TTT CAT GAT GAA GTT AAG GAG CTC AGA GAA CGT GCC AAG GAA ATC CCT
PHE HIS ASP GLU VAL LYS GLU LEU ARG GLU ARG ALA LYS GLU ILE PRO>
```

FIG. 10A

```
   510   515   520   525   530   535   540   545   550   555
    *           *           *           *           *
GAT GAT TAT TTT GTT TGT TTG GTG GGA GAC ATG ATT ACC GAG GAA GCT
ASP ASP TYR PHE VAL CYS LEU VAL GLY ASP MET ILE THR GLU GLU ALA>

560   565   570   575   580   585   590   595   600
        *           *           *           *           *
CTA CCA ACA TAC CAG ACT ATG CTT AAC ACC CTC GAC GGT GTC AGA GAT
LEU PRO THR TYR GLN THR MET LEU ASN THR LEU ASP GLY VAL ARG ASP>

605   610   615   620   625   630   635   640   645   650
  *           *           *           *           *
GAG ACA GGT GCA AGC CCC ACT GCC TGG GCT GTT TGG ACG AGG GCA TGG
GLU THR GLY ALA SER PRO THR ALA TRP ALA VAL TRP THR ARG ALA TRP>

655   660   665   670   675   680   685   690   695   700
        *           *           *           *           *
ACT GCT GAG GAG AAC AGG CAT GGT GAT CTG CTC AAC AAG TAT ATG TAC
THR ALA GLU GLU ASN ARG HIS GLY ASP LEU LEU ASN LYS TYR MET TYR>

705   710   715   720   725   730   735   740   745
        *           *           *           *
CTC ACT GGG AGG GTG GAT ATG AGG CAG ATT GAG AAG ACA ATT CAG TAT
LEU THR GLY ARG VAL ASP MET ARG GLN ILE GLU LYS THR ILE GLN TYR>

750   755   760   765   770   775   780   785   790   795
  *           *           *           *           *
CTT ATT GGC TCT GGA ATG GAT CCT AGG ACT GAG AAT AAT CCT TAT CTT
LEU ILE GLY SER GLY MET ASP PRO ARG THR GLU ASN ASN PRO TYR LEU>

800   805   810   815   820   825   830   835   840
     *           *           *           *           *
GGT TTC ATC TAC ACC TCC TTC CAA GAG CGG GCG ACC TTC ATC TCA CAC
GLY PHE ILE TYR THR SER PHE GLN GLU ARG ALA THR PHE ILE SER HIS>

845   850   855   860   865   870   875   880   885   890
        *           *           *           *           *
GGG AAC ACT GCT CGT CAC GCC AAG GAC TTT GGC GAC TTA AAG CTT GCA
GLY ASN THR ALA ARG HIS ALA LYS ASP PHE GLY ASP LEU LYS LEU ALA>

895   900   905   910   915   920   925   930   935   940
        *           *           *           *           *
CAA ATC TGC GGC ATC ATC GCC TCA GAT GAG AAG CGA CAT GAA ACT GCG
GLN ILE CYS GLY ILE ILE ALA SER ASP GLU LYS ARG HIS GLU THR ALA>

945   950   955   960   965   970   975   980   985
        *           *           *           *
TAC ACC AAG ATC GTG GAG AAG CTG TTT GAG ATC GAC CCT GAT GGT ACC
TYR THR LYS ILE VAL GLU LYS LEU PHE GLU ILE ASP PRO ASP GLY THR>

990   995  1000  1005  1010  1015  1020  1025  1030  1035
  *           *           *           *           *
GTG GTC GCT CTG GCT GAC ATG ATG AGG AAG AAG ATC TCA ATG CCT GCC
VAL VAL ALA LEU ALA ASP MET MET ARG LYS LYS ILE SER MET PRO ALA>
```

FIG. 10B

```
     1040 1045  1050  1055 1060  1065  1070 1075  1080
        *           *           *           *           *
   CAC CTG ATG TTT GAC GGG CAG GAC GAC AAG CTG TTC GAG CAC TTC TCC
   HIS LEU MET PHE ASP GLY GLN ASP ASP LYS LEU PHE GLU HIS PHE SER>

1085 1090  1095  1100 1105  1110  1115 1120  1125  1130
        *           *           *           *           *
   ATG GTC GCG CAG AGG CTT GGC GTT TAC ACC GCC AGG GAC TAC GCC GAC
   MET VAL ALA GLN ARG LEU GLY VAL TYR THR ALA ARG ASP TYR ALA ASP>

1135  1140  1145  1150  1155  1160 1165  1170  1175 1180
           *           *           *           *           *
   ATC CTC GAG TTC CTC GTC GAC AGG TGG AAG GTG GCG AGC CTG ACT GGT
   ILE LEU GLU PHE LEU VAL ASP ARG TRP LYS VAL ALA SER LEU THR GLY>

1185  1190  1195  1200   1205 1210   1215  1220  1225
              *           *           *           *
   CTG TCG GGT GAA GGG AAC AAG GCG CAG GAC TAC CTT TGC ACC CTT GCT
   LEU SER GLY GLU GLY ASN LYS ALA GLN ASP TYR LEU CYS THR LEU ALA>

1230  1235  1240  1245  1250  1255  1260  1265  1270  1275
     *           *           *           *           *
   TCA AGA ATC AGG AGG CTG GAG GAG AGG GCC CAG AGC AGA GCC AAG AAA
   SER ARG ILE ARG ARG LEU GLU GLU ARG ALA GLN SER ARG ALA LYS LYS>

1280  1285  1290  1295  1300  1305  1310  1315  1320
              *           *           *           *           *
   GCC GGC ACG CTG CCT TTC AGC TGG GTA TAC GGT AGG GAC GTC CAA CTG
   ALA GLY THR LEU PRO PHE SER TRP VAL TYR GLY ARG ASP VAL GLN LEU>
1325 1330 1335 1340  1345 1350  1355 1360  1365 1370  1375 1380
   *           *           *           *           *           *
TGA GAT CGGAAACCTG CTGCGGTCTG CTTAGACAAG ACCTGCTGTG TCTGCGTTAC
***>

1385 1390  1395 1400  1405 1410  1415 1420  1425 1430  1435 1440
         *           *           *           *           *           *
ATAGGTCTCC AGGTTTTGAT CAAATGGTCC CGTGTCGTCT TATAGAGCGA TAGGAGAACG 1445 1450  1455 1460  1465 1470  1475 1480  1485 1490  1495 1500
         *           *           *           *           *           *
TGTTGGTCTG TGGTGTAGCT TTGTTTTTAT TTTGTATTTT TCTGCTTTGA TGTACAACCT 1505 1510  1515 1520  1525 1530  1535 1540  1545 1550  1555 1560
         *           *           *           *           *           *
GTGGCCGCAT GAACTGGGGC GTGGAGATGG GAGCGACCAT GCCGTACTTT GTCTGTCGCT 1565 1570  1575 1580  1585 1590  1595 1600  1605 1610  1615 1620
         *           *           *           *           *           *
GGCGGTGTGT TTCGGTATGT TATTTGAGTT GCTCAGATCT GTTAAAAAAA AAAAAAAAA
A
```

FIG. 10C

Figure 12: Plant Fatty Acid Biosynthesis

1. Delta 9 desaturase

*Figure 17:* Delta-9 Desaturase Multimer Ribozyme Construct

*Figure 18:* Delta-9 Desaturase Multimer Ribozyme Construct

Figure 23: Delta-9 Desaturase Multimer Ribozyme

| RIBOZYMES | PERCENT CLEAVED |
|---|---|
| 453 MULTIMER | 79.2 |
| 453 | 47 |
| 464 | ≥ 1 |
| 475 | 20 |
| 484 | 33 |
| 252 MULTIMER | 55.2 |
| 252 | 55 |
| 271 | 20 |
| 313 | 20 |
| 326 | 5 |
| 238 MULTIMER | 30.9 |
| 238 HP | ≥ 1 |
| 252 | 33 |
| 259 | ≥ 1 |
| 271 | 67 |
| 259 MULTIMER | 24 |
| 259 HP | 9 |
| 271 | 40 |
| 313 | 51 |

FIG. 24

SEQUENCE OF NUCLEOTIDES 1-91:

```
HIND III   SSE8387 I   SPH I PST I FSE I   PAC I   NOT I   PME I   SRF I   SWA I   ASC I   SGF I   BGL II
AAGCTTGCATGCCTGCAGGCCGGCCTTAATTAAGGCGGCCGCGTTTAAACGCCCGGGCATTTAAATGGCGCGCCGCGATCGCTTGCAGATCT
TTCGAACGTACGGACGTCCGGCCGGAATTAATTCCGCCGGCGCAAATTTGCGGGCCCGTAAATTTACCGCGCGGCGCTAGCGAACGTCTAGA
```

NUCLEIC ACID ENCODING DELTA-9 DESATURASE

This application is a continuation-in-part of: 1) a Non-Provisional application by Edington, entitled "Method for the production of transgenic plants deficient in starch granule bound glucose starch glycosyl transferase activity" filed on Sep. 2, 1994 as U.S. Ser. No. of 08/300,726; and 2) a Provisional application by Zwick et al., entitled "Composition and method for modification of fatty acid saturation profile in plants" filed on Jul. 13, 1995, as U.S. Ser. No. 60/001,135. Both of these applications in their entirety, including drawings, are hereby incorporated by reference herein.

BACKGROUND OF THE INVENTION

The present invention concerns compositions and methods for the modulation of gene expression in plants, specifically using enzymatic nucleic acid molecules.

The following is a brief description of regulation of gene expression in plants. The discussion is not meant to be complete and is provided only for understanding of the invention that follows. This summary is not an admission that any of the work described below is prior art to the claimed invention.

There are a variety of strategies for modulating gene expression in plants. Traditionally, antisense RNA (reviewed in Bourque, 1995 *Plant Sci* 105, 125–149) and co-suppression (reviewed in Jorgensen, 1995 *Science* 268, 686–691) approaches have been used to modulate gene expression. Insertion mutagenesis of genes have also been used to silence gene expression. This approach, however, cannot be designed to specifically inactivate the gene of interest. Applicant believes that ribozyme technology offers an attractive new means to alter gene expression in plants.

Naturally occurring antisense RNA was first discovered in bacteria over a decade ago (Simons and Kleckner, 1983 *Cell* 34, 683–691). It is thought to be one way in which bacteria can regulate their gene expression (Green et al., 1986 *Ann. Rev. Biochem.* 55: 567–597; Simons 1988 *Gene* 72: 35–44). The first demonstration of antisense-mediated inhibition of gene expression was reported in mammalian cells (Izant and Weintraub 1984 *Cell* 36: 1007–1015). There are many examples in the literature for the use of antisense RNA to modulate gene expression in plants. Following are a few examples:

Shewmaker et al., U.S. Pat. Nos. 5,107,065 and 5,453,566 disclose methods for regulating gene expression in plants using antisense RNA.

It has been shown that an antisense gene expressed in plants can act as a dominant suppressor gene. Transgenic potato plants have been produced which express RNA antisense to potato or cassava granule bound starch synthase (GBSS). In both of these cases, transgenic plants have been constructed which have reduced or no GBSS activity or protein. These transgenic plants give rise to potatoes containing starch with dramatically reduced amylose levels (Visser et al. 1991, *Mol. Gen. Genet.* 225: 2889–296; Salehuzzaman et al. 1993, *Plant Mol. Biol.* 23: 947–962).

Kull et al., 1995, *J. Genet. & Breed.* 49, 69–76 reported inhibition of amylose biosynthesis in tubers from transgenic potato lines mediated by the expression of antisense sequences of the gene for granule-bound starch synthase (GBSS). The authors, however, indicated a failure to see any in vivo activity of ribozymes targeted against the GBSS RNA.

Antisense RNA constructs targeted against Δ-9 desaturase enzyme in canola have been shown to increase the level of stearic acid (C18:0) from 2% to 40% (Knutzon et. al., 1992 *Proc. Natl. Acad. Sci.* 89, 2624). There was no decrease in total oil content or germination efficiency in one of the high stearate lines. Several recent reviews are available which illustrate the utility of plants with modified oil composition (Ohlrogge, J. B. 1994 *Plant Physiol.* 104, 821; Kinney, A. J. 1994 *Curr. Opin. Cell Biol.* 5, 144; Gibson et al. 1994 *Plant Cell Envir.* 17, 627).

Homologous transgene inactivation was first documented in plants as an unexpected result of inserting a transgene in the sense orientation and finding that both the gene and the transgene were down-regulated (Napoli et al., 1990 *Plant Cell* 2: 279–289). There appears to be at least two mechanisms for inactivation of homologous genetic sequences. One appears to be transcriptional inactivation via methylation, where duplicated DNA regions signal endogenous mechanisms for gene silencing. This approach of gene modulation involves either the introduction of multiple copies of transgenes or transformation of plants with transgenes with homology to the gene of interest (Ronchi et al. 1995 *EMBO J.* 14: 5318–5328). The other mechanism of co-suppression is post-transcriptional, where the combined levels of expression from both the gene and the transgene is thought to produce high levels of transcript which triggers threshold-induced degradation of both messages (van Bokland et al., 1994 *Plant J.* 6: 861–877). The exact molecular basis for co-suppression is unknown.

Unfortunately, both antisense and co-suppression technologies are subject to problems in heritability of the desired trait (Finnegan and McElroy 1994 *Bio/Technology* 12: 883–888). Currently, there is no easy way to specifically inactivate a gene of interest at the DNA level in plants (Pazkowski et al., 1988 *EMBO J.* 7: 4021–4026). Transposon mutagenesis is inefficient and not a stable event, while chemical mutagenesis is highly non-specific.

Applicant believes that ribozymes present an attractive alternative and because of their catalytic mechanism of action, have advantages over competing technologies. However, there have been difficulties in demonstrating the effectiveness of ribozymes in modulating gene expression in plant systems (Mazzolini et al., 1992 *Plant Mol. Biol.* 20: 715–731; Kull et al., 1995 *J. Genet. & Breed.* 49: 69–76). Although there are reports in the literature of ribozyme activity in plants cells, almost all of them involve down regulation of exogenously introduced genes, such as reporter genes in transient assays (Steinecke et al., 1992 *EMBO J.* 11:1525–1530; Perriman et al., 1993 *Antisense Res. Dev.* 3: 253–263; Perriman et al., 1995, *Proc. Natl. Acad. Sci. USA*, 92, 6165).

There are also several publications, [e.g., Lamb and Hay, 1990, *J. Gen. Virol.* 71, 2257–2264; Gerlach et al., International PCT Publication No. WO 91/13994; Xu et al., 1992, Science in China (Ser. B) 35, 1434–1443; Edington and Nelson, 1992, in *Gene Regulation*: Biology of antisense RNA and DNA, eds. R. P. Erickson and J. G. Izant, pp 209–221, Raven Press, NY.; Atkins et al., International PCT Publication No. WO 94/00012; Lenee et al., International PCT Publication Nos. WO 94/19476 and WO 9503404, Atkins et al., 1995, *J. Gen. Virol.* 76, 1781–1790; Gruber et al., 1994, *J. Cell. Biochem. Suppl.* 18A, 110 (X1-406) and Feyter et al., 1996, *Mol. Gen. Genet.* 250, 329–338], that propose using hammerhead ribozymes to modulate: virus replication, expression of viral genes and/or reporter genes. None of these publications report the use of ribozymes to modulate the expression of plant genes.

Mazzolini et al., 1992, *Plant. Mol. Bio.* 20, 715–731; Steinecke et al., 1992, *EMBO J.* 11, 1525–1530; Perriman et al., 1995, *Proc. Natl. Acad. Sci. USA.*, 92, 6175–6179; Wegener et al., 1994, *Mol. Gen. Genet.* 245, 465–470; and Steinecke et al., 1994, *Gene*, 149, 47–54, describe the use of hammerhead ribozymes to inhibit expression of reporter genes in plant cells.

Bennett and Cullimore, 1992 *Nucleic Acids Res.* 20, 831–837 demonstrate hammerhead ribozyme-mediated in vitro cleavage of glna, glnb, glng and glnd RNA, coding for glutamine synthetase enzyme in *Phaseolus vulgaris*.

Hitz et al., (WO 91/18985) describe a method for using the soybean Δ-9 desaturase enzyme to modify plant oil composition. The application describes the use of soybean Δ-9 desaturase sequence to isolate Δ-9 desaturase genes from other species.

The references cited above are distinct from the presently claimed invention since they do not disclose and/or contemplate the use of ribozymes in maize. Furthermore, Applicant believes that the references do not disclose and/or enable the use of ribozymes to down regulate genes in plant cells, let alone plants.

SUMMARY OF THE INVENTION

The invention features modulation of gene expression in plants specifically using enzymatic nucleic acid molecules. Preferably, the gene is an endogenous gene. The enzymatic nucleic acid molecule with RNA cleaving activity may be in the form of, but not limited to, a hammerhead, hairpin, hepatitis delta virus, group I intron, group II intron, RNaseP RNA, Neurospora VS RNA and the like. The enzymatic nucleic acid molecule with RNA cleaving activity may be encoded as a monomer or a multimer, preferably a multimer. The nucleic acids encoding for the enzymatic nucleic acid molecule with RNA cleaving activity may be operably linked to an open reading frame. Gene expression in any plant species may be modified by transformation of the plant with the nucleic acid encoding the enzymatic nucleic acid molecules with RNA cleaving activity. There are also numerous technologies for transforming a plant: such technologies include but are not limited to transformation with Agrobacterium, bombarding with DNA coated microprojectiles, whiskers, or electroporation. Any target gene may be modified with the nucleic acids encoding the enzymatic nucleic acid molecules with RNA cleaving activity. Two targets which are exemplified herein are delta 9 desaturase and granule bound starch synthase (GBSS).

Until the discovery of the inventions herein, nucleic acid-based reagents, such as enzymatic nucleic acids (ribozymes), had yet to be demonstrated to modulate and/or inhibit gene expression in plants such as monocot plants (e.g., corn). Ribozymes can be used to modulate a specific trait of a plant cell, for example, by modulating the activity of an enzyme involved in a biochemical pathway. It may be desirable, in some instances, to decrease the level of expression of a particular gene, rather than shutting down expression completely: ribozymes can be used to achieve this. Enzymatic nucleic acid-based techniques were developed herein to allow directed modulation of gene expression to generate plant cells, plant tissues or plants with altered phenotype.

Ribozymes (i.e., enzymatic nucleic acids) are nucleic acid molecules having an enzymatic activity which is able to repeatedly cleave other separate RNA molecules in a nucleotide base sequence-specific manner. Such enzymatic RNA molecules can be targeted to virtually any RNA transcript, and efficient cleavage has been achieved in vitro and in vivo (Zaug et al., 1986, *Nature* 324, 429; Kim et al., 1987, *Proc. Natl. Acad. Sci. USA* 84, 8788; Dreyfus, 1988, Einstein Quarterly *J. Bio. Med.*, 6, 92; Haseloff and Gerlach, 1988, *Nature* 334 585; Cech, 1988, *JAMA* 260, 3030; Murphy and Cech, 1989, *Proc. Natl. Acad. Sci. USA.*, 86, 9218; Jefferies et al., 1989, *Nucleic Acids Research* 17, 1371).

Because of their sequence-specificity, trans-cleaving ribozymes may be used as efficient tools to modulate gene expression in a variety of organisms including plants, animals and humans (Bennett et al., supra; Edington et al., supra; Usman & McSwiggen, 1995 *Ann. Rep. Med. Chem.* 30, 285–294; Christoffersen and Marr, 1995 *J. Med. Chem.* 38, 2023–2037). Ribozymes can be designed to cleave specific RNA targets within the background of cellular RNA. Such a cleavage event renders the mRNA non-functional and abrogates protein expression from that RNA. In this manner, synthesis of a protein associated with a particular phenotype and/or disease state can be selectively inhibited.

Other features and advantages of the invention will be apparent from the following description of the preferred embodiments thereof, and from the claims.

BRIEF DESCRIPTION OF THE FIGURES

FIG. 1 is a diagrammatic representation of the hammerhead ribozyme domain known in the art. Stem II can be $\geq 2$ base-pairs long. Each N is any nucleotide and each • represents a base pair.

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H refers to bases A, U, or C. Y refers to pyrimidine bases. "—" refers to a covalent bond.

FIG. 4 is a representation of the general structure of the hepatitis Δ virus ribozyme domain known in the art.

FIG. 5 is a representation of the general structure of the self-cleaving VS RNA ribozyme domain.

FIG. 6 is a schematic representation of an RNaseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

FIG. 7 is a graphical representation of RNaseH accessibility of GBSS RNA.

FIG. 8 is a graphical representation of GBSS RNA cleavage by ribozymes at different temperatures.

FIG. 9 is a graphical representation of GBSS RNA cleavage by multiple ribozymes.

FIGS. 10A–C list the nucleotide sequence of Δ-9 desaturase cDNA isolated from *Zea mays*.

FIG. 11 has been adapted from Gibson et al., 1994, *Plant Cell Envir.* 17, 627.

FIG. 24 shows cleavage of Δ-9 desaturase RNA by ribozymes. 453 Multimer, represents a multimer ribozyme construct targeted against hammerhead ribozyme sites 453, 464, 475 and 484. 252 Multimer, represents a multimer ribozyme construct targeted against hammerhead ribozyme sites 252, 271, 313 and 326. 238 Multimer, represents a multimer ribozyme construct targeted against three hammerhead ribozyme sites 252, 259 and 271 and one hairpin ribozyme site 238 (HP). 259 Multimer, represents a multimer ribozyme construct targeted against two hammerhead ribozyme sites 271 and 313 and one hairpin ribozyme site 259 (HP).

DETAILED DESCRIPTION OF THE INVENTION

Figure 11:
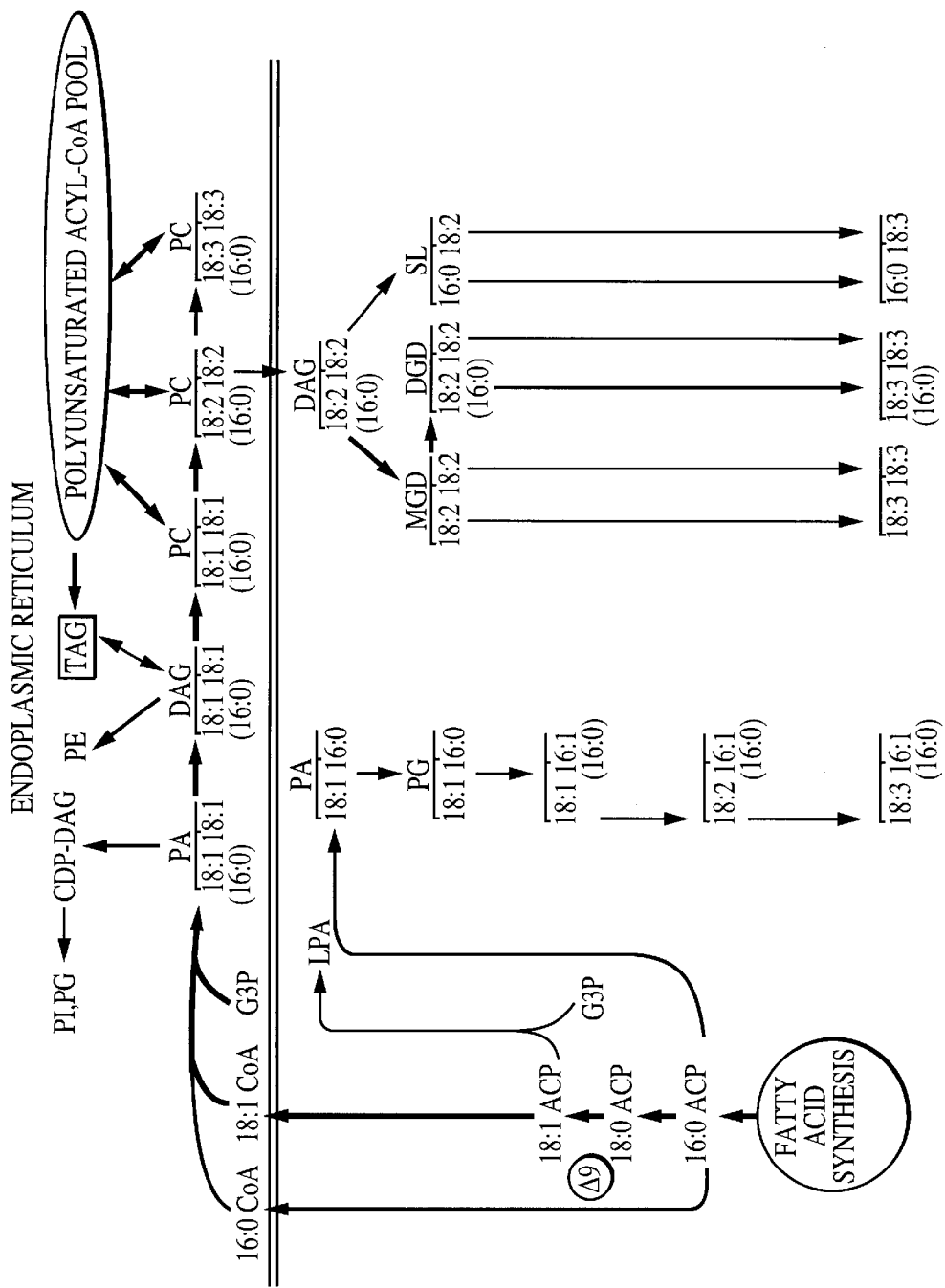
FIGS. 11 and 12 are diagrammatic representations of fatty acid biosynthesis in plants.

The present invention concerns compositions and methods for the modulation of gene expression in plants specifically using enzymatic nucleic acid molecules.

The Following Phrases and Terms are Defined Below

By "inhibit" or "modulate" is meant that the activity of enzymes such as GBSS and Δ-9 desaturase or level of mRNAs encoded by these genes is reduced below that observed in the absence of an enzymatic nucleic acid and preferably is below that level observed in the presence of an inactive RNA molecule able to bind to the same site on the mRNA, but unable to cleave that RNA.

By "enzymatic nucleic acid molecule" it is meant a nucleic acid molecule which has complementarity in a substrate binding region to a specified gene target, and also has an enzymatic activity which is active to specifically cleave that target. That is, the enzymatic nucleic acid molecule is able to internolecularly cleave RNA (or DNA) acid thereby inactivate a target RNA molecule. This complementarty functions to allow sufficient hybridization of the enzymatic nucleic acid molecule to the target RNA to allow the cleavage to occur. One hundred percent complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, nucleozyme, DNAzyme, RNA enzyme, RNAzyme, polyribozymes, molecular scissors, self-splicing RNA, self-cleaving RNA, cis-cleaving RNA, autolytic RNA, endoribonuclease, minizyme, leadzyme or DNA enzyme. All of these terminologies describe nucleic acid molecules with enzymatic activity. The term encompasses enzymatic RNA molecule which include one or more ribonucleotides and may include a majority of other types of nucleotides or abasic moieties, as described below.

By "complementarity" is meant a nucleic acid that can form hydrogen bond(s) with other RNA sequences by either traditional Watson-Crick or other non-traditional types (for example, Hoogsteen type) of base-paired interactions.

By "vectors" is meant any nucleic acid- and/or viral-based technique used to deliver and/or express a desired nucleic acid.

By "gene" is meant a nucleic acid that encodes an RNA.

By "plant gene" is meant a gene encoded by a plant.

By "endogenous" gene is meant a gene normally found in a plant cell in its natural location in the genome.

By "foreign" or "heterologous" gene is meant a gene not normally found in the host plant cell, but that is introduced by standard gene transfer techniques.

By "nucleic acid" is meant a molecule which can be single-stranded or double-stranded, composed of nucleotides containing a sugar, a phosphate and either a purine or pyrimidine base which may be same or different, and may be modified or unmodified.

By "genome" is meant genetic material contained in each cell of an organism and/or a virus.

By "mRNA" is meant RNA that can be translated into protein by a cell.

By "cDNA" is meant DNA that is complementary to and derived from a mRNA.

By "dsDNA" is meant a double stranded cDNA.

By "sense" RNA is meant RNA transcript that comprises the mRNA sequence.

By "antisense RNA" is meant an RNA transcript that comprises sequences complementary to all or part of a target RNA and/or mRNA and that blocks the expression of a target gene by interfering with the processing, transport and/or translation of its primary transcript and/or mRNA. The complementarity may exist with any part of the target RNA, i.e., at the 5' non-coding sequence, 3' non-coding sequence, introns, or the coding sequence. Antisense RNA is normally a mirror image of the sense RNA.

By "expression", as used herein, is meant the transcription and stable accumulation of the enzymatic nucleic acid molecules, mRNA and/or the antisense RNA inside a plant cell. Expression of genes involves transcription of the gene and translation of the mRNA into precursor or mature proteins.

By "cosuppression" is meant the expression of a foreign gene, which has substantial homology to an gene, and in a plant cell causes the reduction in activity of the foreign and/or the endogenous protein product.

By "altered levels" is meant the level of production of a gene product in a transgenic organism is different from that of a normal or non-transgenic organism.

By "promoter" is meant nucleotide sequence element within a gene which controls the expression of that gene. Promoter sequence provides the recognition for RNA polymerase and other transcription factors required for efficient transcription. Promoters from a variety of sources can be used efficiently in plant cells to express ribozymes. For example, promoters of bacterial origin, such as the octopine synthetase promoter, the nopaline synthase promoter, the manopine synthetase promoter; promoters of viral origin, such as the cauliflower mosaic virus (35S); plant promoters, such as the ribulose-1,6-biphosphate (RUBP) carboxylase small subunit (ssu), the beta-conglycinin promoter, the phaseolin promoter, the ADH promoter, heat-shock promoters, and tissue specific promoters. Promoter may also contain certain enhancer sequence elements that may improve the transcription efficiency.

By "enhancer" is meant nucleotide sequence element which can stimulate promoter activity (Adh).

By "constitutive promoter" is meant promoter element that directs continuous gene expression in all cells types and at all times (actin, ubiquitin, CaMV 35S).

By "tissue-specific" promoter is meant promoter element responsible for gene expression in specific cell or tissue types, such as the leaves or seeds (zein, oleosin, napin, ACP).

By "development-specific" promoter is meant promoter element responsible for gene expression at specific plant developmental stage, such as in early or late embryogenesis.

By "inducible promoter" is meant promoter element which is responsible for expression of genes in response to a specific signal, such as: physical stimulus (heat shock genes); light (RUBP carboxylase); hormone (Em); metabolites; and stress.

By a "plant" is meant a photosynthetic organism, either eukaryotic and prokaryotic.

By "angiosperm" is meant a plant having its seed enclosed in an ovary (e.g., coffee, tobacco, bean, pea).

By "gymnosperm" is meant a plant having its seed exposed and not enclosed in an ovary (e.g., pine, spruce).

By "monocotyledon" is meant a plant characterized by the presence of only one seed leaf (primary leaf of the embryo). For example, maize, wheat, rice and others.

By "dicotyledon" is meant a plant producing seeds with two cotyledons (primary leaf of the embryo). For example, coffee, canola, peas and others.

By "transgenic plant" is meant a plant expressing a foreign gene.

By "open reading frame" is meant a nucleotide sequence, without introns, encoding an amino acid sequence, with a defined translation initiation and termination region.

The invention provides a method for producing a class of enzymatic cleaving agents which exhibit a high degree of specificity for the RNA of a desired target. The enzymatic nucleic acid molecule may be targeted to a highly specific sequence region of a target such that specific gene inhibition can be achieved. Alternatively, enzymatic nucleic acid can be targeted to a highly conserved region of a gene family to inhibit gene expression of a family of related enzymes. The ribozymes can be expressed in plants that have been transformed with vectors which express the nucleic acid of the present invention.

The enzymatic nature of a ribozyme is advantageous over other technologies, since the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

In one of the preferred embodiments of the inventions herein, the enzymatic nucleic acid molecule is formed in a hammerhead or hairpin motif, but may also be formed in the motif of a hepatitis Δ virus, group I intron, group II intron or RNaseP RNA (in association with an RNA guide sequence) or Neurospora VS RNA. Examples of such hammerhead motifs are described by Dreyfus, supra, Rossi et al., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene*, 82, 43, and Hampel et al., 1990 *Nucleic Acids Res.* 18, 299; of the hepatitis Δ virus motif is described by Perrotta and Been, 1992 *Biochemistry* 31, 16; of the RNaseP motif by Guerrier-Takada et al., 1983 *Cell* 35, 849; Forster and Altman, 1990, *Science* 249, 783; Li and Altman, 1996, *Nucleic Acids Res.* 24, 835; Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J.* 14, 363); Group II introns are described by Griffin et al., 1995, *Chem. Biol.* 2, 761; Michels and Pyle, 1995, *Biochemistry* 34, 2965; and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The enzymatic nucleic acid molecules of the instant invention will be expressed within cells from eukaryotic promoters [e.g., Gerlach et al., International PCT Publication No. WO 91/13994; Edington and Nelson, 1992, in *Gene Regulation: Biology of Antisense RNA and DNA*, eds. R. P. Erickson and J. G. Izant, pp 209–221, Raven Press, NY.; Atkins et al., International PCT Publication No. WO 94/00012; Lenee et al., International PCT Publication Nos. WO 94/19476 and WO 9503404, Atkins et al., 1995, *J. Gen. Virol.* 76, 1781–1790; McElroy and Brettell, 1994, *TIBTECH* 12, 62; Gruber et al., 1994, *J. Cell. Biochem.* Suppl. 18A, 110 (X1-406)and Feyter et al., 1996, *Mol. Gen. Genet.* 250, 329–338; all of these are incorporated by reference herein]. Those skilled in the art will realize from the teachings herein that any ribozyme can be expressed in eukaryotic plant cells from an appropriate promoter. The ribozymes expression is under the control of a constitutive promoter, a tissue-specific promoter or an inducible promoter.

To obtain the ribozyme mediated modulation, the ribozyme RNA is introduced into the plant. Although examples are provided below for the construction of the plasmids used in the transformation experiments illustrated herein, it is well within the skill of an artisan to design numerous different types of plasmids which can be used in the transformation of plants, see Bevan, 1984, *Nucl. Acids Res.* 12, 8711–8721, which is incorporated by reference. There are also numerous ways to transform plants. In the examples below embryogenic maize cultures were helium blasted. In addition to using the gene gun (U.S. Pat. No. 4,945,050 to Cornell and U.S. Pat. No. 5,141,131 to DowElanco), plants may be transformed using Agrobacterium technology, sec U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to MaxPlanck, European Patent Applications 604662 and 627752 to Japan Tobacco, European Patent Applications 0267159, and 0292435 and U.S. Pat. No. 5,231,019 all to Ciba Geigy, U.S. Pat. Nos. 5,463, 174 and 4,762,785 both to Calgene, and U.S. Pat. Nos. 5,004,863 and 5,159,135 both to Agracetus; whiskers technology, see U.S. Pat. Nos. 5,302,523 and 5,464,765 both to Zeneca; electroporation technology, see WO 87/06614 to Boyce Thompson Institute, U.S. Pat. No. 5,472,869 and U.S. Pat. No. 5,384,253 both to Dekalb, WO9209696 and WO9321335 both to PGS; all of which are incorporated by reference herein in totality. In addition to numerous technologies for transforming plants, the type of tissue which is contacted with the foreign material (typically plasmids containing RNA or DNA) may vary as well. Such tissue would include but would not be limited to embryogenic tissue, callus tissue type I and II, and any tissue which is receptive to transformation and subsequent regeneration into a transgenic plant. Another variable is the choice of a selectable marker. The preference for a particular marker is at the discretion of the artisan, but any of the following selectable markers may be used along with any other gene not listed herein which could function as a selectable marker. Such selectable markers include but are not limited to chlorosulfuron, hygromyacin, PAT and/or bar, bromoxynil, kanamycin and the like. The bar gene may be isolated from Strptomuces, particularly from the hygroscopicus or viridochromogenes species. The bar gene codes for phosphinothricin acetyl transferase (PAT) that inactivates the active ingredient in the herbicide bialaphos phosphinothricin (PPT). Thus, numerous combinations of technologies may be used in employing ribozyme mediated modulation.

The ribozymes may be expressed individually as monomers, i.e., one ribozyme targeted against one site is expressed per transcript. Alternatively, two or more ribozymes targeted against more than one target site are expressed as part of a single RNA transcript. A single RNA transcript comprising more than one ribozyme targeted against more than one cleavage site are readily generated to achieve efficient modulation of gene expression. Ribozymes within these multimer constructs are the same or different. For example, the multimer construct may comprise a plurality of hammerhead ribozymes or hairpin ribozymes or other ribozyme motifs. Alternatively, the multimer construct may be designed to include a plurality of different ribozyme motifs, such as hammerhead and hairpin ribozymes. More specifically, multimer ribozyme constructs arc designed, wherein a series of ribozyme motifs are linked together in tandem in a single RNA transcript. The ribozymes are linked to each other by nucleotide linker sequence, wherein the linker sequence may or may not be complementary to the target RNA. Multimer ribozyme constructs (polyribozymes) are likely to improve the effectiveness of ribozyme-mediated modulation of gene expression.

The activity of ribozymes can also be augmented by their release from the primary transcript by a second ribozyme (Draper et al., PCT WO 93/23569, and Sullivan et al., PCT WO 94/02595, both hereby incorporated in their totality by reference herein; Ohkawa, J., et al., 1992, Nucleic Acids Symp. Ser., 27, 15–6; Taira, K., et al., 1991, Nucleic Acids Res., 19, 5125–30; Ventura, M., et al., 1993, Nucleic Acids Res., 21, 3249–55; Chowrira et al., 1994 J. Biol. Chem. 269, 25856).

Ribozyme-mediated modulation of gene expression can be practiced in a wide variety of plants including angiosperms, gymnosperms, monocotyledons, and dicotyledons. Plants of interest include but are not limited to: cereals, such as rice, wheat, barley, maize; oil-producing crops, such as soybean, canola, sunflower, cotton, maize, cocoa, safflower, oil palm, coconut palm, flax, castor, peanut; plantation crops, such as coffee and tea; fruits, such as pineapple, papaya, mango, banana, grapes, oranges, apples; vegetables, such as cauliflower, cabbage, melon, green pepper, tomatoes, carrots, lettuce, celery, potatoes, broccoli; legumes, such as soybean, beans, peas; flowers, such as carnations, chrysanthemum, daisy, tulip, gypsophila, alstromeria, marigold, petunia, rose; trees such as olive, cork, poplar, pine; nuts, such as walnut, pistachio, and others. Following are a few non-limiting examples that describe the general utility of ribozymes in modulation of gene expression.

Ribozyme-mediated down regulation of the expression of genes involved in caffeine synthesis can be used to significantly change caffeine concentration in coffee beans. Expression of genes, such as 7-methylxanthosine and/or 3-methyl transferase in coffee plants can be readily modulated using ribozymes to decrease caffeine synthesis (Adams and Zarowitz, U.S. Pat. No. 5,334,529; incorporated by reference herein).

Transgenic tobacco plants expressing ribozymes targeted against genes involved in nicotine production, such as N-methylputrescine oxidase or putrescine N-methyl transferase (Shewmaker et al., supra), would produce leaves with altered nicotine concentration.

Transgenic plants expressing ribozymes targeted against genes involved in ripening of fruits, such as ethylene-forming enzyme, pectin methyltransferase, pectin esterase, polygalacturonase, 1-amininocyclopropane carboxylic acid (ACC) synthase, ACC oxidase genes (Smith et al., 1988, Nature, 334, 724; Gray et al., 1992, Pl. Mol. Biol., 19, 69; Tieman et al., 1992, Plant Cell, 4, 667; Picton et al., 1993, The Plant J. 3, 469; Shewmaker et al., supra; James et al., 1996, Bio/Technology, 14, 56), would delay the ripening of fruits, such as tomato and apple.

Transgenic plants expressing ribozymes targeted against genes involved in flower pigmentation, such as chalcone synthase (CHS), chalcone flavanone isomerase (CHI), phenylalanine ammonia lyase, or dehydroflavonol (DF) hydroxylases, DF reductase (Krol van der, et al., 1988, Nature, 333, 866; Krol van der, et al., 1990, Pl. Mol. Biol., 14, 457; Shewmaker et al., supra; Jorgensen, 1996, Science, 268, 686), would produce flowers, such as roses, petunia, with altered colors.

Lignins are organic compounds essential for maintaining mechanical strength of cell walls in plants. Although essential, lignins have some disadvantages. They cause indigestibility of sillage crops and are undesirable to paper production from wood pulp and others. Transgenic plants expressing ribozymes targeted against genes involved in lignin production such as, O-methyltransferase, cinnamoyl-CoA:NADPH reductase or cinnamoyl alcohol dehydrogenase (Doorsselaere et al., 1995, The Plant J. 8, 855; Atanassova et al., 1995, The Plant J. 8, 465; Shewmaker et al., supra; Dwivedi et al., 1994, Pl. Mol. Biol., 26, 61), would have altered levels of lignin.

Other useful targets for useful ribozymes are disclosed in Draper et al., International PCT Publication No. WO 93/23569, Sullivan et al., International PCT Publication No. WO 94/02595, as well as by Stinchcomb et al., International PCT Publication No. WO 95/31541, and hereby incorporated by reference herein in totality.

Modulation of Granule Bound Starch Synthase Gene Expression in Plants

In plants, starch biosynthesis occurs in both chloroplasts (short term starch storage) and in the amyloplast (long term starch storage). Starch granules normally consist of a linear chain of $\alpha(1\text{-}4)$-linked $\alpha$-D-glucose units (amylose) and a branched form of amylose cross-linked by $\alpha(1\text{–}6)$ bonds (amylopectin). An enzyme involved in the synthesis of starch in plants is starch synthase which produces linear chains of $\alpha(1\text{-}4)$-glucose using ADP-glucose. Two main forms of starch synthase are found in plants: granule bound starch synthase (GBSS) and a soluble form located in the stroma of chloroplasts and in amyloplasts (soluble starch synthase). Both forms of this enzyme utilize ADP-D-glucose while the granular bound form also utilizes UDP-D-glucose, with a preference for the former. The GBSS, known as waxy protein, has a molecular mass of between 55 to about 70 kDa in a variety of plants in which it has been characterized. Mutations affecting the GBSS gene in several plant species has resulted in the loss of amylose, while the total amount of starch has remained relatively unchanged. In addition to a loss of GBSS activity, these mutants also contain altered, reduced levels, or no GBSS protein (Mac Donald and Preiss, Plant Physiol. 78: 849–852 (1985), Sano, Theor. Appl. Genet. 68: 467–473 (1984), Hovenkamp-Hermelink et al.

Theor. Appl. Genet. 75: 217–221 91987), Shure et al. Cell 35, 225–233 (1983), Echt and Schwartz Genetics 99: 275–284 (1981)). The presence of a branching enzyme as well as a soluble ADP-glucose starch glycosyl transferase in both GBSS mutants and wild type plants indicates the existence of independent pathways for the formation of the branched chain polymer amylopectin and the straight chain polymer amylose.

The Wx (waxy) locus encodes a granule bound glucosyl transferase involved in starch biosynthesis. Expression of this enzyme is limited to endosperm, pollen and the embryo sac in maize. Mutations in this locus have been termed waxy due to the appearance of mutant kernels, which is the phenotype resulting from an reduction in amylose composition in the kernels. In maize, this enzyme is transported into the amyloplast of the developing endosperm where it catalyses production of amylose. Corn kernels are about 70% starch, of which 27% is linear amylose and 73% is amylopectin. Waxy is a recessive mutation in the gene encoding granule bound starch synthase (GBSS). Plants homozygous for this recessive mutation produce kernels that contain 100% of their starch in the form of amylopectin.

Ribozymes, with their catalytic activity and increased site specificity (as described below), represent more potent and perhaps more specific inhibitory molecules than antisense oligonucleotides. Moreover, these ribozymes are able to inhibit GBSS activity and the catalytic activity of the ribozymes is required for their inhibitory effect. For those of ordinary skill in the art, it is clear from the examples that other ribozymes may be designed that cleave target mRNAs required for GBSS activity in plant species other than maize.

Thus, in a preferred embodiment, the invention features ribozymes that inhibit enzymes involved in amylose production, e.g., by reducing GBSS activity. These endogenously expressed RNA molecules contain substrate binding domains that bind to accessible regions of the target mRNA. The RNA molecules also contain domains that catalyze the cleavage of RNA. The RNA molecules are preferably ribozymes of the hammerhead or hairpin motif. Upon binding, the ribozymes cleave the target mRNAs, preventing translation and protein accumulation. In the absence of the expression of the target gene, amylose production is reduced or inhibited. Specific examples are provided below infra.

Preferred embodiments include the ribozymes having binding arms which are complementary to the binding sequences in Tables IIIA, VA and VB. Examples of such ribozymes are shown in Tables IIIB–V. Those in the art will recognize that while such examples are designed to one plant's (e.g., maize) mRNA, similar ribozymes can be made complementary to other plant species' mRNA. By complementary is thus meant that the binding arms enable ribozymes to interact with the target RNA in a sequence-specific manner to cause cleavage of a plant mRNA target. Examples of such ribozymes consist essentially of sequences shown in Tables IIIB–V.

Preferred embodiments are the ribozymes and methods for their use in the inhibition of starch granule bound ADP (UDP)-glucose: α-1,4-D-glucan 4-α-glucosyl transferase i.e., granule bound starch synthase (GBSS) activity in plants. This is accomplished through the inhibition of genetic expression, with ribozymes, which results in the reduction or elimination of GBSS activity in plants.

In another aspect of the invention, ribozymes that cleave target molecules and inhibit amylose production are expressed from transcription units inserted into the plant genome. Preferably, the recombinant vectors capable of stable integration into the plant genome and selection of transformed plant lines expressing the ribozymes are expressed either by constitutive or inducible promoters in the plant cells. Once expressed, the ribozymes cleave their target mRNAs and reduce amylose production of their host cells. The ribozymes expressed in plant cells are under the control of a constitutive promoter, a tissue-specific promoter or an inducible promoter.

Modification of corn starch is an important application of ribozyme technology which is capable of reducing specific gene expression. A high level of amylopectin is desirable for the wet milling process of corn and there is also some evidence that high amylopectin corn leads to increased digestibility and therefore energy availability in feed. Nearly 10% of wet-milled corn has the waxy phenotype, but because of its recessive nature the traditional waxy varieties are very difficult for the grower to handle Ribozymes targeted to cleave the GBSS mRNA and thus reduce GBSS activity in plants and in particular, corn endosperm will act as a dominant trait and produce corn plants with the waxy phenotype that will be easier for the grower to handle.

Modification of Fatty Acid Saturation Profile in Plants

Fatty acid biosynthesis in plant tissues is initiated in the chloroplast. Fatty acids are synthesized as thioesters of acyl carrier protein (ACP) by the fatty acid synthase complex (FAS). Fatty acids with chain lengths of 16 carbons follow one of three paths: they are released, immediately after synthesis, and transferred to glycerol 3-phosphate (G3P) by a chloroplast acyl transferase for further modification within the chloroplast; 2) they are released and transferred to Co-enzyme A (CoA) upon export from the plastid by thioesterases; or 3) they are further elongated to C18 chain lengths. The C18 chains are rapidly desaturated at the C9 position by stearoyl-ACP desaturase. This is followed by immediate transfer of the oleic acid (18:1) group to G3P within the chloroplast, or by export from the chloroplast and conversion to oleoyl-CoA by thioesterases (Somerville and Browse, 1991 *Science* 252: 80–87). The majority of C16 fatty acids follow the third pathway.

Figure 12:
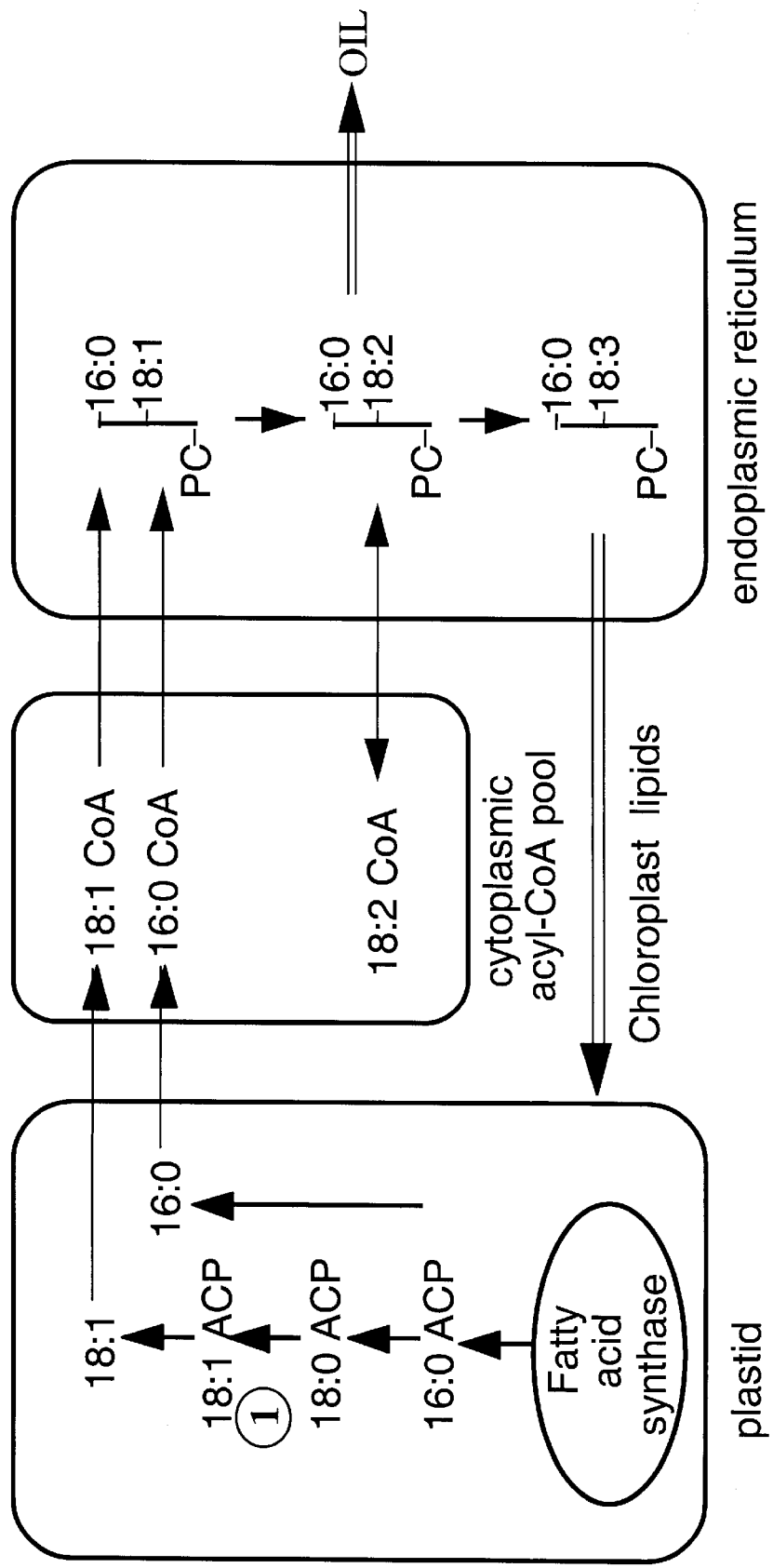

In corn seed oil the predominant triglycerides are produced in the endoplasmic reticulum. Most oleic acids (18:1) and some palmitic acids (16:0) are transferred to G3P from phosphatidic acids, which are then converted to diacyl glycerides and phosphatidyl choline. Further desaturation of the acyl chains on phosphatidyl choline by membrane bound desaturases takes place in the endoplasmic reticulum. Di- and tri-unsaturated chains are then released into the acyl-CoA pool and transferred to the C3 position of the glycerol backbone in diacyl glycerol in the production of triglycerides (Frentzen, 1993 in *Lipid Metabolism in Plants.*, p.195–230, (ed. Moore, T. S.) CRC Press, Boca Raton, Fla.). A schematic of the plant fatty acid biosynthesis pathway is shown in FIGS. 11 and 12. The three predominant fatty acids in corn seed oil are linoleic acid (18:2, ~59%), oleic acid (18:1, ~26%), and palmitic acid (16:0, ~11%). These are average values and may be somewhat different depending on the genotype; however, composite samples of US Corn Belt produced oil analyzed over the past ten years have consistently had this composition (Glover and Mertz, 1987 in: Nutritional Quality of Cereal Grains: genetic and agronomic improvement., p.183–336, (eds. Olson, R. A. and Frey, K. J.) Am. Soc. Agronomy. Inc. Madison, Wis.; Fitch-Haumann, 1985 *J. Am. Oil Chem. Soc.* 62: 1524–1531; Strecker et al., 1990 in Edible fats and oils processing: basic principles and modern practices (ed. Erickson, D. R.) Am. Oil Chemists Soc. Champaign, Ill.). This predominance of C18 chain lengths may reflect the abundance and activity of several key enzymes, such as the fatty acid synthase responsible for production of C18 carbon chains, the stearoyl-ACP desaturase (Δ-9 desaturase) for production of 18:1 and a microsomal Δ-12 desaturase for conversion of 18:1 to 18:2.

Δ-9 desaturase (also called stearoyl-ACP desaturase) of plants is a soluble chloroplast enzyme which uses C18 and occasionally C16-acyl chains linked to acyl carrier protein (ACP) as a substrate (McKeon, T. A. and Stumpf, P. K., 1982 *J. Biol. Chem.* 257: 12141–12147). This contrasts to the mammalian, lower eukaryotic and cyanobacterial Δ-9 desaturases. Rat and yeast Δ-9 desaturases are membrane bound microsomal enzymes using acyl-CoA chains as substrates, whereas cyanobacterial Δ-9 desaturase uses acyl chains on diacyl glycerol as substrate. To date several Δ-9 desaturase cDNA clones from dicotelydenous plants have been isolated and characterized (Shanklin and Somerville, 1991 *Proc. Natl. Acad. Sci. USA* 88: 2510–2514; Knutzon et al., 1991 *Plant Physiol.* 96: 344–345; Sato et al., 1992 *Plant Physiol.* 99: 362–363; Shanklin et al., 1991 *Plant Physiol.* 97: 467–468; Slocombe et al., 1992 *Plant. Mol. Biol.* 20: 151–155; Taylor et al., 1992 *Plant Physiol.* 100: 533–534; Thompson et al., 1991 *Proc. Natl. Acad. Sci. USA* 88: 2578–2582). Comparison of the different plant Δ-9 desaturase sequences suggests that this is a highly conserved enzyme, with high levels of identity both at the amino acid level (~90%) and at the nucleotide level (~80%). However, as might be expected from its very different physical and enzymological properties, no sequence similarity exists between plant and other Δ-9 desaturases (Shanklin and Somerville, supra).

Purification and characterization of the castor bean desaturase (and others) indicates that the Δ-9 desaturase is active as a homodimer; the subunit molecular weight is ~41 kDa. The enzyme requires molecular oxygen, NADPH, NADPH ferredoxin oxidoreductase and ferredoxin for activity in vitro. Fox et al., 1993 (*Proc. Natl. Acad. Sci. USA* 90: 2486–2490) showed that upon expression in *E. coli* the castor bean enzyme contains four catalytically active ferrous atoms per homodimer. The oxidized enzyme contains two identical diferric clusters, which in the presence of dithionite are reduced to the diferrous state. In the presence of stearoyl-CoA and $O_2$ the clusters return to the diferric state. This suggests that the desaturase belongs to a group of $O_2$ activating proteins containing diiron-oxo clusters. Other members of this group are ribonucleotide reductase and methane monooxygenase hydroxylase. Comparison of the predicted primary structure for these catalytically diverse proteins shows that all contain a conserved pair of amino acid sequences (Asp/Glu)-Glu-Xaa-Arg-His separated by ~80–100 amino acids.

Traditional plant breeding programs have shown that increased stearate levels can be achieved without deleterious consequences to the plant. In safflower (Ladd and Knowles, 1970 *Crop Sci.* 10: 525–527) and in soybean (Hammond and Fehr, 1984 *J. Amer. Oil Chem. Soc.* 61: 1713–1716; Graef et al., 1985 *Crop Sci.* 25: 1076–1079) stearate levels have been increased significantly. This demonstrates the flexibility in fatty acid composition of seed oil.

Increases in Δ-9 desaturase activity have been achieved by the transformation of tobacco with the Δ-9 desaturase genes from yeast (Polashock et al., 1992 *Plant Physiol.* 100, 894) or rat (Grayburn et. al., 1992 *BioTechnology* 10, 675). Both sets of transgenic plants had significant changes in fatty acid composition, yet were phenotypically identical to control plants.

Corn (maize) has been used minimally for the production of margarine products because it has traditionally not been utilized as an oil crop and because of the relatively low seed oil content when compared with soybean and canola. However, corn oil has low levels of linolenic acid (18:3) and relatively high levels of palmitic (16:0) acid (desirable in margarine). Applicant believes that reduction in oleic and linoleic acid levels by down-regulation of Δ-9 desaturase activity will make corn a viable alternative to soybean and canola in the saturated oil market.

Margarine and confectionary fats are produced by chemical hydrogenation of oil from plants such as soybean. This process adds cost to the production of the margarine and also causes both cis and trans isomers of the fatty acids. Trans isomers are not naturally found in plant derived oils and have raised a concern for potential health risks. Applicant believes that one way to eliminate the need for chemical hydrogenation is to genetically engineer the plants so that desaturation enzymes are down-regulated. Δ-9 desaturase introduces the first double bond into 18 carbon fatty acids and is the key step effecting the extent of desaturation of fatty acids.

Thus, in a preferred embodiment, the invention concerns compositions (and methods for their use) for the modification of fatty acid composition in plants. This is accomplished through the inhibition of genetic expression, with ribozymes, antisense nucleic acid, cosuppression or triplex DNA, which results in the reduction or elimination of certain enzyme activities in plants, such as Δ-9 desaturase. Such activity is reduced in monocotyledon plants, such as maize, wheat, rice, palm, coconut and others. Δ-9 desaturase activity may also be reduced in dicotyledon plants such as sunflower, safflower, cotton, peanut, olive, sesame, cuphea, flax, jojoba, grape and others.

Thus, in one aspect, the invention features ribozymes that inhibit enzymes involved in fatty acid unsaturation, e.g., by reducing Δ-9 desaturase activity. These endogenously expressed RNA molecules contain substrate binding domains that bind to accessible regions of the target mRNA. The RNA molecules also contain domains that catalyze the cleavage of RNA. The RNA molecules are preferably ribozymes of the hammerhead or hairpin motif. Upon binding, the ribozymes cleave the target mRNAs, preventing translation and protein accumulation. In the absence of the expression of the target gene, stearate levels are increased and unsaturated fatty acid production is reduced or inhibited. Specific examples are provided below in the Tables listed directly below.

In preferred embodiments, the ribozymes have binding arms which are complementary to the sequences in the Tables VI and VIII. Those in the art will recognize that while such examples are designed to one plant's (e.g., corn) mRNA, similar ribozymes can be made complementary to other plant's mRNA. By complementary is thus meant that the binding arms of the ribozymes are able to interact with the target RNA in a sequence-specific manner and enable the ribozyme to cause cleavage of a plant mRNA target. Examples of such ribozymes are typically sequences defined in Tables VII and VIII. The active ribozyme typically contains an enzymatic center equivalent to those in the examples, and binding arms able to bind plant mRNA such that cleavage at the target site occurs. Other sequences may be present which do not interfere with such binding and/or cleavage.

The sequences of the ribozymes that are particularly useful in this study, are shown in Tables VII and VIII.

Those in the art will recognize that ribozyme sequences listed in the Tables are representative only of many more such sequences where the enzymatic portion of the ribozyme (all but the binding arms) is altered to affect activity. For example, stem-loop II sequence of hammerhead ribozymes listed in Table IV (5'-GGCGAAAGCC-3')(SEQ ID NO. 1237) can be altered (substitution, deletion, and/or insertion) to contain any sequences, preferably provided that a minimum of a two base-paired stem structure can form. Similarly, stem-loop IV sequence of hairpin ribozymes listed in Tables V and VIII (5'-CACGUUGUG-3') (SEQ ID NO. 1238) can be altered (substitution, deletion, and/or insertion) to contain any sequence, preferably provided that a minimum of a two base-paired stem structure can form. Such ribozymes are equivalent to the ribozymes described specifically in the Tables.

In another aspect of the invention, ribozymes that cleave target molecules and reduce unsaturated fatty acid content in plants are expressed from transcription units inserted into the plant genome. Preferably, the recombinant vectors capable of stable integration into the plant genome and selection of transformed plant lines expressing the ribozymes are expressed either by constitutive or inducible promoters in the plant cells. Once expressed, the ribozymes cleave their target mRNAs and reduce unsaturated fatty acid production of their host cells. The ribozymes expressed in plant cells are under the control of a constitutive promoter, a tissue-specific promoter or an inducible promoter.

Modification of fatty acid profile is an important application of nucleic acid-based technologies which are capable of reducing specific gene expression. A high level of saturated fatty acid is desirable in plants that produce oils of commercial importance.

In a related aspect, this invention features the isolation of the cDNA sequence encoding Δ-9 desaturase in maize.

In preferred embodiments, hairpin and hammerhead ribozymes that cleave Δ-9 desaturase mRNA are also described. Those of ordinary skill in the art will understand from the examples described below that other ribozymes that cleave target mRNAs required for Δ-9 desaturase activity may now be readily designed and are within the scope of the invention.

While specific examples to corn RNA are provided, those in the art will recognize that the teachings are not limited to corn. Furthermore, the same target may be used in other plant species. The complementary arms suitable for targeting the specific plant RNA sequences are utilized in the ribozyme targeted to that specific RNA. The examples and teachings herein are meant to be non-limiting, and those skilled in the art will recognize that similar embodiments can be readily generated in a variety of different plants to modulate expression of a variety of different genes, using the teachings herein, and are within the scope of the inventions.

Standard molecular biology techniques were followed in the examples herein. Additional information may be found in Sambrook, J., Fritsch, E. F., and Maniatis, T. (1989), Molecular Cloning a Laboratory Manual, second edition, Cold Spring Harbor: Cold Spring Harbor Laboratory Press, which is incorporated herein by reference.

EXAMPLES

Example 1

Isolation of Δ9 Desaturase cDNA from *Zea mays*

Degenerate PCR primers were designed and synthesized to two conserved peptides involved in diiron-oxo group binding of plant Δ-9 desaturases. A 276 bp DNA fragment was PCR amplified from maize embryo cDNA and was cloned in to a vector. The predicted amino acid sequence of this fragment was similar to the sequence of the region separated by the two conserved peptides of dicot Δ-9 desaturase proteins. This was used to screen a maize embryo cDNA library. A total of 16 clones were isolated; further restriction mapping and hybridization identified one clone which was sequenced. Features of the cDNA insert are: a 1621 nt cDNA; 145 nt 5' and 294 nt 3' untranslated regions including a 18 nt poly A tail; a 394 amino acid open reading frame encoding a 44.7 kD polypeptide; and 85% amino acid identity with castor bean Δ-9 desaturase gene for the predicted mature protein. The complete sequence is presented in FIG. 10.

Example 2

Identification of Potential Ribozyme Cleavage Sites for Δ9 Desaturase

Approximately two hundred and fifty HH ribozyme sites and approximately forty three HP sites were identified in the corn Δ-9 desaturase mRNA. A HH site consists of a uridine and any nucleotide except guanosine (UH). Tables VI and VIII have a list of HH and HP ribozyme cleavage sites. The numbering system starts with 1 at the 5' end of a Δ-9 desaturase cDNA clone having the sequence shown in FIG. 10.

Ribozymes, such as those listed in Tables VII and VIII, can be readily designed and synthesized to such cleavage sites with between 5 and 100 or more bases as substrate binding arms (see FIGS. 1–5). These substrate binding arms within a ribozyme allow the ribozyme to interact with their target in a sequence-specific manner.

Example 3

Selection of Ribozyme Cleavage Sites for Δ9 Desaturase

The secondary structure of Δ-9 desaturase mRNA was assessed by computer analysis using algorithms, such as those developed by M. Zuker (Zuker, M., 1989 *Science*, 244, 48–52). Regions of the mRNA that did not form secondary folding structures with RNA/RNA stems of over eight nucicotides and contained potential hammerhead ribozyme cleavage sites were identified.

These sites were assessed for oligonucleotide accessibility by RNase H assays (see Example 4 infra).

Example 4

RNaseH Assays for Δ9 Desaturase

Figure 13:
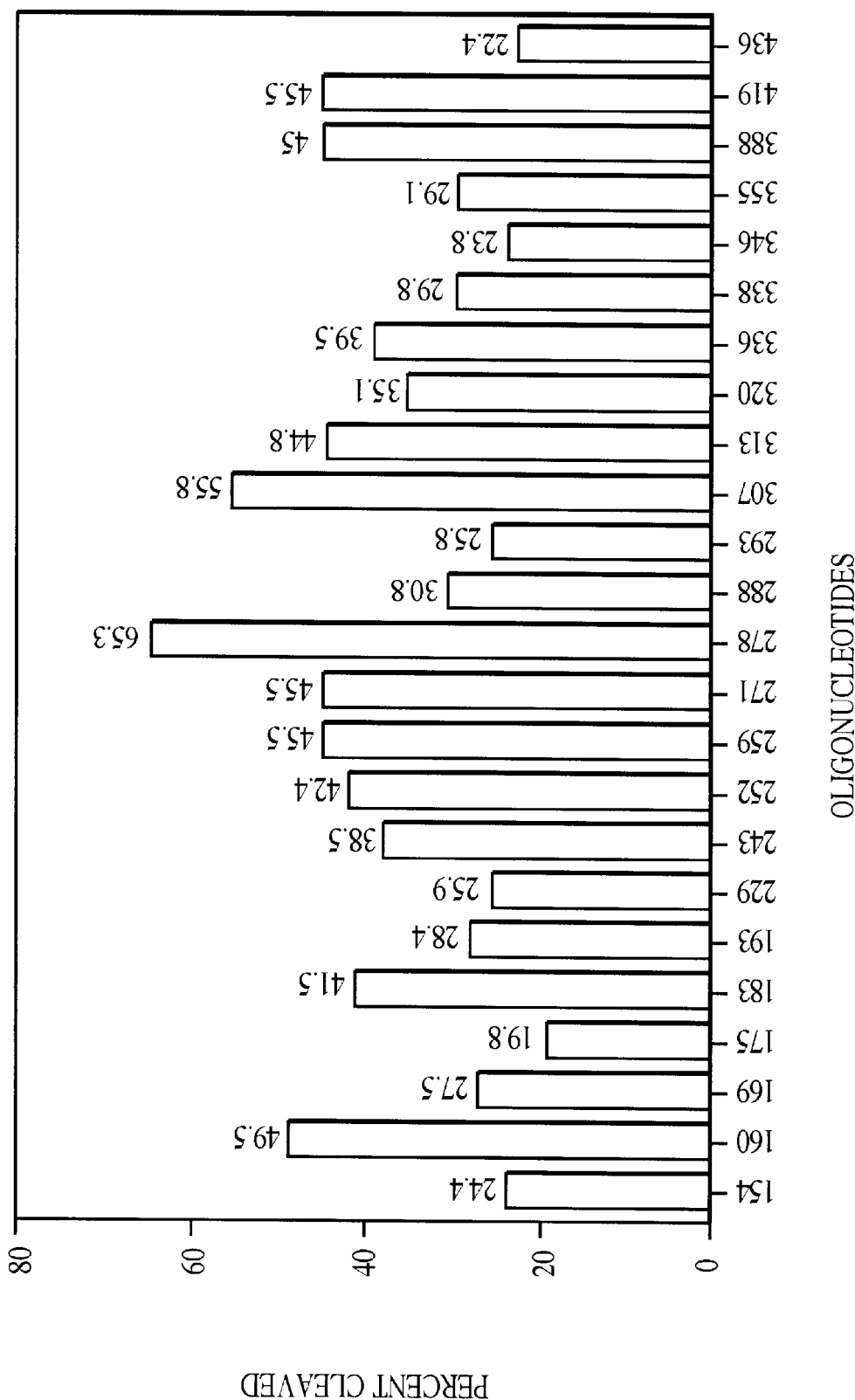
FIGS. 13 and 14 are graphical representations of RNaseH accessibility of Δ-9 desaturase RNA.
Figure 14:
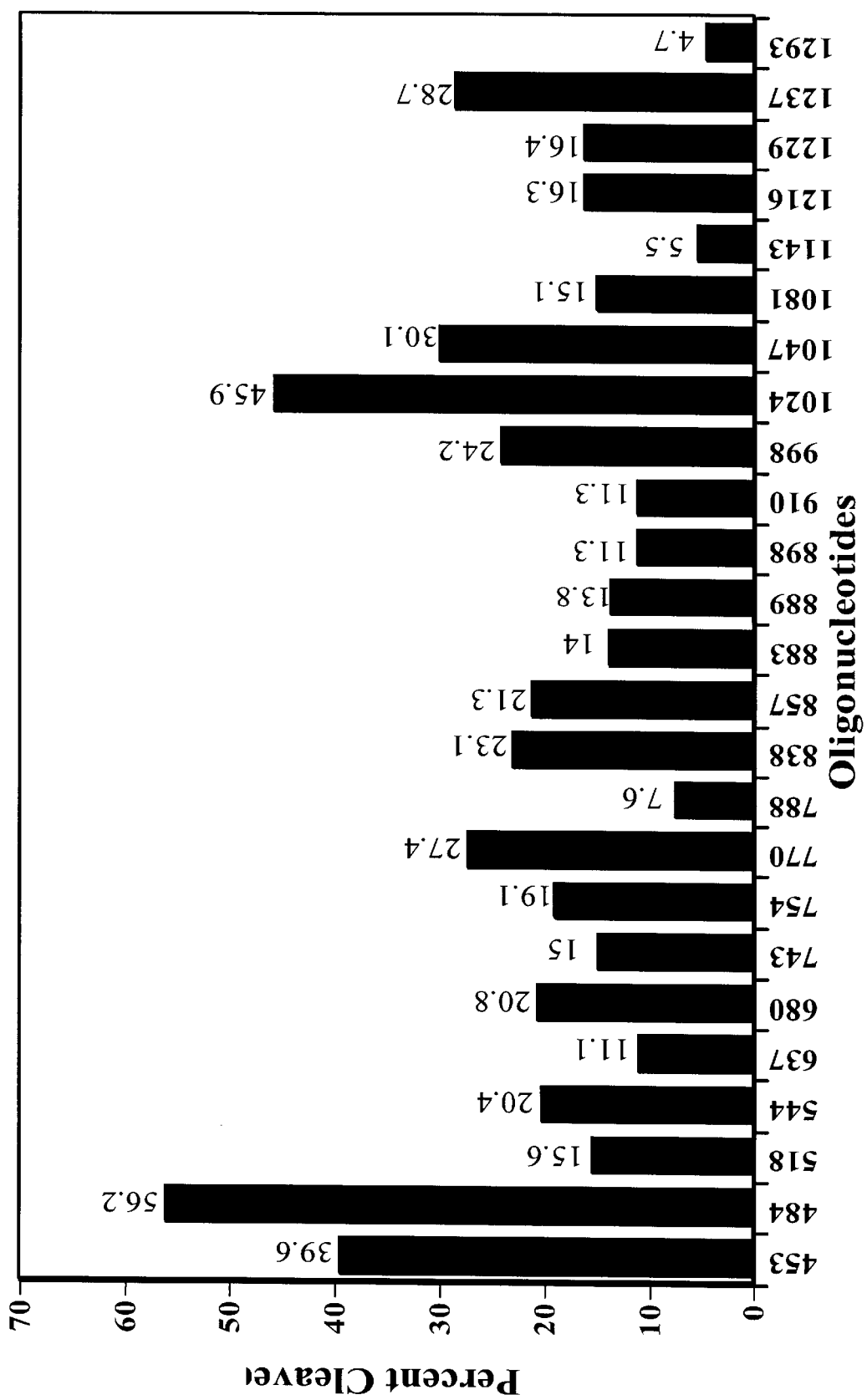

Forty nine DNA oligonucleotides, each twenty one nucleotides long were used in RNase H assays. These oligonucleotides covered 108 sites within Δ-9 desaturase RNA. RNase H assays (FIG. 6) were performed using a full length transcript of the Δ-9 desaturase cDNA. RNA was screened for accessible cleavage sites by the method described generally in Draper et al., supra. Briefly, DNA oligonucleotides representing ribozyme cleavage sites were synthesized. A polymerase chain reaction was used to generate a substrate for T7 RNA polymerase transcription from corn cDNA clones. Labeled RNA transcripts were synthesized in vitro from these templates. The oligonucleotides and the labeled transcripts were annealed, RNaseH was added and the mixtures were incubated for 10 minutes at 37° C. Reactions were stopped and RNA separated on sequencing polyacrylamide gels. The percentage of the substrate cleaved was determined by autoradiographic quantitation using a Molecular Dynamics phosphor imaging system (FIGS. 13 and 14).

Example 5

Hammerhead and Hairpin Ribozymes for Δ9 Desaturase

Hammerhead (HH) and hairpin (HP) ribozymes were designed to the sites covered by the oligos which cleaved best in the RNase H assays. These ribozymes were then subjected to analysis by computer folding and the ribozymes that had significant secondary structure were rejected.

The ribozymes were chemically synthesized. The general procedures for RNA synthesis have been described previously (Usman et al., 1987, *J. Am. Chem. Soc.*, 109, 7845–7854 and in Scaringe et al., 1990, *Nucl. Acids Res.*, 18, 5433–5341; Wincott et al., 1995, *Nucleic Acids Res.* 23, 2677). Small scale syntheses were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table II outlines the amounts, and the contact times, of the reagents used in the synthesis cycle. A 6.5-fold excess (163 μL of 0.1 M=16.3 μmol) of phosphoramidite and a 24-fold excess of S-ethyl tetrazole (238 μL of 0.25 M=59.5 μmol) relative to polymer-bound 5'-hydroxyl was used in each coupling cycle. Average coupling yields on the 394, determined by colorimetric quantitation of the trityl fractions, was 97.5–99%. Other oligonucleotide synthesis reagents for the 394: Detritylation solution was 2% TCA in methylene chloride (ABI); capping was performed with 16% N-Methyl imidazole in THF (ABI) and 10% acetic anhydride/10% 2,6-lutidine in THF (ABI); oxidation solution was 16.9 mM 12, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of EtOH:MeCN:H$_2$O/3:1:1, vortexed and the supernatant was then added to the first supernatant. The combined supernatants, containing the oligoribonucleotide, were dried to a white powder.

The base-deprotected oligoribonucleotide was resuspended in anhydrous TEA•HF/NMP solution (250 μL of a solution of 1.5 mL N-methylpyrrolidinone, 750 μL TEA and 1.0 mL TEA•3HF to provide a 1.4 M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

Inactive hammerhead ribozymes were synthesized by substituting a U for G$_5$ and a U for A$_{14}$ (numbering from (Hertel, K. J., et al., 1992, *Nucleic Acids Res.*, 20, 3252).

The hairpin ribozymes were synthesized as described above for the hammerhead RNAs.

Ribozymes were also synthesized from DNA templates using bacteriophage T7 RNA polymerase (Milligan and Uhlenbeck, 1989, *Methods Enzymol.* 180, 51). Ribozymes were purified by gel electrophoresis using general methods or were purified by high pressure liquid chromatography (HPLC; See Wincott et al., 1996, supra, the totality of which is hereby incorporated herein by reference) and were resuspended in water. The sequences of the chemically synthesized ribozymes used in this study are shown below in Tables VII and VIII.

Example 6

Long Substrate Tests for Δ9 Desaturase Ribozymes

Target RNA used in this study was 1621 nt long and contained cleavage sites for all the HH and HP ribozymes targeted against Δ-9 desaturase RNA. A template containing T7 RNA polymerase promoter upstream of Δ-9 desaturase target sequence, was PCR amplified from a cDNA clone. Target RNA was transcribed from this PCR amplified template using T7 RNA polymerase. The transcript was internally labeled during transcription by including [α-$^{32}$P] CTP as one of the four ribonucleotide triphosphates. The transcription mixture was treated with DNase-I, following transcription at 37° C. for 2 hours, to digest away the DNA template used in the transcription. The transcription mixture was resolved on a denaturing polyacrylamide gel. Bands corresponding to full-length RNA was isolated from a gel slice and the RNA was precipitated with isopropanol and the pellet was stored at 4° C.

Ribozyme cleavage reactions were carried out under ribozyme excess ($k_{cat}/K_M$) conditions (Herschlag and Cech, 1990, *Biochemistry* 29, 10159–10171). Briefly, 1 mM ribozyme and <10 nM internally labeled target RNA were denatured separately by heating to 65° C. for 2 min in the presence of 50 mM Tris.HCl, pH 7.5 and 10 mM MgCl$_2$. The RNAs were renatured by cooling to the reaction temperature (37° C., 26° C. or 20° C.) for 10–20 min. Cleavage reaction was initiated by mixing the ribozyme and target RNA at appropriate reaction temperatures. Aliquots were taken at regular intervals of time and the reaction was quenched by adding equal volume of stop buffer. The samples were resolved on 4% sequencing gel.

Figure 15:
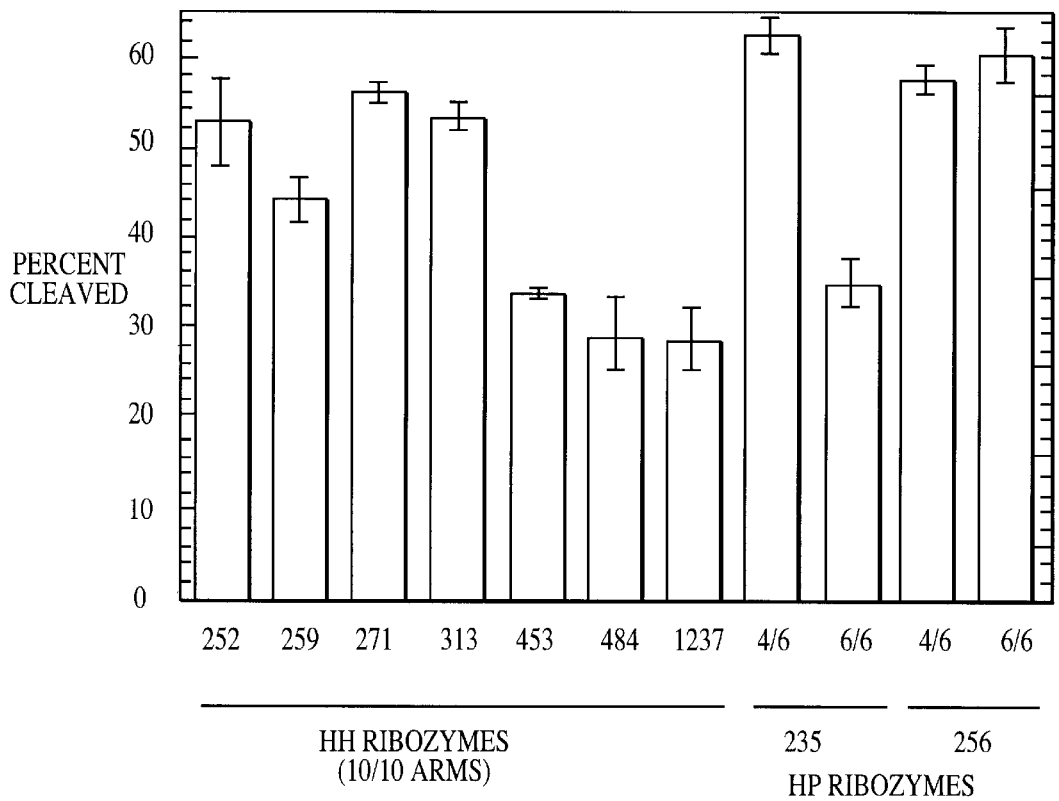
FIG. 15 shows cleavage of Δ-9 desaturase RNA by ribozymes in vitro. 10/10 represents the length of the binding arms of a hammerhead (HH) ribozyme. 10/10 means helix 1 and helix 3 each form 10 base-pairs with the target RNA (FIG. 1). 4/6 and 6/6, represent helix2/helix1 interaction between a hairpin ribozyme and its target. 4/6 means the hairpin (HP) ribozyme forms four base-paired helix 2 and a six base-paired helix 1 complex with the target (see FIG. 3). 6/6 means, the hairpin ribozyme forms a 6 base-paired helix 2 and a six base-paired helix 1 complex with the target. The cleavage reactions were carried out for 120 min at 26° C.
Figure 16:
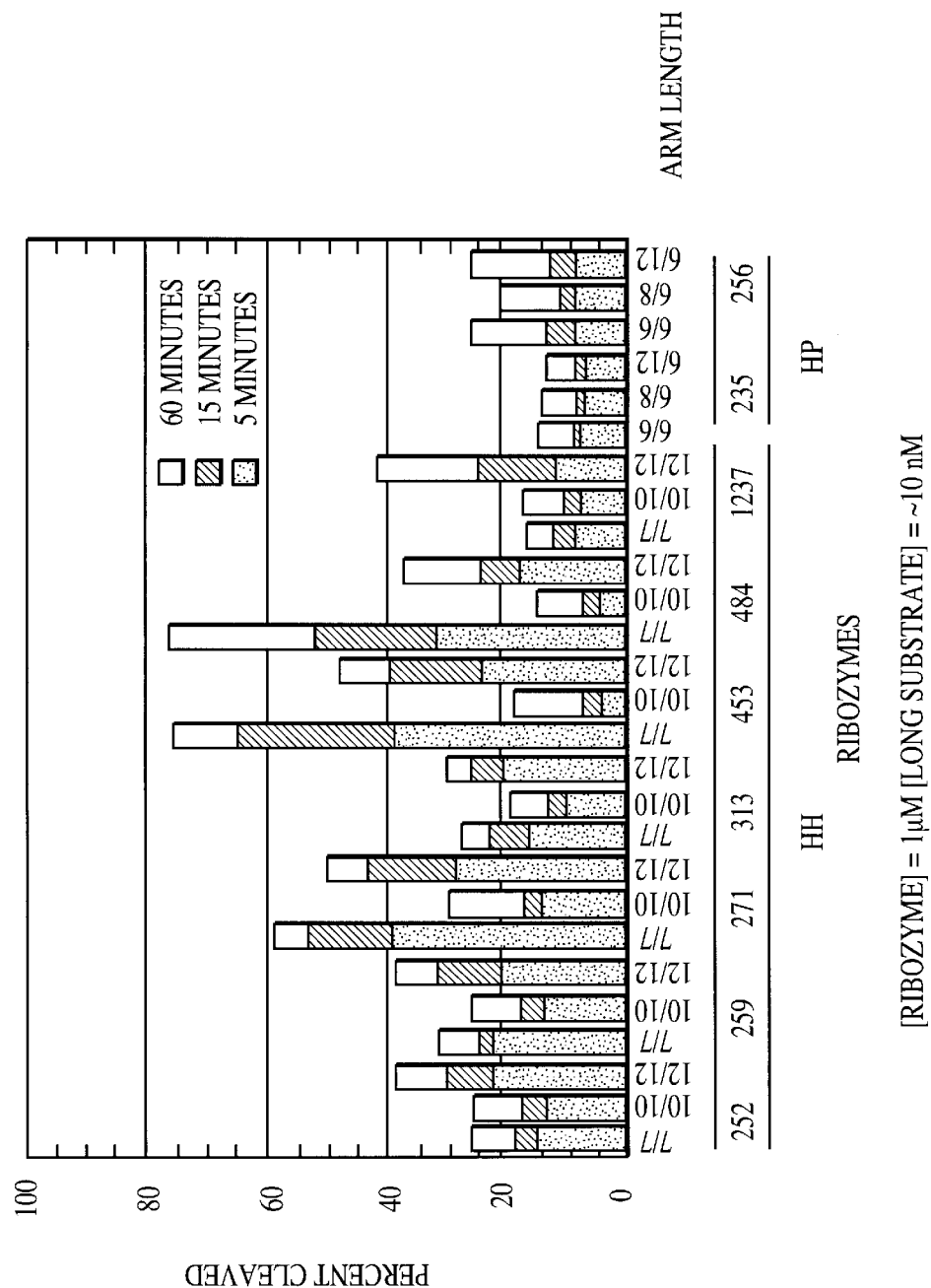
FIG. 16 shows the effect of arm-length variation on the activity of HH and HP ribozymes in vitro. 7/7, 10/10 and 12/12 are essentially as described above for the HH ribozyme. 6/6, 6/8, 6/12 represents varying helix 1 length and a constant (6 bp) helix 2 for a hairpin ribozyme. The cleavage reactions were carried out essentially as described above.

The results from ribozyme cleavage reactions, at 26° C. or 20° C., are summarized in Table IX and FIGS. 15 and 16. Of the ribozymes tested, seven hammerheads and two hairpins showed significant cleavage of Δ-9 desaturase RNA (FIGS. 15 and 16). Ribozymes to other sites showed varied levels of activity.

Example 7

Figure 20:
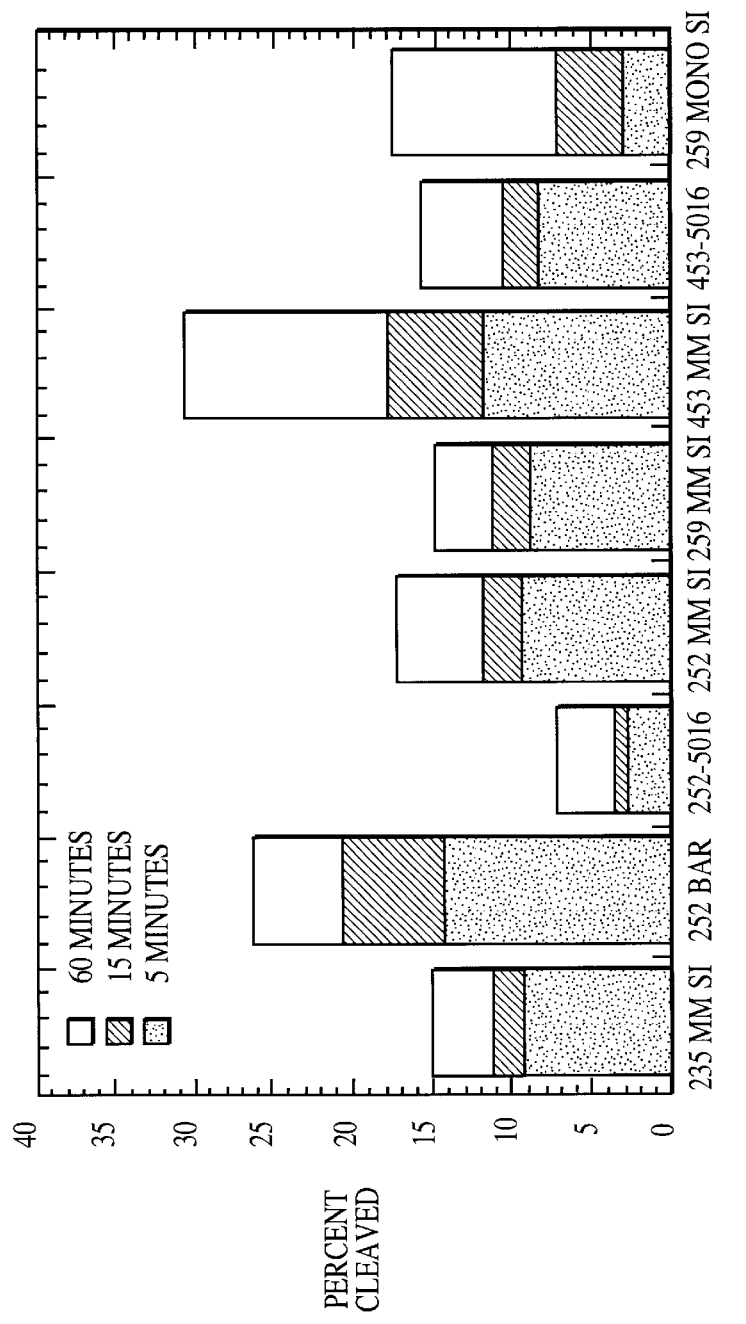
FIGS. 20 and 21 show in vitro cleavage of Δ-9 desaturase RNA by ribozymes that are transcribed from DNA templates using bacteriophage T7 RNA polymerase enzyme.
Figure 21:
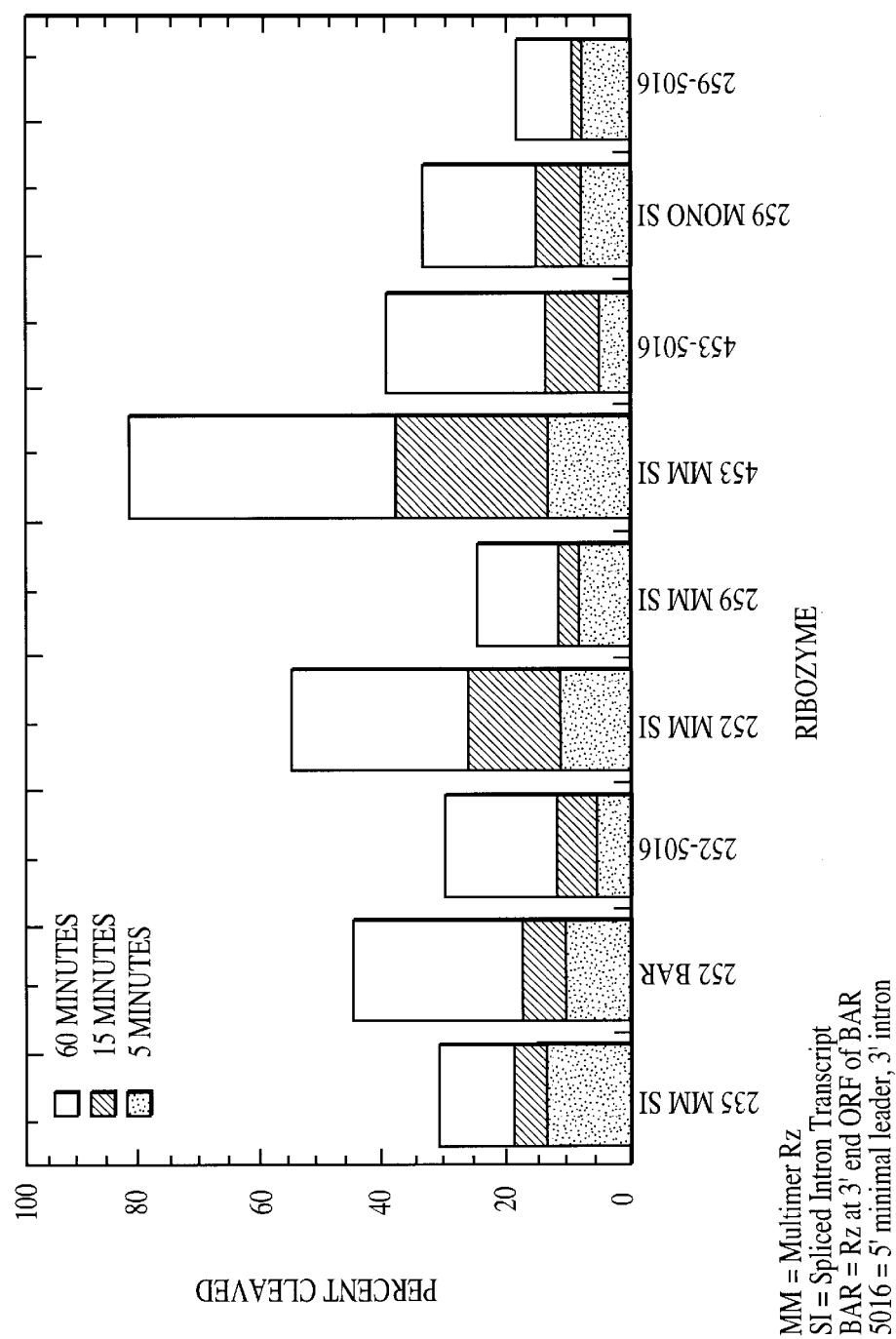
Figure 22:
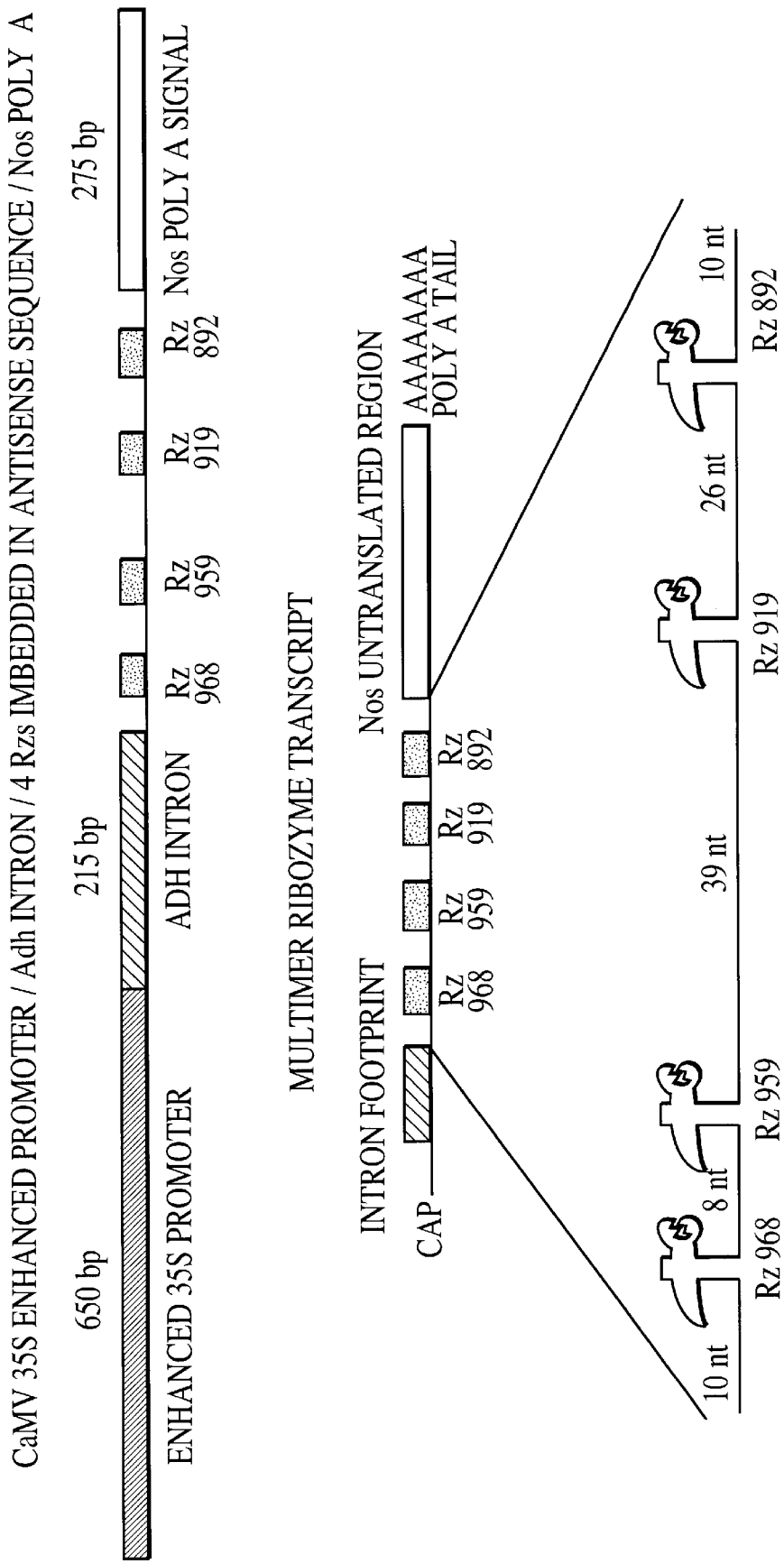
FIG. 22 diagrammatic representation of a non-limiting strategy to construct a transcript comprising multiple ribozyme motifs that are the same or different targeting various sites within GBSS RNA.
Figure 23:
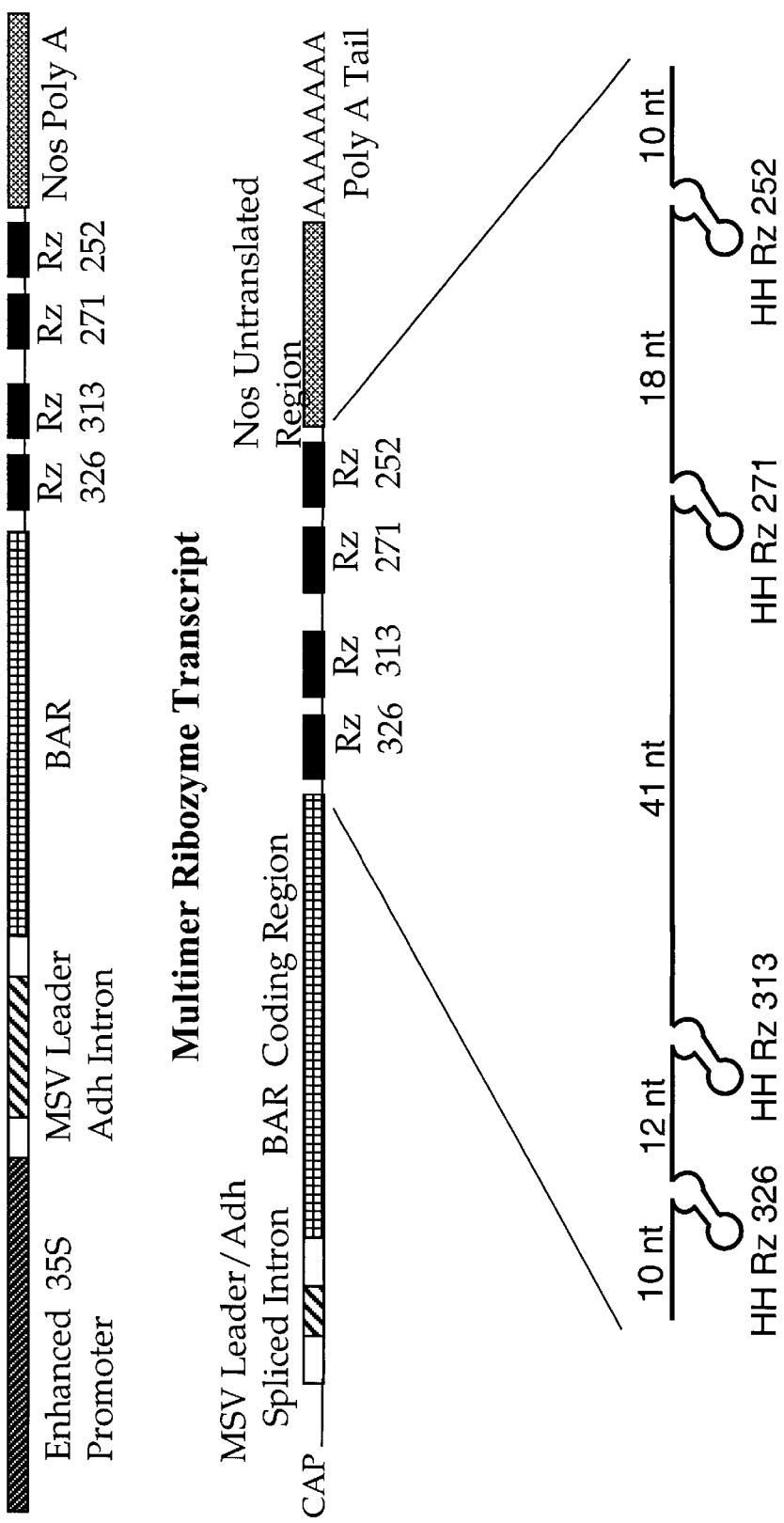

Cleavage of the Target RNA Using Multiple Ribozyme Combinations for Δ9 Desaturase Several of the above ribozymes were incorporated into a multimer ribozyme construct which contains two or more ribozymes embedded in a contiguous stretch of complementary RNA sequence. Non-limiting examples of multimer ribozymes are shown in FIGS. 17, 18, 19 and 23. The ribozymes were made by annealling complementary oligonucleotides and cloning into an expression vector containing the Cauliflower Mosaic Virus 35S enhanced promoter (Franck et al., 1985 *Cell* 21, 285), the maize Adh 1 intron (Dennis et al., 1984 *Nucl. Acids Res.* 12, 3983) and the Nos polyadenylation signal (DePicker et al., 1982 *J. Molec. Appl. Genet.* 1, 561). Cleavage assays with T7 transcripts made from these multimer-containing transcription units are shown in FIGS. 20 and 21. These are non-limiting examples; those skilled in the art will recognize that similar embodiments, consisting of other ribozyme combinations, introns and promoter elements, can be readily generated using techniques known in the art and are within the scope of this invention.

Example 8

Construction of Ribozyme Expressing Transcription Units for Δ9 Desaturase

Ribozymes targeted to cleave Δ-9 desaturase mRNA are endogenously expressed in plants, either from genes inserted into the plant genome (stable transformation) or from episomal transcription units (transient expression) which are part of plasmid vectors or viral sequences. These ribozymes can be expressed via RNA polymerase I, II, or III plant or plant virus promoters (such as CaMV). Promoters can be either constitutive, tissue specific, or developmentally expressed.

Δ9 259 Monomer Ribozyme Constructs (RPA 114, 115)

These are the Δ-9 desaturase 259 monomer hammerhead ribozyme clones. The ribozymes were designed with 3 bp long stem II and 20 bp (total) long substrate binding arms targeted against site 259. The active version is RPA114, the inactive is RPA 115. The parent plasmid, pDAB367, was digested with Not I and filled in with Klenow to make a blunt acceptor site. The vector was then digested with Hind III restriction enzyme. The ribozyme containing plasmids were cut with Eco RI, filled-in with Klenow and recut with Hind III. The insert containing the entire ribozyme transcription unit was gel-purified and ligated into the pDAB 367 vector. The constructs are checked by digestion with SgfI/Hind III and Xba I/Sst I and confirmed by sequencing.

Δ9 453 Multimer Ribozyme Constructs (RPA 118, 119)

Figure 17:
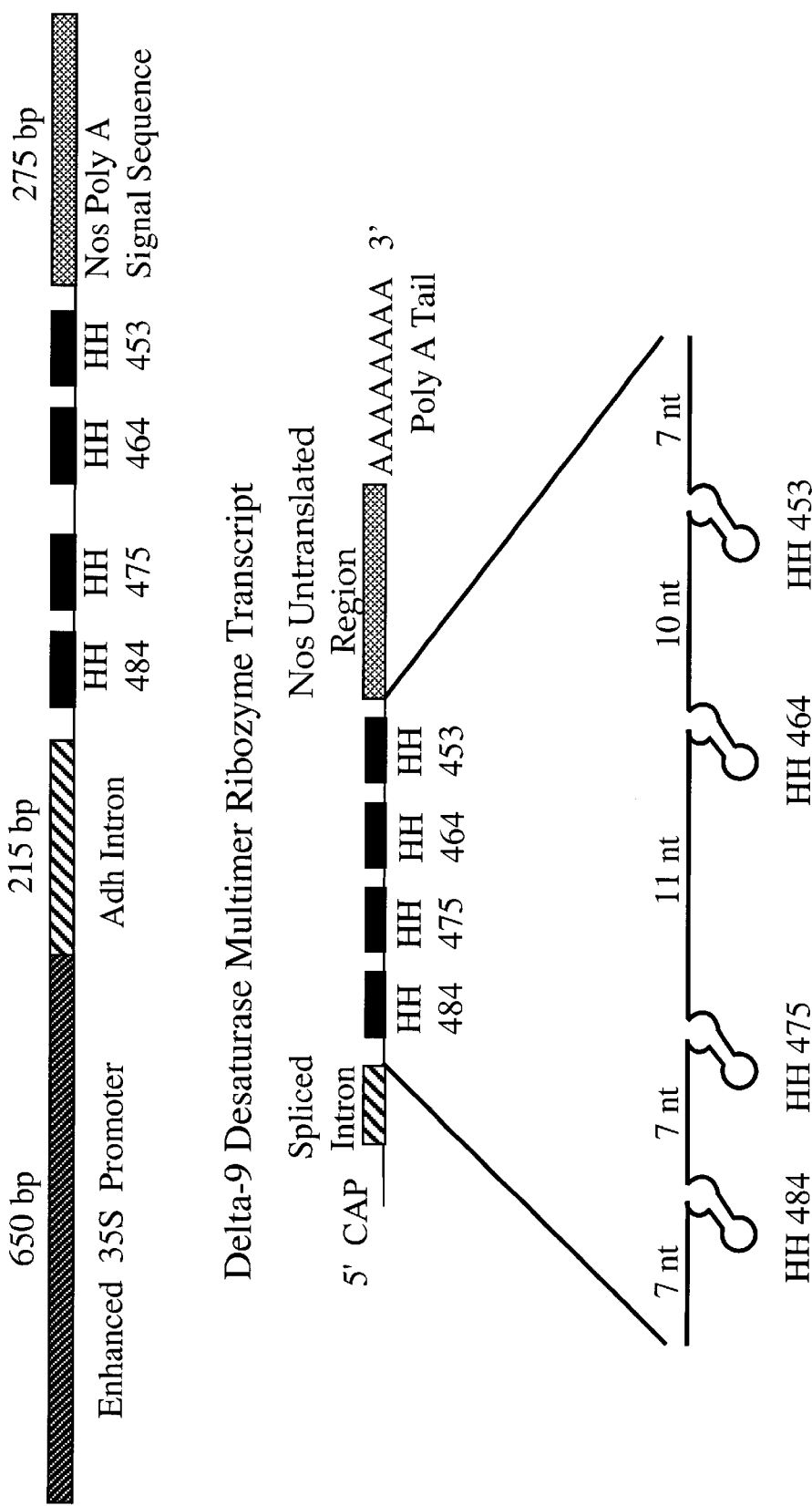
FIGS. 17, 18, 19 and 23 are diagrammatic representations of non-limiting strategies to construct a transcript comprising multiple ribozyme motifs that are the same or different, targeting various sites within Δ-9 desaturase RNA.
Figure 18:
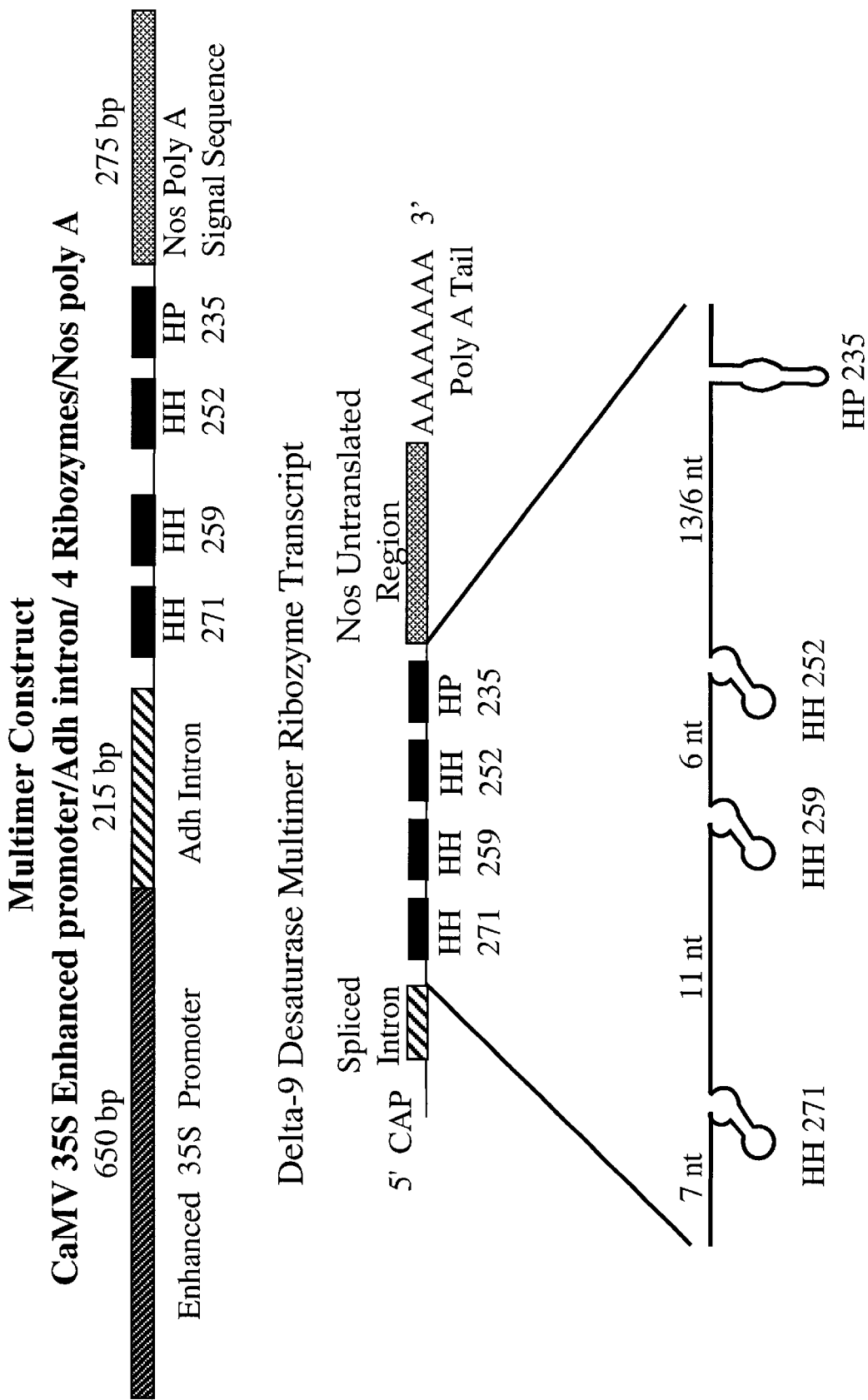
Figure 19:
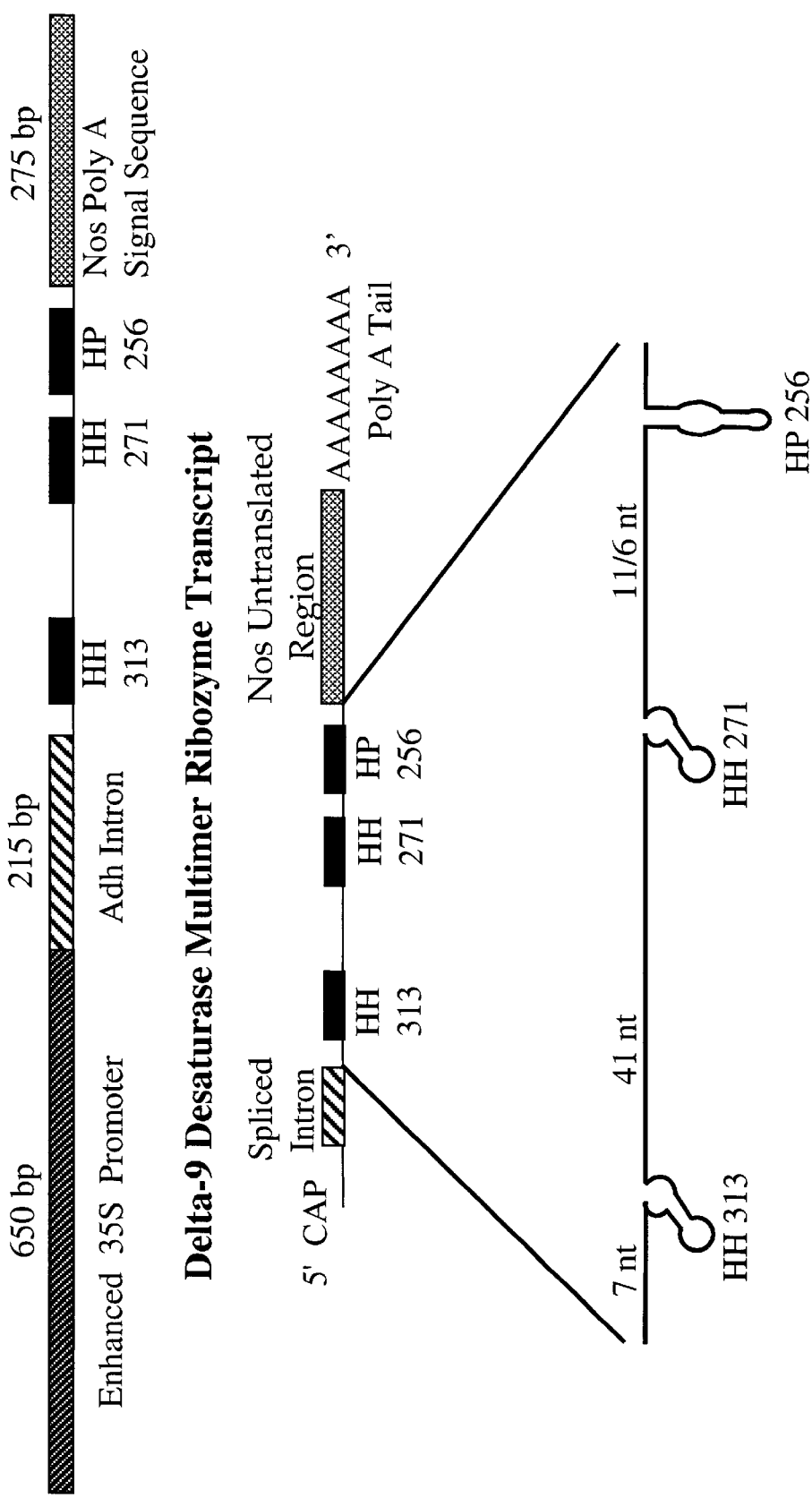

These are the Δ-9 desaturase 453 Multimer hammerhead ribozyme clones (see FIG. 17). The ribozymes were designed with 3 bp long stem II regions. Total length of the substrate binding anms of the multimer construct was 42 bp. The active version is RPA 118, the inactive is 119. The constructs were made as described above for the 259 monomer. The multimer construct was designed with four hammerhead ribozymes targeted against sites 453, 464, 475 and 484 within Δ-9 desaturase RNA.

Δ9 252 Multimer Ribozyme Constructs (RPA 85, 113)

These are the Δ-9 desaturase 252 multimer ribozyme clones placed at the 3' end of bar (phosphoinothricin acetyl transferase; Thompson et al., 1987 *EMBO J.* 6: 2519–2523) open reading frame. The multimer contructs were designed with 3 bp long stem II regions. Total length of the substrate binding arms of the multimer construct was 91 bp. RPA 85 is the active ribozyme, RPA 113 is the inactive. The vector was constructed as follows: The parent plasmid pDAB 367 was partially digested with Bgl II and the single cut plasmid was gel-purified. This was recut with Eco RI and again gel-purified to isolate the correct Bgl II/Eco RI cut fragment. The Bam HI/Eco RI inserts from the ribozyme constructs were gel-isolated (this contains the ribozyme and the NOS poly A region) and ligated into the 367 vector. The identitiy of positive plasmids were confinned by performing a Nco I/Sst I digest and sequencing.

Useful transgenic plants can be identified by standard assays. The transgenic plants can be evaluated for reduction in Δ-9 desaturase expression and Δ-9 desaturase activity as discussed in the examples infra.

Example 9

Identification of Potential Ribozyme Cleavage Sites in GBSS RNA

Two hundred and forty one hammer-head ribozyme sites were identified in the corn GBSS mRNA polypeptide coding region (see table IIIA). A hammer-head site consists of a uridine and any nucleotide except guanine (UH). Following is the sequence of GBSS coding region for corn (SEQ. I.D. No. 25). The numbering system starts with 1 at the 5' end of a GBSS cDNA clone having the following sequence (5' to 3'):

```
1                                                                      72 (SEQ I.D. NO.
                                                                          25).
GACCGATCGATCGCCACAGCCAACACCACCCGCCGAGGCGACGCGACAGCCGCCAGGAGGAAGGAATAAACT 73                                                                     144
CACTGCCAGCCAGTGAAGGGGAGAAGTGTACTGCTCCGTCCACCAGTGCGCGCACCGCCCGGCAGGGCTGC 145                                                                    216
TCATCTCGTCGACGACCAGTGGATTAATCGGCATGGCGGCTCTAGCCACGTCGCAGCTCGTCGCAACGCGCG 217                                                                    288
CCGGCCTGGGCGTCCCGGACGCGTCCACGTTCCGCCGCGGCGCCGCGCAGGGCCTGAGGGGGGCCGGACGG 289                                                                    360
CGTCGGCGGCGGACACGCTCAGCATTCGGACCAGCGCGCGCGGCGCCCAGGCTCCAGCACCAGCAGCAGC 361                                                                    432
AGCAGGCGCGCCGCGGGGCCAGGTTCCCGTCGCTCGTCGTGTGCGCCAGCGCCGGCATGAACGTCGTCTTCG 433                                                                    504
TCGGCGCCGAGATGGCGCCGTGGAGCAAGACCGGCGGCCTCGGCGACGTCCTCGGCGGCCTGCCGCCGGCCA 505                                                                    576
TGGCCGCGAATGGGCACCGTGTCATGGTCGTCTCTCCCCGCTACGACCAGTACAAGGACGCCTGGGACACCA 577                                                                    648
GCGTCGTGTCCGAGATCAAGATGGGAGACAGGTACGAGACGGTCAGGTTCTTCCACTGCTACAAGCGCGGAG
```

```
                                                           -continued
649                                                                                              720
TGGACCGCGTGTTCGTTGACCACCCACTGTTCCTGGAGAGGGTTTGGGGAAAGACCGAGGAGAAGATCTACG 721                                                                                              792
GGCCTGACGCTGGAACGGACTACAGGGACAACCAGCTGCGGTTCAGCCTGCTATGCCAGGCAGCACTTGAAG 793                                                                                              864
CTCCAAGGATCCTGAGCCTCAACAACAACCCATACTTCTCCGGACCATACGGGGAGGACGTCGTGTTCGTCT 865                                                                                              936
GCAACGACTGGCACACCGGCCCTCTCTCGTGCTACCTCAAGAGCAACTACCAGTCCCACGGCATCTACAGGG 937                                                                                             1008
ACGCAAAGACCGCTTTCTGCATCCACAACATCTCCTACCAGGGCCGGTTCGCCTTCTCCGACTACCCGGAGC 1009                                                                                            1080
TGAACCTCCCGGAGAGATTCAAGTCGTCCTTCGATTTCATCGACGGCTACGAGAAGCCCGTGGAAGGCCGGA 1081                                                                                            1152
AGATCAACTGGATGAAGGCCGGGATCCTCGAGGCCGACAGGGTCCTCACCGTCAGCCCCTACTACGCCGAGG 1153                                                                                            1224
AGCTCATCTCCGGCATCGCCAGGGGCTGCGAGCTCGACAACATCATGCGCCTCACCGGCATCACCGGCATCG 1225                                                                                            1296
TCAACGGCATGGACGTCAGCGAGTGGGACCCCAGCAGGGACAAGTACATCGCCGTGAAGTACGACGTGTCGA 1297                                                                                            1368
CGGCCGTGGAGGCCAAGGCGCTGAACAAGGAGGCGCTGCAGGCGGAGGTCGGGCTCCCGGTGGACCGGAACA 1369                                                                                            1440
TCCCGCTGGTGGCGTTCATCGGCAGGCTGGAAGAGCAGAAGGGACCCGACGTCATGGCGGCCGCCATCCCGC 1441                                                                                            1512
AGCTCATGGAGATGGTGGAGGACGTGCAGATCGTTCTGCTGGGCACGGGCAAGAAGAAGTTCGAGCGCATGC 1513                                                                                            1584
TCATGAGCGCCGAGGAGAAGTTCCCAGGCAAGGTGCGCGCCGTGGTCAAGTTCAACGCGGCGCTGGCGCACC 1585                                                                                            1656
ACATCATGGCCGGCGCCGACGTGCTCGCCGTCACCAGCCGCTTCGAGCCCTGCGGCCTCATCCAGCTGCAGG 1657                                                                                            1728
GGATGCGATACGGAACGCCCTGCGCCTGCGCGTCCACCGGTGGACTCGTCGACACCATCATCGAAGGCAAGA 1729                                                                                            1800
CCGGGTTCCACATGGGCCGCCTCAGCGTCGACTGCAACGTCGTGGAGCCGGCGGACGTCAAGAAGGTGGCCA 1801                                                                                            1872
CCACCTTGCAGCGCGCCATCAAGGTGGTCGGCACGCCGGCGTACGAGGAGATGGTGAGGAACTGCATGATCC 1873                                                                                            1944
AGGATCTCTCCTGGAAGGGCCCTGCCAAGAACTGGGAGAACGTGCTGCTCAGCCTCGGGGTCGCCGGCGGCG 1945                                                                                            2016
AGCCAGGGGTCGAAGGCGAGGAGATCGCGCCGCTCGCCAAGGAGAACGTGGCCGCGCCCTGAAGAGTTCGGC 2017                                                                                            2088
CTGCAGGCCCCCTGATCTCGCGCGTGGTGCAAACATGTTGGGACATCTTCTTATATATGCTGTTTCGTTTAT 2089                                                                                            2160
GTGATATGGACAAGTATGTGTAGCTGCTTGCTTGTGCTAGTGTAATATAGTGTAGTGGTGGCCAGTGGCACA 2161                                                                                            2232
ACCTAATAAGCGCATGAACTAATTGCTTGCGTGTGTAGTTAAGTACCGATCGGTAATTTTATATTGCGAGTA

2233
AATAAATGGACCTGTAGTGGTGGAAAAAAAAAAAA
```

There are approximately 53 potential hairpin ribozyme sites in the GBSS mRNA. The ribozyme and target sequences are listed in Table V.

Ribozymes can be readily designed and synthesized to such sites with between 5 and 100 or more bases as substrate binding arms (see FIGS. 1–5) as described above.

Example 10

Selection of Ribozyme Cleavage Sites for GBSS

The secondary structure of GBSS mRNA was assessed by computer analysis using folding algorithms, such as the ones developed by M. Zuker (Zuker, M., 1989 Science, 244, 48–52. Regions of the mRNA that did not form secondary folding structures with RNA/RNA stems of over eight nucleotides and contained potential hammerhead ribozyme cleavage sites were identified.

These sites which were then assessed for oligonucleotide accessibility with RNase H assays (see FIG. 6). Fifty-eight DNA oligonucleotides, each twenty one nucleotides long were used in these assays. These oligonucleotides covered 85 sites. The position and designation of these oligonucleotides were 195, 205, 240, 307, 390, 424, 472, 481, 539, 592, 625, 636, 678, 725, 741, 811, 859, 891, 897, 912, 918, 928, 951, 958, 969, 993, 999, 1015, 1027, 1032, 1056, 1084, 1105, 1156, 1168, 1186, 1195, 1204, 1213, 1222, 1240, 1269, 1284, 1293, 1345, 1351, 1420, 1471, 1533, 1563, 1714, 1750, 1786, 1806, 1819, 1921, 1954, and 1978. Secondary sites were also covered and included 202, 394, 384, 385, 484, 624, 627, 628, 679, 862, 901, 930, 950, 952, 967, 990, 991, 1026, 1035, 1108, 1159, 1225, 1273, 1534, 1564, 1558, and 1717.

Example 11

RNaseH Assays for GBSS

RNase H assays (FIG. 7) were performed using a full length transcript of the GBSS coding region, 3' noncoding region, and part of the 5' noncoding region. The GBSS RNA was screened for accessible cleavage sites by the method described generally in Draper et al., supra. hereby incorporated by reference herein. Briefly, DNA oligonucleotides representing hammerhead ribozyme cleavage sites were synthesized. A polymerase chain reaction was used to generate a substrate for T7 RNA polymerase transcription from corn cDNA clones. Labeled RNA transcripts were synthesized in vitro from these templates. The oligonucleotides and the labeled transcripts were annealed, RNAseH was added and the mixtures were incubated for 10 minutes at 37° C. Reactions were stopped and RNA separated on sequencing polyacrylamide gels. The percentage of the substrate cleaved was determined by autoradiographic quantitation using a phosphor imaging system (FIG. 7).

Example 12

Hammerhead Ribozymes for GBSS

Hammerhead ribozymes with 10/10 (i.e., able to form 10 base pairs on each arm of the ribozyme) nucleotide binding arms were designed to the sites covered by the oligos which cleaved best in the RNase H assays. These ribozymes were then subjected to analysis by computer folding and the ribozymes that had significant secondary structure were rejected. As a result of this screening procedure 23 ribozymes were designed to the most open regions in the GBSS mRNA, the sequences of these ribozymes are shown in Table IV.

The ribozymes were chemically synthesized. The method of synthesis used follows the procedure for normal RNA synthesis as described above (and in Usman et al., supra, Scaringe et al., and Wincott et al., supra) and are incorporated by reference herein, and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from (Hertel et al., supra). Hairpin ribozymes were synthesized in two parts and annealed to reconstruct the active ribozyme (Chowrira and Burke, 1992, Nucleic Acids Res., 20, 2835-). All ribozymes were modified to enhance stability by modification of five ribonucleotides at both the 5' and 3' ends with 2'-O-methyl groups. Ribozymes were purified by gel electrophoresis using general methods. (Ausubel et al., 1990 Current Protocols in Molecular Biology Wiley & Sons, NY) or were purified by high pressure liquid chromatography, as described above and were resuspended in water.

Example 13

Long Substrate Tests for GBSS

Target RNA used in this study was 900 nt long and contained cleavage sites for all the 23 HH ribozymes targeted against GBSS RNA. A template containing T7 RNA polymerase promoter upstream of GBSS target sequence, was PCR amplified from a cDNA clone. Target RNA was transcribed from this PCR amplified template using T7 RNA polymerase. The transcript was internally labeled during transcription by including [$\alpha$-$^{32}$P] CTP as one of the four ribonucleotide tripbospbates. The transcription mixture was treated with DNase-1, following transcription at 37° C. for 2 hours, to digest away the DNA template used in the transcription. The transcription mixture was resolved on a denaturing polyacrylamide gel. Bands corresponding to full-length RNA was isolated from a gel slice and the RNA was precipitated with isopropanol and the pellet was stored at 4° C.

Ribozyme cleavage reactions were carried out under ribozyme excess ($k_{cat}/K_M$) conditions (Herschlag and Cech, supra). Briefly, 1000 nM ribozyme and <10 nM internally labeled target RNA were denatured separately by heating to 90° C. for 2 min. in the presence of 50 mM Tris.HCl, pH 7.5 and 10 mM MgCl$_2$. The RNAs were renatured by cooling to the reaction temperature (37° C., 26° C. and 20° C.) for 10–20 min. Cleavage reaction was initiated by mixing the ribozyme and target RNA at appropriate reaction temperatures. Aliquots were taken at regular intervals of time and the reaction was quenched by adding equal volume of stop buffer. The samples were resolved on 4% sequencing gel.

The results from ribozyme cleavage reactions, at the three different temperatures, summarized in FIG. 8. Seven lead ribozymes were chosen (425, 892, 919, 959, 968, 1241, and 1787). One of the active ribozymes (811) produced a strange pattern of cleavage products; as a result, it was not chosen as one of our lead ribozymes.

Example 14

Cleavage of the GBSS RNA Using Multiple Ribozyme Combinations

Four of the lead ribozymes (892, 919, 959, 1241) were incubated with internally labeled target RNA in the following combinations: 892 alone; 892+919; 892+919+959; 892+919+959+1241. The fraction of RNA cleavage increased in an additive manner with an increase in the number of ribozymes used in the cleavage reaction (FIG. 9). Ribozyme cleavage reactions were carried out at 20° C. as described above. These data suggest that multiple ribozymes targeted to different sites on the same mRNA will increase the reduction of target RNA in an additive manner.

Example 15

Construction of Ribozvme Expressing Transcription Units for GBSS

Cloning of GBSS Multimer Ribozymes RPA 63 (active) and RPA 64 (inactive) A multimer ribozyme was constructed which contained four hammerhead ribozymes targeting sites 892, 919, 959 and 968 of the GBSS mRNA. Two DNA oligonucleotides (Macromolecular Resourses, Fort Collins, Colo.) were ordered which overlap by 18 nucleotides. The sequences were as follows:

Oligo 1: CGC GGA TCC TGG TAG GAC TGA TGA GGC CGA AAG GCC GAA ATG TTG TGC TGA TGA GGC CGA AAG GCC GAA ATG CAG AAA GCG GTC TTT GCG TCC CTG TAG ATG CCG TGG C (SEQ ID NO. 1238)

Oligo 2: CGC GAG CTC GGC CCT CTC TTT CGG CCT TTC GGC CTC ATC AGG TGC TAC CTC AAG AGC AAC TAC CAG TTT CGG CCT TTC GGC CTC ATC AGC CAC GGC ATC TAC AGG G (SEQ ID NO. 1239)

Inactive versions of the above were made by substituting T for G5 and T for A14 within the catalytic core of each ribozyme motif.

These were annealed in 1 × Klenow Buffer (Gibco/BRL) at 90° C. for 5 minutes and slow cooled to room temperature (22° C.). NTPs were added to 0.2 mM and the oligos extended with Klenow enzyme at 1 unit/ul for one hour at 37° C. This was phenol/chloroform extracted and ethanol precipitated, then resuspended in 1×React 3 buffer (Gibco/BRL) and digested with Bam HI and Sst I for 1 hour at 37° C. The DNA was gel purified on a 2% agarose gel using the Qiagen gel extraction kit.

The DNA fragments were ligated into BamHI/Sst I digested pDAB 353. The ligation was transformed into competent DH5α F' bacteria (Gibco/BRL). Potential clones were screened by digestion with Bam HI/Eco RI. Clones were confirmed by sequencing. The total length of homology with the target sequence is 96 nucleotides.

919 Monomer Ribozyme (RPA 66)

A single ribozyme to site 919 of the GBSS mRNA was constructed with 10/10 arms as follows. Two DNA oligos were ordered:

Oligo 1: GAT CCG ATG CCG TGG CTG ATG AGG CCG AAA GGC CGA AAC TGG TAG TT (SEQ ID NO. 1240)

Oligo 2: AAC TAC CAG TTT CGG CCT TTC GGC CTC ATC AGC CAC GGC ATC G (SEQ ID NO. 1241)

The oligos are phosphorylated individually in 1×kinase buffer (Gibco/BRL) and heat denatured and annealed by combining at 90° C. for 10 min, then slow cooled to room temperature (22° C.). The vector was prepared by digestion of pDAB 353 with Sst I and blunting the ends with T4 DNA polymerase. The vector was redigested with Bam HI and gel purified as above. The annealed oligos are ligated to the vector in 1×ligation buffer (Gibco/BRL) at 16° C. overnight. Potential clones were digested with Bam HI/Eco RI and confirmed by sequencing.

Example 16

Plant Transformation Plasmids pDAB 367, Used in the Δ9 Ribozyme Experiments, and pDAB353 Used in the GBSS Ribozyme Experiments Part A pDAB367

Plasmid pDAB367 has the following DNA structure: beginning with the base after the final C residue of the Sph I site of pUC 19 (base 441; Ref. 1), and reading on the strand contiguous to the LacZ gene coding strand, the linker sequence CTGCAGGCCGGCC TTAATTAAGCGGC-CGCGTTTAAACGCCCGGGCATTTAAATG-GCGCGCCGCGA TCGCTTGCAGATCTGCATGGGTG (SEQ ID NO. 1242), nucleotides 7093 to 7344 of CaMV DNA (2), the linker sequence CATCGATG, nucleotides 7093 to 7439 of CaMV, the linker sequence GGG-GACTCTAGAGGATCCAG (SEQ ID NO. 1243), nucleotides 167 to 186 of MSV (3), nucleotides 188 to 277 of MSV (3), a C residue followed by nucleotides 119 to 209 of maize Adh 1S containing parts of exon 1 and intron 1 (4), nucleotides 555 to 672 containing parts of Adh 1S intron 1 and exon 2 (4), the linker sequence GACGGATCTG (SEQ ID NO. 1244), and nucleotides 278 to 317 of MSV. This is followed by a modified BAR coding region from pIJ4104 (5) having the AGC serine codon in the second position replaced by a GCC alanine codon, and nucleotide 546 of the coding region changed from G to A to eliminate a Bgl II site. Next, the linker sequence TGAGATCTGAGCTC-GAATTTCCCC (SEQ ID NO. 1245), nucleotides 1298 to 1554 of Nos (6), and a G residue followed by the rest of the pUC 19 sequence (including the Eco RI site).

PartB pDAB353

Plasmid pDAB353 has the following DNA structure: beginning with the base after the final C residue of the Sph I site of pUC 19 (base 441; Ref. 1), and reading on the strand contiguous to the LacZ gene coding strand, the linker sequence CTGCAGATCTGCATGGGTG (SEQ ID NO. 1246), nucleotides 7093 to 7344 of CaMV DNA (2), the linker sequence CATCGATG, nucleotides 7093 to 7439 of CaMV, the linker sequence GGGGACTCTAGAG (SEQ ID NO. 1247), nucleotides 119 to 209 of maize Adh 1S containing parts of exon 1 and intron 1 (4), nucleotides 555 to 672 containing parts of Adh 1S intron 1 and exon 2 (4), the linker sequence GACGGATCCGTCGACC (SEQ ID NO. 1248), where GGATCC represents the recognition sequence for BamH I restriction enzyme. This is followed by the beta-glucuronidase (GUS) gene from pRAJ275 (7), cloned as an Nco I/Sac I fragment, the linker sequence GAATTTCCCC (SEQ ID NO. 1249), the poly A region in nucleotides 1298 to 1554 of Nos (6), and a G residue followed by the rest of the pUC 19 sequence (including the Eco RI site).

The following are herein incorporated by reference:
1. Messing, J. (1983) in "Methods in Enzymology" (Wu, R. et al., Eds) 101:20–78.
2. Franck, A., H. Guilley, G. Jonard, K. Richards, and L. Hirth (1980) Nucleotide sequence of Cauliflower Mosaic Virus DNA. Cell 21:285–294.
3. Mullineaux, P. M., J. Donson, B. A. M. Morris-Krsinich, M. I. Boulton, and J. W. Davies (1984) The nucleotide sequence of Maize Streak Virus DNA. *EMBO J.* 3:3063–3068.
4. Dennis, E. S., W. L. Gerlach, A. J. Pryor, J. L. Bennetzen, A. Inglis, D. Llewellyn, M. M. Sachs, R. J. Ferl, and W. J. Peacock (1984) Molecular analysis of the alcohol dehydrogenase (Adh1) gene of maize. Nucl. Acids Res. 12:3983–4000.
5. White, J., S-Y Chang, M. J. Bibb, and M. J. Bibb (1990) A cassette containing the bar gene of *Streptomyces hygroscopicus*: a selectable marker for plant transformation. Nucl. Acids. Res. 18:1062.
6. DePicker, A., S. Stachel, P. Dhaese, P. Zambryski, and H. M. Goodman (1982) Nopaline Synthase: Transcript mapping and DNA sequence. J. Molec. Appl. Genet. 1:561–573.
7. Jefferson, R. A. (1987) Assaying chimeric genes in plants: The GUS gene fusion system. Plant Molec. Biol. Reporter 5:387–405.

Example 17

Plasmid pDAB359 a Plant Transformation Plasmid which Contains the Gamma-Zein Promoter, the Antisense GBSS, and a the Nos Polyadenylation Sequence Plasmid pDAB359 is a 6702 bp double-stranded, circular DNA that contains the following sequence elements: nucleotides 1–404 from pUC18 which include lac operon sequence from base 238 to base 404 and ends with the HindIII site of the M13mp18 polylinker (1,2); the Nos polyadenylation sequence from nucleotides 412 to 668 (3); a synthetic adapter sequence from nucleotides 679–690 which converts a Sac I site to an Xho I site by changing GAGCTC to GAGCTT and adding CTCGAG; maize granule bound starch synthase cDNA from bases 691 to 2953, corresponding to nucleotides 1–2255 of SEQ. I.D. No. 25. The GBSS sequence in plasmid pDAB359 was modified from the original cDNA by the addition of a 5' Xho I and a 3' Nco I site as well as the deletion of internal Nco I and Xho I sites using Klenow to fill in the enzyme recognition sequences. Bases 2971 to 4453 are 5' untranslated sequence of the maize 27 kD gamma-zein gene corresponding to nucleotides 1078 to 2565 of the published sequence (4). The gamma-zein sequence was modified to contain a 5' Kpn I site and 3' BamH/SalI/Nco I sites. Additional changes in the gamma-zein sequence relative to the published sequence include a T deletion at nucleotide 104, a TACA deletion at nucleotide 613, a C to T conversion at nucleotide 812, an A deletion at nucleotide 1165 and an A insertion at nucleotide 1353. Finally, nucleotides 4454 to 6720 of pDAB359 are identical to puc18 bases 456 to 2686 including the Kpn I/EcoRI/Sac I sites of the M13/mp18 polylinker from 4454 to 4471, a lac operon fragment from 4471 to 4697, and the β-lacatmase gene from 5642 to 6433 (1, 2).

The following are incorporated by reference herein:
pUC18—Norrander, J., Kempe, T., Messing, J. Gene (1983) 26: 101–106; Pouwels, P. H., Enger-Valk, B. E., Brammar, W. J. Cloning Vectors, Elsevier 1985 and supplements
NosA—DePicker, A., Stachel, S., Dhaese, P., Zambryski, P., and Goodman, H. M. (1982) Nopaline Synthase: Transcript Mapping and DNA Sequence J. Molec. Appl. Genet. 1:561–573.
Maize 27 kD gamma-zein—Das, O. P., Poliak, E. L., Ward, K., Messing, J. Nucleic Acids Research 19, 3325–3330 (1991).

Example 18

Construction of Plasmid pDAB430, Containing Antisense Δ9 Desaturase, Expressed by the Ubiquitin Promoter/intron (Ubi1)

Part A Construction of plasmid pDAB421

Plasmid pDAB421 contains a unique blunt-end SrfI cloning site flanked by the maize Ubiquitin promoter/intron and the nopaline synthase polyadenylation sequences. pDAB421 was prepared as follows: digestion of pDAB355 with restriction enzymes KpnI and BamHI drops out the R coding region on a 2.2 kB fragment. Following gel purification, the vector was ligated to an adapter composed of two annealed oligonucleotides OF235 and OF236. OF235 has the sequence 5'-GAT CCG CCC GGG GCC CGG GCG GTA C-3' (SEQ ID NO. 1250) and OF236 has the sequence 5'-CGC CCG GGC CCC GGG CG-3' (SEQ ID NO. 1251). Clones containing this adapter were identified by digestion and linearization of plasmid DNA with the enzymes SrfI and SmaI which cut in the adapter, but not elsewhere in the plasmid. One representative clone was sequenced to verify that only one adapter was inserted into the plasmid. The resulting plasmid pDAB421 was used in subsequent construction of the Δ9 desaturase antisense plasmid pDAB430.

Part B Construction of plasmid pDAB430 (antisense Δ9 desaturase)

The antisense Δ9 desaturase construct present in plasmid pDAB430 was produced by cloning of an amplification product in the blunt-end cloning site of plasmid pDAB421. Two constructs were produced simultaneously from the same experiment. The first construct contains the Δ9 desaturase gene in the sense orientation behind the ubiquitin promoter, and the c-myc tag fused to the C-terminus of the Δ9 desaturase open reading frame for immunological detection of overproduced protein in transgenic lines. This construct was intended for testing of ribozymes in a system which did not express maize Δ9 desaturase. This construct was never used, but the primers used to amplify and construct the Δ9 desaturase antisense gene were the same. The Δ9 desaturase cDNA sequence described herein was amplified with two primers. The N-terminal primer OF279 has the sequence 5'-GTG CCC ACA ATG GCG CTC CGC CTC AAC GAC-3' (SEQ ID NO. 1252). The underlined bases correspond to nucleotides 146–166 of the cDNA sequence. C-terminal primer OF280 has the sequence 5'-TCA TCA CAG GTC CTC CTC GCT GAT CAG CTT CTC CTC CAG TTG GAC CTG CCT ACC GTA-3' (SEQ ID NO. 1253) and is the reverse complement of the sequence 5'-TAC GGT AGG GAC GTC CAA CTG GAG GAG AAG CTG ATC AGC GAG GAG GAC CTG TGA TGA-3' (SEQ ID NO. 1254). In this sequence the underlined bases correspond to nucleotides 1304–1324 of the cDNA sequence, the bases in italics correspond to the sequence of the c-myc epitope. The 1179 bp of amplification product was purified through a 1.0% agarose gel, and ligated into plasmid pDAB421 which was linearized with the restriction enzyme Srf I. Colony hybridization was used to select clones containing the pDAB421 plasmid with the insert. The orientation of the insert was determined by restriction digestion of plasmid DNA with diagnostic enzymes KpnI and BamHI. A clone containing the Δ9 desaturase coding sequence in the sense orientation relative to the Ubiquitin promoter/intron was recovered and was named pDAB429. An additional clone containing the Δ9 desaturase coding sequence in the anit-sense orientation relative to the promoter was named pDAB430. Plasmid pDAB430 was subjected to sequence analysis and it was determined that the sequence contained three PCR induced errors compared to the expected sequence. One error was found in the sequence corresponding to primer OF280 and two nucleotide changes were observed internal to the coding sequence. These errors were not corrected, because antisense downregulation does not require 100% sequence identity between the antisense transcript and the downregulation target.

Example 19

Helium Blasting of Embryogenic Maize Cultures and the Subsequent Regeneration of Transgenic Progeny Part A Establishment of embryogenic maize cultures. The tissue cultures employed in transformation experiments were initiated from immature zygotic embryos of the genotype "Hi-II". Hi-II is a hybrid made by intermating 2 $R_3$ lines derived from a B73×A188 cross (Armstrong et al. 1990). When cultured, this genotype produces callus tissue known as Type II. Type II callus is friable, grows quickly, and exhibits the ability to maintain a high level of embryogenic activity over an extended time period.

Type II cultures were initiated from 1.5–3.0 mm immature embryos resulting from controlled pollinations of greenhouse grown Hi-II plants. The initiation medium used was N6 (Chu, 1978) which contained 1.0 mg/L 2,4-D, 25 mM L-proline, 100 mg/L casein hydrolysate, 10 mg/L $AgNO_3$, 2.5 g/L gelrite and 2% sucrose adjusted to pH 5.8. For approximately 2–8 weeks, selection occurred for Type II callus and against nonembryogenic and/or Type I callus. Once Type II callus was selected, it was transferred to a maintenance medium in which $AgNO_3$ was omitted and L-proline reduced to 6 mM.

After approximately 3 months of subculture in which the quantity and quality of embryogenic cultures was increased, the cultures were deemed acceptable for use in transformation experiments.

Part B Preparation of plasmid DNA. Plasmid DNA was adsorbed onto the surface of gold particles prior to use in transformation experiments. The experiments for the GBSS target used gold particles which were spherical with diameters ranging from 1.5–3.0 microns (Aldrich Chemical Co., Milwaukee, Wis.). Transformation experiments for the Δ9 desaturase target used 1.0 micron spherical gold particles (Bio-Rad, Hercules, Calif.). All gold particles were surface-sterilized with ethanol prior to use. Adsorption was accomplished by adding 74 μl of 2.5 M calcium chloride and 30 μl of 0.1 M spermidine to 300 μl of plasmid DNA and sterile $H_2O$. The concentration of plasmid DNA was 140 μg. The DNA-coated gold particles were immediately vortexed and allowed to settle out of suspension. The resulting clear supernatent was removed and the particles were resuspended in 1 ml of 100% ethanol. The final dilution of the suspension ready for use in helium blasting was 7.5 mg DNA/gold per ml of ethanol.

Part C Preparation and helium blasting of tissue targets. Approximately 600 mg of embryogenic callus tissue per target was spread over the surface of petri plates containing Type II callus maintenance medium plus 0.2 M sorbitol and 0.2 M mannitol as an osmoticum. After an approximately 4 hour pretreatment, all tissue was transferred to petri plates containing 2% agar blasting medium (maintenance medium plus osmoticum plus 2% agar).

Helium blasting involved accelerating the suspended DNA-coated gold particles towards and into prepared tissue targets. The device used was an earlier prototype to the one described in a DowElanco U.S. Pat. No. 5,141,131) which is incorporated herein by reference, although both function in a similar manner. The device consisted of a high pressure helium source, a syringe containing the DNA/gold suspension, and a pneumatically-operated multipurpose valve which provided controlled linkage between the helium source and a loop of pre-loaded DNA/gold suspension.

Prior to blasting, tissue targets were covered with a sterile 104 micron stainless steel screen, which held the tissue in place during impact. Next, targets w ere placed under vacuum in the main chamber of the device. The DNA-coated gold particles were accelerated at the target 4 times using a helium pressure of 1500 psi. Each blast delivered 20 μl of DNA/gold suspension. Immediately post-blasting, the targets were placed back on maintenance medium plus osmoticum for a 16 to 24 hour recovery period.

Part D Selection of transformed tissue and the regeneration of plants from transgenic cultures. After 16 to 24 hours post-blasting, the tissue was divided into small pieces and transferred to selection medium (maintenance medium plus 30 mg/L Basta™). Every 4 weeks for 3 months, the tissue pieces were non-selectively transferred to fresh selection medium. After 8 weeks and up to 24 weeks, any sectors found proliferating against a background of growth inhibited tissue were removed and isolated. Putatively transformed tissue was subcultured onto fresh selection medium. Transgenic cultures were established after 1 to 3 additional subcultures.

Once Basta™ resistant callus was established as a line, plant regeneration was initiated by transferring callus tissue to petri plate containing cytokinin-based induction medium which were then placed in low light (125 ft-candles) for one week followed by one week in high light (325 ft-candles). The induction medium was composed of MS salts and vitamins (Murashige and Skoog, 1962), 3 0 g/L sucrose, 100 mg/L myo-inositol, 5 mg/L 6-benzylaminopurine, 0.025 mg/L 2,4-D, 2.5 g/L gelrite adjusted to pH 5.7. Following the two week induction period, the tissue was non-selectively transferred to hormone-free regeneration medium and kept in high light. The regeneration medium was composed of MS salts and vitamins, 30 g/L sucrose and 2.5 g/L gelrite adjusted to pH 5.7. Both induction and regeneration media contained 30 mg/L Basta™. Tissue began differentiating shoots and roots in 2–4 weeks. Small (1.5–3 cm) plantlets were removed and placed in tubes containing SH medium. SH medium is composed of SH salts and vitamins (Schenk and Hildebrandt, 1972), 10 g/L sucrose, 100 mg/L myo-inositol, 5 mL/L FeEDTA, and either 7 g/L Agar or 2.5 g/L Gelrite adjusted to pH 5.8. Plantlets were transferred to 10 cm pots containing approximately 0.1 kg of Metro-Mix® 360 (The Scotts Co., Marysville, Ohio) in the greenhouse as soon as they exhibited growth and developed a sufficient root system (1–2 weeks). At the 3–5 leaf stage, plants were trans ferred to 5 gallon pots containing approximately 4 kg Metro-Mix® 360 and grown to maturity. These $R_0$ plants were self-pollinated and/or cross-pollinated with non-transgenic inbreds to obtain transgenic progeny. In the case of transgenic plants produced for the GBSS target, $R_1$ seed produced from $R_0$ pollinations was replanted. The $R_1$ plants were grown to maturity and pollinated to produce $R_2$ seed in the quantities needed for the analyses.

Example 20

Production and Regeneration of Δ9 Transgenic Material

Part A Transformation and isolation of embryogenic callus. Six ribozyme constructs, described previously, targeted to Δ9 desaturase were transformed into regenerable Type II callus cultures as described herein. These 6 constructs consisted of 3 active/inactive pairs; namely, RPA85/RPA113, RPA114/RPA115, and RPA118/RPA119. A total of 1621 tissue targets were prepared, blasted, and placed into selection. From these blasting experiments 334 independent Basta®-resistant transformation events ("lines") were isolated from selection. Approximately 50% of these lines were analyzed via DNA PCR or GC/FAME as a means of determining which ones to move forward to regeneration and which ones to discard. The remaining 50% were not analyzed either because they had become non-embryogenic or contaminated.

Part B Regeneration of Δ9 plants from transgenic callus. Following analyses of the transgenic callus, twelve lines were chosen per ribozyme construct for regeneration, with 15 $R_0$ plants to be produced per line. These lines generally consisted of 10 analysis-positive lines plus 2 negative controls, however, due to the poor regenerability of some of the cultures, plants were produced from less than 12 lines for constructs RPA113, RPA115, RPA118, and RPA119. An overall total of 854 $R_0$ plants were regenerated from 66 individual lines (see Table X). When the plants reached maturity, self- or sib-pollinations were given the highest priority, however, when this was not possible, cross-pollinations were made using the inbreds CQ806, CS716, OQ414, or $HO_1$ as pollen donors, and occasionally as pollen recipients. Over 715 controlled pollinations have been made, with the majority (55%) being comprised of self- or sib-pollinations and the minority (45%) being comprised of F1 crosses. $R_1$ seed was collected approximately 45 days post-pollination.

Example 21

Production and Regeneration of Transgenic Maize for the GBSS

Part A Transformation of embryogenic maize callus and the subsequent selection and establishment of transgenic cultures. RPA63 and RPA64, an active/inactive pair of ribozyme multimers targeted to GBSS, were inserted along with bar selection plasinid pDAB308 into Type II callus as described herein. A total of 115 Basta™-resistant independent transformation events were recovered from the selection of 590 blasted tissue targets. Southern analysis was performed on callus samples from established cultures of all events to determine the status of the gene of interest.

Part B Regeneration of plants from cultures transformed with ribozymes targeted to GBSS as well as the advancement to the $R_2$ generation. Plants were regenerated from Southern "positive" transgenic cultures and grown to maturity in a greenhouse. The primary regenerates were pollinated to produce $R_1$ seed. From 30 to 45 days after pollination, seed was harvested, dried to the correct moisture content, and replanted. A total of 752 $R_1$ plants, representing 16 original lines, were grown to sexual maturity and pollinated. Approximately 19 to 22 days after pollination, ears were harvested and 30 kernels were randomly excised per ear and frozen for later analyses.

Example 22

Testing of GBSS-Targeted Ribozymes in Maize Black Mexican Sweet (BMS) Stably Transformed Callus Part A Production of BMS callus stably transformed with GBSS and GBSS-targeted ribozymes. BMS does not produce a GBSS mRNA which is homologous to that found endogenously in maize. Therefore, a double transformation system was developed to produce transformants which expressed both target and ribozymes. "ZM" BMS suspensions (obtained from Jack Widholm, University of Illinois, also see W. F. Sheridan, "Black Mexican Sweet Corn: Its Use for Tissue Cultures" in *Maize for Biological Research*, W. F. Sheridan, editor. University Press. University of North Dakokta, Grand Forks, N. Dak., 1982, pp. 385–388) were prepared for helium blasting four days after subculture by transfer to a 100×20 mm Petri plate (Fisher Scientific, Pittsburgh, Pa.) and partial removal of liquid medium, forming a thin paste of cells. Targets consisted of 100–125 mg fresh weight of cells on a ½" antibiotic disc (Schleicher and Schuell, Keene, N.H.) placed on blasting medium, DN6 [N6 salts and vitamins (Chu et al., 1978), 20 g/L sucrose, 1.5 mg/L 2,4-dichlorophenoxyacetic acid (2,4-D), 25 mM L-proline; pH=5.8 before autoclaving 20 minutes at 121° C.] solidified with 2% TC agar (JRH Biosciences, Lenexa, Kas.) in 60×20 mm plates. DNA was precipitated onto gold particles. For the first transformation, pDAB 426 (Ubi/GBSS) and pDAB 308 (35T/Bar) were used. Targets were individually shot using DowElanco Helium Blasting Device I. With a vacuum pressure of 650 mm Hg and at a distance of 15.5 cm from target to device nozzle, each sample was blasted once with DNA/gold mixture at 500 psi. Immediately after blasting, the antibiotic discs were transferred to DN6 medium made with 0.8% TC agar for one week of target tissue recovery. After recovery, each target was spread onto a 5.5 cm Whatman #4 filter placed on DN6 medium minus proline with 3 mg/L Basta® (Hoechst, Frankfort, Germany). Two weeks later, the filters were transferred to fresh selection medium with 6 mg/L Basta®. Subsequent transfers were done at two week intervals. Isolates were picked from the filters and placed on AMCF-ARM medium (N6 salts and vitamins, 20 g/L sucrose, 30 g/L mannitol, 100 mg/L acid casein hydrolysate, and 1 mg/L 2,4-D, 24 mM L-proline; pH=5.8 before autoclaving 20 minutes at 121° C.) solidified with 0.8% TC agar containing 6 mg/L Basta®. Isolates were maintained by subculture to fresh medium every two weeks.

Basta®-resistant isolates which expressed GBSS were subjected to a second transformation. As with BMS suspensions, targets of transgenic callus were prepared 4 days after subculture by spreading tissue onto ½" filters. However, AMCF-ARM with 2% TC agar was used for blasting, due to maintenance of transformants on AMCF-ARM selection media. Each sample was covered with a sterile 104 μm mesh screen and blasting was done at 1500 psi. Target tissue was co-bombarded with pDAB 319 (35S-ALS; 35T-GUS) and RPA63 (active ribozyme multimer) or pDAB3 19 and RPA64 (inactive ribozyme multimer), or shot with pDAB 319 alone. Immediately after blasting, all targets were transferred to nonselective medium (AMCF-ARM) for one week of recovery. Subsequently, the targets were placed on AMCF-ARM medium containing two selection agents, 6 mg/L Basta® and 2 μg/L chlorsulfuron (CSN). The level of CSN was increased to 4 ug/L after 2 weeks. Continued transfer of the filters and generation of isolates was done as described in the first transformation, with isolates being maintained on AMCF-ARM medium containing 6 mg/L Basta and 4 μg/L CSN.

Part B Analysis of BMS stable transformants expressing GBSS and GBSS-targeted ribozymes. Isolates from the first transformation were evaluated by Northern blot analysis for detection of a functional target gene (GBSS) and to detennine relative levels of expression. In 12 of 25 isolates analyzed, GBSS transcript was detected. A range of expression was observed, indicating an independence of transformation events. Isolates generated from the second transformation were evaluated by Northern blot analysis for detection of continued GBSS expression and by RT-PCR to screen for the presence of ribozyme transcript. Of 19 isolates tested from one previously transformed line, 18 expressed the active ribozyme, RPA63, and all expressed GBSS. GBSS was detected in each of 6 vector controls; ribozyme was not expressed in these samples. As described herein, RNase protection assay (RPA) and Northern blot analysis were performed on ribozyme-expressing and vector control tissues to compare levels of GBSS transcript in the presence or absence of active ribozyme. GBSS values were normalized to an internal control (Δ9 desaturase); Northern blot data is shown in FIG. (25). Northern blot results revealed a significantly lower level of GBSS message in the presence of ribozyme, as compared to vector controls. RPA data showed that some of the individual samples expressing active ribozyme ("L" and "O") were significantly different from vector controls and similar to a nontransformed control.

Example 23

Analysis of Plant and Callus Materials

Plant material co-transformed with the pDAB308 and one of the following ribozyme containing vectors, pRPA63, pRPA64, pRPA85, pRPA113, pRPA114, pRPA115, pRPA118 or pRPA119 were analyzed at the callus level, Ro level and select lines analyzed at the F1 level. Leaf material was harvested when the plantlets reached the 6–8 leaf stage. DNA from the plant and callus material was prepared from lyophilized tissue as described by Saghai-Maroof et al. (supra). Eight micrograms of each DNA was digested with the restriction enzymes specific for each construct using conditions suggested by the manufacturer (Bethesda Research Laboratory, Gaithersburg, Md.) and separated by agarose gel electrophoresis. The DNA was blotted onto nylon membrane as described by Southern, E. 1975 "Detection of specific sequences among DNA fragments separated by gel electrophoresis," J Mol. Biol. 98:503 and Southern, E. 1980 "Gel electrophoresis of restriction fragments" Methods Enzmol. 69:152, which are incorporated by reference herein.

Probes specific for the ribozyme coding region were hybridized to the membranes. Probe DNA was prepared by boiling 50 ng of probe DNA for 10 minutes then quick cooling on ice before being added to the Ready-To-Go DNA labeling beads (Pharmacia LKB, Piscataway, N.J.) with 50 microcuries of $\alpha^{32}$P-dCTP (Amersham Life Science, Arlington Heights, Ill.). Probes were hybridized to the genomic DNA on the nylon membranes. The membranes were washed at 60° C. in 0.25×SSC and 0.2% SDS for 45 minutes, blotted dry and exposed to XAR-5 film overnight with two intensifying screens.

The DNA from the RPA63 and RPA64 was digested with the restriction enzymes HindIII and EcoRI and the blots containing these samples were hybridized to the RPA63 probe. The RPA63 probe consists of the RPA63 ribozyme multimer coding region and should produce a single 1.3 kb hybridization product when hybridized to the RPA63 or RPA64 materials. The 1.3 kb hybridization product should contain the enhanced 35S promoter, the AdhI intron, the ribozyme coding region and the nopaline synthase poly A 3' end. The DNA from the RPA85 and RPA113 was digested with the restriction enzymes HindIII and EcoRI and the blots containing these samples were hybridized to the RPA122 probe. RPA122 is the 252 multimer ribozyme in pDAB 353 replacing the GUS reporter. The RPA122 probe consists of the RPA122 ribozyme multimer coding region and the nopaline synthase 3' end and should produce a single 2.1 kb hybridization product when hybridized to the RPA85 or RPA113 materials. The 2.1 kb hybridization product should contain the enhanced 35S promoter, the AdhI intron, the bar gene, the ribozyme coding region and the nopaline synthase poly A 3' end. The DNA from the RPA114 and RPA115 was digested with the restriction enzymes HindIII and SmaI and the blots containing these samples were hybridized to the RPA115 probe. The RPA115 probe consist of the RPA115 ribozyme coding region and should produce a single 1.2 kb hybridization product when hybridized to the RPA114 or RPA115 materials. The 1.2 kb hybridization product should contain the enhanced 35S promoter, the AdhI intron, the ribozyme coding region and the nopaline synthase poly A 3' end. The DNA from the RPA118 and RPA119 was digested with the restriction enzymes HindIII and SmaI and the blots containing these samples were hybridized to the RPA118 probe. The RPA118 probe consist of the RPA118 ribozyme coding region and should produce a single 1.3 kb hybridization product when hybridized to the RPA118 or RPA119 materials. The 1.3 kb hybridization product should contain the enhanced 35S promoter, the AdhI intron, the ribozyme coding region and the nopaline synthase poly A 3' end.

Example 24

Extraction of Genomic DNA from Transgenic Callus

Three hundred mg of actively growing callus were quick frozen on dry ice. It was ground to a fine powder with a chilled Bessman Tissue Pulverizer (Spectrum, Houston, Tex.) and extracted with 400 µl of 2×CTAB buffer (2% Hexadecyltrimethylammonium Bromide, 100 mM Tris pH 8.0, 20 mM EDTA, 1.4 M NaCl, 1% polyvinylpyrrolidone). The suspension was lysed at 65° C. for 25 minutes, then extracted with an equal volume of chloroform:isoamyl alcohol. To the aqueous phase was added 0.1 volumes of 10% CTAB buffer (10% Hexadecyltrimethylammonium Bromide, 0.7 M NaCl). Following extraction with an equal volume of chloroform:isoamyl alcohol, 0.6 volumes of cold isopropyl alcohol was added to the aqueous phase, and placed at −20° C. for 30 minutes. After a 5 minute centrifugation at 14,000 rpm, the resulting precipitant was dried for 10 minutes under vacuum. It was resuspended in 200 µl TE (10 mM Tris, 1 mM EDTA, pH 8.0) at 65° C. for 20 minutes. 20% Chelex (Biorad,) was added to the DNA to a final concentration of 5% and incubated at 56° C. for 15–30 minutes to remove impurities. The DNA concentration was measured on a Hoefer Fluorimeter (Hoefer, San Francisco).

Example 25

PCR Analysis of Genomic Callus DNA

Use of Polymerase Chain Reaction (PCR) to demonstrate the stable insertion of ribozyme genes into the chromosome of transgenic maize calli.

Part A Method used to detect ribozyme DNA

The Polymerase Chain Reaction (PCR) was performed as described in the suppliers protocol using AmpliTaq DNA Polymerase (GeneAmp PCR kit, Perkin Elmer, Cetus). Aliquots of 300 ng of genomic callus DNA, 1 µl of a 50 µM downstream primer (5' CGC AAG ACC GGC AAC AGG 3'; SEQ ID NO. 1255), 1 µl of an upstream primer and 1 µl of Perfect Match (Stratagene, Calif.) PCR enhancer were mixed with the components of the kit. The PCR reaction was performed for 40 cycles using the following parameters; denaturation at 94° C. for 1 minute, annealing at 55° C. for 2 minutes, and extension at 72° C. for 3 mins. An aliquot of 0.2×vol. of each PCR reaction was electrophoresised on a 2% 3:1 Agarose (FMC) gel using standard TAE agarose gel conditions.

Part B Upstream primer used for detection of Δ9 desaturase ribozyme genes

RPA85/RPA113 251 multimer fused to BAR 3' ORF
RPA114/RPA115 258 ribozyme monomer
RPA118/RPA119 452 ribozyme multimer 5'TGG ATT GAT GTG ATA TCT CCA C 3' (SEQ ID NO. 1256) This primer is used to amplify across the Eco RV site in the 35S promoter. Primers were prepared using standard oligo synthesis protocols on an Applied Biosystems Model 394 DNA/RNA synthesizer.

Example 26

Preparation of Total RNA from Transgenic Maize Calli and Plant

Part A Preparation of total RNA from transgenic non-regenerable and regenerable callus tissue. Three hundred milligrams of actively growing callus was quick frozen on dry ice. The tissue was ground to a fine powder with a chilled Bessman Tissue Pulverizer (Spectrum, Houston, Tex.) and extracted with RNA Extraction Buffer (50 mM Tris-HCl pH 8.0, 4% para-amino salicylic acid, 1% Tri-isopropylnapthalenesulfonic acid, 10 mM dithiothreitol, and 10 mM Sodium meta-bisulfite) by vigorous vortexing. The homogenate was then extracted with an equal volume of phenol containing 0.1% 8-hydroxyquinoline. After centrifugation, the aqueous layer was extracted with an equal volume of phenol containing chloroform:isoamyl alcohol (24:1), followed by extraction with chloroform:octanol (24:1). Subsequently, 7.5 M Ammonium acetate was added to a final concentration of 2.5 M, the RNA was precipitated for 1 to 3 hours at 4° C. Following 4° C. centrifugation at 14,000 rpm, RNA was resuspended in sterile water, precipitated with 2.5 M NH$_4$OAc and 2 volumes of 100% ethanol and incubated overnite at −20° C. The harvested RNA pellet was washed with 70% ethanol and dried under vacuum. RNA was resuspended in sterile H$_2$O and stored at −80° C.

Part B Preparation of total RNA from transgenic maize plants. A five cm section (~150 mg) of actively growing maize leaf tissue was excised and quick frozen in dry ice. The leaf was ground to a fine powder in a chilled mortar. Following manufactorers instructions, total RNA was purified from the powder using a Qaigen RNeasy Plant Total RNA kit (Qiagen Inc., Chatsworth, Calif.). Total RNA was released from the RNeasy columns by two sequential elution spins of prewarmed (50° C.) sterile water (30 µl each) and stored at −80° C.

Example 27

Use of RT-PCR Analysis to Demonstrate Expression of Ribozyme RNA in Transgenic Maize Calli and Plants Part A Method used to detect ribozyme RNA. The Reverse Transcription-Polyinerase Chain Reaction (RT-PCR) was performed as described in the suppliers protocol using a thermostable rTth DNA Polymerase (rTth DNA Polymerase RNA PCR kit, Perkin Elmer Cetus). Aliquots of 300 ng of total RNA (leaf or callus) and 1 µl of a 15 µM downstream primer (5' CGC AAG ACC GGC AAC AGG 3'; SEQ ID NO. 1257) were mixed with the RT components of the kit. The reverse transcription reaction was performed in a 3 step ramp up with 5 minute incubations at 60° C., 65° C., and 70° C. For the PCR reaction, 1 µl of upstream primer specific for the ribozyme RNA being analyzed was added to the RT reaction with the PCR components. The PCR reaction was performed for 35 cycles using the following parameters; incubation at 96° C. for 1 minute, denaturation at 94° C. for 30 seconds, annealing at 50° C. for 30 seconds, and extension at 72° C. for 3 mins. An aliquot of 0.2×vol. of each RT-PCR reaction was electrophoresed on a 2% 3:1 Agarose (FMC) gel using standard TAE agarose gel conditions.

Part B Specific upstream primers used for detection of GBSS ribozymes.

GBSS Active and Inactive Multimer

5' CAG ATC AAG TGC AAA GCT GCG GAC GGA TCT G 3' (SEQ ID NO. 1258). This primer covers the Adh I intron footprint upstream of the first ribozyme arm. GBSS 918 Intron (−) Monomer:

5' ATC CGA TGC CGT GGC TGA TG 3' (SEQ ID NO. 1259). This primer covers the 10 base pair ribozyme arm and the first 6 bases of the ribozyme catalytic domain. GBSS ribozyrne expression in transgenic callus and plants was confirmed by RT-PCR.

GBSS multimer ribozyme expression in stably transformed callus was also determined by Ribonuclease Protection Assay.

Part C Specific upstream primers used for detection of Δ9 desaturase ribozymes.

RPA85/RPA113 252 multimer fused to BAR 3' ORF

5' GAT GAG ATC CGG TGG CAT TG 3' (SEQ ID NO. 1260)

This primer spans the junction of the BAR gene and the RPA85/113 ribozyme. RPA114/RPA115 259 ribozyme monomer

5' ATC CCC TTG GTG GAC TGA TG 3' (SEQ ID NO. 1261)

This primer covers the 10 base pair ribozyme arm and the first 6 bases of the ribozyme catalytic domain. RPA118/RPA119 453 ribozyme multimer

5' CAG ATC AAG TGC AAA GCT GCG GAC GGA TCT G 3' (SEQ ID NO. 1262)

This primer covers the Adh I intron footprint upstream of the first ribozyme arm. Expression of Δ9 desaturase ribozymes in transgenic plant lines 85-06, 113-06 and 85-15 were confirmed by RT-PCR.

Primers were prepared using standard oligo synthesis protocols on an Applied Biosystems Model 394 DNA/RNA synthesizer.

Example 28

Demonstration of Ribozyme Mediated Reduction in Target mRNA Levels in Transgenic Maize Callus and Plants Part A Northern analysis method which was used to demonstrated reductions in target mRNA levels. Five µg of total RNA was dried under vacuum, resuspended in loading buffer (20 mM phosphate buffer pH 6.8, 5 mM EDTA; 50% formamide: 16% formaldehyde: 10% glycerol) and denatured for 10 minutes at 65° C. Electrophoresis was at 50 volts through 1% agarose gel in 20 mM phosphate buffer (pH 6.8) with buffer recirculation. BRL 0.24–9.5 Kb RNA ladder (Gibco/BRL, Gaithersburg, Md.) were stained in gels with ethiduim bromide. RNA was transferred to GeneScreen membrane filter (DuPont NEN, Boston Mass.) by capillary transfer with sterile water. Hybridization was performed as described by DeLeon et al. (1983) at 42° C., the filters were washed at 55° C. to remove non-hybridized probe. The blot was probed sequentially with cDNA fragments from the target gene and an internal RNA control gene. The internal RNA standard was utilized to distinguish variation in target mRNA levels due to loading or handling errors from true ribozyme mediated RNA reductions. For each sample the level of target mRNA was compared to the level of control mRNA within that sample. Fragments were purified by Qiaex resin (Qaigen Inc. Chatsworth, Calif.) from 1× TAE agarose gels. They were nick-translated using an Amersham Nick Translation Kit (Amersham Corporation, Arlington Heights, Ill.) with alpha $_{32}$P dCTP. Autoradiography was at −70° C. with intensifying screens (DuPont, Wilmington Del.) for one to three days. Autoradiogram signals for each probe were measured after a 24 hour exposure by densitometer and a ratio of target/internal control mRNA levels was calculated.

Ribonuclease protection assays were performed as follows: RNA was prepared using the Qiagen RNeasy Plant Total RNA Kit from either BMS protoplasts or callus material. The probes were made using the Ambion Maxiscript kit and were typically $10^8$ cpm/microgram or higher. The probes were made the same day they were used. They were gel purified, resuspended in RNase-free 10 mM Tris (pH 8) and kept on ice. Probes were diluted to 5×$10^5$ cpm/ul immediately before use. 5 μg of RNA derived from callus or 20 μg of RNA derived from protoplasts was incubated with 5×10$^5$ cpm of probe in 4M Guanidine Buffer. [4M Guanidine Buffer: 4M Guanidine Thiocyanate/0.5% Sarcosyl/25 mM Sodium Citrate (pH 7.4)]. 40 ul of PCR mineral oil was added to each tube to prevent evaporation. The samples were heated to 95° for 3 minutes and placed immediately into a 45° water bath. Incubation continued overnight. 600 μl of RNase Treatment Mix was added per sample and incubated for 30 minutes at 37° C. (RNase Treatment Mix: 400 mM NaCl, 40 units/ml RNase A and T1). 12 μl of 20% SDS were added per tube, immediately followed by addition of 12 ul (20 mg/ml) Proteinase K to each tube. The tubes were vortexed gently and incubated for 30 minutes at 37° C. 750 ul of room temperature RNase-free isopropanol was added to each tube, and mixed by inverting repeatedly to get the SDS into solution. The samples were then microfuged at top speed at room temperature for 20 minutes. The pellets were air dried for 45 minutes. 15 ul of RNA Running Buffer was added to each tube, and vortexed hard for 30 seconds. (RNA Running Buffer: 95% Formamide/20 mM EDTA/0.1% Bromophenol Blue/0.1% Xylene Cyanol). The sample was heated to 95° C. for 3 minutes, and loaded onto an 8% denaturing acrylamide gel. The gel was vacuum dried and exposed to a phosphorimager screens for 4 to 12 hours.

Part B Results demonstrating reductions in GBSS mRNA levels in nongenerable callus expressing both a GBSS and GBSS targeted ribozyme RNA. The production of nonregenerable callus expressing RNAs for the GBSS target gene and an active multimer ribozyme targeted to GBSS mRNA was performed. Also produced were transgenics expressing GBSS and a ribozyme (−) control RNA. Total RNA was prepared from the transgenic lines. Northern analysis was performed on 7 ribozyme (−) control transformants and 8 active RPA63 lines. Probes for this analysis were a full length maize GBSS cDNA and a maize Δ9 cDNA fragment. To distinguish variation in GBSS mRNA levels due to loading or handling errors from true ribozyme mediated RNA reductions, the level of GBSS mRNA was compared to the level of Δ9 mRNA within that sample. The level of full length GBSS transcript was compared between ribozyme expressing and ribozyme minus calli to identify lines with ribozyme mediated target RNA reductions. Blot to blot variation was controlled by performing duplicate analyses.

Figure 25:
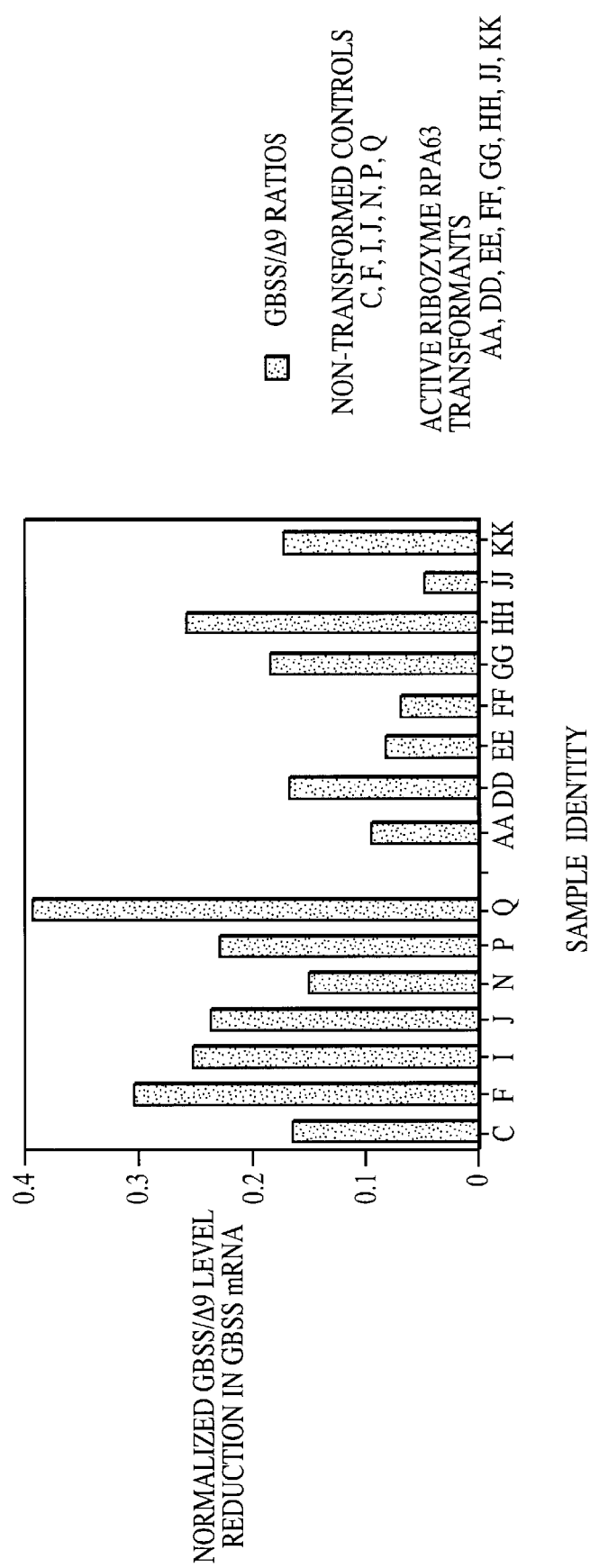
FIG. 25 illustrates GBSS mRNA levels in Ribozyme minus Controls (C, F, I, J, N, P, Q) and Active Ribozyme RPA63 Transformants (AA, DD, EE, FF, GG, HH, JJ, KK).

A range in GBSS/Δ9 ratio was observed between ribozyme (−) transgenics. The target mRNA is produced by a transgene and may be subject to more variation in expression then the endogenous Δ9 mRNA. Active lines (RPA 63) AA, EE, KK, and JJ were shown to reduce the level of GBSS/Δ9 most significantly, as much as 10 fold as compared to ribozyme (−) control transgenics this is graphed in FIG. 25. Those active lines were shown to be expressing GBSS targeted ribozyme by RT-PCR as described herein.

Reductions in GBSS mRNA compared to Δ9 mRNA were also seen by RNAse protection assay.

Figure 26:
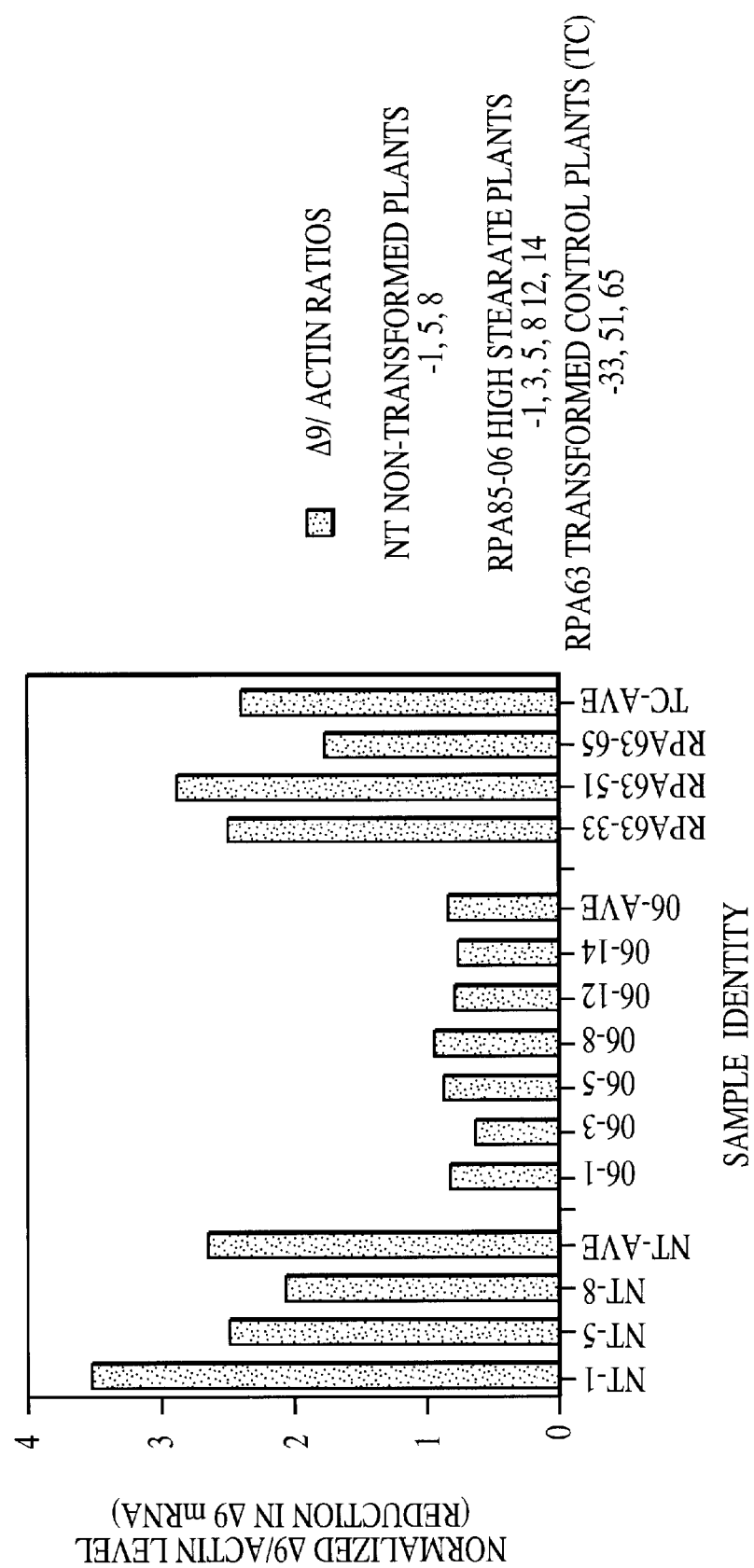
FIG. 26 illustrates Δ9 desaturase mRNA levels in Non-transformed plants (NT), 85-06 High Stearate Plants (1, 3, 5, 8, 12, 14), and Transformed (irrelevant ribozyme)
Figure 27:
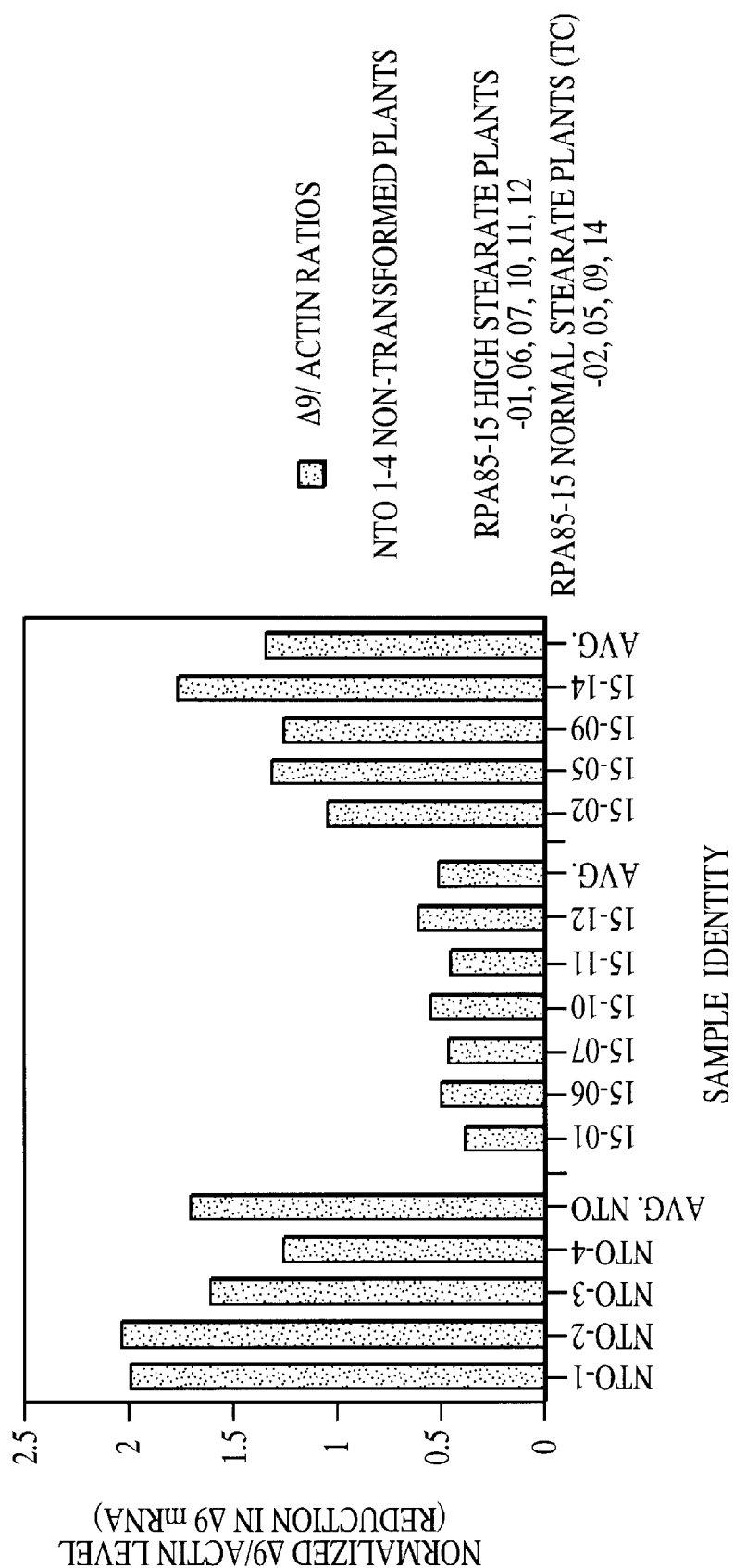
FIG. 27 illustrates Δ9 desaturase mRNA levels in Non-transformed plants (NTO), 85-15 High Stearate Plants (01, 06, 07, 10, 11, 12), and 85-15 Normal Stearate Plants (02, 05, 09, 14).

Part C Demonstration of reductions in Δ9 desaturasc levels in transgenic plants expressing ribozymes targeted to Δ9 desaturase mRNA. The high stearate transgenics, RPA85-06 and RPA85-15, each contained an intact copy of the fused ribozyme multimer gene. Within each line, plants were screened by RT-PCR for the presence of ribozyme RNA. Using the protocol described in Example 27. RPA85 ribozyme expression was demonstrated in plants of the 85-06 and 85-15 lines which contained high stearic acid in their leaves. Northern analysis was performed on the six high stearate plants from each line as well as non-transformed (NT) and transformed control (TC) plants. The probes for this analysis were cDNA fragments from a maize Δ9 desaturase cDNA and a maize actin cDNA. To distinguish variation in Δ9 mRNA levels due to loading or handling errors from true ribozyme mediated RNA reductions, the level of Δ9 mRNA was compared to the level of actin mRNA within that sample. Using densitometer readings described above a ratio was calculated for each sample. Δ9/actin ratio values ranging from 0.55 to 0.88 were calculated for the 85-06 plants. The average Δ9/actin value for non-transformed controls was 2.7. There is an apparent 4 fold reduction in Δ9/actin ratios between 85-06 and NT leaves. Comparing Δ9/actin values between 85-06 high stearate and TC plants, on average a 3 fold reduction in Δ9/actin was observed for the 85-06 plants. This data is graphed in FIG. 26. Ranges in Δ9/actin ratios from 0.35 to 0.53, with an average of 0.43 were calculated for the RPA85-15 high stearate transgenics. In this experiment the average Δ9/actin ratio for the NT plants was 1.7. Comparing the average Δ9/actin ratio between NT controls and 85–15 high stearate plants, a 3.9 fold reduction in 85-15 Δ9 mRNA was demonstrated. An apparent 3 fold reduction in Δ9 mRNA level was observed for RPA85-15 high stearate transgenics when Δ9/actin ratios were compared between 85-15 high stearate and normal stearate (TC) plants. These data are graphed in FIG. 27. These data indicate ribozyme-mediated reduction of Δ9-desaturase mRNA in transgenic plants expressing RPA85 ribozyme, and producing increased levels of stearic acid in the leaves.

Example 29

Figure 28:
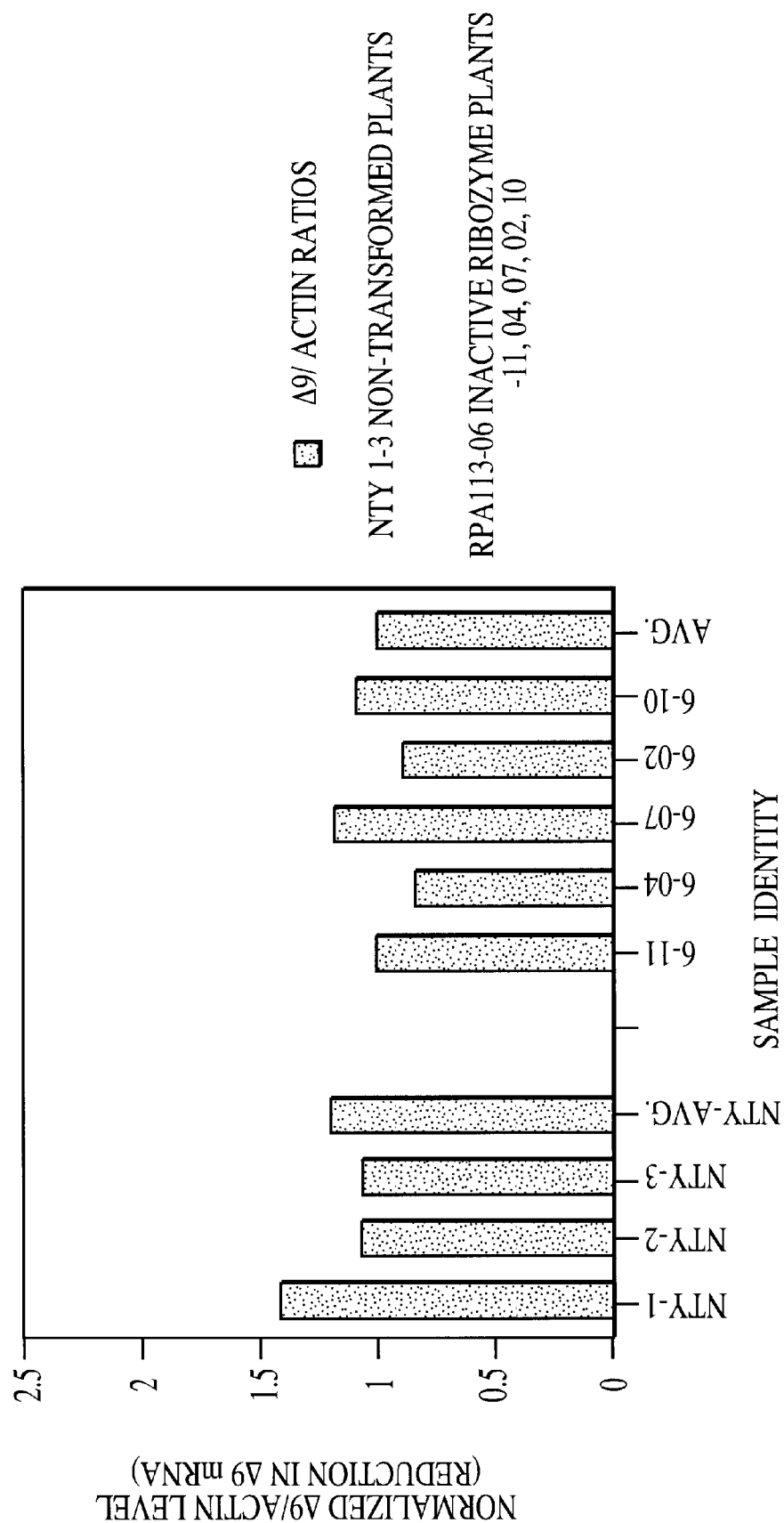
FIG. 28 illustrates Δ9 desaturase mRNA levels in Non-transformed plants (NTY), 113-06 Inactive Ribozyme Plants (02, 04, 07, 10, 11).

Evidence of Δ9 Desaturase Down Regulation in Maize Leaves as a Result of Active Ribozyme Activity Plants were produced which were transformed with inactive versions of the Δ9 desaturase ribozyme genes. Data was presented demonstrating control levels of leaf stearate in the inactive Δ9 ribozyme transgenic lines RPA113-06 and 113-17. Ribozyme expression and northern analysis was performed for the RPA113-06 line. Δ9 desaturase protein levels were determined in plants of the RPA113-17 line. Ribozyme expression was measured as described herein. Plants 113-06-04, -07, and -10 expressed detectable levels of RPA 113 inactive Δ9 ribozyme. Northern analysis was performed on 5 plants of the 113-06 line with leaf stearate ranging from 1.8–3.9%, all of which fall within the range of controls. No reduction in Δ9 desaturase mRNA correlating with ribozyme expression or elevations in leaf stearate were found in the RPA113-06 plants as compared to controls, graphed in FIG. 28. Protein analysis did not indicate any reduction in Δ9 desaturase protein levels correlating with elevated leaf stearate in the RPA113-17 plants. This data is graphed in FIG. 29(a). Taken together, the data from the two RPA113 inactive transgenic lines indicate ribozyme activity is responsible for the high strearate phenotype observed in the RPA85 lines. The RPA85 ribozyme is the active version of the RPA113 ribozyme.

Example 30

Demonstration of Ribozyme Mediated Reduction in Stearoyl-ACP Δ9 Desaturase Levels in Maize Leaves (RO) Δ9 Desaturase Levels in Maize Leaves (R0)

Part A Partial purification of stearoyl-ACP Δ9-desaturase from maize leaves. All procedures were performed at 4° C. unless stated otherwise. Maize leaves (50 mg) were harvested and ground to a fine powder in liquid $N_2$ with a mortar and pestle. Proteins were extracted in one equal volume of Buffer A consisting of 25 mM sodium-phosphate pH 6.5, 1 mM ethylenediaminetetraacetic acid, 2 mM dithiothreitol, 10 mM phenylmethylsulfonyl fluoride, 5 mM leupeptin, and 5 mM antipapin. The crude homogenate was centrifuged for 5 minutes at 10,000×g. The supernatant was assayed for total protein concentration by Bio-Rad protein assay kit (Bio-Rad Laboratories, Hercules, Calif.). One hundred micrograms of total protein was brought up to a final volume of 500 μl in Buffer A, added to 50 μl of mixed SP-sepharose beads (Pharmacia Biotech Inc., Piscataway, N.J.), and resuspended by vortexing briefly. Proteins were allowed to bind to sepharose. beads for 10 minutes while on ice. After binding, the Δ9 desaturase-sepharose material was centrifuged (10,000×g) for 10 seconds, decanted, washed three times with Buffer A (500 μl), and washed one time with 200 mM sodium chloride (500 μl). Proteins were eluted by boiling in 50 μl of Treatment buffer (125 mM Tris-Cl pH 6.8, 4% sodium dodecyl sulfate, 20% glycerol, and 10% 2-mercaptoethanol) for 5 mintues. Samples were centrifuged (10,000 ×g) for 5 minutes. The supernatant was saved for Western anaylsis and the pellet consisting of sepharose beads was discarded.

Part B Western analysis method which was used to demonstrate reductions in stearoyl-ACP Δ9 desaturase. Partially purified proteins were separated on sodium dodecyl sulfate (SDS)-polyacrylamide gels (10% PAGE) as described by Laemmli, U.K. (1970) Cleavage of structural proteins during assembly of the head of phage T4, *Nature* 227, 660–685. To distinguish variation in Δ9 desaturase levels, included on each blot as a reference was purified and quantified overexpressed Δ9 desaturase from *E. coli* as described hereforth. Proteins were electrophoretically transferred to ECL™ nitrocellulose membranes (Amersham Life Sciences, Arlington Heights, Ill.) using a Phannacia Semi-Dry Blotter (Pharmacia Biotech Inc., Piscataway, N.J.), using Towbin buffer (Towbin et al. 1979). The nonspecific binding sites were blocked with 10% dry milk in phosphate buffer saline for 1 h. Immunoreactive polypeptides were detected using the ECL™ Western Blotting Detection Reagent (Amersham Life Sciences, Arlington Heights, Ill.) with rabbit antiserum raised against *E. coli* expressed maize Δ9 desaturase. The antibody was produced according to standard protocols by Berkeley Antibody Co. The secondary antibody was goat antirabbit serum conjugated to horseradish peroxidase (BioRad). Autoradiograms were scanned with a densitometer and quantified based on the relative amount of purified *E. coli* Δ9 desaturase. These experiments were duplicated and the mean reduction was recorded.

Figure 29B:
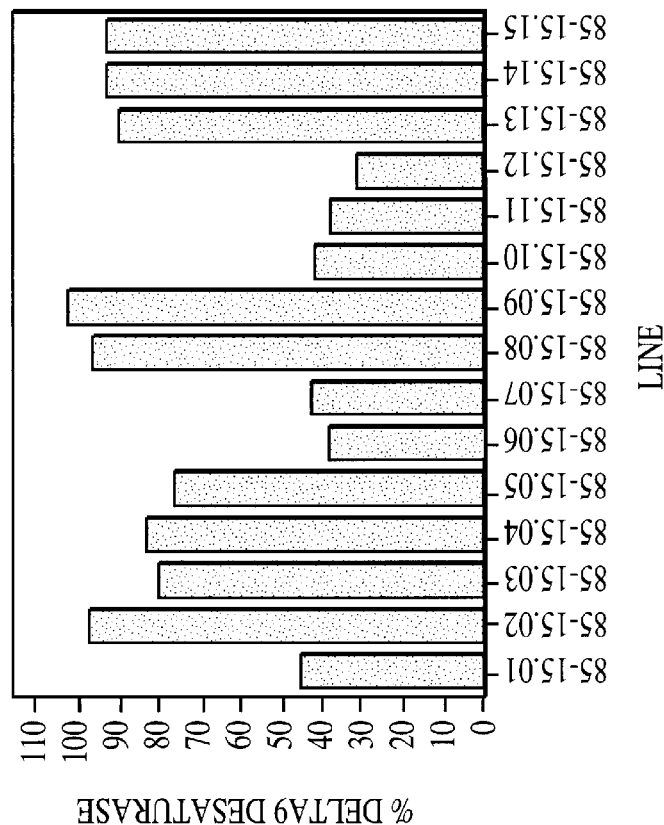
FIGS. 29a and 29b illustrate Δ9 desaturase protein levels in maize leaves (R0). (a) Line HiII, plants a-e nontransformed and ribozyme inactive line RPA113-17, plants 1–6. (b) Ribozyme active line RPA85-5, plants 1–15.
Figure 29A:
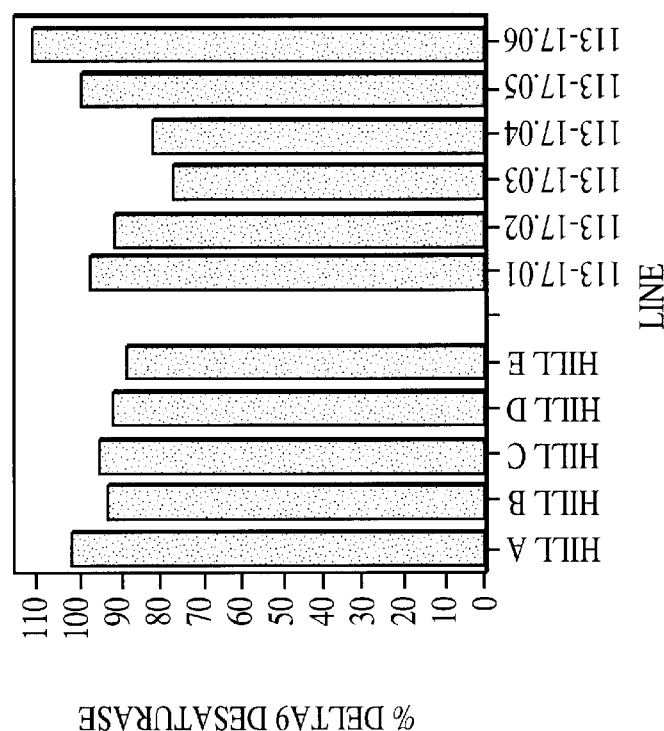

Part C Demonstration of Reductions in Δ9 desaturase levels in R0 maize leaves expressing ribozymes targeted to Δ9 desaturase mRNA. The high stearate transgenic line, RPA85-15, contains an intact copy of the fused multimer gene. Δ9 desaturase was partially purified from R0 maize leaves, using the protocol described herein. Western analysis was performed on ribozyme active (RPA85-15) and ribozyme inactive (RPA113-17) plants and nontransformed (HiII) plants as described above in part B. The natural variation of Δ9 desaturase was determined for the nontransformed line (HiII) by Western analysis see FIG. 29A. No reduction in Δ9 desaturase was observed with the ribozyme inactive line RPA113-17, all of which fell within the range as compared to the nontransformed line (HiII). An apparent 50% reduction of Δ9 desaturase was observed in six plants of line RPA85-15 (FIG. 29B) as compared with the controls. Concurrent with this, these same six plants also had increased stearate and reduced Δ9 desaturase mRNA (As described in Examples 28 and 32). However, nine active ribozyme plants from line RPA85-15 did not have any significant reduction as compared with nontransformed line (HiII) and inactive ribozyme line (RPA113-17) (FIGS. 29A and B). Collectively, these results suggest that the ribozyme activity in the six plants from line RPA85-15 is responsible for the reduced Δ9 desaturase.

Example 31

*E. coli* Expression and Purification of Maize Δ-9 Desaturase Enzyme

Part A The mature protein encoding portion of the maize Δ-9 desaturase cDNA was inserted into the bacterial T7 expression vector pET9D (Novagen Inc., Madison, Wis.). The mature protein encoding region was deduced from the mature castor bean polypeptide sequence. The alanine at position 32 (nts 239–241 of cDNA) was designated as the first residue. This is found within the sequence Ala.Val.Ala.Ser.Met.Thr. Restriction endonuclease Nhe I site was engineered into the maize sequence by PCR, modifying GCCTCC to GCTAGC and a BamHI site was added at the 3' end. This does not change the amino acid sequence of the protein. The cDNA sequence was cloned into pET9d vector using the Nhe I and Bam HI sites. The recombinant plasmid is designated as pDAB428. The maize Δ-9 desaturase protein expressed in bacteria has an additional methionine residue at the 5' end. This pDAB428 plasmid was transformed into the bacterial strain BL21 (Novagen, Inc., Madison, Wis.) and plated on LB/kanamycin plates (25 mg/ml). Colonies were resuspended in 10 ml LB with kanamycin (25 mg/ml) and IPTG (1 mM) and were grown in a shaker for 3 hours at 37° C. The cells were harvested by centrifugation at 1000×g at 4° C. for 10 minutes. The cells were lysed by freezing and thawing the cell pellet 2×, followed by the addition of 1 ml lysis buffer (10 mM Tris-HCl pH 8.0, 1 mM EDTA, 150 mM NaCl, 0.1% Triton X100, 100 ug/ml DNAse I, 100 ug/ml RNAse A, and 1 mg/ml lysozyme). The mixture was incubated for 15 minutes at 37° C. and then centrifuged at 1000×g for 10 minutes at 4° C. The supernatant is used as the soluble protein fraction.

The supernatant, adjusted to 25 mM sodium phosphate buffer (pH 6.0), was chilled on ice for 1 hr. Afterwards, the resulting flocculant precipitant was removed by centrifugation. The ice incubation step was repeated twice more after which the solution remained clear. The clarified solution was loaded onto a Mono S HR 10/10 column (Pharmacia) that had been equilibrated in 25 mM sodium phosphate buffer (pH 6.0). Basic proteins bound to the column matrix were eluted using a 0–500 mM NaCl gradient over 1 hr (2 ml/min; 2 ml fractions). The putative protein of interest was subjected to SDS-PAGE, blotted onto PVDF membrane, visualized with coomassie blue, excised, and sent to Harvard Microchem for amino-terminal sequence analysis. Comparison of the protein's amino terminal sequence to that encoded by the cDNA clone revealed that the protein was indeed Δ9. Spectrophotometric analysis of the diiron-oxo component associated with the expressed protein (Fox et al., 1993 *Proc. Natl. Acad. Sci. USA*. 90, 2486–2490), as well as identification using a specific nonheme iron stain (Leong et al., 1992 *Anal. Biochem.* 207, 317–320) confirmed that the purified protein was Δ-9.

Part B Production of polyclonal antiserum

The *E. coli* produced Δ-9 protein, as determined by amino terminal sequencing, was gel purified via SDS-PAGE, excised, and sent in the gel matrix to Berkeley Antibody Co., Richmond, Calif., for production of polyclonal sera in rabbits. Titers of the antibodies against Δ-9 were performed via western analysis using the ECL Detection system (Amersham, Inc.)

Part C Purification of Δ9 desaturase from corn kernels

Protein Precipitation: Δ9 was purified from corn kernels following homogenization using a Warring blender in 25 mM sodium phosphate buffer (pH 7.0) containing 25 mM sodium bisulfite and a 2.5% polyvinylpolypyrrolidone. The crude homogenate was filtered through cheesecloth, centrifuged (10,000×g) for 0.25 h and the resulting supernatant was filtered once more through cheesecloth. In some cases, the supernatant was fractionated via saturated ammonium sulfate precipitation by precipitation at 20% v/v followed by 80% v/v. Extracts obtained from high oil germplasm were fractionated by adding a 50% polyethylene glycol solution (mw=8000) at final concentrations of 5- and 25% v/v. In all cases, the Δ9 protein precipitated at either 80% ammonium sulfate or 25% polyethylene glycol. The resulting pellets were then dialyzed extensively in 25 mM sodium phosphate buffer (pH 6.0).

Cation Exchange Chromatography: The solubilized pellet material described above was clarified via centrifugation and applied to Mono S HR10/10 column equilibrated in 25 mM sodium phosphate buffer (pH 6.0). After extensive column washing, basic proteins bound to the column matrix were eluted using a 0–500 mM NaCl gradient over 1 hr (2 ml/min: 2 ml fractions). Typically, the Δ9 protein eluted between 260- and 350 mM NaCl., as determined by enzymatic and western analysis. After dialysis, this material was further fracionated by acyl carrier protein (ACP)-sepharose and phenyl superose chromatography.

Acyl Carrier Protein-Sepharose Chromatography: ACP was purchased from Sigma Chemical Company and purified via precipitation at pH 4.1 (Rock and Cronan, 1981 *J. Biol. Chem.* 254, 7116–7122) before linkage to the beads. ACP-sepharose was prepared by covalently binding 100 mg of ACP to cyanogen bromide activated sepharose 4B beads, essentially as described by Pharmacia, Inc., in the package insert. After linkage and blocking of the remaining sites with glycine, the ACP-sepharose material was packed into a HR 5/5 column (Pharmacia, Inc.) and equilibrated in 25 mM sodium phosphate buffer (pH 7.0). The dialyzed fractions identified above were then loaded onto the column (McKeon and Stumpf, 1982 *J. Biol. Chem.* 257, 12141–12147; Thompson et al., 1991, *Proc. Natl. Acad. Sci. USA* 88, 2578–2582). After extensive column washing, ACP-binding proteins were eluted using 1 M NaCl. Enzymatic and western analysis, followed by amino terminal sequencing, indicated that the eluent contained Δ-9 protein. The Δ-9 protein purified from corn was determined to have a molecular size of approximately 38 kDa by SDS-PAGE analysis (Hames, 1981 in Gel Electrophoresis of Proteins: A Practical Approach, eds Hames B D and Rickwood, D., IRL Press, Oxford).

Phenyl Sepharose Chromatography: The fractions containing Δ9 obtained from the ACP-Sepharose column were adjusted to 0.4 M ammonium sulfate (25 mM sodium phosphate, pH 7.0) and loaded onto a Pharmacia Phenyl Superose column (HR 10/10). Proteins were eluted by running a gradient (0.4–0.0 M ammonium sulfate) at 2 ml/min for 1 hour. The Δ9 protein typically eluted between 60- and 30 mM ammonium sulfate as determined by enzymatic and western analysis.

Example 32

Evidence for the Increase in Stearic Acid in Leaves as a Result of Transformation of Plants with Δ9 Desaturase Ribozymes Part A Method used to determine the stearic acid levels in plant tissues. The procedure for extraction and esterification of fatty acids from plant tissue was modified from a described procedure (Browse et. al., 1986, Anal. Biochem. 152, 141–145). One to 20 mg of plant tissue was placed in Pyrex 13 mm screw top test tubes. After addition of 1 ml of methanolic HCL (Supelco, Bellefonte, Pa.), the tubes were purged with nitrogen gas and sealed. The tubes were heated at 80° C. for 1 hour and allowed to cool. The heating in the presence of the methanolic HCL results in the extraction as well as the esterification of the fatty acids. The fatty acid methyl esters were removed from the reaction mixture by extraction with hexane. One ml of hexane and 1 ml of 0.9% (w/v) NaCl was added followed by vigorous shaking of the test tubes. After centrifugation of the tubes at 2000 rpm for 5 minutes the top hexane layer was removed and used for fatty acid methyl ester analysis. Gas chromatograph analysis was performed by injection of 1 μl of the sample on a Hewlett Packard (Wilmington, Del.) Series II model 5890 gas chromatograph equipped with a flame ionization detector and a J&W Scientific (Folsom, Calif.) DB-23 column. The oven temperature was 150° C. throughout the run and the flow of the carrier gas (helium) was 80 cm/sec. The run time was 20 minutes. The conditions allowed for the separation of the 5 fatty acid methyl esters of interest: C16:0, palmityl methyl ester; C18:0, stearyl methyl ester; C18:1, oleoyl methyl ester; C18:2, linolcoyl methyl ester; and C18:3, linolenyl methyl ester. Data collection and analysis was performed with a Hewlett Packard Series II Model 3396 integrator and a PE Nelson (Perkin Elmer, Norwalk, Conn.) data collection system. The percentage of each fatty acid in the sample was taken directly from the readouts of the data collection system. Quantitative amounts of each fatty acid were calculated using the peak areas of a standard (Matreya, Pleasant Gap, Pa.) which consisted of a known amount of the five fatty acid methyl esters. The amount calculated was used to estimate the percentage, of total fresh weight, represented by the five fatty acids in the sample. An adjustment was not made for loss of fatty acids during the extraction and esterification procedure. Recovery of the standard sample, after subjecting it to the extraction and esterification procedure (with no tissue present), ranged from 90 to 100% depending on the original amount of the sample. The presence of plant tissue in the extraction mixture had no effect on the recovery of the known amount of standard.

Figure 30:
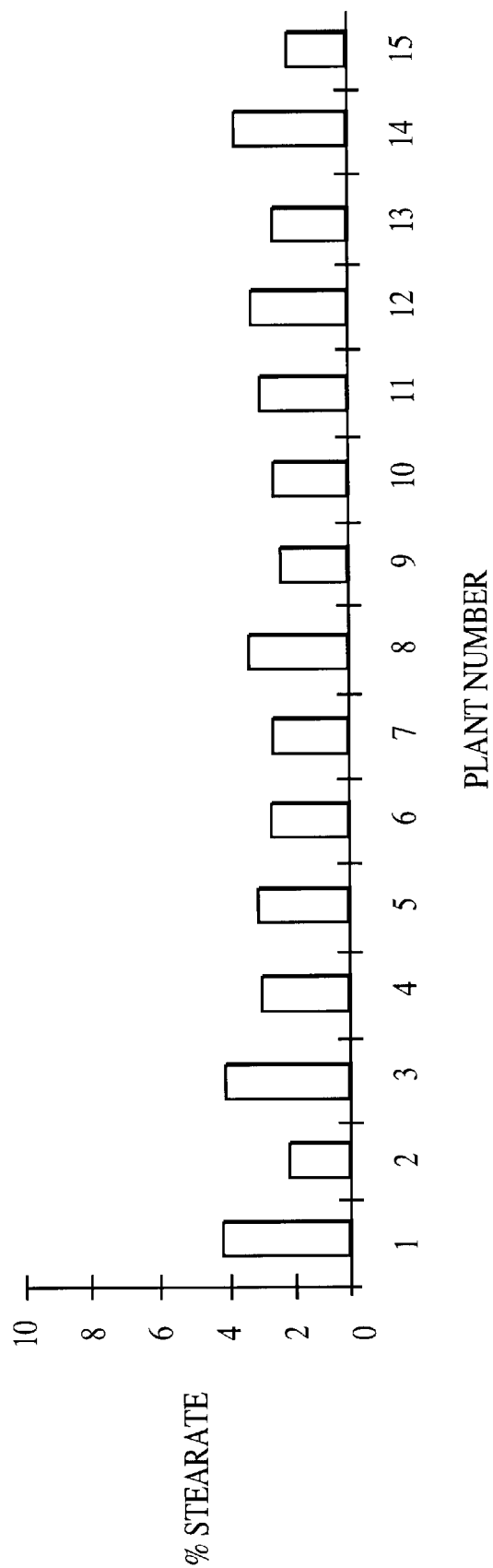
FIG. 30 illustrates stearic acid in leaves of RPA85-06 plants.
Figure 31:
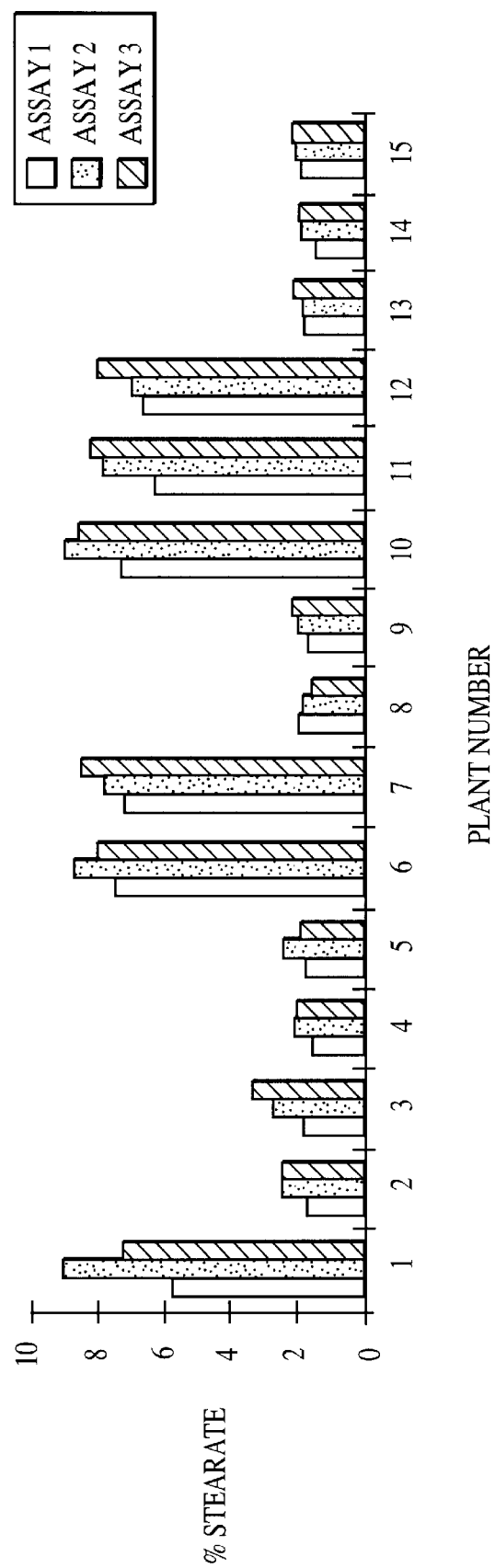
FIG. 31 illustrates stearic acid in leaves of RPA85-15 plants, results of three assays.
Figure 32:
FIG. 32 illustrates stearic acid in leaves of RPA113-06 plants.
Figure 33:
FIG. 33 illustrates stearic acid in leaves of RPA113-17 plants.
Figure 34:
FIG. 34 illustrates stearic acid in leaves of control plants.

Part B Demonstration of an increase in stearic acid in leaves due to introduction of Δ9 desaturase ribozymes. Leaf tissue from individual plants was assayed for stearic acid as described in Part A. A total of 428 plants were assayed from 35 lines transfonned with active Δ9 desaturase ribozymes (RPA85, RPA114, RPA118) and 406 plants from 31 lines transformed with Δ9 desaturase inactive ribozymes (RPA113, RPA115, RPA119). Table XI summarizes the results obtained for stearic acid levels in these plants. Seven percent of the plants from the active lines had stearic acid levels greater than 3%, and 2% had levels greater than 5%. Only 3% of the plants from the inactive lines had stearic acid levels greater than 3%. Two percent of the control plants had leaves with stearate greater than 3%. The controls included 49 non-transformed plants and 73 plants transformed with a gene not related to Δ9 desaturase. There were no plants from the inactive lines or controls that had leaf stearate greater than 4%. Two of the lines transformed with the active Δ9 desaturase ribozyme RPA85 produced many plants which exhibited increased stearate in their leaves. Line RPA85-06 had 6 out of the 15 plants assayed with stearic acid levels which were between 3 and 4%, about 2-fold greater than the average of the controls (FIG. 30) The average stearic acid content of the control plants (122 plants) as 1.69% (SD+/−0.49%). The average stearic acid content of leaves from line RPA85-06 as 2.86% (+/−0.57%). Line RPA85-15 had 6 out of 15 plants assayed with stearic acid levels which were approximately 4-fold greater than the average of the controls (FIG. 31). The average leaf stearic acid content of line RPA85-15 was 3.83% (+/−2.53%). When the leaf analysis was repeated for RPA85-15 plants, the stearic acid level in leaves from plants previously shown to have normal stearic acid levels remained normal and leaves from plants with high stearic acid were again found to be high (FIG. 31). The stearic acid levels in leaves of plants from two lines which were transformed with an inactive Δ9 desaturase ribozyme, RPA113, is shown in FIGS. 32 and 33. RPA113-06 had three plants with a stearic acid content of 3% or higher. The average stearic acid content of leaves from line RPA113-06 was 2.26% (+/−0.65%). RPA113-17 had no plants with leaf stearic acid content greater than 3%. The average stearic acid content of leaves from line RPA113-17 was 1.76% (+/−0.29%). The stearic acid content of leaves from 15 control plants is shown in FIG. 34. The average stearic acid content for these 15 control plants was 1.70% (+/−0.6%). When compared to the control and inactive Δ9 desaturase ribozyme data, the results obtained for stearic acid content in RPA85-06 and RPA85-15 demonstrate an increase in stearic acid content due to the introduction of the Δ9 desaturase ribozyme.

Example 33

Inheritance of the High Stearic Acid Trait in Leaves

Figure 35:
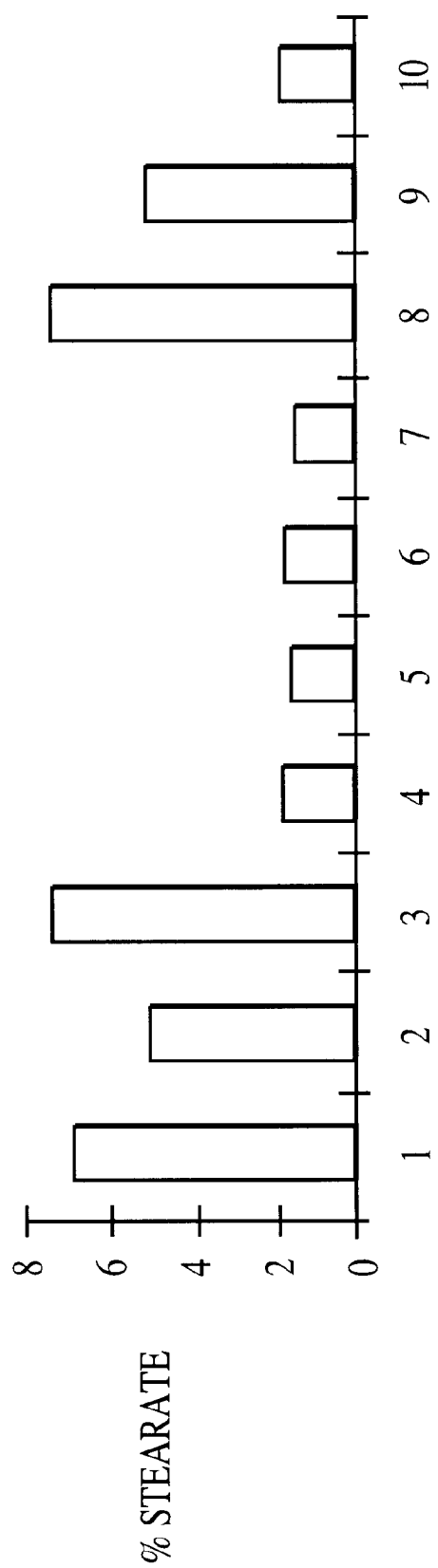
FIG. 35 illustrates leaf stearate in R1 plants from a high stearate plant cross (RPA85-15.07 self).

Part A Results obtained with stearic acid levels in leaves from offspring of high stearic acid plants. Plants from line RPA85-15 were pollinated as described herein. Twenty days after pollination zygotic embryos were excised from immature kernels from these RPA85-15 plants and placed in a tube on media as described herein for growth of regenerated plantlets. After the plants were transferred to the greenhouse, fatty acid analysis was performed on the leaf tissue. FIG. 35 shows the stearic acid levels of leaves from 10 different plants for one of the crosses, RPA85-15.07 selfed. Fifty percent of the plants had high leaf stearic acid and 50% had normal leaf stearic acid. Table XII shows the results from 5 different crosses of RPA85-15 plants. The number of plants with high stearic acid ranged from 20 to 50%.

Figure 36:
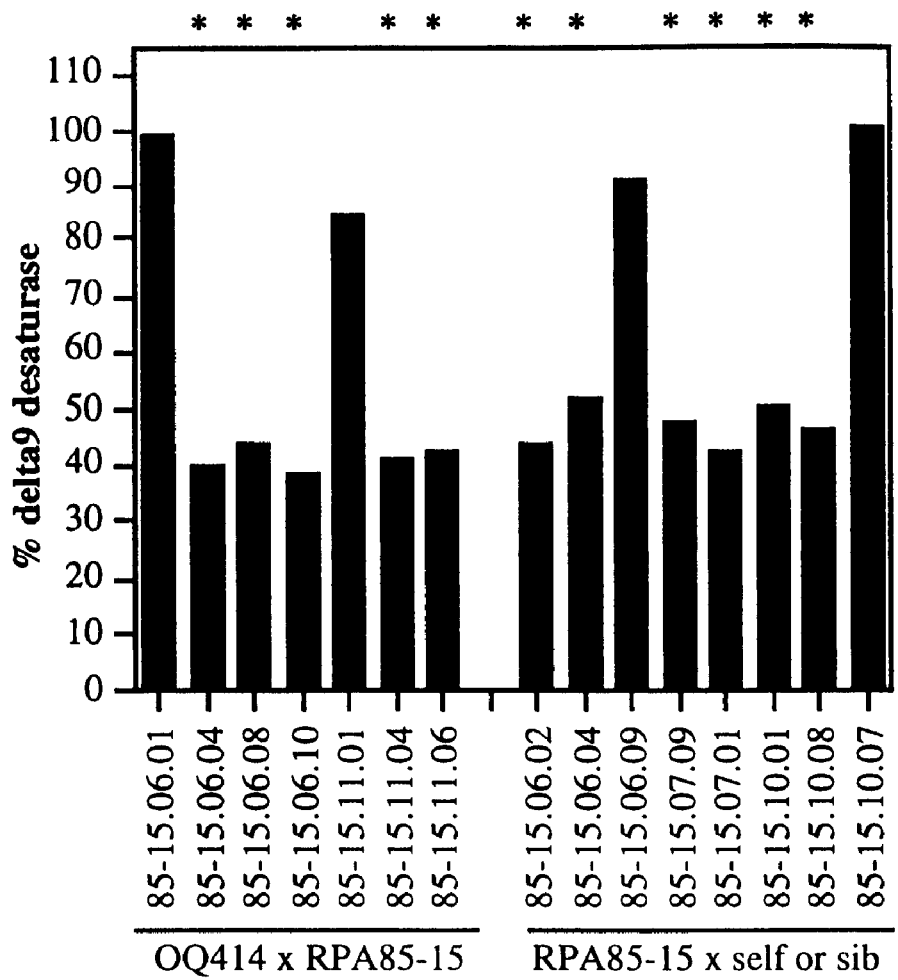
FIG. 36 illustrates Δ9 desaturase levels in next generation maize leaves (R1). * indicates those plants that showed a high stearate content.

Part B Results demonstrating reductions in Δ9 desaturase levels in next generation (R1) maize leaves expressing ribozymes targeted to Δ9 desaturase mRNA. In next generation maize plants that showed a high stearate content (see above Part A), Δ9 desaturase was partially purified from R1 maize leaves, using the protocol described herein. Western analysis was performed on several of the high stearate plants. In leaves of next generation plants, a 40–50% reduction of Δ9 desaturase was observed in those plants that had high stearate content (FIG. 36). The reduction was comparable to R0 maize leaves. This reduction was observed in either OQ414 plants crossed with RPA85-15 pollen or RPA85-15 plants crossed with self or siblings. Therefore, this suggests that the gene encoding the ribozyme is heritable.

Example 34

Increase in Stearic Acid in Plant Tissues Using Antisense-Δ9 Desaturase

Part A Method for culturing somatic embryos of maize. The production and regeneration of maize embryogenic callus has been described herein. Somatic embryos make up a large part of this embryogenic callus. The somatic embryos continued to form in callus because the callus was transferred every two weeks. The somatic embryos in embryogenic callus continued to proliferate but usually remained in an early stage of embryo development because of the 2,4-D in the culture medium. The somatic embryos regenerated into plantlets because the callus was subjected to a regeneration procedure described herein. During regeneration the somatic embryo formed a root and a shoot, and ceases development as an embryo. Somatic embryos were made to develop as seed embryos, i.e., beyond the early stage of development found in embryogenic callus and no regeneration, by a specific medium treatment. This medium treatment involved transfer of the embryogenic callus to a Murashige and Skoog medium (MS; described by Murashige and Skoog in 1962) which contains 6% (w/v) sucrose and no plant hormones. The callus was grown on the MS medium with 6% sucrose for 7 days and then the somatic embryos were individually transferred to MS medium with 6% sucrose and 10 μM abscisic acid (ABA). The somatic embryos were assayed for fatty acid composition as described herein after 3 to 7 days of growth on the ABA medium. The fatty acid composition of somatic embryos grown on the above media was compared to the fatty acid composition of embryogenic callus and maize zygotic embryos 12 days after pollination (Table XIII). The fatty acid composition of the somatic embryos was different than that of the embryogenic callus. The embryogenic callus had a higher percentage of C16:0 and C18:3, and a lower percentage of C18:1 and C18:2. The percentage of lipid represented by the fresh weight was different for the embryogenic callus when compared to the somatic embryos; 0.4% versus 4.0%. The fatty acid composition of the zygotic embryos and somatic embryos were very similar and their percentage of lipid represented by the fresh weight were nearly identical. It was concluded that the somatic embryo culture system described above would be an useful in vitro system for testing the effect of certain genes on lipid synthesis in developing embryos of maize.

Figure 37:
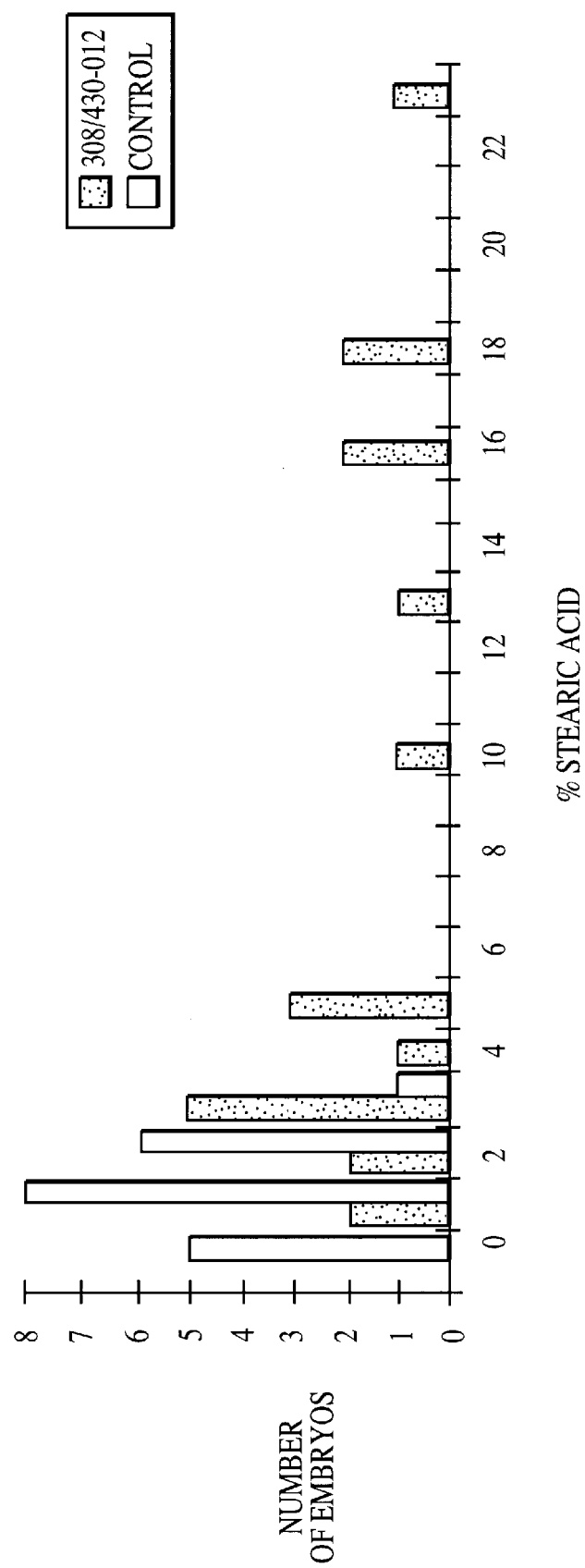
FIG. 37 illustrates stearic acid in individual somatic embryos from a culture (308/430-012) transformed with antisense Δ9 desaturase.
Figure 38:
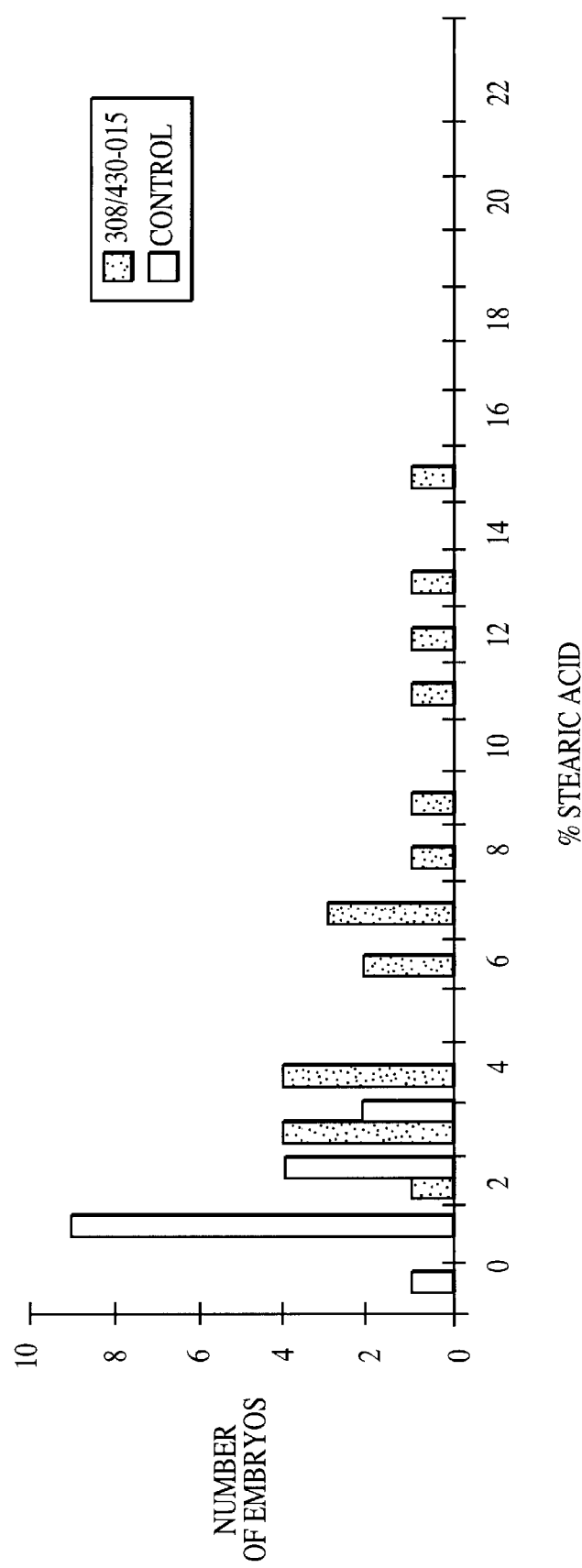
FIG. 38 illustrates stearic acid in individual somatic embryos from a culture (308/430-015) transformed with antisense Δ9 desaturase.

Part B Increase in stearic acid in somatic embryos of maize as a result of the introduction of an antisense-Δ9 desaturase gene. Somatic embryos were produced using the method described herein from embryogenic callus transformed with pDAB308/pDAB430. The somatic embryos from 16 different lines were assayed for fatty acid composition. Two lines, 308/430-12 and 308/430-15, were found to produce somatic embryos with high levels of stearic acid. The stearic acid content of somatic embryos from these two lines is compared to the stearic acid content of somatic embryos from their control lines in FIGS. 37 and 38. The control lines were from the same culture that the transformed lines came from except that they were not transformed. For line 308/430-12, stearic acid in somatic embryos ranged from 1 to 23% while the controls ranged from 0.5 to 3%. For line 308/430-15, stearic acid in somatic embryos ranged from 2 to 15% while the controls ranged from 0.5 to 3%. More than 50% of the somatic embryos had stearic acid levels which were above the range of the controls in both the transformed lines. The above results indicate that an antisense-Δ9 desaturase gene can be used to raise the stearic acid levels in somatic embryos of maize.

Figure 39:
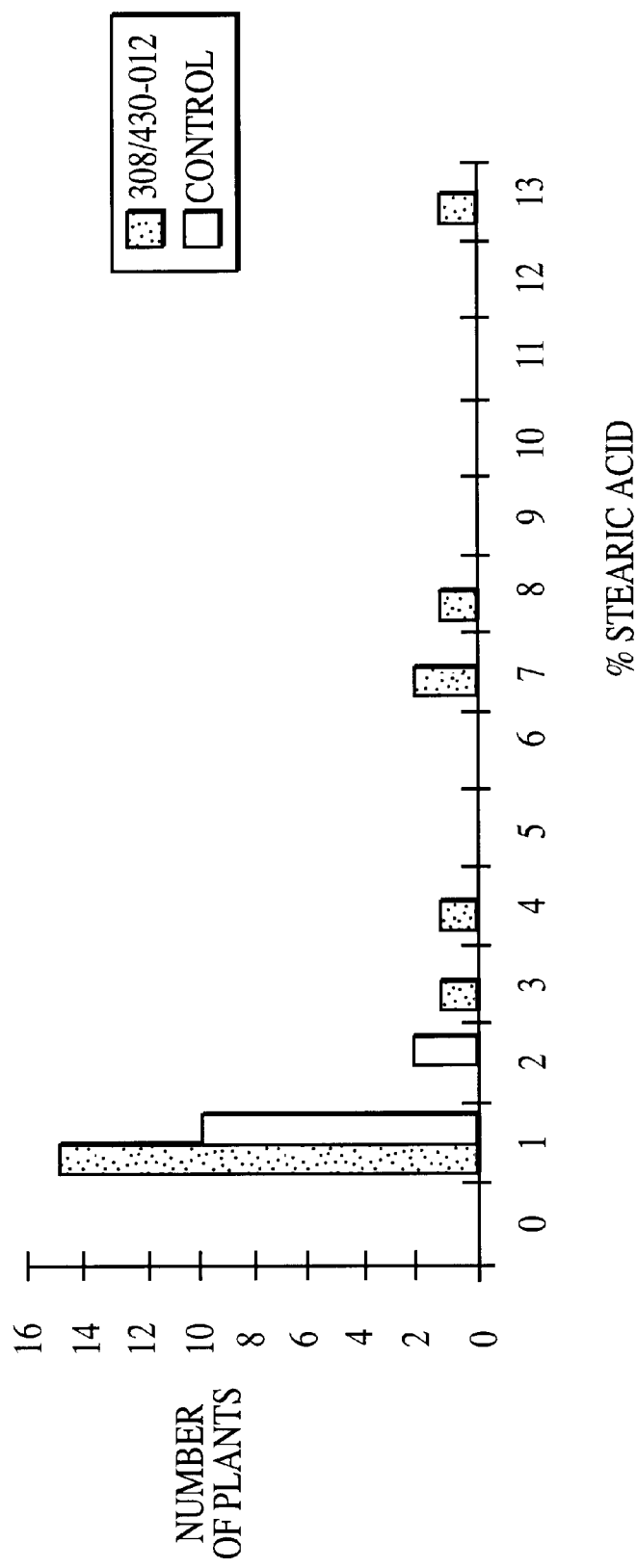
FIG. 39 illustrates stearic acid in individual leaves from plants regenerated from a culture (308/430-012) transformed with antisense Δ9 desaturase.

Part C Demonstration of an increase in stearic acid in leaves due to introduction of an antisense-Δ9 desaturase gene. Embryogenic cultures from lines 308/430-12 and 308/430-15 were used to regenerate plants. Leaves from these plants were analyzed for fatty acid composition using the method previously described. Only 4 plants were obtained from the 308/430-15 culture and the stearic acid level in the leaves of these plants were normal, 1–2%. The stearic acid levels in leaves from plants of line 308/430-12 are shown in FIG. 39. The stearic acid levels in leaves ranged from 1 to 13% in plants from line 308/430-12. About 30% of the plants from line 308/430-12 had stearic acid levels above the range observed in the controls, 1–2%. These results indicate that the stearic acid levels can be raised in leaves of maize by introduction of an antisense-Δ9 desaturase gene.

By "antisense" is meant a non-enzymatic nucleic acid molecule that binds to a RNA (target RNA) by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

Example 35

Amylose Content Assay of Maize Pooled Starch Sample and Single Kernel

The amylose content was assayed by the method of Hovenkamp-Hermelink et al. (Potato Research 31:241–246) with modifications. For pooled starch sample, 10 mg to 100 mg starch was dissolved in 5 ml 45% perchloric acid in plastic culture tube. The solution was mixed occasionally by vortexing. After one hour, 0.2 ml of the starch solution was diluted to 10 ml by $H_2O$. 0.4 ml of the diluted solution was then mixed with 0.5 ml diluted Lugol's solution (Sigma) in 1 ml cuvet. Readings at 618 nm and 550 nm were immediately taken and the R ratio (618 nm/550 nm) was calculated. Using standard equation P (percentage of amylose)= (4.5R-2.6)/(7.3-3R) generated from potato amylose and maize amylopectin (Sigma, St. Louis), ainylose content was determined. For frozen single kernel sample, same procedure as above was used except it was extracted in 45% perchloric acid for 20 min instead for one hour.

Example 36

Starch Purification and Granular Bound Starch Synthase (GBSS) Assay

The purification of starch and following GBSS activity assay were modified from the methods of Shure et al. (Cell, 35:225–233, 1983) and Nelson et al. (Plant Physiology, 62:383–386, 1978). Maize kernel was homogenized in 2 volume (v/w) of 50 mM Tris-HCl, pH 8.0, 10 mM EDTA and filtrated through 120 μm nylon membrane. The material was then centrifuged at 5000 g for 2 min and the supernatant was discarded. The pellet was washed three times by resuspending in water and removing supernatant by centrifugation. After washing, the starch was filtrated through 20 μm nylon membrane and centrifuged. Pellet was then lyophilized and stored in −20° C. until used for activity assay.

A standard GBSS reaction mixture contained 0.2 M Tricine, pH 8.5, 25 mM Glutathione, 5 mM EDTA, 1 mM $^{14}C$ ADPG (6 nci/μmol), and 10 mg starch in a total volume of 200 μl. Reactions were conducted at 37° C. for 5 min and terminated by adding 200 μl of 70% ethanol (v/v) in 0.1 M KCl. The material was centrifuged and unincorporated ADPG in the supernatant is removed. The pellet was then washed four time with 1 ml water each in the same fashion. After washing, pellet was suspended in 500 μl water, placed into scintillation vial, and the incorporated ADPG was counted by a Beckman (Fullerton, Calif.) scintillation counter. Specific activity was given as pmoles of ADPG incorporated into starch per min per mg starch.

Example 37

Analysis of Antisense-GBSS Plants

Because of the segregation of R2 seeds, single kernels should therefore be analyzed for amylose content to identify phenotype. Because of the large amount of samples generated in this study, a two-step screening strategy was used. In the first step, 30 kernels were taken randomly from the same ear, freeze-dried and homogenized into starch flour. Amylose assays on the starch flours were carried out. Lines with reduced amylose content were identified by statistical analysis. In the second step, amylose content of the single kernels in the lines with reduced amylose content was further analyzed (25 to 50 kernels per ear). Two sets of controls were used in the screening, one of the sets were untransformed lines with the same genetic background and the other were transformed lines which did not carry transgene due to segregation (Southern analysis negative line).

Figure 40:
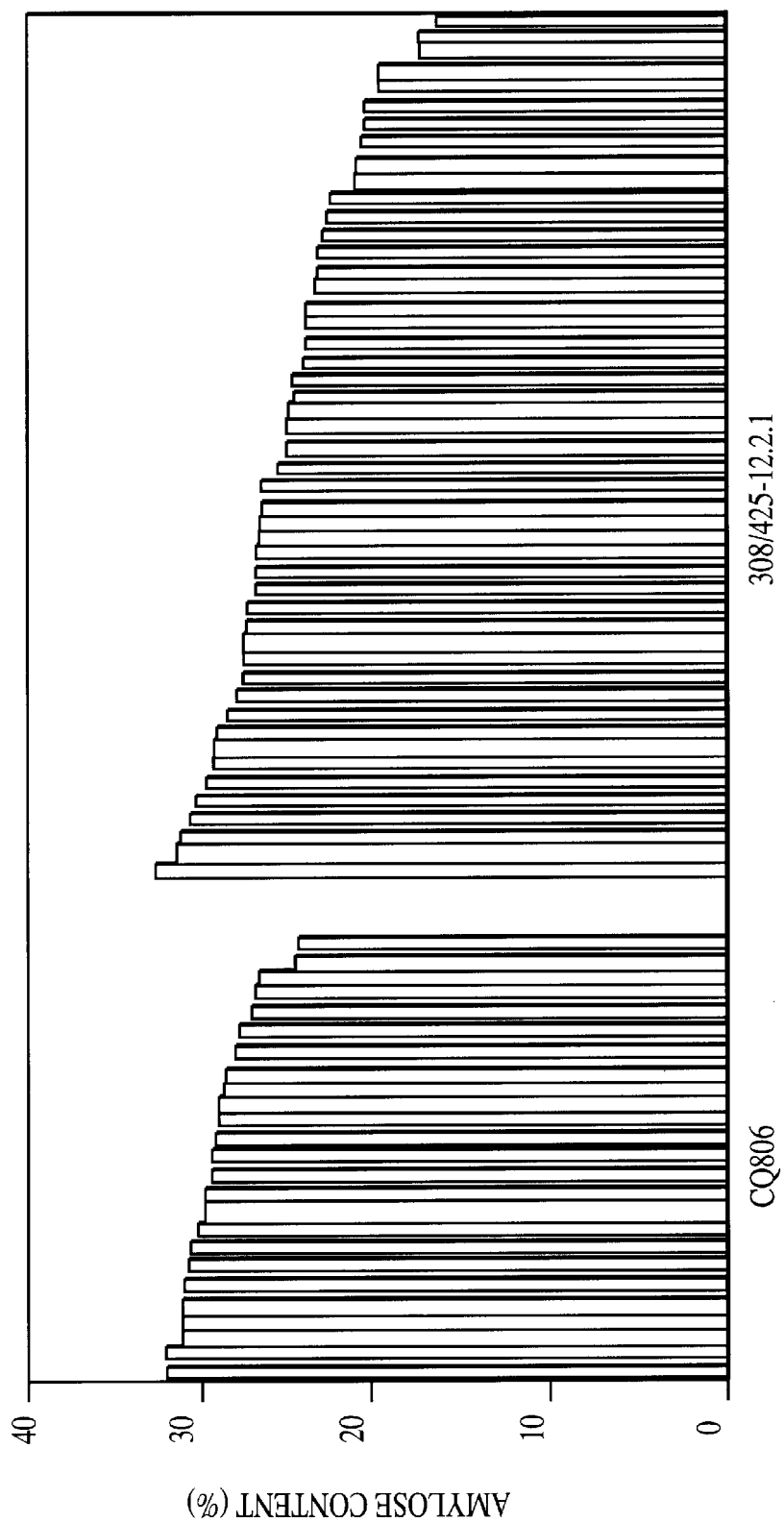
FIG. 40 illustrates amylose content in a single kernel of untransformed control line (Q806 and antisense line 308/425-12.2.1.

81 lines representing 16 transformation events were examined at the pooled starch level. Among those lines, six with significant reduction of amylose content by statistical analysis were identified for further single kernel analysis. One line, 308/425-12.2.1, showed significant reduction of amylose content (FIG. 40).

Twenty five individual kernels of CQ806, a conventional maize inbred line, were analyzed. The amylose content of CQ806 ranged from 24.4% to 32.2%, averaging 29.1%. The single kernel distribution of amylose content is skewed slightly towards lower amylose contents. Forty nine single kernels of 308/425-12.2.1.1 were analyzed. Given that 308/425-12.2.1.1 resulted from self pollination of a hemizygous individual, the expected distribution would consist of 4 distinct genetic classes present in equal frequencies since endosperm is a triploid tissue. The 4 genetic classes consist of individuals carrying 0, 1, 2, and 3 copies of the antisense construct. If there is a large dosage effect for the transgene, then the distribution of amylose contents would be tetramodal. One of the modes of the resulting distribution should be indistinguishable from the non-transgenic parent. If there is no dosage effect for the transgene (individuals carrying 1, 2 or 3 copies of the transgene are phenotypically equivalent), then the distribution should be bimodal with one of the modes identical to the parent. The number of individuals included in the modes should be 3:1 of transgenic:parental. The distribution for 308/425-12.2.1.1 is distinctly trimodal. The central mode is approximately twice the size of either other mode. The two distal modes are of approximately equal size. Goodness of fit to a 1:2:1 ratio was tested and the fit was excellent.

Further evidence was available demonstrating that the mode with the highest amylose content was identical to the non-transgenic parent. This was done using discriminant analysis. The CQ806 and 308/425-12.2.1.1 data sets were combined for this analysis. The distance metrics used in the analysis were calculated using amylose contents only. The estimates of variance from the individual analyses were used in all tests. No pooled estimate of variance was employed. The original data was tested for reclassification. Based on the discriminant analysis, the entire mode of the 308/425-12.2.1.1 distribution with the highest amylose content would be more appropriately classified as parental. This is strong confirmation that this mode of the distribution is parental. Of the remaining two modes, the central mode is approximately twice the size of the lowest amylose content mode. This would be expected if the central mode includes two genetic classes: individuals with 1 or 2 copies of the antisense construct. The mode with the lowest amylose content thus represents those individuals which are fully homozygous (3 copies) for the antisense construct. The 2:1 ratio was tested and could not be rejected on the basis of the data.

This analysis indicates that the antisense GBSS gene as functioning in 308/425-12.2.1.1 demonstrates a dosage dependent reduction in amylose content of maize kernels.

Example 38

Analysis of Ribozyme-GBSS Plants

The same two-step screening strategy as in the antisense study (Example 37) was used to analyze ribozyme-GBSS plants. 160 lines representing 11 transformation events were examined in the pooled starch level. Among the control lines (both untransformed line and Southern negative line), the amylose content varied from 28% to 19%. No significant reduction was observed among all lines carrying ribozyme gene (Southern positive line). More than 20 selected lines were further analyzed in the single kernel level, no significant amylose reduction as well as segregation pattern were found. It was apparent that ribozyme did not cause any alternation in the phenotypic level.

Transformed lines were further examined by their GBSS activity (as described in Example 36). For each line, 30 kernels were taken from the frozen ear and starch was purified. Table XIV shows the results of 9 plants representing one transformation event of the GBSS activity in the pooled starch samples, amylose content in the pooled starch samples, and Southern analysis results. Three southern negative lines: RPA63.0283, RPA63.0236, and RPA63.0219 were used as control.

The GBSS activities of control lines RPA63.0283, RPA63.0236, and RPA63.0219 were around 300 units/mg starch, In lines RPA63.021 1, RPA63.021 8, RPA63.0209, and RPA63.0210, a reduction of GBSS activity to more than 30% was observed. The correlation of varied GBSS activity to the Southern analysis in this group (from RPA63.0314 to RPA63.0210 of Table XIV) indicated that the reduced GBSS activity was caused by the expression of ribozyme gene incorporated into the maize genome.

Figure 41:
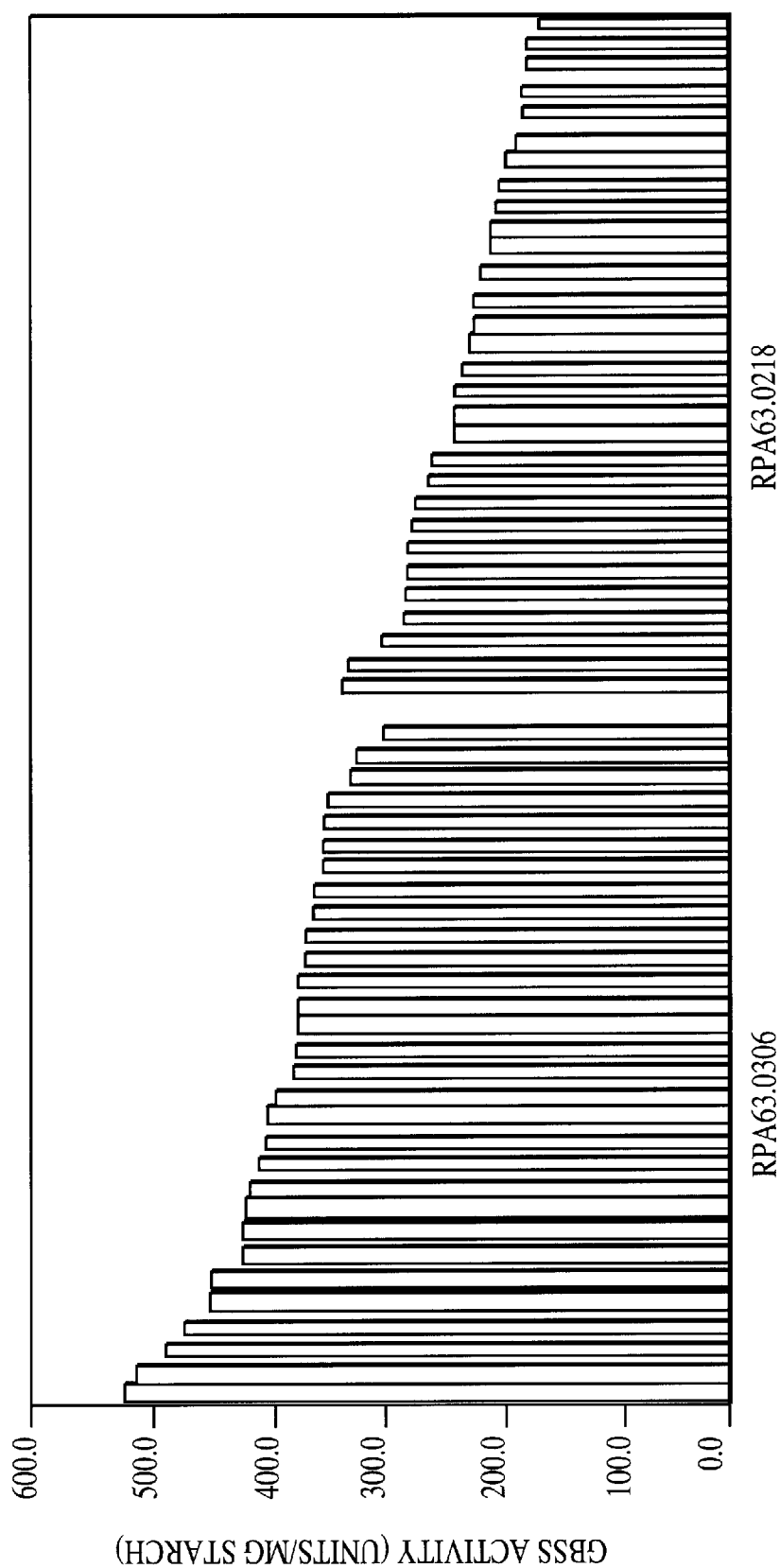
FIG. 41 illustrates GBSS activity in single kernels of a southern negative line (RPA63-0306) and Southern positive line RPA63-0218.
Figure 42:
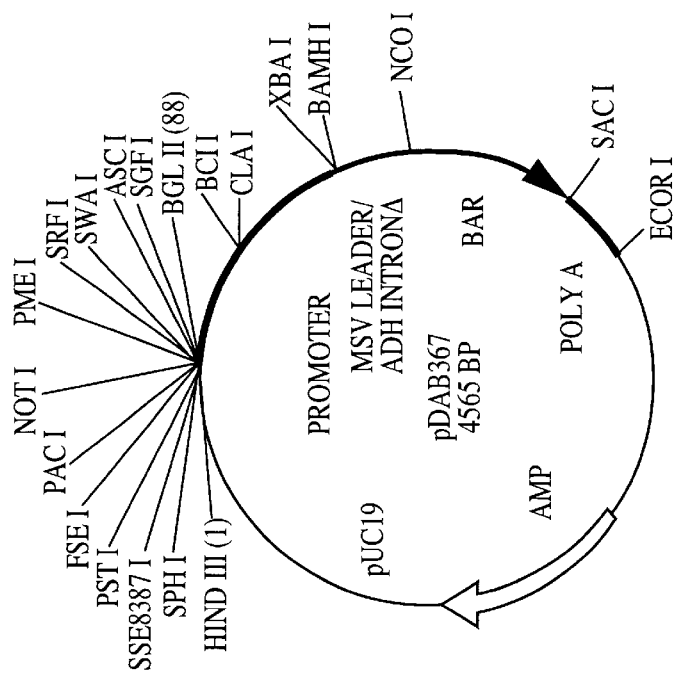
FIG. 42 illustrates a transformation vector that can be used to express the enzymatic nucleic acid of the present invention.

GBSS activities at the single kernel level of line RPA63.0218 (Southern positive and reduced GBSS activity in pooled starch) was further examined, using RPA63.0306 (Southern negative and GBSS activity normal in pooled starch) as control. About 30 kernels from each line were taken, and starch samples were purified from each kernel individually. FIG. 41 clearly indicated reduced GBSS activity in line RPA63.0218 compared to RPA63.0306.

Other embodiments are within the following claims.

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintainance of the active structure [1].

-continued

Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [2, 3].
Complete kinetic framework established for one ribozyme [4, 5, 6, 7].
Studies of ribozyme folding and substrate docking underway [8, 9, 10].
Chemical modification investigation of important residues well established [11, 12].
The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [13].
RNAse P RNA (M1 RNA)

Size: ~290 to 400 nucleotides.
RNA portion of a ubiquitous ribonucleoprotein enzyme.
Cleaves tRNA precursors to form mature tRNA [14].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [15, 16]
Important phosphate and 2' OH contacts recently identified [17, 18]
Group II Introns Size: >1000 nucleotides.
Trans cleavage of target RNAs recently demonstrated [19, 20].
Sequence requirements not fully determined.
Reaction mechanism: 2'-OH of an internal adenosine generates cleavage products with 3'-OH and a "lariat" RNA containing a 3'–5' and a 2'–5' branch point.
Only natural ribozyme with demonstrated participation in DNA cleavage [21, 22] in addition to RNA cleavage and ligation.
Major structural features largely established through phylogenetic comparisons [23].
Important 2' OH contacts beginning to be identified [24]
Kinetic framework under development [25]
Neurospora VS RNA Size: ~144 nucleotides.
Trans cleavage of hairpin target RNAs recently demonstrated [26].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.
Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [ ]
Minimal ligation activity demonstrated (for engineering through in vitro selection) [ ]
Complete kinetic framework established for two or more ribozymes [ ].
Chemical modification investigation of important residues well established [ ].
Hairpin Ribozyme Size: ~50 nucleotides.
Requires the target sequence GUC immediately 3' of the cleavage site.
Binds 4–6 nucleotides at the 5'-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [27, 28, 29, 30]

-continued

Ligation activity (in addition to cleavage activity) makes ribozyme amenable to engineering through in vitro selection [31]
Complete kinetic framework established for one ribozyme [32].
Chemical modification investigation of important residues begun [33, 34].
Hepatitis Delta Virus (HDV) Ribozyme Size: ~60 nucleotides.
Trans cleavage of target RNAs demonstrated [35].
Binding sites and structural requirements not fully determined, although no sequences 5' of cleavage site are required. Folded ribozyme contains a pseudoknot structure [36].
Reaction mechanism: attack by 2'-OH 5' to the scissile bond to generate cleavage products with 2',3'-cyclic phosphate and 5'-OH ends.
Only 2 known members of this class. Found in human HDV.
Circular form of HDV is active and shows increased nuclease stability [37]

1. Mohr, G.; Caprara, M. G.; Guo, Q.; Lambowitz, A. M. Nature, 370, 147–150 (1994).
2. Michel, Francois; Westhof, Eric. Slippery substrates. Nat. Struct. Biol. (1994), 1(1), 5–7.
3. Lisacek, Frederique; Diaz, Yolande; Michel, Francois. Automatic identification of group I intron cores in genomic DNA sequences. J. Mol. Biol. (1994), 235(4), 1206–17.
4. Herschlag, Daniel; Cech, Thomas R.. Catalysis of RNA cleavage by the Tetrahymena thermophila ribozyme. 1. Kinetic description of the reaction of an RNA substrate complementary to the active site. Biochemistry (1990), 29(44), 10159–71.
5. Herschlag, Daniel; Cech, Thomas R.. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
6. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
7. Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.
8. Li, Yi; Bevilacqua, Philip C.; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
9. Banerjee, Aloke Raj; Turner, Douglas H.. The time dependence of chemical modification reveals slow steps in the folding of a group I ribozyme. Biochemistry (1995), 34(19), 6504–12.
10. Zarrinkar, Patrick P.; Williamson, James R.. The P9.1–P9.2 peripheral extension helps guide folding of the Tetrahymena ribozyme. Nucleic Acids Res. (1996), 24(5), 854–8.
11. Strobel, Scott A.; Cech, Thomas R.. Minor groove recognition of the conserved G.cntdot.U pair at the Tetrahymena ribozyme reaction site. Science (Washington, D.C.) (1995), 267(5198), 675–9.
12. Strobel, Scott A.; Cech, Thomas R.. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
13. Sullenger, Bruce A.; Cech, Thomas R.. Ribozyme-mediated repair of defective mRNA by targeted trans-splicing. Nature (London) (1994), 371 (6498), 619–22.
14. Robertson, H. D.; Altman, S.; Smith, J. D. J. Biol. Chem., 247, 5243–5251 (1972).
15. Forster, Anthony C.; Altman, Sidney. External guide sequences for an RNA enzyme. Science (Washington, D.C., 1883–) (1990), 249(4970), 783–6.
16. Yuan, Y.; Hwang, E. S.; Altman, S. Targeted cleavage of mRNA by human RNase P. Proc. Natl. Acad. Sci. USA (1992) 89, 8006–10.
17. Harris, Michael E.; Pace, Norman R.. Identification of phosphates involved in catalysis by the ribozyme RNase P RNA. RNA (1995), 1(2), 210–18.
18. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
19. Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.
20. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
21. Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.
22. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
23. Michel, Francois; Ferat, Jean Luc. Structure and activities of group II introns. Annu. Rev. Biochem. (1995), 64, 435–61.
24. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
25. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256 (1), 31–49.
26. Guo, Hans C. T.; Collins, Richard A.. Efficient trans-cleavage of a stem-loop RNA substrate by a ribozyme derived from Neurospora VS RNA. EMBO J. (1995), 14(2), 368–76.
27. Hampel, Arnold; Tritz, Richard; Hicks, Margaret; Cruz, Phillip. 'Hairpin' catalytic RNA model: evidence for helices and sequence requirement for substrate RNA. Nucleic Acids Res. (1990), 18(2), 299–304.
28. Chowrira, Bharat M.; Berzal-Herranz, Alfredo; Burke, John M.. Novel guanosine requirement for catalysis by the hairpin ribozyme. Nature (London) (1991), 354(6351), 320–2.
29. Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
30. Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
31. Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
32. Hegg, Lisa A.; Fedor, Martha J.. Kinetics and Thermodynamics of Intermolecular Catalysis by Hairpin Ribozymes. Biochemistry (1995), 34(48), 15813–28.
33. Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068–76.
34. Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
35. Perrotta, Anne T.; Been, Michael D.. Cleavage of oligoribonucleotides by a ribozyme derived from the hepatitis .delta. virus RNA sequence. Biochemistry (1992), 31(1), 16–21.
36. Perrotta, Anne T.; Been, Michael D.. A pseudoknot-like structure required for efficient self-cleavage of hepatitis delta virus RNA. Nature (London) (1991), 350(6317), 434–6.
37. Puttaraju, M.; Perrotta, Anne T.; Been, Michael D.. A circular trans-acting hepatitis delta virus ribozyme. Nucleic Acids Res. (1993), 21(18), 4253–8.

TABLE II 2.5 µmol RNA Synthesis Cycle

| Reagent | Equivalents | Amount | Wait Time* |
|---|---|---|---|
| Phosphoramidites | 6.5 | 163 µL | 2.5 |
| S-Ethyl Tetrazole | 23.8 | 238 µL | 2.5 |
| Acetic Anhydride | 100 | 233 µL | 5 sec |
| N-Methyl Imidazole | 186 | 233 µL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

TABLE IIIA

GBSS Hammerhead Substrate Sequence

| nt. Position | Substrate |
|---|---|
| 12 | CGAUCGAUC GCCACAGC |
| 68 | GAAGGAAUA AACUCACU |
| 73 | AAUAAACUC ACUGCCAG |
| 103 | AGAAGUGUA CUGCUCCG |
| 109 | GUACUGCUC CGUCCACC |
| 113 | UGCUCCGUC CACCAGUG |
| 146 | GGGCUGCUC AUCUCGUC |
| 149 | CUGCUCAUC UCGUCGAC |
| 151 | GCUCAUCUC GUCGACGA |
| 154 | CAUCUCGUC GACGACCA |
| 169 | CAGUGGAUU AAUCGGCA |
| 170 | AGUGGAUUA AUCGGCAU |
| 173 | GGAUUAAUC GGCAUGGC |
| 186 | UGGCGGCUC UAGCCACG |
| 188 | GCGGCUCUA GCCACGUC |
| 196 | AGCCACGUC GCAGCUCG |
| 203 | UCGCAGCUC GUCGCAAC |
| 206 | CAGCUCGUC GCAACGCG |
| 230 | CUGGGCGUC CCGGACGC |
| 241 | GGACGCGUC CACGUUCC |
| 247 | GUCCACGUU CCGCCGCG |
| 248 | UCCACGUUC CGCCGCGG |
| 292 | GACGGCGUC GGCGGCGG |
| 308 | GACACGCUC AGCAUUCG |
| 314 | CUCAGCAUU CGGACCAG |
| 315 | UCAGCAUUC GGACCAGC |
| 344 | CCCAGGCUC CAGCACCA |
| 385 | GGCCAGGUU CCCGUCGC |
| 386 | GCCAGGUUC CCGUCGCU |
| 391 | GUUCCCGUC GCUCGUCG |
| 395 | CCGUCGCUC GUCGUGUG |
| 398 | UCGCUCGUC GUGUGCGC |
| 425 | AUGAACGUC GUCUUCGU |
| 428 | AACGUCGUC UUCGUCGG |
| 430 | CGUCGUCUU CGUCGGCG |
| 431 | GUCGUCUUC GUCGGCGC |
| 434 | GUCUUCGUC GGCGCCGA |

TABLE IIIA-continued

GBSS Hammerhead Substrate Sequence

| nt. Position | Substrate |
|---|---|
| 473 | GGCGGCCUC GGCGACGU |
| 482 | GGCGACGUC CUCGGCGG |
| 485 | GACGUCCUC GGCGGCCU |
| 527 | CACCGUGUC AUGGUCGU |
| 533 | GUCAUGGUC GUCUCUCC |
| 536 | AUGGUCGUC UCUCCCCG |
| 538 | GGUCGUCUC UCCCCGCU |
| 540 | UCGUCUCUC CCCGCUAC |
| 547 | UCCCCGCUA CGACCAGU |
| 556 | CGACCAGUA CAAGGACG |
| 581 | ACCAGCGUC GUGUCCGA |
| 586 | CGUCGUGUC CGAGAUCA |
| 593 | UCCGAGAUC AAGAUGGG |
| 610 | AGACAGGUA CGAGACGG |
| 620 | GAGACGGUC AGGUUCUU |
| 625 | GGUCAGGUU CUUCCACU |
| 626 | GUCAGGUUC UUCCACUG |
| 628 | CAGGUUCUU CCACUGCU |
| 629 | AGGUUCUUC CACUGCUA |
| 637 | CCACUGCUA CAAGCGCG |
| 661 | CCGCGUGUU CGUUGACC |
| 662 | CGCGUGUUC GUUGACCA |
| 665 | GUGUUCGUU GACCACCC |
| 679 | CCCACUGUU CCUGGAGA |
| 680 | CCACUGUUC CUGGAGAG |
| 692 | GAGAGGGUU UGGGGAAA |
| 693 | AGAGGGUUU GGGGAAAG |
| 716 | GAGAAGAUC UACGGGCC |
| 718 | GAAGAUCUA CGGGCCUG |
| 742 | AACGGACUA CAGGGACA |
| 763 | GCUGCGGUU CAGCCUGC |
| 764 | CUGCGGUUC AGCCUGCU |
| 773 | AGCCUGCUA UGCCAGGC |
| 788 | GCAGCACUU GAAGCUCC |
| 795 | UUGAAGCUC CAAGGAUC |
| 803 | CCAAGGAUC UGAGCCU |
| 812 | CUGAGCCUC AACAACAA |

TABLE IIIA-continued

GBSS Hammerhead Substrate Sequence

| nt. Position | Substrate |
|---|---|
| 826 | CAACCCAUA CUUCUCCG |
| 829 | CCCAUACUU CUCCGGAC |
| 830 | CCAUACUUC UCCGGACC |
| 832 | AUACUUCUC CGGACCAU |
| 841 | CGGACCAUA CGGGGAGG |
| 854 | GAGGACGUC GUGUUCGU |
| 859 | CGUCGUGUU CGUCUGCA |
| 860 | GUCGUGUUC GUCUGCAA |
| 863 | GUGUUCGUC UGCAACGA |
| 888 | CCGGCCCUC UCUCGUGC |
| 890 | GGCCCUCUC UCGUGCUA |
| 892 | CCCUCUCUC GUGCUACC |
| 898 | CUCGUGCUA CCUCAAGA |
| 902 | UGCUACCUC AAGAGCAA |
| 913 | GAGCAACUA CCAGUCCC |
| 919 | CUACCAGUC CCACGGCA |
| 929 | CACGGCAUC UACAGGGA |
| 931 | CGGCAUCUA CAGGGACG |
| 951 | AGACCGCUU UCUGCAUC |
| 952 | GACCGCUUU CUGCAUCC |
| 953 | ACCGCUUUC UGCAUCCA |
| 959 | UUCUGCAUC CACAACAU |
| 968 | CACAACAUC UCCUACCA |
| 970 | CAACAUCUC CUACCAGG |
| 973 | CAUCUCCUA CCAGGGCC |
| 985 | GGGCCGGUU CGCCUUCU |
| 986 | GGCCGGUUC GCCUUCUC |
| 991 | GUUCGCCUU CUCCGACU |
| 992 | UUCGCCUUC UCCGACUA |
| 994 | CGCCUUCUC CGACUACC |
| 1000 | CUCCGACUA CCCGGAGC |
| 1016 | CUGAACCUC CCGGAGAG |
| 1027 | GGAGAGAUU CAAGUCGU |
| 1028 | GAGAGAUUC AAGUCGUC |
| 1033 | AUUCAAGUC GUCCUUCG |
| 1036 | CAAGUCGUC CUUCGAUU |
| 1039 | GUCGUCCUU CGAUUUCA |

TABLE IIIA-continued

GBSS Hammerhead Substrate Sequence

| nt. Position | Substrate |
|---|---|
| 1040 | UCGUCCUUC GAUUUCAU |
| 1044 | CCUUCGAUU UCAUCGAC |
| 1045 | CUUCGAUUU CAUCGACG |
| 1046 | UUCGAUUUC AUCGACGG |
| 1049 | GAUUUCAUC GACGGCUA |
| 1057 | CGACGGCUA CGAGAAGC |
| 1085 | CGGAAGAUC AACUGGAU |
| 1106 | GCCGGGAUC CUCGAGGC |
| 1109 | GGGAUCCUC GAGGCCGA |
| 1124 | GACAGGGUC CUCACCGU |
| 1127 | AGGGUCCUC ACCGUCAG |
| 1133 | CUCACCGUC AGCCCCUA |
| 1141 | CAGCCCCUA CUACGCCG |
| 1144 | CCCCUACUA CGCCGAGG |
| 1157 | GAGGAGCUC AUCCCGG |
| 1160 | GAGCUCAUC UCCGGCAU |
| 1162 | GCUCAUCUC CGGCAUCG |
| 1169 | UCCGGCAUC GCCAGGGG |
| 1187 | UGCGAGCUC GACAACAU |
| 1196 | GACAACAUC AUGCGCCU |
| 1205 | AUGCGCCUC ACCGGCAU |
| 1214 | ACCGGCAUC ACCGGCAU |
| 1223 | ACCGGCAUC GUCAACGG |
| 1226 | GGCAUCGUC AACGGCAU |
| 1241 | AUGGACGUC AGCGAGUG |
| 1270 | GGACAAGUA CAUCGCCG |
| 1274 | AAGUACAUC GCCGUGAA |
| 1285 | CGUGAAGUA CGACGUGU |
| 1294 | CGACGUGUC GACGGCCG |
| 1346 | GCGGAGGUC GGGCUCCC |
| 1352 | GUCGGGCUC CCGGUGGA |
| 1370 | CGGAACAUC CCGCUGGU |
| 1384 | GGUGGCGUU CAUCGGCA |
| 1385 | GUGGCGUUC AUCGGCAG |
| 1388 | GCGUUCAUC GGCAGGCU |
| 1421 | CCCGACGUC AUGGCGGC |
| 1436 | GCCGCCAUC CCGCAGCU |

TABLE IIIA-continued

GBSS Hammerhead Substrate Sequence

| nt. Position | Substrate |
|---|---|
| 1445 | CCGCAGCUC AUGGAGAU |
| 1472 | GUGCAGAUC GUUCUGCU |
| 1475 | CAGAUCGUU CUGCUGGG |
| 1476 | AGAUCGUU UGCUGGGC |
| 1501 | GAAGAAGUU CGAGCGCA |
| 1502 | AAGAAGUUC GAGCGCAU |
| 1514 | CGCAUGCUC AUGAGCGC |
| 1534 | GGAGAAGUU CCCAGGCA |
| 1535 | GAGAAGUUC CCAGGCAA |
| 1559 | GCCGUGGUC AAGUUCAA |
| 1564 | GGUCAAGUU CAACGCGG |
| 1565 | GUCAAGUUC AACGCGGC |
| 1589 | CACCACAUC AUGGCCGG |
| 1610 | GACGUGCUC GCCGUCAC |
| 1616 | CUCGCCGUC ACCAGCCG |
| 1627 | CAGCCGCUU CGAGCCCU |
| 1628 | AGCCGCUUC GAGCCCUG |
| 1643 | UGCGGCCUC AUCCAGCU |
| 1646 | GGCCUCAUC CAGCUGCA |
| 1666 | GAUGCGAUA CGGAACGC |
| 1690 | CUGCGCGUC CACCGGUG |
| 1703 | GGUGGACUC GUCGACAC |
| 1706 | GGACUCGUC GACACCAU |
| 1715 | GACACCAUC AYCGAAGG |
| 1718 | ACCAYCAYC GAAGGCAA |
| 1735 | GACCGGGUU CCACAUGG |
| 1736 | ACCGGGUUC CACAUGGG |
| 1751 | GGCCGCCUC AGCGUCGA |
| 1757 | CUCAGCGUC GACUGCAA |
| 1769 | UGCAACGUC GUGGAGCC |
| 1787 | GCGGACGUC AAGAAGGU |
| 1807 | CACCACCUU GCAGCGCG |
| 1820 | CGCGCCAUC AAGGUGGU |
| 1829 | AAGGUGGUC GGCACGCC |
| 1843 | GCCGGCGUA CGAGGAGA |
| 1871 | UGCAUGAUC CAGGAUCU |
| 1878 | UCCAGGAUC UCUCCUGG |

TABLE IIIA-continued

GBSS Hammerhead Substrate Sequence

| nt. Position | Substrate |
|---|---|
| 1880 | CAGGAUCUC UCCUGGAA |
| 1882 | GGAUCUCUC CUGGAAGG |
| 1922 | GUGCUGCUC AGCCUCGG |
| 1928 | CUCAGCCUC GGGGUCGC |
| 1934 | CUCGGGGUC GCCGGCGG |
| 1955 | CCAGGGGUC GAAGGCGA |
| 1970 | GAGGAGAUC GCGCCGCU |
| 1979 | GCGCCGCUC GCCAAGGA |
| 2012 | UGAAGAGUU CGGCCUGC |
| 2013 | GAAGAGUUC GGCCUGCA |
| 2033 | CCCCUGAUC UCGCGCGU |
| 2035 | CCUGAUCUC GCGCGUGG |
| 2055 | AAACAUGUU GGGACAUC |
| 2063 | UGGGACAUC UUCUUAUA |
| 2065 | GGACAUCUU CUUAUAUA |
| 2066 | GACAUCUUC UUAUAUAU |
| 2068 | CAUCUUCUU AUAUAUGC |
| 2069 | AUCUUCUUA UAUAUGCU |
| 2071 | CUUCUUAUA UAUGCUGU |
| 2073 | UCUUAUAUA UGCUGUUU |
| 2080 | UAUGCUGUU UCGUUUAU |
| 2081 | AUGCUGUUU CGUUUAUG |
| 2082 | UGCUGUUUC GUUUAUGU |
| 2085 | UGUUUCGUU UAUGUGAU |
| 2086 | GUUUCGUUU AUGUGAUA |
| 2087 | UUUCGUUUA UGUGAUAU |
| 2094 | UAUGUGAUA UGGAVAAG |
| 2104 | GGACAAGUA UGUGUAGC |
| 2110 | GAUAGUGUA GCUGCUUG |
| 2117 | UAGCUGCUU GCUUGUGC |
| 2121 | UGCUUGCUU GUGCUAGU |
| 2127 | CUUGUGCUA GUGUAAUA |
| 2132 | GCUAGUGUA AUAUAGUG |
| 2135 | AGUGUAAUA UAGUGUAG |
| 2137 | UGUAAUAUA GUGUAGUG |
| 2142 | UAUAGUGUA GUGGUGGC |
| 2165 | CACAACCUA AUAAGCGC |

TABLE IIIA-continued

GBSS Hammerhead Substrate Sequence

| nt. Position | Substrate |
|---|---|
| 2168 | AACCUAAUA AGCGCAUG |
| 2181 | CAUGAACUA AUUGCUUG |
| 2184 | GAACUAAUU GCUUGCGU |
| 2188 | UAAUUGCUU GCGUGUGU |
| 2197 | GCGUGUGUS GUUAAGUA |
| 2200 | UGUGUAGUU AAGUACCG |
| 2201 | GUGUAGUUA AGUACCGA |
| 2205 | AGUUAAGUA CCGAUCGG |
| 2211 | GUACCGAUC GGUAAUUU |
| 2215 | CGAUCGGUA AUUUUAUA |
| 2218 | UCGGUAAUU UUAUAUUG |
| 2219 | CGGUAAUUU UAUAUUGC |
| 2220 | GGUAAUUUU AUAUUGCG |
| 2221 | GUAAUUUUA UAUUGCGA |
| 2223 | AAUUUUAUA UUGCGAGU |
| 2225 | UUUUAUAUU GCGAGUAA |
| 2232 | UUGCGAGUA AAUAAAUG |
| 2236 | GAGUAAAUA AAUGGACC |
| 2248 | GGACCUGUA GUGGUGGA |

TABLE III B

Hammerhead Robozyme Sequence Targeted Against GBSS mRNA

| nt. Position | HH Ribozyme Sequence |
|---|---|
| 12 | UGGCUGUGGC CUGAUGA X GAA AUCGAUCGGU |
| 68 | GCAGUGAGUU CUGAUGA X GAA AUUCCUUCCU |
| 73 | GGCUGGCAGU CUGAUGA X GAA AGUUUAUUCC |
| 103 | GACGGAGCAG CUGAUGA X GAA ACACUUCUCC |
| 109 | CUGGUGGACG CUGAUGA X GAA AGCAGUACAC |
| 113 | CGCACUGGUG CUGAUGA X GAA ACGGAGCAGU |
| 146 | UCGACGAGAU CUGAUGA X GAA AGCAGCCCUG |
| 149 | UCGUCGACGA CUGAUGA X GAA AUGAGCAGCC |
| 151 | GGUCGUCGAC CUGAUGA X GAA AUGAGCAGCC |
| 154 | ACUGGUCGUC CUGAUGA X GAA ACGAGAUGAG |
| 169 | CAUGCCGAUU CUGAUGA X GAA AUCCACUGGU |
| 170 | CCAUGCCGAU CUGAUGA X GAA AUCCACUGGU |
| 173 | CCGCCAUGCC CUGAUGA X GAA AUUAAUCCAC |
| 186 | GACGUGGCUA CUGAUGA X GAA AGCCGCCAUG |
| 188 | GCGACGUGGC CUGAUGA X GAA AGAGCCGCCA |
| 196 | GACGAGCUGC CUGAUGA X GAA ACGUGGCUAG |
| 203 | GCGUUGCGAC CUGAUGA X GAA AGCUGCGACG |
| 206 | CGCGCGUUGC CUGAUGA X GAA ACGAGCUGCG |
| 230 | ACGCGUCCGG CUGAUGA X GAA ACGCCCAGGC |
| 241 | GCGGAACGUG CUGAUGA X GAA ACGCGUCCGG |
| 247 | GCCGCGGCGG CUGAUGA X GAA ACGUGGACGC |
| 248 | CGCCGCGGCG CUGAUGA X GAA AACGUGGACG |
| 292 | GUCCGCCGCC CUGAUGA X GAA ACGCCGUCCG |
| 308 | UCCGAAUGCU CUGAUGA X GAA AGCGUGUCCG |
| 314 | CGCUGGUCCG CUGAUGA X GAA AUGCUGAGCG |
| 315 | GCGCUGGUCC CUGCUGA X GAA AAUGCUGAGC |
| 344 | GCUGGUGCUG CUGAUGA X GAA AGCCUGGGCG |
| 385 | GAGCGACGGG CUGAUGA X GAA ACCUGGCCCC |
| 386 | CGAGCGACGG CUGAUGA X GAA AACCUGGCCC |
| 391 | CACGACGAGC CUGAUGA X GAA ACGGGAACCU |
| 395 | CGCACACGAC CUGAUGA X GAA AGCGACGGGA |
| 398 | UGGCGCACAC CUGAUGA X GAA ACGAGCGACG |
| 425 | CGACGAAGAC CUGAUGA X GAA ACGUUCAUGC |
| 428 | CGCCGACGAA CUGAUGA X GAA AGACGACGUU |
| 430 | GGCGCCGACG CUGAUGA X GAA AGACGACGUU |
| 431 | CGGCGCCGAC CUGAUGA X GAA AAGACGACGU |
| 434 | UCUCGGCGCC CUGAUGA X GAA ACGAAGACGA |
| 473 | GGACGUCGCC CUGAUGA X GAA AGGCCGCCGG |
| 482 | GGCCGCCGAG CUGAUGA X GAA ACGUCGCCGA |
| 485 | GCAGGCCGCC CUGAUGA X GAA AGGACGUCGC |
| 527 | AGACGACCAU CUGAUGA X GAA ACACGGUGCC |
| 533 | GGGGAGAGAC CUGAUGA X GAA ACCAUGACAC |
| 536 | AGCGGGGAGA CUGAUGA X GAA ACGACCAUGA |
| 538 | GUAGCGGGGA CUGAUGA X GAA AGACGACCAU |
| 540 | UCGUAGCGGG CUGAUGA X GAA AGAGACGACC |
| 547 | GUACUGGUCG CUGAUGA X GAA AGCGGGGAGA |
| 556 | GGCGUCCUUG CUGCUGA X GAA ACUGGUCGUA |
| 581 | UCUCGGACAC CUGAUGA X GAA ACGCUGGUGU |
| 586 | CUUGAUCUCG CUGAUGA X GAA ACACGACGCU |

TABLE III B-continued

Hammerhead Robozyme Sequence Targeted Against GBSS mRNA

| nt. Position | HH Ribozyme Sequence |
|---|---|
| 593 | CUCCCAUCUU CUGAUGA X GAA AUCUCGGACA |
| 610 | GACCGUCUCG CUGAUGA X GAA ACCUGUCUCC |
| 620 | GGAAGAACCU CUGAUGA X GAA ACCGUCUCGU |
| 625 | GCAGUGGAAG CUGAUGA X GAA ACCUGACCGU |
| 626 | AGCAGUGGAA CUGAUGA X GAA AACCUGACCG |
| 628 | GUAGCACUGG CUGAUGA X GAA AGAACCUGAC |
| 629 | UGUAGCAGUG CUGAUGA X GAA AAGAACCUGA |
| 637 | UCCGCGCUUG CUGAUGA X GAA AGCAGUGGAA |
| 661 | GUGGUCAACG CUGAUGA X GAA ACACGCGGUC |
| 662 | GGUGGUCAAC CUGAUGA X GAA AACACGCGGU |
| 665 | GUGGGUGGUC CUGAUGA X GAA ACGAACACGC |
| 679 | CCUCUCCAGG CUGAUGA X GAA ACAGUGGGUG |
| 680 | CCCUCUCCAH CUGAUGA X GAA AACAGUGGGU |
| 692 | UCUUUCCCCA CUGAUGA X GAA ACCCUCUCCA |
| 693 | GUCUUUCCCC CUGAUGA X GAA AACCCUCUCC |
| 716 | CAGGCCCGUA CUGAUGA X GAA AUCUUCUCCU |
| 718 | GUCAGGCCCG CUGAUGA X GAA AGAUCUUCUC |
| 742 | GUUGUCCCUG CUGAUGA X GAA AGUCCGUUCC |
| 763 | UAGCAGGCUG CUGAUGA X GAA ACCGCAGCUG |
| 764 | AUAGCAGGCU CUGAUGA X GAA AACCGCAGCU |
| 773 | CUGCCUGGCA CUGAUGA X GAA AGCAGGCUGA |
| 788 | UUGGAGCUUC CUGAUGA X GAA AGUGCUGCCU |
| 795 | AGGAUCCUUG CUGAUGA X GAA AGCUUCAAGU |
| 803 | UGAGGCUCAG CUGAUGA X GAA AUCCUUGGAG |
| 812 | GGUUGUUGUU CUGAUGA X GAA AGGCUCAGGA |
| 826 | UCCGGAGAAG VUGAUGA X GAA AUGGGUUGUU |
| 829 | UGGUCCGGAG CUGAUGA X GAA AGUAUGGGUU |
| 830 | AUGGUCCGGA CUGAUGA X GAA AAGUAUGGGC |
| 832 | GUAUGGUCCG CUGAUGA X GAA AGAACUAUGG |
| 841 | GUCCUCCCCG CUGAUGA X GAA AUGGUCCGGA |
| 854 | AGACGAACAC CUGAUGA X GAA ACGUCCUCCC |
| 859 | GUUGCAGACG CUGAUGA X GAA ACACGACGUC |
| 860 | CGUUGCAGAC CUGAUGA X GAA AACACGACGU |
| 863 | AGUCGUUGCA CUGAUGA X GAA ACGAACACGA |
| 888 | UAGCACGAGA CUGAUGA X GAA AGGGCCGGUG |
| 890 | GGUAGCACGA CUGAUGA X GAA AGAGGGCCGG |
| 892 | GAGGUAGCAC CUGUAGA x GAA AGAGAGGGCC |
| 898 | GCUCUUGAGG CUGAUGA X GAA AGCACGAGAG |
| 902 | AGUUGCUCUU CUGAUGA X GAA AGGUAGCACG |
| 913 | GUGGGACUGG CUGAUGA X GAA AGUUGCUCUU |
| 919 | GAUGCCGUGG CUGAUGA X GAA ACUGGUAGUU |
| 929 | CGUCCCUGUA CUGAUGA X GAA AUGCCGUGGG |
| 931 | UGCGUCCCUG CUGAUGA X GAA AGAUGCCGUG |
| 951 | UGGAUGCAGA CUGAUGA X GAA AGCGGUCUUU |
| 952 | GUGGAUGCAG CUGAUGA X GAA AAGCGGUCUU |
| 953 | UGUGGAUGCA CUGAUGA X GAA AAAGCGGUCU |
| 959 | AGAUGUUGUG CUGAUGA X GAA AUGCAGAAAG |
| 968 | CCUGGUAGGA CUGAUGA X GAA AUGUUGUGGA |
| 970 | GCCCUGGUAG CUGAUGA X GAA AGAUGUUGUG |
| 973 | CCGGCCCUGG CUGAUGA X GAA AGGAGAUGUU |
| 985 | GGAGAAGGCG CUGAUGA X GAA ACCGGCCCUG |
| 986 | CGGAGAAGGC CUGAUGA X GAA AACCGGCCCU |
| 991 | GUAGUCGGAG CUGAUGA X GAA AGGCGAACCG |
| 992 | GGUAGUCGGA CUGAUGA X GAA AAGGCGAACC |
| 994 | CGGGAUGUCG CUGAUGA X GAA AGAAGGCGAA |
| 1000 | CAGCUCCGGG CUGAUGA X GAA AGUCGGAGAA |
| 1016 | AUCUCCGG CUGAUGA X GAA AGGUUCAGCU |
| 1027 | GGACGACUUG CUGAUGA X GAA AUCUCUCCGG |
| 1028 | AGGACGACUU CUGAUGA X GAA AAUCUCUCCG |
| 1033 | AUCGAAGGAC CUGAUGA X GAA ACUUGAAUCU |
| 1036 | GAAAUCGAAG CUGAUGA X GAA ACGACUUGAA |
| 1039 | GAUGAAAUCG CUGAUGA X GAA AGGACGACUU |
| 1040 | CGAUGAAAUC CUGAUGA X GAA AAGGACGACU |
| 1044 | CCGUCGAUGA CUGAUGA X GAA AUCGAAGGAC |
| 1045 | GCCGUCGAUG CUGAUGA X GAA AAUCGAAGGA |
| 1046 | AGCCGUCGAU CUGAUGA X GAA AAAUCGAAGG |
| 1049 | CGUAGCCGUC CUGAUGA X GAA AUGAAAUCGA |
| 1057 | GGGCUUCUCG CUGAUGA X GAA AGCCGUCGAU |
| 1085 | UCAUCCAGUU CUGAUGA X GAA AUCUUCCGGC |
| 1106 | CGGCCUCGAG CUGAUGA X GAA AUCCCGGCCU |
| 1109 | UGUCGGCCUC CUGAUGA X GAA AGGAUCCCGG |
| 1124 | UGACGGUGAG CUGAUGA X GAA ACCCUGUCGG |
| 1127 | GGCUGACGGU CUGAUGA X GAA AGGACCCUGU |

TABLE III B-continued

Hammerhead Ribozyme Sequence Targeted Against GBSS mRNA

| nt. Position | HH Ribozyme Sequence |
|---|---|
| 1133 | AGUAGGGGCU CUGAUGA X GAA ACGGUGAGGA |
| 1141 | CUCGGCGUAG CUGAUGA X GAA AGGGGCUGAC |
| 1144 | CUCCUCGGCG CUGAUGA X GAA AGUAGGGGCU |
| 1157 | UGCCGGAGAU CUGAUGA X GAA AGCUCCUCGG |
| 1160 | CGAUGCCGGA CUGAUGA X GAA AUGAGCUCCU |
| 1162 | GGCGAUGCCG CUGAUGA X GAA AGAUGAGCUC |
| 1169 | AGCCCCUGGC CUGAUGA X GAA AUGCCGGAGA |
| 1187 | UGAUGUUCUG CUGAUGA X GAA AGCUCGCAGC |
| 1196 | UGAGGCGCAU CUGAUGA X GAA AUGUUGUCGA |
| 1205 | UGAUGCCGGU CUGAUGA X GAA AGGCGCAUGA |
| 1214 | CGAUGCCGGU CUGAUGA X GAA AUGCCGGUGA |
| 1223 | UGCCGUUGAC CUGAUGA X GAA AUGCCGGUGA |
| 1226 | CCAUGCCGUU CUGAUGA X GAA ACGAUGCCGG |
| 1241 | CCCACUCGCU CUGAUGA X GAA ACGUCCAUGC |
| 1270 | CACGGCGAUG CUGAUGA X GAA ACUUCUCCCU |
| 1274 | ACUUCACGGC CUGAUGA X GAA AUGUACUUGU |
| 1285 | CGACACGUCG CUGAUGA X GAA ACUUCACGGC |
| 1294 | CACGGCCGUC CUGAUGA X GAA ACACGUCGUA |
| 1346 | CCGGGAGCCC CUGAUGA X GAA ACCUCCGCCU |
| 1352 | GGUCCACCGG CUGAUGA X GAA AGCCCGACCU |
| 1370 | CCACCAGCGG CUGAUGA X GAA AUGUUCCGGU |
| 1384 | CCUGCCGAUG CUGAUGA X GAA ACGCCACCAG |
| 1385 | GCCUGCCGAU CUGAUGA X GAA AACGCCACCA |
| 1388 | CCAGCCUGCC CUGAUGA X GAA AUGAACGCCA |
| 1421 | CGGCCGCCAU CUGAUGA X GAA ACGUCGGGUC |
| 1436 | UGAGCUGCGG CUGAUGA X GAA AUGGCGGCCG |
| 1445 | CCAUCUCCAU CUGAUGA X GAA AGCUGCGGGA |
| 1472 | CCAGCAGAAC CUGAUGA X GAA AUCUGCACGU |
| 1475 | UGCCCAGCAG CUGAUGA X GAA ACGAUCUGCA |
| 1476 | GUGCCCAGCA CUGAUGA X GAA AACGAUCUGC |
| 1501 | CAUGCGCUCG CUGAUGA X GAA ACUUCUUCUU |
| 1502 | GCAUGCGCUC CUGAUGA X GAA AACUUCUUCU |
| 1514 | CGGCGCUCAU CUGAUGA X GAA ACUUCUCCUC |
| 1534 | CUUGCCUGGG CUGAUGA X GAA ACUUCUCCUC |
| 1535 | CCUUGCCUGG CUGAUGA X GAA AACUUCUCCU |
| 1559 | CGUUGAACUU CUGAUGA X GAA ACCACGGCGC |
| 1564 | CGCCGCGUUG CUGAUGA C GAA ACUUGACCAC |
| 1565 | GCGCCGCGUU CUGAUGA X GAA AACUUGACCA |
| 1589 | CGCCGGCCAU CUGAUGA X GAA AUGUGGUGCG |
| 1610 | UGGUGACGGC CUGAUGA C GAA AGCACGUCGG |
| 1616 | AGCGGCUGGU CUGAUGA X GAA ACGGCGAGCA |
| 1627 | GCAGGGCUCG CUGAUGA X GAA AGCGGCUGGU |
| 1628 | CGCAGGGCUC CUGAUGA X GAA AAGCGGCUGG |
| 1643 | GCAGCUGGAU CUGAUGA X GAA AGGCCGCAGG |
| 1646 | CCUGCAGCUG CUGAUGA X GAA AUGAGGCCGC |
| 1666 | GGGCGUUCCG CUGAUGA X GAA AUCGCAUCCC |
| 1690 | UCCACCGGUG CUGAUGA X GAA ACGCGCAGGC |
| 1703 | UGGUGUCGAC CUGAUGA X GAA AGUCCACCGG |
| 1706 | UGAUGGUGUC CUGAUGA X GAA ACGAGUCCAC |
| 1715 | UGCCUUCGAU CUGAUGA X GAA AUGGUGUCGA |
| 1718 | UCUUGCCUUC CUGAUGA X GAA AUGAUGGUGU |
| 1735 | GCCCAUGUGG CUGAUGA X GAA ACCCGGUCUU |
| 1736 | GGCCCAUGUG CUGAUGA X GAA AACCCGGUCU |
| 1751 | AGUCGACGCU CUGAUGA X GAA AGGCGGCCCA |
| 1757 | CGUUGCAGUC CUGAUGA X GAA ACGCUGAGGC |
| 1769 | CCGGCUCCAC CUGAUGA X GAA ACGUUGCAGU |
| 1787 | CCACCUUCUU CUGAUGA X GAA ACGUCCGCCG |
| 1807 | GGCGCGCUGC CUGAUGA X GAA AGGUGGUGGC |
| 1820 | CGACCACCUU CUGAUGA X GAA AUGGCGCGCU |
| 1829 | CCGGCGUGCC CUGAUGA X GAA ACCACCUUGA |
| 1843 | CAUCUCCUCG CUGAUGA X GAA ACGCCGGCGU |
| 1871 | AGAGAUCCUG CUGAUGA X GAA AUCAUGCAGU |
| 1878 | UUCCAGGAGA CUGAUGA X GAA AUCCUGGAUC |
| 1880 | CCUUCCAGGA CUGAUGA X GAA AGAUCCUGGA |
| 1882 | GCCCUUCCAG CUGAUGA X GAA AGAGAUCCUG |
| 1922 | CCCCGAGGCU CUGAUGA X GAA AGCAGCACGU |
| 1928 | CGGCGACCCC CUGAUGA X GAA AGGCUGAGCA |
| 1934 | CGCCGCCGGC CUGAUGA X GAA ACCCCGAGGC |
| 1955 | CCUCGCCUUC CUGAUGA X GAA ACCCCUGGCU |
| 1970 | CGAGCGGCGC CUGAUGA X GAA AUCUCCUCGC |
| 1979 | UCUCCUUGGC CUGAUGA X GAA AGCGGCGCGA |
| 2012 | CUGCAGGCCG CUGAUGA X GAA ACUCUUCAGG |
| 2013 | CCUGCAGGCC CUGAUGA X GAA AACUCUUCAG |

TABLE III B-continued

Hammerhead Robozyme Sequence Targeted Against GBSS mRNA

| nt. Position | HH Ribozyme Sequence |
|---|---|
| 2033 | CCACGCGCGA CUGAUGA X GAA AUCAGGGGC |
| 2035 | CACCACGCGC CUGAUGA X GAA AGAUCAGGGG |
| 2055 | AAGAUGUCCC CUGAUGA X GAA ACAUGUUUGC |
| 2063 | UAUAUAAGAA CUGAUGA X GAA AUGUCCCAAC |
| 2065 | CAUAUAUAAG CUGAUGA X GAA AGAUGUCCCA |
| 2066 | GCAUAUAUAA CUGAUGA X GAA AAGAUGUCCC |
| 2068 | CAGCAUAUAU CUGAUGA X GAA AGAAGAUGUC |
| 2069 | ACAGCAYAYA CYGAYGA X GAA AAGAAGAUGU |
| 2071 | AAACAGCAUA CUGAUGA X GAA AUAAGAAGAU |
| 2073 | CGAAACAGCA CUGAUGA X GAA AUAUAAGAAG |
| 2080 | ACAUAAACGA CUGAUGA X GAA ACAGCAUAUA |
| 2081 | CACAUAAACG CUGAUGA X GAA AACAGCAUAU |
| 2082 | UCACAUAAAC CUGAUGA X GAA AAACAGCAUA |
| 2085 | AUAUCACAUA CUGAUGA X GAA ACGAAACAGC |
| 2086 | CAUAUCACAU CUGAUGA X GAA AACGAAACAG |
| 2087 | CCAUAUCACA CUGAUGA X GAA AAACGAAACA |
| 2094 | UACUUGUCCA CUGAUGA X GAA AUCACAUAAA |
| 2104 | CAGCUACACA CUGAUGA X GAA ACUUGUCCAU |
| 2110 | AGCAAGCAGC CUGAUGA X GAA ACACAUACUU |
| 2117 | UAGCACAAGC CUGAUGA X GAA AGCAGCUACA |
| 2121 | ACACUAGCAC CUGAUGA X GAA AGCAAGCAGC |
| 2127 | UAUAUUACAC CUGAUGA X GAA AGCACAAGCA |
| 2132 | UACACUAUAU CUGAUGA X GAA ACACUAGCAC |
| 2135 | CACUACUCUA CUGAUGA X GAA AUUACACUAG |
| 2137 | ACCACUACAC CUGAUGA X GAA AUAUUACACU |
| 2142 | UGGCCACCAC CUGAUGA X GAA ACACUAUAUU |
| 2165 | AUGCGCUUAU CUGAUGA X GAA AGGUUGUGCC |
| 2168 | UUCAUGCGCU CUGAUGA X GAA AUUAGGUUGU |
| 2181 | CGCAAGCAAU CUGAUGA X GAA AGUUCAUGCG |
| 2184 | ACACGCAAGC CUGAUGA X GAA AUUAGUUCAU |
| 2188 | CUACACACGC CUGAUGA X GAA AGCAAUUAGU |
| 2197 | GGUACUUAAC CUGAUGA X GAA ACACACGCAA |
| 2200 | AUCGGUACUU CUGAUGA X GAA ACUACACACG |
| 2201 | GAUCGGUACU CUGAUGA X GAA AACUACACAC |
| 2205 | UACCGAUCGG CUGAUGA X GAA ACUUAACUAC |
| 2211 | UAAAAUUACC CUGAUGA X GAA AUCGGUACUU |
| 2215 | AAUAUAAAAU CUGAUGA X GAA ACCGAUCGGU |
| 2218 | CGCAAUAUAA CUGAUGA X GAA AUUACCGAUC |
| 2219 | UCGCAAUAUA CUGAUGA X GAA AAUUACCGAU |
| 2220 | CUCGCAAUAU CUGAUGA X GAA AAAUUACCGA |
| 2221 | ACUCGCAAUA CUGAUGA X GAA AAAAUUACCG |
| 2223 | UUACUCGCAA CUGAUGA X GAA AUAAAAUUAC |
| 2225 | AUUUACUCGC CUGAUGA X GAA AUAUAAAAUU |
| 2232 | UCCAUUUAUU CUGAUGA X GAA ACUCGCAAUA |
| 2236 | CAGGUCCAUU CUGAUGA X GAA AUUUACUCGC |
| 2248 | UUUCCACCAC CUGAUGA X GAA ACAGGUCCAU |

Where "X" represents stem II region of a HH ribozyme (Hertel et al., 1992 Nucleic acids Res. 20 3252). The length of stem II may be ≧2 base-pairs.

TABLE IV

HH Ribozyme Sequences Tested against GBSS mRNA

| nt. Position | HH Ribozyme Sequence | Sequence I.D. |
|---|---|---|
| 425 | CGACGAAGAC CUGAUGAGGCCGAAAGGCCGAA ACGUUCAUGC | 2 |
| 593 | CUCCCAUCUU CUGAUGAGGCCGAAAGGCCGAA AUCUCGGACA | 3 |
| 742 | GUUGUCCCUG CUGAUGAGGCCGAAAGGCCGAA AGUCCGUUCC | 4 |
| 812 | GGUUGUUGUU CUGAUGAGGCCGAAAGGCCGAA AGGCUCAGAA | 5 |

TABLE IV-continued

HH Ribozyme Sequences Tested against GBSS mRNA

| nt. Position | HH Ribozyme Sequence | Sequence I.D. |
|---|---|---|
| 892 | GAGGUAGCAC CUGAUGAGGCCGAAAGGCCGAA AGAGAGGGCC | 6 |
| 913 | GUGGGACUGG CUGAUGAGGCCGAAAGGCCGAA AGUUGCUCUU | 7 |
| 919 | GAUGCCGUGG CUGAUGAGGCCGAAAGGCCGAA ACUGGUAGUU | 8 |
| 953 | UGUGGAUGCA CUGAUGAGGCCGAAAGGCCGAA AAAGCGGUCU | 9 |
| 959 | AGAUGUUGUG CUGAUGAGGCCGAAAGGCCGAA AUGCAGAAAG | 10 |
| 968 | CCUGGUAGGA CUGAUGAGGCCGAAAGGCCGAA AUGUUGUGGA | 11 |
| 1016 | AUCUCUCCGG CUGAUGAGGCCGAAAGGCCGAA AGGUUCAGCU | 12 |
| 1028 | AGGACGACUU CUGAUGAGGCCGAAAGGCCGAA AAUCUCUCCG | 13 |
| 1085 | UCAUCCAGUU CUGAUGAGGCCGAAAGGCCGAA AUCUUCCGGC | 14 |
| 1187 | UGAUGUUGUC CUGAUGAGGCCGAAAGGCCGAA AGCUCGCAGC | 15 |
| 1196 | UGAGGCGCAU CUGAUGAGGCCGAAAGGCCGAA AUGUUGUCGA | 16 |
| 1226 | CCAUGCCGUU CUGAUGAGGCCGAAAGGCCGAA ACGAUGCCGG | 17 |
| 1241 | CCCACUCGCU CUGAUGAGGCCGAAAGGCCGAA ACGUCCAUGC | 18 |
| 1270 | CACGGCGAUG CUGAUGAGGCCGAAAGGCCGAA ACUUGUCCCU | 19 |
| 1352 | GGUCCACCGG CUGAUGAGGCCGAAAGGCCGAA AGCCCGACCU | 20 |
| 1421 | CGGCCGCCAU CUGAUGAGGCCGAAAGGCCGAA ACGUCGGGUC | 21 |
| 1534 | CUUGCCUGGG CUGAUGAGGCCGAAAGGCCGAA ACUUCUCCUC | 22 |
| 1715 | UGCCUUCGAU CUGAUGAGGCCGAAAGGCCGAA AUGGUGUCGA | 23 |
| 1787 | CCACCUUCUU CUGAUGAGGCCGAAAGGCCGAA ACGUCCGCCG | 24 |

TABLE V A

GBSS Hairpin Ribozyme and Substrate Sequences

| nt. Position | Hairpin Ribozyme Sequence | Substrate |
|---|---|---|
| 48 | CUCCUGGC AGAA GUCG ACCAGAGAAACACACGUUGUGGUACAUUACCUGGUA | CGACA GCC GCCAGGAG |
| 129 | CCCUGCCG AGAA GUGC ACCAGAGAAACACACGUUGUGGUACAUUACCUGGUA | GCACC GCC CGGCAGGG |
| 468 | GUCGCCGA AGAA GCCG ACCAGAGAAACACACGUUGUGGUACAUUACCUGGUA | CGGCG GCC UCGGCGAC |
| 489 | CGGCGGCA AGAA GCCG ACCAGAGAAACACACGUUGUGGUACAUUACCUGGUA | CGGCG GCC UGCCGCCG |
| 496 | CCAUGGCC AGAA GCAG ACCAGAGAAACACACGUUGUGGUACAUUACCUGGUA | CUGCC GCC GGCCAUGG |
| 676 | UCUCCAGG AGAA GUGG ACCAGAGAAACACACGUUGUGGUACAUUACCUGGUA | CCACU GUU CCUGGAGA |
| 737 | UCCCUGUA AGAA GUUC ACCAGAGAAACACACGUUCUGGUACAUUACCUGGUA | GAACG GAC AUCAGGGA |
| 760 | GCAGGCUG AGAA GCAG ACCAGAGAAACACACGUUGUGGUACAUUACCUGGUA | CUGCG GUU CAGCCUGC |
| 1298 | GCCUCCAC AGAA GUCG ACCAGAGAAACACACGUUGUGGUACAUUACCUGGUA | CGACG GCC GUGGAGGC |
| 1427 | GGGAUGGC AGAA GCCA ACCAGAGAAACACACGUUGUGGUACAUUACCUGGUA | UGGCG GCC GCCAUCCC |
| 1601 | GCGAGCAC AGAA GCGC ACCAGAGAAACACACGUUGUGGUACAUUACCUGGUA | GCGCC GAC GUGCUCGC |

TABLE V A-continued

GBSS Hairpin Ribozyme and Substrate Sequences

| nt. Position | Hairpin Ribozyme Sequence | Substrate |
|---|---|---|
| 1638 | CUGGAUGA AGAA GCAG ACCAGAGAAACACACGUUGUGGUACAUUACCUGGUA | CUGCG GCC UCAUCCAG |
| 1746 | GACGCUGA AGAA GCCC ACCAGAGAAACACACGUUGUGGUACAUUACCUGGUA | GGGCC GCC UCAGCGUC |
| 1781 | UUCUUGAC AGAA GCCG ACCAGAGAAACACACGUUGUGGUACAUUACCUGGUA | CGGCG GAC GUCAAGAA |
| 2077 | AUAAACGA AGAA GCAU ACCAGAGAAACACACGUUGUGGUACAUUACCUGGUA | AUGCU GUU UCGUUUAU |

TABLE VB

GBSS Hairpin Ribozyme and Substrate Sequences

| nt. Position | Ribozyme Sequence | Substrate |
|---|---|---|
| 31 | GUCGCCUC AGAA GGUGGU ACCAGAGAAACACACGUUGUGGUACAUUACCUGGUA | ACCACCC GCC GAGGCGAC |
| 48 | CUCCUGGC AGAA GUCGCG ACCAGAGAAACACACGUUGUGGUACAUUACCUGGUA | CGCGACA GCC GCCAGGAG |
| 105 | GUGGACGG AGAA GUACAC ACCAGAGAAACACACGUUGUGGUACAUUACCUGGUA | GUGUACU GCU CCGUCCAC |
| 110 | CACUGGUG AGAA GAGCAG ACCAGAGAAACACACGUUGUGGUACAUUACCUGGUA | CUGCUCC GUC CACCAGUG |
| 129 | CCCUGCCG AGAA GUGCGC ACCAGAGAAACACACGUUGUGGUACAUUACCUGGUA | GCGCACC GCC CGGCAGGG |
| 142 | ACGAGAUG AGAA GCCCUG ACCAGAGAAACACACGUUGUGGUACAUUACCUGGUA | CAGGGCU GCU CAUCUCGU |
| 182 | GUGGCUAG AGAA GCCUAG ACCAGAGAAACACACGUUGUGGUACAUUACCUGGUA | CAUGGCG GCU CUAGCCAC |
| 199 | UUGCGACG AGAA GCGACG ACCAGAGAAACACACGUUGUGGUACAUUACCUGGUA | CGUCGCA GCU CGUCGCAA |
| 219 | GACGCCCA AGAA GGCGCG ACCAGAGAAACACACGUUGUGGUACAUUACCUGGUA | CGCGCCG GCC UGGGCGUC |
| 233 | GUGGACGC AGAA GGGACG ACCAGAGAAACACACGUUGUGGUACAUUACCUGGUA | CGUCCCG GAC GCGUCCAC |
| 249 | GGCGCCGC AGAA GAACGU ACCAGAGAAACACACGUUGUGGUACAUUACCUGGUA | ACGUUCC GCC GCGGCGCC |
| 283 | CCGACGCC AGAA GGCCCC ACCAGAGAAACACACGUUGUGGUACAUUACCUGGUA | GGGGCCG GAC GGCGUCGG |
| 316 | GCGCGCUG AGAA GAAUGC ACCAGAGAAACACACGUUGUGGUACAUUACCUGGUA | GCAUUCG GAC CAGCGCGC |
| 388 | CGACGAGC AGAA GGAACC ACCAGAGAAACACACGUUGUGGUACAUUACCUGGUA | GGUUCCC GUC GCUCGUCG |
| 468 | GUCGCCGA AGAA GCCGGU ACCAGAGAAACACACGUUGUGGUACAUUACCUGGUA | ACCGGCG GCC ACGGCGAC |
| 489 | CGGCGGCA AGAA GCCGAG ACCAGAGAAACACACGUUGUGGUACAUUACCUGGUA | CUCGGCG GCC UGCCGCCG |
| 493 | UGGCCGGC AGAA GGCCGC ACCAGAGAAACACACGUUGUGGUACAUUACCUGGUA | GCGGCCU GCC GCCGGCCA |
| 496 | CCAUGGCC AGAA GCAGGC ACCAGAGAAACACACGUUGUGGUACAUUACCUGGUA | GCCUGCC GCC GGCCAUGG |
| 676 | UCUCCAGG AGAA GUGGGU ACCAGAGAAACACACGUUGUGGUACAUUACCUGGUA | ACCCACU GUU CCUGGAGA |
| 725 | GUUCCAGC AGAA GGCCCG ACCAGAGAAACACACGUUGUGGUACAUUACCUGGUA | CGGGCCU GAC GCUGGAAC |
| 737 | UCCCUGUA AGAA GUUCCA ACCAGAGAAACACACGUUGUGGUACAUUACCUGGUA | UGGAACG GAC AUCAGGGA |
| 754 | UGAACCGC AGAA GGUUGU ACCAGAGAAACACACGUUGUGGUACAUUACCUGGUA | ACAACCA GCU GCGGUUCA |
| 760 | GCAGGCUG AGAA GCAGCU ACCAGAGAAACACACGUUGUGGUACAUUACCUGGUA | AGCUGCG GUU CAGCCUGC |
| 765 | GCAUAGCA AGAA GAACCG ACCAGAGAAACACACGUUGUGGUACAUUACCUGGUA | CGGUUCA GCC UGCUAUGC |
| 834 | CCCGUAUG AGAA GGAGAA ACCAGAGAAACACACGUUGUGGUACAUUACCUGGUA | UUCUCCG GAC CAUACGGG |
| 882 | CGAGAGAG AGAA GGUGUG ACCAGAGAAACACACGUUGUGGUACAUUACCUGGUA | CACACCG GCC CUCUCUCG |
| 916 | UGCCGUGG AGAA GGUAGU ACCAGAGAAACACACGUUGUGGUACAUUACCUGGUA | ACUACCA GUC CCACGGCA |
| 947 | AUGCAGAA AGAA GUCUUU ACCAGAGAAACACACGUUGUGGUACAUUACCUGGUA | AAAGACC GCU UUCUGCAU |

TABLE VB-continued

GBSS Hairpin Ribozyme and Substrate Sequences

| nt. Position | Ribozyme Sequence | Substrate |
|---|---|---|
| 982 | AGAAGGCG AGAA GGCCCU ACCAGAGAAACACACGUUGUGGUACAUUACCUGGUA | AGGGCCG GUU CGCCUUCU |
| 995 | UCCGGGUA AGAA GAGAAG ACCAGAGAAACACACGUUGUGGUACAUUACCUGGUA | CUUCUCC GAC UACCCGGA |
| 1134 | GUAGUAGG AGAA GACGGU ACCAGAGAAACACACGUUGUGGUACAUUACCUGGUA | ACCGUCA GCC CCUACUAC |
| 1298 | GCCUCCAC AGAA GUCGAC ACCAGAGAAACACACGUUGUGGUACAUUACCUGGUA | GUCGACG GCC GUGGAGGC |
| 1372 | ACGCCACC AGAA GGAUGU ACCAGAGAAACACACGUUGUGGUACAUUACCUGGUA | ACAUCCC GCU GGUGGCGU |
| 1415 | GCCAUGAC AGAA GGUCCC ACCAGAGAAACACACGUUGUGGUACAUUACCUGGUA | GGGACCC GAC GUCAUGGC |
| 1427 | GGGAUGGC AGAA GCCAUG ACCAGAGAAACACACGUUGUGGUACAUUACCUGGUA | CAUGGCG GCC GCCAUCCC |
| 1441 | UCUCCAUG AGAA GCGGGA ACCAGAGAAACACACGUUGUGGUACAUUACCUGGUA | UCCCGCA GCU CAUGGAGA |
| 1468 | GCAGAACG AGAA GCACGU ACCAGAGAAACACACGUUGUGGUACAUUACCUGGUA | ACGUGCA GAU CGUUCUGC |
| 1477 | CCGUGCCC AGAA GAACGA ACCAGAGAAACACACGUUGUGGUACAUUACCUGGUA | UCGUUCU GCU GGGCACGG |
| 1601 | GCGAGCAC AGAA GCGCCG ACCAGAGAAACACACGUUGUGGUACAUUACCUGGUA | CGGCGCC GAC GUGCUCGC |
| 1620 | CUCGAAGC AGAA GGUGAC ACCAGAGAAACACACGUUGUGGUACAUUACCUGGUA | GUCACCA GCC GCUUCGAG |
| 1623 | GGGCACGA AGAA GCUGGU ACCAGAGAAACACACGUUGUGGUACAUUACCUGGUA | ACCAGCC GCU UCGAGCCC |
| 1638 | CUGGAUGA AGAA GCAGGG ACCAGAGAAACACACGUUGUGGUACAUUACCUGGUA | CCCUGCG GCC UCAUCCAG |
| 1648 | UCCCCUGC AGAA GGAUGA ACCAGAGAAACACACGUUGUGGUACAUUACCUGGUA | UCAUCCA GCU GCAGGGGA |
| 1746 | GACGCUGA AGAA GCCCAU ACCAGAGAAACACACGUUGUGGUACAUUACCUGGUA | AUGGGCC GCC UCAGCGUC |
| 1781 | UUCUUGAC AGAA GCCGGC ACCAGAGAAACACACGUUGUGGUACAUUACCUGGUA | GCCGGCG GAC GUCAAGAA |
| 1918 | CGAGGCUG AGAA GCACGU ACCAGAGAAACACACGUUGUGGUACAUUACCUGGUA | ACGUGCU GCU CAGCCUCG |
| 1923 | GACCCCGA AGAA GAGCAG ACCAGAGAAACACACGUUGUGGUACAUUACCUGGUA | CUGCUCA GCC UCGGGGUC |
| 1975 | CCUUGGCG AGAA GCGCGA ACCAGAGAAACACACGUUGUGGUACAUUACCUGGUA | UCGCGCC GCU CGCCAAGG |
| 2014 | GGCCUGCA AGAA GAACUC ACCAGAGAAACACACGUUGUGGUACAUUACCUGGUA | GAGUUCC GCC UGCAGGCC |
| 2029 | CGCGCGAG AGAA GGGGGC ACCAGAGAAACACACGUUGUGGUACAUUACCUGGUA | GCCCCCU GAU CUCGCGCG |
| 2077 | AUAAACGA AGAA GCAUAU ACCAGAGAAACACACGUUGUGGUACAUUACCUGGUA | AUAUGCU GUU UVHUUUAU |
| 2113 | CACAAGCA AGAA GCUACA ACCAGAGAAACACACGUUGUGGUACAUUACCUGGUA | UGUAGCU GCU UGCUUGUG |
| 2207 | AAUUACCG AGAA GUACUU ACCAGAGAAACACACGUUGUGGUACAUUACCUGGUA | AAGUACC GAU CGGUAAUU |

TABLE VI

Delta-9 Desaturase HH Ribozyme Target Sequences

| nt. Position | Substrate |
|---|---|
| 13 | CGCGCCCUC UGCCGCUU |
| 21 | CUGCCGCUU GUUCGUUC |
| 24 | CCGCUUGUU CGUUCCUC |
| 25 | CGCUUGUUC GUUCCUCG |
| 28 | UUGUUCGUU CCUCGCGC |
| 29 | UGUUCGUUC CUCGCGCU |
| 32 | UCGUUCCUC GCGCUCGC |
| 38 | CUCGCGCUC GCCACCAG |
| 63 | ACACACAUC CCAAUCUC |
| 69 | AUCCCAAUC UCGCGAGG |
| 71 | CCCAAUCUC GCGAGGGC |
| 92 | AGCAGGGUC UGCGGCGG |
| 117 | GCCGCGCUU CCGGCUCC |
| 118 | CCGCGCUUC CGGCUCCC |
| 124 | UUCCGGCUC CCCUUCCC |
| 129 | GCUCCCCUU CCCAUUGG |
| 130 | CUCCCCUUC CCAUUGGC |
| 135 | CUUCCCAUU GGCUCCA |
| 141 | AUUGGCCUC CACGAUGG |
| 154 | AUGGCGCUC CGCCUCAA |
| 160 | CUCCGCCUC AACGACGU |
| 169 | AACGACGUC GCGCUCUG |
| 175 | GUCGCGCUC UGCCUCUC |
| 181 | CUCUGCCUC UCCCCGCC |
| 183 | CUGCCUCUC CCCGCCGC |
| 193 | CCGCCGCUC GCCGCCCG |

TABLE VI-continued

Delta-9 Desaturase HH Ribozyme Target Sequences

| nt. Position | Substrate |
|---|---|
| 228 | CGGCAGGUU CGUCGCCG |
| 229 | GGCAGGUUC GUCGCCGU |
| 232 | AGGUUCGUC GCCGUCGC |
| 238 | GUCGCCGUC GCCUCCAU |
| 243 | CGUCGCCUC CAUGACGU |
| 252 | CAUGACGUC CGCCGUCU |
| 259 | UCCGCCGUC UCCACCAA |
| 261 | CGCCGUCUC CACCAAGG |
| 271 | ACCAAGGUC GAGAAUAA |
| 278 | UCGAGAAUA AGAAGCCA |
| 288 | GAAGCCAUU UGCUCCUC |
| 289 | AAGCCAUUU GCUCCUCC |
| 293 | CAUUUGCUC CUCCAAGG |
| 296 | UUGCUCCUC CAAGGGAG |
| 307 | AGGGAGGUA CAUGUCCA |
| 313 | GUACAUGUC CAGGUUAC |
| 319 | GUCCAGGUU ACACAUUC |
| 320 | UCCAGGUUA CACAUUCA |
| 326 | UUACACAUU CAAUGCCA |
| 327 | UACACAUUC AAUGCCAC |
| 338 | UGCCACCUC ACAAGAUU |
| 346 | CACAAGAUU GAAAUUUU |
| 352 | AUUGAAAUU UUCAAGUC |
| 353 | UUGAAAUUU UCAAGUCG |
| 354 | UGAAAUUUU CAAGUCGC |
| 355 | GAAAUUUUC AAGUCGCU |
| 360 | UUUCAAGUC GCUUGAUG |
| 364 | AAGUCGCUU GAUGAUUG |
| 371 | UUGAUGAUU GGGCAUGA |
| 377 | AUUGGGCUA GAGAUAAU |
| 383 | CUAGAGAUA AUAUCUUG |
| 386 | GAGAUAAUA UCUUGACG |
| 388 | GAUAAUAUC UUGACGCA |
| 390 | UAAUAUCUU GACGCAUC |
| 398 | UGACGCAUC UCAAGCCA |
| 400 | ACGCAUCUC AAGCCAGU |
| 409 | AAGCCAGUC GAGAAGUG |
| 419 | AGAAGUGUU GGCAGCCA |
| 434 | CACAGGAUU UCCUCCCG |
| 435 | ACAGGAUUU CCUCCCGG |
| 436 | CAGGAUUUC CUCCCGGA |
| 439 | GAUUUCCUC CCGGACCC |
| 453 | CCCAGCAUC UGAAGGAU |
| 462 | UGAAGGAUU UCAUGAUG |
| 463 | GAAGGAUUU CAUGAUGA |
| 464 | AAGGAUUUC AUGAUGAA |
| 475 | GAUGAAGUU AAGGAGCU |
| 476 | AUGAAGUUA AGGAGCUC |
| 484 | AAGGAGCUC AGAGAACG |
| 505 | AAGGAAAUC CCUGAUGA |
| 515 | CUGAUGAUU AUUUUGUU |
| 516 | UGAUGAUUA UUUUGUUU |
| 518 | AUGAUUAUU UUGUUUGU |
| 519 | UGAUUAUUU UGUUUGUU |
| 520 | GAUUAUUUU GUUUGUUU |
| 523 | UAUUUUGUU UGUUUGGU |
| 524 | AUUUUGUUU GUUUGGUG |
| 527 | UUGUUUGUU UGGUGGGA |
| 528 | UGUUUGUUU GGUGGGAG |
| 544 | GACAUGAUU ACCGAGGA |
| 545 | ACAUGAUUA CCGAGGAA |
| 557 | AGGAAGCUC UACCAACA |
| 559 | GAAGCUCUA CCAACAUA |
| 567 | ACCAACAUA CCAGACUA |
| 575 | ACCAGACUA UGCUUAAC |
| 580 | ACUAUGCUU AACACCCU |
| 581 | CUAUGCUUA ACACCCUC |
| 589 | AACACCCUC GACGGUGU |
| 598 | GACGGUGUC AGAGAUGA |
| 637 | UGGGCUGUU UGGACGAG |
| 638 | GGGCUGUUU GGACGAGG |
| 680 | AUGGUGAUC UGCUCAAC |
| 685 | CAACAAGUA UAUGUACC |
| 693 | CAACAAGUA UAUGUACC |
| 695 | ACAAGUAUA UGUACCUC |
| 699 | GUAUAUGUA CCUCACUG |
| 703 | AUGUACCUC ACUGGGAG |
| 719 | GGGUGGAUA UGAGGCAG |
| 730 | AGGCAGAUU GAGAAGAC |
| 742 | AAGACAAUU CAGUAUCU |
| 743 | AGACAAUUC AGUAUCUU |
| 747 | AAUUCAGUA UCUAUUG |
| 749 | UUCAGUAUC UUAUUGGC |
| 751 | CAGUAUCUU AUUGGCUC |
| 752 | AGUAUCUUA UUGGCUCU |
| 754 | UAUCUUAUU GGCUCUGG |
| 759 | UAUUGGCUC UGGAAUGG |
| 770 | GAAUGGAUC CUAGGACU |
| 773 | UGGAUCCUA GGACUGAG |
| 785 | CUGAGAAUA UCCUUAUU |
| 788 | AGAAUAAUC CUUAUCUU |
| 791 | AUAAUCCUU AUCUUGGU |
| 792 | UAAUCCUUA UCUUGGUU |
| 794 | AUCCUUAUC UUGGUUUC |
| 796 | CCUUAUCUU GGUUUCAU |
| 800 | AUCUUGGUU UCAUCUAC |
| 801 | UCUUGGUUU CAUCUACA |
| 802 | CUUGGUUUC AUCUACAC |
| 805 | GGUUUCAUC UACACCUC |
| 807 | UUUCAUCUA CACCUCCU |
| 813 | CUACACCUC CUUCCAAG |
| 816 | CACCUCCUU CCAAGAGC |
| 817 | ACCUCCUUC CAAGAGCG |
| 834 | GGCGACCUU CAUCUCAC |
| 835 | GCGACCUUC AUCUCACA |
| 838 | ACCUUCAUC UCACACGG |
| 840 | CUUCAUCUC ACACGGGA |
| 857 | ACACUGCUC GUCACGCC |
| 860 | CUGCUCGUC ACGCCAAG |
| 873 | CAAGGACUU UGGCGACU |
| 874 | AAGGACUUU GGCGACUU |
| 882 | UGGCGACUU AAAGCUUG |
| 883 | GGCGACUUA AAGCUUGC |
| 889 | UUAAAGCUU GCACAAAU |
| 898 | GCACAAAUC UGCGGCAU |
| 907 | UGCGGCAUC AUCGCCUC |
| 910 | GGCAUCAUC GCCACAGA |
| 915 | CAUCGCCUC AGAUGAGA |
| 942 | AACUGCGUA CACCAAGA |
| 952 | ACCAAGAUC GUGGAGAA |
| 966 | GAAGCUGUU UGAGAUCG |
| 967 | AAGCUGUUU GAGAUCGA |
| 973 | UUUGAGAUC GACCCUGA |
| 986 | CUGAUGGUA CCGUGGUC |
| 994 | ACCGUGGUC GCUCUGGC |
| 998 | UGGUCGCUC UGGCUGAC |
| 1024 | AAGAAGAUC UCAAUGCC |
| 1026 | GAAGAUCUC AAUGCCUG |
| 1047 | CCUGAUGUU UGACGGGC |
| 1048 | CUGAUGUUU GACGGGCA |
| 1071 | CAAGCUGUU CGAGCACU |
| 1072 | AAGCUGUUC GAGCACUU |
| 1080 | CGAGCACUU CUCCAUGG |
| 1081 | GAGCACUUC UCCAUGGU |
| 1083 | GCACUUCUC CAUGGUCG |
| 1090 | UCCAUGGUC GCGCAGAG |
| 1102 | CAGAGGCUU GGCGUUUA |
| 1108 | CUUGGCGUU UACACCGC |
| 1109 | UUGGCGUUU ACACCGCC |
| 1110 | UGGCGUUUA CACCGCCA |
| 1125 | CAGGGACUA CGCCGACA |
| 1135 | GCCGACAUC UCGAGUU |
| 1138 | GACAUCCUC GAGUUCCU |
| 1143 | CCUCGAGUU CCUCGUCG |
| 1144 | CUCGAGUUC CUCGUCGA |
| 1147 | GAGUUCCUC GUCGACAG |
| 1150 | UUCCUCGUC GACAGGUG |
| 1181 | UGACUGGUC UGUCGGGU |

TABLE VI-continued

Delta-9 Desaturase HH Ribozyme Target Sequences

| nt. Position | Substrate |
|---|---|
| 1185 | UGGUCUGUC GGGUGAAG |
| 1212 | GCAGGACUA CCUUUGCA |
| 1216 | GACUACCUU UGCACCCU |
| 1217 | ACUACCUUU GCACCCUU |
| 1225 | UGCACCCUU GCUUCAAG |
| 1229 | CCCUUGCUU CAAGAAUC |
| 1230 | CCUUGCUUC AAGAAUCA |
| 1237 | UCAAGAAUC AGGAGGCU |
| 1292 | CGCUGCCUU UCAGCUGG |
| 1293 | GCUGCCUUU CAGCUGGG |
| 1294 | CUGCCUUUC AGCUGGGU |
| 1303 | AGCUGGGUA UACGGUAG |
| 1305 | CUGGGUAUA CGGUAGGG |
| 1310 | UAUACGGUA GGGACGUC |
| 1318 | AGGGACGUC CAACUGUG |
| 1331 | UGUGAGAUC GGAAACCU |
| 1348 | GCUGCGGUC UGCUUAGA |
| 1353 | GGUCUGCUU AGACAAGA |
| 1354 | GUCUGCUUA GACAAGAC |
| 1372 | UGCUGUGUC UGCGUUAC |
| 1378 | GUCUGCGUU ACAUAGGU |
| 1379 | UCUGCGUUA CAUAGGUC |
| 1383 | CGUUACAUA GGUCUCCA |
| 1387 | ACAUAGGUC UCCAGGUU |
| 1389 | AUAGGUCUC CAGGUUUU |
| 1395 | CUCCAGGUU UUGAUCAA |
| 1396 | UCCAGGUUU UGAUCAAA |
| 1397 | CCAGGUUUU GAUCAAAU |
| 1401 | GUUUUGAUC AAAUGGUC |
| 1409 | CAAAUGGUC CCGUGUCG |
| 1416 | UCCCGUGUC GUCUUAUA |
| 1419 | CGUGUCGUC UUAUAGAG |
| 1421 | UGUCGUCUU AUAGAGCG |
| 1422 | GUCGUCUUA UAGAGCGA |
| 1424 | CGUCUUAUA GAGCGAUA |
| 1432 | AGAGCGAUA GGAGAACG |
| 1444 | GAACGUGUU GGUCUGUG |
| 1448 | GUGUUGGUC UGUGGUGU |
| 1457 | UGUGGUGUA GCUUUGUU |
| 1461 | GUGUAGCUU UGUUUUUA |
| 1462 | UGUAGCUUU GUUUUUAU |
| 1465 | AGCUUUGUU UUUAUUUU |
| 1466 | GCUUUGUUU UUAUUUUG |
| 1467 | CUUUGUUUU UAUUUUGU |
| 1468 | UUUGUUUUU AUUUUGUA |
| 1469 | UUGUUUUUA UUUUGUAU |
| 1471 | GUUUUAUUU UGUAUUUU |
| 1472 | UUUUAUUUU GUAUUUUU |
| 1473 | UUUUAUUUU GUAUUUUU |
| 1476 | UAUUUUGUA UUUUUCUG |
| 1478 | UUUUGUAUU UUUGUGCU |
| 1479 | UUUGUAUUU UUGUGCUU |
| 1480 | UUGUAUUUU UVUGCUUU |
| 1481 | UGUAUUUUU CUGCUUUG |
| 1482 | GUAUUUUUC UGCUUUGA |
| 1487 | UUUCUGCUU UGAUGUAC |
| 1488 | UUCUGCUUU GAUGAUCA |
| 1494 | UUUGAUGUA CAACCGUU |
| 1546 | CAUGCCGUA CUUUGUCU |
| 1549 | GCCGUACUU UGUCUGUC |
| 1550 | CCGUACUUU GUCUGUCG |
| 1553 | UACUUUGUC UGUCGCUG |
| 1557 | UUGUCUGUC GCUGGCGG |
| 1571 | CGGUGUGUU UCGGUAUG |
| 1572 | GGUGUGUUU CGGUAUGU |
| 1573 | GUGUGUUUC GGUAUGUU |
| 1577 | GUUUCGGUA UGUUAUUU |
| 1581 | CGGUAUGUU AUUUGAGU |
| 1582 | GGUAUGUUA UUUGAGUU |
| 1584 | UAUGUUAUU UGAGUUGC |
| 1585 | AUGUUAUUU GAGUUGCU |
| 1590 | AUUUGAGUU GCUCAGAU |
| 1594 | GAGUUGCUC AGAUCUGU |
| 1599 | GCUCAGAUC UGUUAAAA |
| 1603 | AGAUCUGUU AAAAAAAA |
| 1604 | GAUCUGUUA AAAAAAAA |

TABLE VII

Delta-9 Desaturase HH Ribozyme Sequences

| nt. Position | Ribozyme sequence |
|---|---|
| 13 | AAGCGGCA CUGAUGA X GAA AGGGCGCG |
| 21 | GAACGAAC CUGAUGA X GAA AGCGGCAG |
| 24 | GAGGAACG CUGAUGA X GAA ACAAGCGG |
| 25 | CGAGGAAC CUGAUGA X GAA AACAAGCG |
| 28 | GCGCGAGG CUGAUGA X GAA ACGAACAA |
| 29 | AGCGCGAG CUGAUGA X GAA AACGAACA |
| 32 | GCGAGCGC CUGAUGA X GAA AGGAACGA |
| 38 | CUGGUGGC CUGAUGA X GAA AGCGCGAG |
| 63 | GAGAUUGG CUGAUGA X GAA AUGUGUGU |
| 69 | CCUCGCGA CUGAUGA X GAA AUUGGGAU |
| 71 | GCCCUCGC CUGAUGA X GAA AGAUUGGG |
| 92 | CCGCCGCA CUGAUGA X GAA ACCCUGCU |
| 117 | GGAGCCGG CUGAUGA X GAA AGCGCGGC |
| 118 | GGGAGCCG CUGAUGA X GAA AAGCGCGG |
| 124 | GGGAAGGG CUGAUGA X GAA AGCCGGAA |
| 129 | CCAAUGGG CUGAUGA X GAA AGGGGAGC |
| 130 | GCCAAUGG CUGAUGA X GAA AAGGGGAG |
| 135 | UGGGAGCC CUGAUGA X GAA AUGGGAAG |
| 141 | CCAUCGUG CUGAUGA X GAA AGGCCAAU |
| 154 | UUGAGGCG CUGAUGA X GAA AGCGCCAU |
| 160 | ACGUCGUU CUGAUGA X GAA AGGCGGAG |
| 169 | CAGAGCGC CUGAUGA X GAA ACGUCGUU |
| 175 | GAGAGGCA CUGAUGA X GAA AGCGCGAC |
| 181 | GGCGGGGA CUGAUGA X GAA AGGCAGAG |
| 183 | GCGGCGGG CUGAUGA X GAA AGAGGCAG |
| 193 | CGGGCGGC CUGAUGA X GAA AGCGGCGG |
| 228 | CGGCGACG CUGAUGA X GAA ACCUGCCG |
| 229 | ACGGCGAC CUGAUGA X GAA AACCUGCC |
| 232 | GCGACGGC CUGAUGA X GAA ACGAACCU |
| 238 | AUGGAGGC CUGAUGA X GAA ACGGCGAC |
| 243 | ACGUCAUG CUGAUGA X GAA AGGCGACG |
| 252 | AGACGGCG CUGAUGA X GAA ACGUCAUG |
| 259 | UUGGUGGA CUGAUGA X GAA ACGGCGGA |
| 261 | CCUGGGUG CUGAUGA X GAA AGACGGCG |
| 271 | UUAUUCUC CUGAUGA X GAA ACCUUGGU |
| 278 | UGGCUUCU CUGAUGA X GAA AUUCUCGA |
| 288 | GAGGAGCA CUGAUGA X GAA AUGGCUUC |
| 289 | GGAGGAGC CUGAUGA X GAA AAUGGCUU |
| 293 | CCUUGGAG CUGAUGA X GAA AGCAAAUG |
| 296 | CUCCCUUG CUGAUGA X GAA AGGAGCAA |
| 307 | UGGACAUG CUGAUGA X GAA ACCUCCCU |
| 313 | GUAACCUG CUGAUGA X GAA ACAUGUAC |
| 319 | GAAUGUGU CUGAUGA X GAA ACCUGGAC |
| 320 | UGAAUGUG CUGAUGA X GAA AACCUGGA |
| 326 | UGGCAUUG CUGAUGA X GAA AUGUGUAA |
| 327 | GUGGCAUU CUGAUGA X GAA AAUGUGUA |
| 338 | AAUCUUGU CUGAUGA X GAA AGGUGGCA |
| 346 | AAAAUUUC CUGAUGA X GAA AUCUUGUG |
| 352 | GACUUGAA CUGAUGA X GAA AUUUCAAU |
| 353 | CGACUUGA CUGAUGA X GAA AAUUUCAA |
| 354 | GCGACUUG CUGAUGA X GAA AAAUUUCA |
| 355 | AGCGACUU CUGAUGA X GAA AAAAUUUC |
| 360 | CAUCAAGC CUGAUGA X GAA ACUUGAAA |
| 364 | CAAUCAUC CUGAUGA X GAA AGCGACUU |
| 371 | UCUAGCCC CUGAUGA X GAA AUCAUCAA |
| 377 | AUUAUCUC CUGAUGA X GAA AGCCCAAU |
| 383 | CAAGAUAU CUGAUGA X GAA AUCUCUAG |
| 386 | CGUCAAGA CUGAUGA X GAA AUUAUCUC |
| 388 | UGCGUCAA CUGAUGA X GAA AUAUUAUC |
| 390 | GAUGCGUC CUGAUGA X GAA AGAUAUUA |
| 398 | UGGCUUGA CUGAUGA X GAA AUGCGUCA |

TABLE VII-continued

Delta-9 Desaturase HH Ribozyme Sequences

| nt. Position | Ribozyme sequence |
|---|---|
| 400 | ACUGGCUU CUGAUGA X GAA AGAUGCGU |
| 409 | CACUUCUC CUGAUGA X GAA ACUGGCUU |
| 419 | UGGCUGCC CUGAUGA X GAA ACACUUCU |
| 434 | CGGGAGGA CUGAUGA X GAA AUCCUGUG |
| 435 | CCGCGAGG CUGAUGA X GAA AAUCCUGU |
| 436 | UCCGGGAG CUGAUGA X GAA AAAUCCUG |
| 439 | GGGUCCGG CUGAUGA X GAA AGGAAAUC |
| 453 | AUCCUUCA CUGAUGA X GAA AUGCUGGG |
| 462 | CAUCAUGA CUGAUGA X GAA AUCCUUCA |
| 463 | UCAUCAUG CUGAUGA X GAA AAUCCUUC |
| 464 | UUCAUCAU CUGAUGA X GAA AAAUCCUU |
| 475 | AGCUCCUU CUGAUGA X GAA ACUUCAUC |
| 476 | GAGCUCCU CUGAUGA X GAA AACUUCAU |
| 484 | CGUUCUCU CUGAUGA X GAA AGCUCCUU |
| 505 | UCAUCAGG CUGAUGA X GAA AUUUCCUU |
| 515 | AACAAAAU CUGAUGA X GAA AUCAUCAG |
| 516 | AAACAAAA CUGAUGA X GAA AAUCAUCA |
| 518 | ACAAACAA CUGAUGA X GAA AUAAUCAU |
| 519 | AACAACAA CUGAUGA X GAA AAUAAUCA |
| 520 | AAACAAAC CUGAUGA X GAA AAAUAAUC |
| 523 | ACCAAACA CUGAUGA X GAA ACAAAAUA |
| 524 | CACCAAAC CUGAUGA X GAA AACAAAAU |
| 527 | UCCCACCA CUGAUGA X GAA ACAAACAA |
| 528 | CUCCCACC CUGAUGA X GAA AACAAACA |
| 544 | UCCUCGGU CUGAUGA X GAA AUCAUGUC |
| 545 | UUCCUCGG CUGAUGA X GAA AAUCAUGU |
| 557 | UGUUGGUA CUGAUGA X GAA AGCUUCCU |
| 559 | UAUCUUGG CUGAUGA X GAA AGAGCUUC |
| 567 | UAGUCUGG CUGAUGA X GAA AUGUUGGU |
| 575 | GUUAAGCA CUGAUGA X GAA AGUCUGGU |
| 580 | AGGGUGUU CUGAUGA X GAA AGCAUAGU |
| 581 | GAGGGUGU CUGAUGA X GAA AAGCAUAG |
| 589 | ACACCGUC CUGAUGA X GAA AGGGUGUU |
| 598 | UCAUCUCU CUGAUGA X GAA ACACCGUC |
| 637 | CUCGUCCA CUGAUGA X GAA ACAGCCCA |
| 638 | CCUCGUCC CUGAUGA X GAA AACAGCCC |
| 680 | GUUGAGCA CUGAUGA X GAA AUCACCAU |
| 685 | UAGUUGUU CUGAUGA X GAA AGCAGAUC |
| 693 | GGUACAUA CUGAUGA X GAA ACUUGUUG |
| 695 | GAGGUACA CUGAUGA X GAA AUACUUGU |
| 699 | CAGUGAGG CUGAUGA X GAA ACAUAUAC |
| 703 | CUCCCAGU CUGAUGA X GAA AGGUACAU |
| 719 | CUGCCUCA CUGAUGA X GAA AUCCACCC |
| 730 | GUCUUCUC CUGAUGA X GAA AUCUGCCU |
| 742 | AGAUACUG CUGAUGA X GAA AUUGUCUU |
| 743 | AAGAUACU CUGAUGA X GAA AAUUGUCU |
| 747 | CAAUAAGA CUGAUGA X GAA ACUGAAUU |
| 749 | GCCAAUAA CUGAUGA X GAA AUACUGAA |
| 751 | GAGCCAAU CUGAUGA X GAA AGAUACUG |
| 752 | AGAGCCAA CUGAUGA X GAA AAGAUACU |
| 754 | CCAGAGCC CUGAUGA x GAA AUAAGAUA |
| 759 | CCAUUCCA CUGAUGA X GAA AGCCAAUA |
| 770 | AGUCCUAG CUGAUCA X GAA AUCCAUUC |
| 773 | CUCAGUCC CUGAUGA X GAA AGGAUCCA |
| 785 | AUAAGGAU CUGAUGA X GAA AUUCUCAG |
| 788 | AAGAUAAG CUGAUGA X GAA AUUAUUCU |
| 791 | ACCAAGAU CUGAUGA X GAA AGGAUUAU |
| 792 | AACCAAGA CUGAUGA X GAA AAGGAUUA |
| 794 | GAAACCAA CUGAUGA X GAA AUAAGGAU |
| 796 | AUGAAACC CUGAUGA X GAA AGAUAAGG |
| 800 | GUAGAUGA CUGAUGA X GAA ACCAAGAU |
| 801 | UGUAGAUG CUGAUGA X GAA AACCAAGA |
| 802 | GUGUAGAU CUGAUGA X GAA AAAGCAAG |
| 805 | GAGGUGUA CUGAUGA X GAA AUGAAACC |
| 807 | AGGAGGUG CUGAUGA X GAA AGAUGAAA |
| 813 | CUUGGAAG CUGAUGA X GAA AGGUGUAG |
| 816 | GCUCUUGG CUGAUGA X GAA AGGAGGUG |
| 817 | CGCUCUUG CUGAUGA X GAA AAGGAGGU |
| 834 | GUGAGAUG CUGAUGA X GAA AGGUCGCC |
| 835 | UGUGAGAU CUGAUGA X GAA AAGGUCGC |
| 838 | CCGUGUGA CUGAUGA X GAA AUGAAGGU |
| 840 | UCCCGUGU CUGAUGA X GAA AGAUGAAG |
| 857 | GGCGUGAC CUGAUGA X GAA AGCAGUGU |
| 860 | CUUGGCGU CUGAUGA X GAA ACGAGCAG |

TABLE VII-continued

Delta-9 Desaturase HH Ribozyme Sequences

| nt. Position | Ribozyme sequence |
|---|---|
| 873 | AGUCGCCA CUGAUGA X GAA AGUGCUUG |
| 874 | AAGUCGCC CUGAUGA X GAA AAGUCCUU |
| 882 | CAAGCUUU CUGAUGA X GAA AGUCGCCA |
| 883 | GCAAGCUU CUGAUGA X GAA AAGUCGCC |
| 889 | AUUUGUGC CUGAUGA X GAA AGCUUUAA |
| 898 | AUGCCGCA CUGAUGA X GAA AUUUGUGC |
| 907 | GAGGCGAU CUGAUGA X GAA AUGCCGCA |
| 910 | UCUGAGGC CUGAUGA X GAA AUGAUGCC |
| 915 | UCUCAUCU CUGAUGA X GAA AGGCGAUG |
| 942 | UCUUGGUG CUGAUGA X GAA ACGCAGUU |
| 952 | UUCUCCAC CUGAUGA X GAA AUCUUGGU |
| 966 | CGAUCUCA CUGAUGA X GAA ACAGCUUC |
| 967 | UCGAUCUC CUGAUGA X GAA AACAGCUU |
| 973 | UCAGGGUC CUGAUGA X GAA AUCUCAAA |
| 986 | GACCACGG CUGAUGA X GAA ACCAUCAG |
| 994 | GCCAGAGC CUGAUGA X GAA ACCACGGU |
| 998 | GUCAGCCA CUGAUGA X GAA AGCGACCA |
| 1024 | GGCAUUGA CUGAUGA X GAA AUCUUCUU |
| 1026 | CAGGCAUU CUGAUGA X GAA AGAUCUUC |
| 1047 | GCCCGUCA CUGAUGA X GAA ACAUCAGG |
| 1048 | UGCCCGUC CUGAUGA X GAA AACAUCAG |
| 1071 | AGUGCUCG CUGAUGA X GAA ACAGCUUG |
| 1072 | AAGUGCUC CUGAUGA X GAA AACAGCUU |
| 1080 | CCAUGGAG CUGAUGA X GAA AGUGCUCG |
| 1081 | ACCAUGGA CUGAUGA X GAA AAGUGCUC |
| 1083 | CGACCAUG CUGAUGA X GAA AGAAGUGC |
| 1090 | CUCUGCGG CUGAUGA X GAA ACCAUGGA |
| 1102 | UAAACGCC CUGAUGA X GAA AGCCUCUG |
| 1108 | GCGGUGUA CUGAUGA X GAA ACGCAAGG |
| 1109 | GGCGGUGU CUGAUGA X GAA AACGCCAA |
| 1110 | UGGCGGUG CUGAUGA X GAA AAACGCCA |
| 1125 | UGUCGGCG CUGAUGA X GAA AGUCCCUG |
| 1135 | AACUCGAG CUGAUGA X GAA AUGUCGGC |
| 1138 | AGGAACUC CUGAUGA X GAA AGGAUGUC |
| 1143 | CGACGAGG CUGAUGA X GAA ACUCCAGG |
| 1144 | UCGACGAG CUGAUGA X GAA AACUCGAG |
| 1147 | CUGUCGAC CUGAUGA X CAA AGGAACUC |
| 1150 | CACCUGUC CUGAUGA X GAA ACGAGGAA |
| 1181 | ACCCGACA CUGAUGA X GAA ACAGUCA |
| 1185 | CUUCACCC CUGAUGA X GAA ACAGACCA |
| 1212 | UGCAAAGG CUGAUGA X GAA AGUCCUGC |
| 1216 | AGGGUGCA CUGAUGA X GAA AGGUAGUC |
| 1217 | AAGGGUGC CUGAUGA X GAA AAGGUAGU |
| 1225 | CUUGAAGC CUGAUGA X GAA AGGGUGCA |
| 1229 | GAUUCUUG CUGAUGA X GAA AGCAAGGG |
| 1230 | UGAUUCUU CUGAUGA X GAA AAGCAAGG |
| 1237 | AGCCUCCU CUGAUGA X GAA AUUCUUGA |
| 1292 | CCAGCUGA CUGAUGA X GAA AGGCAGCG |
| 1293 | CCCAGCUG CUGAUGA X GAA AAGGCAGC |
| 1294 | ACCCAGCU CUGAUGA X GAA AAAGGCAG |
| 1303 | CUACCGUA CUGAUGA X GAA ACCCAGCU |
| 1305 | CCCUACCG CUGAUGA X GAA AUACCCAG |
| 1310 | GACGUCCC CUGAUGA X GAA ACCGUAUA |
| 1318 | CACAGUUG CUGAUGA X GAA ACGUCCCU |
| 1331 | AGGUUUCC CUGAUGA X GAA AUCUCACA |
| 1348 | UCUAAGCA CUGAUGA X GAA ACCGCAGC |
| 1353 | UCUUGUCU CUGAUGA X GAA AGCAGACC |
| 1354 | GUCUUGUC CUGAUGA X GAA AAGCAGAC |
| 1372 | GUAACGCA CUGAUGA X GAA ACACAGCA |
| 1378 | ACCUAUGU CUGAUGA X GAA ACGCAGAC |
| 1379 | GACCUAUG CUGAUGA x GAA AACGCAGA |
| 1383 | UGGAGACC CUGAUGA X GAA AUGUAACG |
| 1387 | AACCUGGA CUGAUGA X GAA ACCUAUGU |
| 1389 | AAAACCUG CUGAUGA X GAA AGACCUAU |
| 1395 | UUGAUCAA CUGAUGA X GAA ACCUGGAG |
| 1396 | UUUGAUCA CUGAUGA X GAA AACCUGGA |
| 1397 | AUUUGAUC CUGAUGA X GAA AAACCUGG |
| 1401 | GACCAUUU CUGAUGA X GAA AUCAAAAC |
| 1409 | CGACCAUG CUGAUGA X GAA ACCAUUUG |
| 1416 | UAUAAGAC CUGAUGA X GAA ACACGGGA |
| 1419 | CUCUAUAA CUGAUGA X GAA ACGACACG |
| 1421 | CGCUCUAU CUGAUGA X GAA AGACGACA |
| 1422 | UCGCUCUA CUGAUGA X GAA AAGACGAC |
| 1424 | UAUCGCUC CUGAUGA x GAA AUAAGACG |

TABLE VII-continued

Delta-9 Desaturase HH Ribozyme Sequences

| nt. Position | Ribozyme sequence |
|---|---|
| 1432 | CGUUCUCC CUGAUGA X GAA AUCGCUCU |
| 1444 | CACAGACC CUGAUGA X GAA ACACGUUC |
| 1448 | ACACCACA CUGAUGA X GAA ACCAACAC |
| 1457 | AACAAAGC CUGAUGA X GAA ACACCACA |
| 1461 | UAAAAACA CUGAUGA X GAA AGCUACAC |
| 1462 | AUAAAAAC CUGAUGA X GAA AAGCUACA |
| 1465 | AAAAUAAA CUGAUGA X GAA ACAAAGCU |
| 1466 | CAAAAUAA CUGAUGA X GAA AACAAAGC |
| 1467 | ACAAAAUA CUGAUGA X GAA AAACAAAG |
| 1468 | UACAAAAU CUGAUGA X GAA AAAACAAA |
| 1469 | AUACAAAA CUGAUGA X GAA AAAAACAA |
| 1471 | AAAUACAA CUGAUGA X GAA AUAAAAAC |
| 1472 | AAAAUACA CUGAUGA X GAA AAUAAAAA |
| 1473 | AAAAAUAC CUGAUGA X GAA AAAUAAAA |
| 1476 | CAGAAAAA CUGAUGA X GAA ACAAAAUA |
| 1478 | AGCAGAAA CUGAUGA X GAA AUACAAAA |
| 1479 | AAGCAGAA CUGAUGA X GAA AAUACAAA |
| 1480 | AAAGCAGA CUGAUGA X GAA AAAUACAA |
| 1481 | CAAAGCAG CUGAUGA X GAA AAAAUACA |
| 1482 | UCAAAGCA CUGAUGA X GAA AAAAAUAC |
| 1487 | GUACAUCA CUGAUGA X GAA AGCAGAAA |
| 1488 | UGUACAUC CUGAUGA X GAA AAGCAGAA |
| 1494 | ACAGGUUG CUGAUGA X GAA ACAUCAAA |
| 1546 | AGACAAAG CUGAUGA X GAA ACGGCAUG |
| 1549 | GACAGACA CUGAUGA X GAA AGUACGGC |
| 1550 | CGACAGAC CUGAUGA X GAA AAGUACGG |
| 1553 | CAGCGACA CUGAUGA X GAA ACAAAGUA |
| 1557 | CCGCCAGC CUGAUGA X GAA ACAGAGAA |
| 1571 | CAUACCGA CUGAUGA X GAA ACACACCG |
| 1572 | ACAUACCG CUGAUGA X GAA AACACACC |
| 1573 | AACAUACC CUGAUGA X GAA AAACACAC |
| 1577 | AAAUAACA CUGAUGA X GAA ACCGAAAC |
| 1581 | ACUCAAAU CUGAUGA X GAA ACAUACCG |
| 1582 | AACUCAAA CUGAUGA X GAA AACAUACC |
| 1584 | GCAACUCA CUGAUGA X GAA AUAACAUA |
| 1585 | AGCAACUC CUGAUGA X GAA AAUAACAU |
| 1590 | AUCUGAGC CUGAUGA X GAA ACUCAAAU |
| 1594 | ACAGAUCU CUGAUGA X GAA AGCAACUC |
| 1599 | UUUUAACA CUGAUGA X GAA AUCUGAGC |
| 1603 | UUUUUUUU CUGAUGA X GAA ACAGAUCU |
| 1604 | UUUUUUUU CUGAUGA X GAA AACAGAUC |

Where "X" represents stem II region of a HH ribozyme (Hertel et al., 1992 Nucleic Acids Res. 20 3252). The length of stem II may be ≧2 base-pairs.

TABLE VIII

Delta-9 Desaturase Hairpin Ribozyme and Substrate Sequences

| nt. Position | Ribozyme | Substrate |
|---|---|---|
| 14 | GAACAAGC AGAA GAGGGC ACCAGAGAAACACACGUUGUGGUACAUUACCUGGUA | GCCCUCU GCC GCUUGUUC |
| 17 | AACGAACA AGAA GCAGAG ACCAGAGAAACACACGUUGUGGUACAUUACCUGGUA | CUCUGCC GCU UGUUCGUU |
| 108 | GGAAGCGC AGAA GCCGCC ACCAGAGAAACACACGUUGUGGUACAUUACCUGGUA | GGCGGCG GCC GCGCUUCC |
| 120 | GGAAGGGG AGAA GGAAGC ACCAGAGAAACACACGUUGUGGUACAUUACCUGGUA | GCUUCCG GCU CCCCUUCC |
| 155 | GUCGUUGA AGAA GAGCGC ACCAGAGAAACACACGUUGUGGUACAUUACCUGGUA | GCGCUCC GCC UCAACGAC |
| 176 | CGGGGAGA AGAA GAGCGC ACCAGAGAAACACACGUUGUGGUACAUUACCUGGUA | GCGCUCU GCC UCUCCCCG |
| 186 | CGGCGAGC AGAA GGGAGA ACCAGAGAAACACACGUUGUGGUACAUUACCUGGUA | UCUCCCC GCC GCUCGCCG |
| 189 | GGGCGGCG AGAA GCGGGG ACCAGAGAAACACACGUUGUGGUACAUUACCUGGUA | CCCCGCC GCU CGCCGCCC |
| 196 | CGGCGGCG AGAA GCGAGC ACCAGAGAAACACACGUUGUGGUACAUUACCUGGUA | GCUCGCC GCC CGCCGCCG |
| 200 | GCGGCGGC AGAA GGCGGC ACCAGAGAAACACACGUUGUGGUACAUUACCUGCUA | GCCGCCC GCC GCCGCCGC |
| 203 | GCGGCGGC AGAA GCGGGC ACCAGAGAAACACACGUUGUGGUACAUUACCUGGUA | GCCCGCC GCC GCCGCCGC |
| 206 | GCUGCGGC AGAA GCGGCG ACCAGAGAAACACACGUUGUGGUACAUUACCUGGUA | CGCCGCC GCC GCCGCAGC |
| 209 | GCUGCUGC AGAA GCGGCG ACCAGAGAAACACACGUUGUGGUACAUUACCUGGUA | CGCCGCC GCC GCAGCAGC |

TABLE VIII-continued

Delta-9 Desaturase Hairpin Ribozyme and Substrate Sequences

| nt. Position | Ribozyme | Substrate |
|---|---|---|
| 235 | AUGGAGGC AGAA GCGACG ACCAGAGAAACACACGUUGUGGUACAUUACCUGGUA | CGUCGCC GUC GCCUCCAU |
| 253 | GUGGAGAC AGAA GACGUC ACCAGAGAAACACACGUUGUGGUACAUUACCUGGUA | GACGUCC GCC GUCUCCAC |
| 256 | UUGGUGGA AGAA GCGGAC ACCAGAGAAACACACGUUGUGGUACAUUACCUGGUA | GUCCGCC GUC UCCACCAA |
| 406 | CACUUCUC AGAA GGCUUG ACCAGAGAAACACACGUUGUGGUACAUUACCUGGUA | CAAGCCA GUC GAGAAGUG |
| 442 | GAUGCUGG AGAA GGGAGG ACCAGAGAAACACACGUUGUGGUACAUUACCUGGGA | CCUCCCG GAC CCAGCAUC |
| 508 | AAAUAAUC AGAA GGGAUU ACCAGAGAAACACACGUUGUGGUACAUUACCUCGUA | AAUCCCU GAU GAUUAUUU |
| 570 | UAAGCAUA AGAA GGUAUG ACCAGAGAAACACACGUUGUGGUACAUUACCUGGUA | CAUACCA GAC UAUGCUUA |
| 625 | ACAGCCCA AGAA GUGGGG ACCAGAGAAACACACGUUGUGGUACAUUACCUGGUA | CCCCACU GCC UGGGCUGU |
| 634 | CUCGUCCA AGAA GCCCAG ACCAGAGAAACACACGUUGUGGUACAUUACCUGGUA | CUGGGCU GUU UGGACGAG |
| 655 | UUCUCCUC AGAA GUCCAU ACCAGAGAAACACACGUUGUGGUACAUUACCUGGUA | AUGGACU GCU GAGGAGAA |
| 681 | ACUUGUUG AGAA GAUCAC ACCAGAGAAACACACGUUGUGGUACAUUACCUGGUA | GUGAUCU GCU CAACAAGU |
| 726 | UCUUCUCA AGAA GCCUCA ACCAGAGAAACACACGUUGUGGUACAUUACCUGGUA | UGAGGCA GAU UGAGAAGA |
| 853 | GCGUGACG AGAA GUGUUC ACCAGAGAAACACACGUUGUGGUACAUUACCUGGUA | GAACACU GCU CGUCACGC |
| 916 | CGCUUCUC AGAA GAGGCG ACCAGAGAAACACACGUUGUGGUACAUUACCUGGUA | CGCCUCA GAU GAGAAGCG |
| 963 | CGAUCUCA AGAA GCUUCU ACCAGAGAAACACACCUUGUCGUACAUUACCUGGUA | AGAAGCU GUU UGAGAUCG |
| 979 | ACGGUACC AGAA GGGUCG ACCAGAGAAACACACGUUGUGGUACAUUACCUGGUA | CGACCCU GAU GGUACCGU |
| 1033 | AUCAGGUG AGAA GGCAUU ACCAGAGAAACACACGUUGUGGUACAUUACCUGGUA | AAUGCCU GCC CACCUGAU |
| 1041 | CGUCAAAC AGAA GGUGGG ACCAGAGAAACACACGUUGUGGUACAUUACCUGGUA | CCCACCU GAU GUUUGACG |
| 1068 | AGUGCUCG AGAA GCUUGU ACCAGAGAAACACACGUUGUGGUACAUUACCUGGUA | ACAAGCU GUU CGAGCACU |
| 1173 | ACAGACCA AGAA GGCUCG ACCAGAGAAACACACGUUGUGGUACAUUACCUGGUA | CGAGCCU GAC UGGUCUGU |
| 1182 | CUUCACCC AGAA GACCAG ACCAGAGAAACACACGUUGUGGUACAUUACCUGGUA | CUGGUCU GUC GGGUGAAG |
| 1287 | AGCUGAAA AGAA GCGUGC ACCAGAGAAACACACGUUGUGGUACAUUACCUGGUA | GCACGCU GCC UUUCAGCU |
| 1295 | GUAUACCC AGAA GAAAGG ACCAGAGAAACACACGUUGUGGUACAUUACCUGGUA | CCUUUCA GCU GGGUAUAC |
| 1339 | CAGACCGC AGAA GGUUUC ACCAGAGAAACACACGUUGUGGUACAUUACCUGGUA | GAAACCU GCU GCGGUCUG |
| 1345 | UCUAAGCA AGAA GCAGCA ACCAGAGAAACACACGUUGUGGUACAUUACCUGGUA | UGCUGCG GUC UGCUUAGA |
| 1349 | CUUGUCUA AGAA GACCGC ACCAGAGAAACACACGUUGUGGUACAUUACCUGGUA | GCGGUCU GCU UAGACAAG |
| 1364 | GCAGACAC AGAA GGUCUU ACCAGAGAAACACACGUUGUGGUACAUUACCUGGUA | AAGACCU GCU GUGUCUGC |
| 1483 | UACAUCAA AGAA GAAAAA ACCAGAGAAACACACGUUGUGGUACAUUACCUGGUA | UUUUUCU GCU UUGAUGUA |
| 1554 | CCGCCAGC AGAA GACAAA ACCAGAGAAACACACGUUGUGGUACAUUACCUGGUA | UUUGUCU GUC GCUGGCGG |
| 1595 | UUUAACAG AGAA GAGCAA ACCAGAGAAACACACGUUGUGGUACAUUACCUGGUA | UUGCUCA GAU CUGUUAAA |

TABLE IX

Cleavage of Delta-9 Desaturase RNA by HH Ribozymes

| | Percent Cleaved | | | |
|---|---|---|---|---|
| | 20° C. | | 26° C. | |
| nt. Position | 10 min | 120 min | 10 min | 120 min |
| 183 | 6.3 | 7.0 | 10.45 | 11.8 |
| 252 | 25.2 | 51.2 | 33.1 | 52.9 |
| 259 | 20.3 | 41.3 | 24.8 | 44.0 |
| 271 | 17.2 | 52.4 | 21.5 | 56.3 |
| 278 | 9.9 | 25.7 | 13.3 | 33.6 |
| 307 | 10.3 | 24.2 | 9.2 | 32.4 |
| 313 | 16.9 | 43.0 | 23.8 | 53.4 |
| 320 | 10.6 | 23.6 | 15.0 | 31.3 |
| 326 | 5.7 | 14.6 | 8.0 | 17.1 |
| 338 | 10.0 | 17.5 | 10.4 | 12.9 |
| 353 | 10.2 | 11.3 | 10.7 | 14.7 |
| 390 | 8.6 | 8.9 | 7.8 | 9.8 |
| 419 | 6.3 | 10.1 | 5.8 | 10.9 |
| 453 | 7.3 | 29.0 | 8.0 | 33.8 |
| 484 | 7.8 | 28.9 | 6.9 | 29.2 |
| 545 | 4.8 | 8.5 | 3.6 | 8.9 |
| 773 | 4.5 | 11.5 | 4.4 | 8.9 |
| 1024 | 11.9 | 17.1 | 13.3 | 23.8 |
| 1026 | 11.6 | 12.6 | 13.1 | 17.2 |
| 1237 | 23.1 | 32.4 | 13.8 | 28.6 |

TABLE X

| Construct Number | Targets Blasted | Isolates Recovered | Greenhouse Lines | Plants Produced |
|---|---|---|---|---|
| RPA85 | 231 | 70 | 13 | 161 |
| RPA113 | 292 | 82 | 9 | 116 |
| RPA114 | 244 | 35 | 12 | 152 |
| RPA115 | 285 | 42 | 11 | 165 |
| RPA118 | 268 | 38 | 10 | 125 |
| RPA119 | 301 | 67 | 11 | 135 |
| Totals | 1621 | 334 | 66 | 854 |

TABLE XI

Stearic acid levels in leaves from plants transformed with active and inactive ribozymes compared to control leaves.
Stearic Acid in Leaves Transformed with Active and Inactive Ribozymes
(Percentage of total plants with certain levels of leaf stearic acid)

| Stearic Acid | Ribozyme Actives (428 plants from 35 lines) | Ribozyme Inactives (406 plants from 31 lines) | Controls (122 plants) |
|---|---|---|---|
| >3% | 7% | 3% | 2% |
| >5% | 2% | 0 | 0 |
| >10% | 0 | 0 | 0 |

TABLE XII

Inheritance of the high stearic acid trait in leaves from crosses of high stearic acid plants.
Inheritance of high stearate in leaves.

| Cross | R1 Plants with Normal Leaf Stearate | R1 Plants with High Leaf Stearate | % of Plants with High Stearate |
|---|---|---|---|
| RPA85-15.06 × RPA85-15.12 | 6 | 3 | 33% |
| RPA85-15.07 self | 5 | 5 | 50% |
| RPA85-15.10 self | 8 | 2 | 20% |
| OQ414 × RPA85-15.06 | 5 | 3 | 38% |
| OQ414 × RPA85-15.11 | 6 | 4 | 40% |

TABLE XIII

Comparison of fatty acid composition of embryogenic callus, somatic embryos and zygotic embryos.

| Tissue and/or Media Treatment | Fatty Acid Composition | | | | | % Lipid of Fresh Weight |
|---|---|---|---|---|---|---|
| | C16:0 | C18:0 | C18:1 | C18:2 | C18:3 | |
| embryogenic callus | 19.4 +/- 0.9 | 1.1 +/- 0.1 | 6.2 +/- 2.0 | 55.7 +/- 3.1 | 8.8 +/- 2.0 | 0.4 +/- 0.1 |
| somatic embryo grown on MS + 6% sucrose + 10 mM ABA | 12.6 +/- 0.7 | 1.6 +/- 0.8 | 18.2 +/- 4.9 | 60.7 +/- 5.1 | 1.9 +/- 0.3 | 4.0 +/- 1.1 |
| zygotic embryo 12 days after pollination | 14.5 +/- 0.4 | 1.1 +/- 0.1 | 18.5 +/- 1.0 | 60.2 +/- 1.5 | 1.4 +/- 0.2 | 3.9 +/- 0.6 |

TABLE XIV

GBSS activity, amylose content, and Southern analysis results of selected Ribozyme Lines

| Line | GBSS activity (Units/mg starch) | Amylose Content (%) | Southern |
|---|---|---|---|
| RPA63.0283 | 321.5 ± 31.2 | 23.3 ± 0.5 | − |
| RPA63.0236 | 314.6 ± 9.2 | 27.4 ± 0.3 | − |
| RPA63.0219 | 299.8 ± 10.4 | 21.5 ± 0.3 | − |
| RPA63.0314 | 440.4 ± 17.1 | 19.1 ± 0.8 | − |
| RPA63.0316 | 346.5 ± 8.5 | 17.9 ± 0.5 | − |
| RPA63.0311 | 301.5 ± 17.4 | 19.5 ± 0.4 | − |
| RPA63.0309 | 264.7 ± 19 | 21.7 ± 0.1 | + |
| RPA63.0218 | 190.8 ± 7.8 | 21.0 ± 0.3 | + |
| RPA63.0209 | 203 ± 2.4 | 22.6 ± 0.6 | + |
| RPA63.0306 | 368.2 ± 7.5 | 19.0 ± 0.4 | − |
| RPA63.0210 | 195.1 ± 7 | 22.1 ± 0.2 | + |

What is claimed is:

1. An isolated nucleic acid fragment comprising SEQ ID NO. 1.

2. A maize plant transformed with a construct comprising in the 5' to 3' direction of Transcription:
   a promoter functional in said plant;
   a double strand DNA (dsDNA) comprising SEQ ID NO. 1, wherein the transcript strand of said dsDNA is complementary to RNA endogenous to said plant; and
   a termination region functional in said plant.

3. A transgenic plant that is a progeny of the maize plant of claim 2.

4. An expression vector comprising a nucleic acid sequence encoding at least one nucleic acid of claim 1, in a manner which allows expression of said nucleic acid.

5. A plant cell comprising the expression vector of claim 4.

6. A maize plant transformed with the expression vector of claim 4.

7. A transgenic plant that is a progeny of the maize plant of claim 6.

8. The transgenic plant of claim 2, 3, 6, or 7, wherein the plant is transformed by Agrobacterium, electroporation, whiskers, or by bombardment with DNA coated microprojectiles.

9. The transgenic plant of claim 8, wherein said bombardment with DNA coated microprojectiles is done with a gene gun.

10. The transgenic plant of claim 2, 3, 6, or 7, wherein the plant contains a selectable marker comprising the bar gene or a gene encoding resistance to a selection agent selected from the group consisting of chlorosulfuron, hygromycin, bromoxynil, and kanamycin.

11. The transgenic plant of claim 2 or 3, wherein the double strand DNA is operably linked to a cauliflower mosaic virus (35S) promoter or a promoter from a gene encoding a protein selected from the group consisting of octopine synthetase, nopaline synthase, mannopine synthetase, ribulose-1,6-bisphosphate (RUBP) carboxylase small subunit (ssu), beta-conglycinin, phaseolin, napin, gamma zein, globulin, ADH, heat shock protein, actin, and ubiquitin.

* * * * *

SEQUENCE LISTING (1) GENERAL INFORMATION:

(iii) NUMBER OF SEQUENCES: 1263

(2) INFORMATION FOR SEQ ID NO: 1:

(i) SEQUENCE CHARACTERISTICS:
      (A) LENGTH: 1621 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 146...1324

(xi) SEQUENCE DESCRIPTION: SEQ ID NO: 1:

```
CGCACGCGCC CTCTGCCGCT TGTTCGTTCC TCGCGCTCGC CACCAGGCAC CACCACACAC        60

ATCCCAATCT CGCGAGGGCA AGCAGCAGGG TCTGCGGCGG CGGCGGCGGC CGCGCTTCCG       120

GCTCCCCTTC CCATTGGCCT CCACG ATG GCG CTC CGC CTC AAC GAC GTC GCG        172
                            Met Ala Leu Arg Leu Asn Asp Val Ala
                             1               5

CTC TGC CTC TCC CCG CCG CTC GCC GCC CGC CGC CGC CGC CGC AGC AGC        220
Leu Cys Leu Ser Pro Pro Leu Ala Ala Arg Arg Arg Arg Arg Ser Ser
 10              15                  20                  25

GGC AGG TTC GTC GCC GTC GCC TCC ATG ACG TCC GCC GTC TCC ACC AAG        268
Gly Arg Phe Val Ala Val Ala Ser Met Thr Ser Ala Val Ser Thr Lys
             30                  35                  40

GTC GAG AAT AAG AAG CCA TTT GCT CCT CCA AGG GAG GTA CAT GTC CAG        316
Val Glu Asn Lys Lys Pro Phe Ala Pro Pro Arg Glu Val His Val Gln
                 45                  50                  55

GTT ACA CAT TCA ATG CCA CCT CAC AAG ATT GAA ATT TTC AAG TCG CTT        364
Val Thr His Ser Met Pro Pro His Lys Ile Glu Ile Phe Lys Ser Leu
             60                  65                  70

GAT GAT TGG GCT AGA GAT AAT ATC TTG ACG CAT CTC AAG CCA GTC GAG        412
Asp Asp Trp Ala Arg Asp Asn Ile Leu Thr His Leu Lys Pro Val Glu
 75                  80                  85

AAG TGT TGG CAG CCA CAG GAT TTC CTC CCG GAC CCA GCA TCT GAA GGA        460
Lys Cys Trp Gln Pro Gln Asp Phe Leu Pro Asp Pro Ala Ser Glu Gly
 90                  95                 100                 105

TTT CAT GAT GAA GTT AAG GAG CTC AGA GAA CGT GCC AAG GAA ATC CCT        508
Phe His Asp Glu Val Lys Glu Leu Arg Glu Arg Ala Lys Glu Ile Pro
                110                 115                 120

GAT GAT TAT TTT GTT TGT TTG GTG GGA GAC ATG ATT ACC GAG GAA GCT        556
Asp Asp Tyr Phe Val Cys Leu Val Gly Asp Met Ile Thr Glu Glu Ala
            125                 130                 135

CTA CCA ACA TAC CAG ACT ATG CTT AAC ACC CTC GAC GGT GTC AGA GAT        604
Leu Pro Thr Tyr Gln Thr Met Leu Asn Thr Leu Asp Gly Val Arg Asp
            140                 145                 150

GAG ACA GGT GCA AGC CCC ACT GCC TGG GCT GTT TGG ACG AGG GCA TGG        652
Glu Thr Gly Ala Ser Pro Thr Ala Trp Ala Val Trp Thr Arg Ala Trp
        155                 160                 165

ACT GCT GAG GAG AAC AGG CAT GGT GAT CTG CTC AAC AAG TAT ATG TAC        700
Thr Ala Glu Glu Asn Arg His Gly Asp Leu Leu Asn Lys Tyr Met Tyr
170                 175                 180                 185

CTC ACT GGG AGG GTG GAT ATG AGG CAG ATT GAG AAG ACA ATT CAG TAT        748
Leu Thr Gly Arg Val Asp Met Arg Gln Ile Glu Lys Thr Ile Gln Tyr
                190                 195                 200

CTT ATT GGC TCT GGA ATG GAT CCT AGG ACT GAG AAT AAT CCT TAT CTT        796
```

```
Leu Ile Gly Ser Gly Met Asp Pro Arg Thr Glu Asn Asn Pro Tyr Leu
            205                 210                 215

GGT TTC ATC TAC ACC TCC TTC CAA GAG CGG GCG ACC TTC ATC TCA CAC        844
Gly Phe Ile Tyr Thr Ser Phe Gln Glu Arg Ala Thr Phe Ile Ser His
            220                 225                 230

GGG AAC ACT GCT CGT CAC GCC AAG GAC TTT GGC GAC TTA AAG CTT GCA        892
Gly Asn Thr Ala Arg His Ala Lys Asp Phe Gly Asp Leu Lys Leu Ala
            235                 240                 245

CAA ATC TGC GGC ATC ATC GCC TCA GAT GAG AAG CGA CAT GAA ACT GCG        940
Gln Ile Cys Gly Ile Ile Ala Ser Asp Glu Lys Arg His Glu Thr Ala
250             255                 260                 265

TAC ACC AAG ATC GTG GAG AAG CTG TTT GAG ATC GAC CCT GAT GGT ACC        988
Tyr Thr Lys Ile Val Glu Lys Leu Phe Glu Ile Asp Pro Asp Gly Thr
                270                 275                 280

GTG GTC GCT CTG GCT GAC ATG ATG AGG AAG AAG ATC TCA ATG CCT GCC        1036
Val Val Ala Leu Ala Asp Met Met Arg Lys Lys Ile Ser Met Pro Ala
                285                 290                 295

CAC CTG ATG TTT GAC GGG CAG GAC GAC AAG CTG TTC GAG CAC TTC TCC        1084
His Leu Met Phe Asp Gly Gln Asp Asp Lys Leu Phe Glu His Phe Ser
                300                 305                 310

ATG GTC GCG CAG AGG CTT GGC GTT TAC ACC GCC AGG GAC TAC GCC GAC        1132
Met Val Ala Gln Arg Leu Gly Val Tyr Thr Ala Arg Asp Tyr Ala Asp
            315                 320                 325

ATC CTC GAG TTC CTC GTC GAC AGG TGG AAG GTG GCG AGC CTG ACT GGT        1180
Ile Leu Glu Phe Leu Val Asp Arg Trp Lys Val Ala Ser Leu Thr Gly
330             335                 340                 345

CTG TCG GGT GAA GGG AAC AAG GCG CAG GAC TAC CTT TGC ACC CTT GCT        1228
Leu Ser Gly Glu Gly Asn Lys Ala Gln Asp Tyr Leu Cys Thr Leu Ala
                350                 355                 360

TCA AGA ATC AGG AGG CTG GAG GAG AGG GCC CAG AGC AGA GCC AAG AAA        1276
Ser Arg Ile Arg Arg Leu Glu Glu Arg Ala Gln Ser Arg Ala Lys Lys
                365                 370                 375

GCC GGC ACG CTG CCT TTC AGC TGG GTA TAC GGT AGG GAC GTC CAA CTG TG     1326
Ala Gly Thr Leu Pro Phe Ser Trp Val Tyr Gly Arg Asp Val Gln Leu
            380                 385                 390

AGATCGGAAA CCTGCTGCGG TCTGCTTAGA CAAGACCTGC TGTGTCTGCG TTACATAGGT     1386

CTCCAGGTTT TGATCAAATG GTCCCGTGTC GTCTTATAGA GCGATAGGAG AACGTGTTGG     1446

TCTGTGGTGT AGCTTTGTTT TTATTTTGTA TTTTTCTGCT TGATGTACA ACCTGTGGCC      1506

GCATGAACTG GGGCGTGGAG ATGGGAGCGA CCATGCCGTA CTTTGTCTGT CGCTGGCGGT     1566

GTGTTTCGGT ATGTTATTTG AGTTGCTCAG ATCTGTTAAA AAAAAAAAA AAAAA           1621

(2) INFORMATION FOR SEQ ID NO: 2:

(i) SEQUENCE CHARACTERISTICS:
        (A) LENGTH:           42 base pairs
        (B) TYPE:             nucleic acid
        (C) STRANDEDNESS:     single
        (D) TOPOLOGY:         linear (xi) SEQUENCE DESCRIPTION: SEQ ID NO: 2:

CGACGAAGAC CUGAUGAGGC CGAAAGGCCG AAACGUUCAU GC                         42

(2) INFORMATION FOR SEQ ID NO: 3:

(i) SEQUENCE CHARACTERISTICS:
        (A) LENGTH:           42 base pairs
        (B) TYPE:             nucleic acid
        (C) STRANDEDNESS:     single
        (D) TOPOLOGY:         linear
```

(xi) SEQUENCE DESCRIPTION: SEQ ID NO: 3:

CUCCCAUCUU CUGAUGAGGC CGAAAGGCCG AAAUCUCGGA CA          42

(2) INFORMATION FOR SEQ ID NO: 4:

(i) SEQUENCE CHARACTERISTICS:
        (A) LENGTH:         42 base pairs
        (B) TYPE:           nucleic acid
        (C) STRANDEDNESS:   single
        (D) TOPOLOGY:       linear (xi) SEQUENCE DESCRIPTION: SEQ ID NO: 4:

GUUGUCCCUG CUGAUGAGGC CGAAAGGCCG AAAGUCCGUU CC          42

(2) INFORMATION FOR SEQ ID NO: 5:

(i) SEQUENCE CHARACTERISTICS:
        (A) LENGTH:         42 base pairs
        (B) TYPE:           nucleic acid
        (C) STRANDEDNESS:   single
        (D) TOPOLOGY:       linear (xi) SEQUENCE DESCRIPTION: SEQ ID NO: 5:

GGUUGUUGUU CUGAUGAGGC CGAAAGGCCG AAAGGCUCAG GA          42

(2) INFORMATION FOR SEQ ID NO: 6:

(i) SEQUENCE CHARACTERISTICS:
        (A) LENGTH:         42 base pairs
        (B) TYPE:           nucleic acid
        (C) STRANDEDNESS:   single
        (D) TOPOLOGY:       linear (xi) SEQUENCE DESCRIPTION: SEQ ID NO: 6:

GAGGUAGCAC CUGAUGAGGC CGAAAGGCCG AAAGAGAGGG CC          42

(2) INFORMATION FOR SEQ ID NO: 7:

(i) SEQUENCE CHARACTERISTICS:
        (A) LENGTH:         42 base pairs
        (B) TYPE:           nucleic acid
        (C) STRANDEDNESS:   single
        (D) TOPOLOGY:       linear (xi) SEQUENCE DESCRIPTION: SEQ ID NO: 7:

GUGGGACUGG CUGAUGAGGC CGAAAGGCCG AAAGUUGCUC UU          42

(2) INFORMATION FOR SEQ ID NO: 8:

(i) SEQUENCE CHARACTERISTICS:
        (A) LENGTH:         42 base pairs
        (B) TYPE:           nucleic acid
        (C) STRANDEDNESS:   single
        (D) TOPOLOGY:       linear (xi) SEQUENCE DESCRIPTION: SEQ ID NO: 8:

GAUGCCGUGG CUGAUGAGGC CGAAAGGCCG AAACUGGUAG UU          42

(2) INFORMATION FOR SEQ ID NO: 9:

(i) SEQUENCE CHARACTERISTICS:
        (A) LENGTH:         42 base pairs
        (B) TYPE:           nucleic acid
        (C) STRANDEDNESS:   single
        (D) TOPOLOGY:       linear (xi) SEQUENCE DESCRIPTION: SEQ ID NO: 9:

UGUGGAUGCA CUGAUGAGGC CGAAAGGCCG AAAAAGCGGU CU                42

(2) INFORMATION FOR SEQ ID NO: 10:

(i) SEQUENCE CHARACTERISTICS:
        (A) LENGTH:         42 base pairs
        (B) TYPE:           nucleic acid
        (C) STRANDEDNESS:   single
        (D) TOPOLOGY:      linear (xi) SEQUENCE DESCRIPTION: SEQ ID NO: 10:

AGAUGUUGUG CUGAUGAGGC CGAAAGGCCG AAAUGCAGAA AG                42

(2) INFORMATION FOR SEQ ID NO: 11:

(i) SEQUENCE CHARACTERISTICS:
        (A) LENGTH:         42 base pairs
        (B) TYPE:           nucleic acid
        (C) STRANDEDNESS:   single
        (D) TOPOLOGY:      linear (xi) SEQUENCE DESCRIPTION: SEQ ID NO: 11:

CCUGGUAGGA CUGAUGAGGC CGAAAGGCCG AAAUGUUGUG GA                42

(2) INFORMATION FOR SEQ ID NO: 12:

(i) SEQUENCE CHARACTERISTICS:
        (A) LENGTH:         42 base pairs
        (B) TYPE:           nucleic acid
        (C) STRANDEDNESS:   single
        (D) TOPOLOGY:      linear (xi) SEQUENCE DESCRIPTION: SEQ ID NO: 12:

AUCUCUCCGG CUGAUGAGGC CGAAAGGCCG AAAGGUUCAG CU                42

(2) INFORMATION FOR SEQ ID NO: 13:

(i) SEQUENCE CHARACTERISTICS:
        (A) LENGTH:         42 base pairs
        (B) TYPE:           nucleic acid
        (C) STRANDEDNESS:   single
        (D) TOPOLOGY:      linear (xi) SEQUENCE DESCRIPTION: SEQ ID NO: 13:

AGGACGACUU CUGAUGAGGC CGAAAGGCCG AAAAUCUCUC CG                42

(2) INFORMATION FOR SEQ ID NO: 14:

(i) SEQUENCE CHARACTERISTICS:
        (A) LENGTH:         42 base pairs
        (B) TYPE:           nucleic acid
        (C) STRANDEDNESS:   single
        (D) TOPOLOGY:      linear (xi) SEQUENCE DESCRIPTION: SEQ ID NO: 14:

UCAUCCAGUU CUGAUGAGGC CGAAAGGCCG AAAUCUUCCG GC                42

(2) INFORMATION FOR SEQ ID NO: 15:

(i) SEQUENCE CHARACTERISTICS:
        (A) LENGTH:         42 base pairs
        (B) TYPE:           nucleic acid
        (C) STRANDEDNESS:   single
        (D) TOPOLOGY:      linear (xi) SEQUENCE DESCRIPTION: SEQ ID NO: 15:

UGAUGUUGUC CUGAUGAGGC CGAAAGGCCG AAAGCUCGCA GC                               42

(2) INFORMATION FOR SEQ ID NO: 16:

(i) SEQUENCE CHARACTERISTICS:
        (A) LENGTH:            42 base pairs
        (B) TYPE:              nucleic acid
        (C) STRANDEDNESS:      single
        (D) TOPOLOGY:          linear (xi) SEQUENCE DESCRIPTION: SEQ ID NO: 16:

UGAGGCGCAU CUGAUGAGGC CGAAAGGCCG AAAUGUUGUC GA                               42

(2) INFORMATION FOR SEQ ID NO: 17:

(i) SEQUENCE CHARACTERISTICS:
        (A) LENGTH:            42 base pairs
        (B) TYPE:              nucleic acid
        (C) STRANDEDNESS:      single
        (D) TOPOLOGY:          linear (xi) SEQUENCE DESCRIPTION: SEQ ID NO: 17:

CCAUGCCGUU CUGAUGAGGC CGAAAGGCCG AAACGAUGCC GG                               42

(2) INFORMATION FOR SEQ ID NO: 18:

(i) SEQUENCE CHARACTERISTICS:
        (A) LENGTH:            42 base pairs
        (B) TYPE:              nucleic acid
        (C) STRANDEDNESS:      single
        (D) TOPOLOGY:          linear (xi) SEQUENCE DESCRIPTION: SEQ ID NO: 18:

CCCACUCGCU CUGAUGAGGC CGAAAGGCCG AAACGUCCAU GC                               42

(2) INFORMATION FOR SEQ ID NO: 19:

(i) SEQUENCE CHARACTERISTICS:
        (A) LENGTH:            42 base pairs
        (B) TYPE:              nucleic acid
        (C) STRANDEDNESS:      single
        (D) TOPOLOGY:          linear (xi) SEQUENCE DESCRIPTION: SEQ ID NO: 19:

CACGGCGAUG CUGAUGAGGC CGAAAGGCCG AAACUUGUCC CU                               42

(2) INFORMATION FOR SEQ ID NO: 20:

(i) SEQUENCE CHARACTERISTICS:
        (A) LENGTH:            42 base pairs
        (B) TYPE:              nucleic acid
        (C) STRANDEDNESS:      single
        (D) TOPOLOGY:          linear (xi) SEQUENCE DESCRIPTION: SEQ ID NO: 20:

GGUCCACCGG CUGAUGAGGC CGAAAGGCCG AAAGCCCGAC CU                               42

(2) INFORMATION FOR SEQ ID NO: 21:

(i) SEQUENCE CHARACTERISTICS:
        (A) LENGTH:            42 base pairs
        (B) TYPE:              nucleic acid
        (C) STRANDEDNESS:      single
        (D) TOPOLOGY:          linear (xi) SEQUENCE DESCRIPTION: SEQ ID NO: 21:

CGGCCGCCAU CUGAUGAGGC CGAAAGGCCG AAACGUCGGG UC                               42

(2) INFORMATION FOR SEQ ID NO: 22:

(i) SEQUENCE CHARACTERISTICS:
        (A) LENGTH:            42 base pairs
        (B) TYPE:              nucleic acid
        (C) STRANDEDNESS:     single
        (D) TOPOLOGY:         linear (xi) SEQUENCE DESCRIPTION: SEQ ID NO: 22:

```
CUUGCCUGGG CUGAUGAGGC CGAAAGGCCG AAACUUCUCC UC              42
```

(2) INFORMATION FOR SEQ ID NO: 23:

(i) SEQUENCE CHARACTERISTICS:
        (A) LENGTH:            42 base pairs
        (B) TYPE:              nucleic acid
        (C) STRANDEDNESS:     single
        (D) TOPOLOGY:         linear (xi) SEQUENCE DESCRIPTION: SEQ ID NO: 23:

```
UGCCUUCGAU CUGAUGAGGC CGAAAGGCCG AAAUGGUGUC GA              42
```

(2) INFORMATION FOR SEQ ID NO: 24:

(i) SEQUENCE CHARACTERISTICS:
        (A) LENGTH:            42 base pairs
        (B) TYPE:              nucleic acid
        (C) STRANDEDNESS:     single
        (D) TOPOLOGY:         linear (xi) SEQUENCE DESCRIPTION: SEQ ID NO: 24:

```
CCACCUUCUU CUGAUGAGGC CGAAAGGCCG AAACGUCCGC CG              42
```

(2) INFORMATION FOR SEQ ID NO: 25:

(i) SEQUENCE CHARACTERISTICS:
        (A) LENGTH:            2267 base pairs
        (B) TYPE:              nucleic acid
        (C) STRANDEDNESS:     single
        (D) TOPOLOGY:         linear (xi) SEQUENCE DESCRIPTION: SEQ ID NO: 25:

```
GACCGATCGA TCGCCACAGC CAACACCACC CGCCGAGGCG ACGCGACAGC CGCCAGGAGG     60
AAGGAATAAA CTCACTGCCA GCCAGTGAAG GGGGAGAAGT GTACTGCTCC GTCCACCAGT    120
GCGCGCACCG CCCGGCAGGG CTGCTCATCT CGTCGACGAC CAGTGGATTA ATCGGCATGG    180
CGGCTCTAGC CACGTCGCAG CTCGTCGCAA CGCGCGCCGG CCTGGGCGTC CCGGACGCGT    240
CCACGTTCCG CCGCGGCGCC GCGCAGGGCC TGAGGGGGGG CCGGACGGCG TCGGCGGCGG    300
ACACGCTCAG CATTCGGACC AGCGCGCGCG CGGCGCCCAG GCTCCAGCAC CAGCAGCAGC    360
AGCAGGCGCG CCGCGGGGCC AGGTTCCCGT CGCTCGTCGT GTGCGCCAGC GCCGGCATGA    420
ACGTCGTCTT CGTCGGCGCC GAGATGGCGC CGTGGAGCAA GACCGGCGGC CTCGGCGACG    480
TCCTCGGCGC CCTGCCGCCG GCCATGGCCG CGAATGGGCA CCGTGTCATG GTCGTCTCTC    540
CCCGCTACGA CCAGTACAAG GACGCCTGGG ACACCAGCGT CGTGTCCGAG ATCAAGATGG    600
GAGACAGGTA CGAGACGGTC AGGTTCTTCC ACTGCTACAA GCGCGGAGTG GACCGCGTGT    660
TCGTTGACCA CCCACTGTTC CTGGAGAGGG TTTGGGGAAA GACCGAGGAG AAGATCTACG    720
GGCCTGACGC TGGAACGGAC TACAGGGACA ACCAGCTGCG GTTCAGCCTG CTATGCCAGG    780
CAGCACTTGA AGCTCCAAGG ATCCTGAGCC TCAACAACAA CCCATACTTC TCCGGACCAT    840
```

```
ACGGGGAGGA CGTCGTGTTC GTCTGCAACG ACTGGCACAC CGGCCCTCTC TCGTGCTACC    900

TCAAGAGCAA CTACCAGTCC CACGGCATCT ACAGGGACGC AAAGACCGCT TTCTGCATCC    960

ACAACATCTC CTACCAGGGC CGGTTCGCCT TCTCCGACTA CCCGGAGCTG AACCTCCCGG   1020

AGAGATTCAA GTCGTCCTTC GATTTCATCG ACGGCTACGA GAAGCCCGTG AAGGCCGGA    1080

AGATCAACTG GATGAAGGCC GGGATCCTCG AGGCCGACAG GGTCCTCACC GTCAGCCCCT   1140

ACTACGCCGA GGAGCTCATC TCCGGCATCG CCAGGGGCTG CGAGCTCGAC AACATCATGC   1200

GCCTCACCGG CATCACCGGC ATCGTCAACG GCATGGACGT CAGCGAGTGG GACCCCAGCA   1260

GGGACAAGTA CATCGCCGTG AAGTACGACG TGTCGACGGC CGTGGAGGCC AAGGCGCTGA   1320

ACAAGGAGGC GCTGCAGGCG GAGGTCGGGC TCCCGGTGGA CCGGAACATC CCGCTGGTGG   1380

CGTTCATCGG CAGGCTGGAA GAGCAGAAGG GACCCGACGT CATGGCGGCC GCCATCCCGC   1440

AGCTCATGGA GATGGTGGAG GACGTGCAGA TCGTTCTGCT GGGCACGGGC AAGAAGAAGT   1500

TCGAGCGCAT GCTCATGAGC GCCGAGGAGA AGTTCCCAGG CAAGGTGCGC GCCGTGGTCA   1560

AGTTCAACGC GGCGCTGGCG CACCACATCA TGGCCGGCGC CGACGTGCTC GCCGTCACCA   1620

GCCGCTTCGA GCCCTGCGGC CTCATCCAGC TGCAGGGGAT GCGATACGGA ACGCCCTGCG   1680

CCTGCGCGTC CACCGGTGGA CTCGTCGACA CCATCATCGA AGGCAAGACC GGGTTCCACA   1740

TGGGCCGCCT CAGCGTCGAC TGCAACGTCG TGGAGCCGGC GGACGTCAAG AAGGTGGCCA   1800

CCACCTTGCA GCGCGCCATC AAGGTGGTCG GCACGCCGGC GTACGAGGAG ATGGTGAGGA   1860

ACTGCATGAT CCAGGATCTC TCCTGGAAGG GCCCTGCCAA GAACTGGGAG AACGTGCTGC   1920

TCAGCCTCGG GGTCGCCGGC GGCGAGCCAG GGGTCGAAGG CGAGGAGATC GCGCCGCTCG   1980

CCAAGGAGAA CGTGGCCGCG CCCTGAAGAG TTCGGCCTGC AGGCCCCCTG ATCTCGCGCG   2040

TGGTGCAAAC ATGTTGGGAC ATCTTCTTAT ATATGCTGTT TCGTTTATGT GATATGGACA   2100

AGTATGTGTA GCTGCTTGCT TGTGCTAGTG TAATATAGTG TAGTGGTGGC CAGTGGCACA   2160

ACCTAATAAG CGCATGAACT AATTGCTTGC GTGTGTAGTT AAGTACCGAT CGGTAATTTT   2220

ATATTGCGAG TAAATAAATG GACCTGTAGT GGTGGAAAAA AAAAAA              2267
```

(2) INFORMATION FOR SEQ ID NO: 26:

(i) SEQUENCE CHARACTERISTICS:
        (A) LENGTH:       17 base pairs
        (B) TYPE:         nucleic acid
        (C) STRANDEDNESS:  single
        (D) TOPOLOGY:     linear (xi) SEQUENCE DESCRIPTION: SEQ ID NO: 26:

CGAUCGAUCG CCACAGC                                    17

(2) INFORMATION FOR SEQ ID NO: 27:

(i) SEQUENCE CHARACTERISTICS:
        (A) LENGTH:       17 base pairs
        (B) TYPE:         nucleic acid
        (C) STRANDEDNESS:  single
        (D) TOPOLOGY:     linear (xi) SEQUENCE DESCRIPTION: SEQ ID NO: 27:

GGUCGUCUCU CCCCGCU                                    17

(2) INFORMATION FOR SEQ ID NO: 28:

(i) SEQUENCE CHARACTERISTICS:
        (A) LENGTH:       17 base pairs

```
            (B) TYPE:              nucleic acid
            (C) STRANDEDNESS:      single
            (D) TOPOLOGY:          linear (xi) SEQUENCE DESCRIPTION: SEQ ID NO: 28:

GAAGGAAUAA ACUCACU                                                    17

(2) INFORMATION FOR SEQ ID NO: 29:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 29:

UCGUCUCUCC CCGCUAC                                                    17

(2) INFORMATION FOR SEQ ID NO: 30:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 30:

AAUAAACUCA CUGCCAG                                                    17

(2) INFORMATION FOR SEQ ID NO: 31:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 31:

UCCCCGCUAC GACCAGU                                                    17

(2) INFORMATION FOR SEQ ID NO: 32:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 32:

AGAAGUGUAC UGCUCCG                                                    17

(2) INFORMATION FOR SEQ ID NO: 33:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 33:

CGACCAGUAC AAGGACG                                                    17

(2) INFORMATION FOR SEQ ID NO: 34:

(i) SEQUENCE CHARACTERISTICS:
            (A) LENGTH:            17 base pairs
            (B) TYPE:              nucleic acid
```

```
        (C) STRANDEDNESS:        single
        (D) TOPOLOGY:            linear (xi) SEQUENCE DESCRIPTION: SEQ ID NO: 34:

GUACUGCUCC GUCCACC                                                      17

(2) INFORMATION FOR SEQ ID NO: 35:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 35:

ACCAGCGUCG UGUCCGA                                                      17

(2) INFORMATION FOR SEQ ID NO: 36:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 36:

UGCUCCGUCC ACCAGUG                                                      17

(2) INFORMATION FOR SEQ ID NO: 37:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 37:

CGUCGUGUCC GAGAUCA                                                      17

(2) INFORMATION FOR SEQ ID NO: 38:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 38:

GGGCUGCUCA UCUCGUC                                                      17

(2) INFORMATION FOR SEQ ID NO: 39:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 39:

UCCGAGAUCA AGAUGGG                                                      17

(2) INFORMATION FOR SEQ ID NO: 40:

(i) SEQUENCE CHARACTERISTICS:
        (A) LENGTH:              17 base pairs
        (B) TYPE:                nucleic acid
        (C) STRANDEDNESS:        single
```

(D) TOPOLOGY:           linear (xi) SEQUENCE DESCRIPTION: SEQ ID NO: 40:

CUGCUCAUCU CGUCGAC                                                     17

(2) INFORMATION FOR SEQ ID NO: 41:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 41:

AGACAGGUAC GAGACGG                                                     17

(2) INFORMATION FOR SEQ ID NO: 42:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 42:

GCUCAUCUCG UCGACGA                                                     17

(2) INFORMATION FOR SEQ ID NO: 43:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 43:

GAGACGGUCA GGUUCUU                                                     17

(2) INFORMATION FOR SEQ ID NO: 44:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 44:

CAUCUCGUCG ACGACCA                                                     17

(2) INFORMATION FOR SEQ ID NO: 45:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 45:

GGUCAGGUUC UUCCACU                                                     17

(2) INFORMATION FOR SEQ ID NO: 46:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 46:

CAGUGGAUUA AUCGGCA                                                17

(2) INFORMATION FOR SEQ ID NO: 47:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 47:

GUCAGGUUCU UCCACUG                                                17

(2) INFORMATION FOR SEQ ID NO: 48:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 48:

AGUGGAUUAA UCGGCAU                                                17

(2) INFORMATION FOR SEQ ID NO: 49:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 49:

CAGGUUCUUC CACUGCU                                                17

(2) INFORMATION FOR SEQ ID NO: 50:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 50:

GGAUUAAUCG GCAUGGC                                                17

(2) INFORMATION FOR SEQ ID NO: 51:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 51:

AGGUUCUUCC ACUGCUA                                                17

(2) INFORMATION FOR SEQ ID NO: 52:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 52:

UGGCGGCUCU AGCCACG                                                      17

(2) INFORMATION FOR SEQ ID NO: 53:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 53:

CCACUGCUAC AAGCGCG                                                      17

(2) INFORMATION FOR SEQ ID NO: 54:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 54:

GCGGCUCUAG CCACGUC                                                      17

(2) INFORMATION FOR SEQ ID NO: 55:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 55:

CCGCGUGUUC GUUGACC                                                      17

(2) INFORMATION FOR SEQ ID NO: 56:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 56:

AGCCACGUCG CAGCUCG                                                      17

(2) INFORMATION FOR SEQ ID NO: 57:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 57:

CGCGUGUUCG UUGACCA                                                      17

(2) INFORMATION FOR SEQ ID NO: 58:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 58:

UCGCAGCUCG UCGCAAC 17

(2) INFORMATION FOR SEQ ID NO: 59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 59:

GUGUUCGUUG ACCACCC 17

(2) INFORMATION FOR SEQ ID NO: 60:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 60:

CAGCUCGUCG CAACGCG 17

(2) INFORMATION FOR SEQ ID NO: 61:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 61:

CCCACUGUUC CUGGAGA 17

(2) INFORMATION FOR SEQ ID NO: 62:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 62:

CUGGGCGUCC CGGACGC 17

(2) INFORMATION FOR SEQ ID NO: 63:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 63:

CCACUGUUCC UGGAGAG 17

(2) INFORMATION FOR SEQ ID NO: 64:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 64:

```
GGACGCGUCC ACGUUCC                                                   17
```

(2) INFORMATION FOR SEQ ID NO: 65:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 65:

```
GAGAGGGUUU GGGGAAA                                                   17
```

(2) INFORMATION FOR SEQ ID NO: 66:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 66:

```
GUCCACGUUC CGCCGCG                                                   17
```

(2) INFORMATION FOR SEQ ID NO: 67:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 67:

```
AGAGGGUUUG GGGAAAG                                                   17
```

(2) INFORMATION FOR SEQ ID NO: 68:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 68:

```
UCCACGUUCC GCCGCGG                                                   17
```

(2) INFORMATION FOR SEQ ID NO: 69:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 69:

```
GAGAAGAUCU ACGGGCC                                                   17
```

(2) INFORMATION FOR SEQ ID NO: 70:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 70:

```
GACGGCGUCG GCGGCGG                                                   17
```

(2) INFORMATION FOR SEQ ID NO: 71:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 71:

GAAGAUCUAC GGGCCUG                                    17

(2) INFORMATION FOR SEQ ID NO: 72:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 72:

GACACGCUCA GCAUUCG                                    17

(2) INFORMATION FOR SEQ ID NO: 73:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 73:

AACGGACUAC AGGGACA                                    17

(2) INFORMATION FOR SEQ ID NO: 74:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 74:

CUCAGCAUUC GGACCAG                                    17

(2) INFORMATION FOR SEQ ID NO: 75:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 75:

GCUGCGGUUC AGCCUGC                                    17

(2) INFORMATION FOR SEQ ID NO: 76:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 76:

UCAGCAUUCG GACCAGC                                    17

(2) INFORMATION FOR SEQ ID NO: 77:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 77:

CUGCGGUUCA GCCUGCU                                           17

(2) INFORMATION FOR SEQ ID NO: 78:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 78:

CCCAGGCUCC AGCACCA                                           17

(2) INFORMATION FOR SEQ ID NO: 79:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 79:

AGCCUGCUAU GCCAGGC                                           17

(2) INFORMATION FOR SEQ ID NO: 80:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 80:

GGCCAGGUUC CCGUCGC                                           17

(2) INFORMATION FOR SEQ ID NO: 81:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 81:

GCAGCACUUG AAGCUCC                                           17

(2) INFORMATION FOR SEQ ID NO: 82:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 82:

GCCAGGUUCC CGUCGCU                                           17

```
(2) INFORMATION FOR SEQ ID NO: 83:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 83:

UUGAAGCUCC AAGGAUC                                                      17

(2) INFORMATION FOR SEQ ID NO: 84:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 84:

GUUCCCGUCG CUCGUCG                                                      17

(2) INFORMATION FOR SEQ ID NO: 85:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 85:

CCAAGGAUCC UGAGCCU                                                      17

(2) INFORMATION FOR SEQ ID NO: 86:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 86:

CCGUCGCUCG UCGUGUG                                                      17

(2) INFORMATION FOR SEQ ID NO: 87:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 87:

CUGAGCCUCA ACAACAA                                                      17

(2) INFORMATION FOR SEQ ID NO: 88:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 88:

UCGCUCGUCG UGUGCGC                                                      17

(2) INFORMATION FOR SEQ ID NO: 89:
```

```
    (i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 89:

CAACCCAUAC UUCUCCG                                                  17

(2) INFORMATION FOR SEQ ID NO: 90:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 90:

AUGAACGUCG UCUUCGU                                                  17

(2) INFORMATION FOR SEQ ID NO: 91:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 91:

CCCAUACUUC UCCGGAC                                                  17

(2) INFORMATION FOR SEQ ID NO: 92:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 92:

AACGUCGUCU UCGUCGG                                                  17

(2) INFORMATION FOR SEQ ID NO: 93:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 93:

CCAUACUUCU CCGGACC                                                  17

(2) INFORMATION FOR SEQ ID NO: 94:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 94:

CGUCGUCUUC GUCGGCG                                                  17

(2) INFORMATION FOR SEQ ID NO: 95:
```

```
    (i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 95:

AUACUUCUCC GGACCAU                                                        17

(2) INFORMATION FOR SEQ ID NO: 96:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 96:

GUCGUCUUCG UCGGCGC                                                        17

(2) INFORMATION FOR SEQ ID NO: 97:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 97:

CGGACCAUAC GGGGAGG                                                        17

(2) INFORMATION FOR SEQ ID NO: 98:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 98:

GUCUUCGUCG GCGCCGA                                                        17

(2) INFORMATION FOR SEQ ID NO: 99:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 99:

GAGGACGUCG UGUUCGU                                                        17

(2) INFORMATION FOR SEQ ID NO: 100:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 100:

GGCGGCCUCG GCGACGU                                                        17

(2) INFORMATION FOR SEQ ID NO: 101:

(i) SEQUENCE CHARACTERISTICS:
```

```
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 101:

CGUCGUGUUC GUCUGCA                                                    17

(2) INFORMATION FOR SEQ ID NO: 102:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 102:

GGCGACGUCC UCGGCGG                                                    17

(2) INFORMATION FOR SEQ ID NO: 103:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 103:

GUCGUGUUCG UCUGCAA                                                    17

(2) INFORMATION FOR SEQ ID NO: 104:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 104:

GACGUCCUCG GCGGCCU                                                    17

(2) INFORMATION FOR SEQ ID NO: 105:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 105:

GUGUUCGUCU GCAACGA                                                    17

(2) INFORMATION FOR SEQ ID NO: 106:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 106:

CACCGUGUCA UGGUCGU                                                    17

(2) INFORMATION FOR SEQ ID NO: 107:

(i) SEQUENCE CHARACTERISTICS:
            (A) LENGTH:              17 base pairs
```

```
          (B) TYPE:               nucleic acid
          (C) STRANDEDNESS:       single
          (D) TOPOLOGY:           linear (xi) SEQUENCE DESCRIPTION: SEQ ID NO: 107:

CCGGCCCUCU CUCGUGC                                                    17

(2) INFORMATION FOR SEQ ID NO: 108:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 108:

GUCAUGGUCG UCUCUCC                                                    17

(2) INFORMATION FOR SEQ ID NO: 109:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 109:

GGCCCUCUCU CGUGCUA                                                    17

(2) INFORMATION FOR SEQ ID NO: 110:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 110:

AUGGUCGUCU CUCCCCG                                                    17

(2) INFORMATION FOR SEQ ID NO: 111:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 111:

CCCUCUCUCG UGCUACC                                                    17

(2) INFORMATION FOR SEQ ID NO: 112:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 112:

CUCGUGCUAC CUCAAGA                                                    17

(2) INFORMATION FOR SEQ ID NO: 113:

(i) SEQUENCE CHARACTERISTICS:
          (A) LENGTH:             17 base pairs
          (B) TYPE:               nucleic acid
```

```
          (C) STRANDEDNESS:        single
          (D) TOPOLOGY:            linear (xi) SEQUENCE DESCRIPTION: SEQ ID NO: 113:

AUGGACGUCA GCGAGUG                                                    17

(2) INFORMATION FOR SEQ ID NO: 114:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 114:

UGCUACCUCA AGAGCAA                                                    17

(2) INFORMATION FOR SEQ ID NO: 115:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 115:

GGACAAGUAC AUCGCCG                                                    17

(2) INFORMATION FOR SEQ ID NO: 116:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 116:

GAGCAACUAC CAGUCCC                                                    17

(2) INFORMATION FOR SEQ ID NO: 117:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 117:

AAGUACAUCG CCGUGAA                                                    17

(2) INFORMATION FOR SEQ ID NO: 118:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 118:

CUACCAGUCC CACGGCA                                                    17

(2) INFORMATION FOR SEQ ID NO: 119:

(i) SEQUENCE CHARACTERISTICS:
          (A) LENGTH:              17 base pairs
          (B) TYPE:                nucleic acid
          (C) STRANDEDNESS:        single
```

(D) TOPOLOGY:          linear (xi) SEQUENCE DESCRIPTION: SEQ ID NO: 119:

CGUGAAGUAC GACGUGU                                                17

(2) INFORMATION FOR SEQ ID NO: 120:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 120:

CACGGCAUCU ACAGGGA                                                17

(2) INFORMATION FOR SEQ ID NO: 121:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 121:

CGACGUGUCG ACGGCCG                                                17

(2) INFORMATION FOR SEQ ID NO: 122:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 122:

CGGCAUCUAC AGGGACG                                                17

(2) INFORMATION FOR SEQ ID NO: 123:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 123:

GCGGAGGUCG GGCUCCC                                                17

(2) INFORMATION FOR SEQ ID NO: 124:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 124:

AGACCGCUUU CUGCAUC                                                17

(2) INFORMATION FOR SEQ ID NO: 125:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 125:

GUCGGGCUCC CGGUGGA                                                              17

(2) INFORMATION FOR SEQ ID NO: 126:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 126:

GACCGCUUUC UGCAUCC                                                              17

(2) INFORMATION FOR SEQ ID NO: 127:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 127:

CGGAACAUCC CGCUGGU                                                              17

(2) INFORMATION FOR SEQ ID NO: 128:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 128:

ACCGCUUUCU GCAUCCA                                                              17

(2) INFORMATION FOR SEQ ID NO: 129:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 129:

GGUGGCGUUC AUCGGCA                                                              17

(2) INFORMATION FOR SEQ ID NO: 130:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 130:

UUCUGCAUCC ACAACAU                                                              17

(2) INFORMATION FOR SEQ ID NO: 131:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 131:

GUGGCGUUCA UCGGCAG                                    17

(2) INFORMATION FOR SEQ ID NO: 132:

(i) SEQUENCE CHARACTERISTICS:
        (A) LENGTH:         17 base pairs
        (B) TYPE:            nucleic acid
        (C) STRANDEDNESS:    single
        (D) TOPOLOGY:        linear (xi) SEQUENCE DESCRIPTION: SEQ ID NO: 132:

CACAACAUCU CCUACCA                                    17

(2) INFORMATION FOR SEQ ID NO: 133:

(i) SEQUENCE CHARACTERISTICS:
        (A) LENGTH:         17 base pairs
        (B) TYPE:            nucleic acid
        (C) STRANDEDNESS:    single
        (D) TOPOLOGY:        linear (xi) SEQUENCE DESCRIPTION: SEQ ID NO: 133:

GCGUUCAUCG GCAGGCU                                    17

(2) INFORMATION FOR SEQ ID NO: 134:

(i) SEQUENCE CHARACTERISTICS:
        (A) LENGTH:         17 base pairs
        (B) TYPE:            nucleic acid
        (C) STRANDEDNESS:    single
        (D) TOPOLOGY:        linear (xi) SEQUENCE DESCRIPTION: SEQ ID NO: 134:

CAACAUCUCC UACCAGG                                    17

(2) INFORMATION FOR SEQ ID NO: 135:

(i) SEQUENCE CHARACTERISTICS:
        (A) LENGTH:         17 base pairs
        (B) TYPE:            nucleic acid
        (C) STRANDEDNESS:    single
        (D) TOPOLOGY:        linear (xi) SEQUENCE DESCRIPTION: SEQ ID NO: 135:

CCCGACGUCA UGGCGGC                                    17

(2) INFORMATION FOR SEQ ID NO: 136:

(i) SEQUENCE CHARACTERISTICS:
        (A) LENGTH:         17 base pairs
        (B) TYPE:            nucleic acid
        (C) STRANDEDNESS:    single
        (D) TOPOLOGY:        linear (xi) SEQUENCE DESCRIPTION: SEQ ID NO: 136:

CAUCUCCUAC CAGGGCC                                    17

(2) INFORMATION FOR SEQ ID NO: 137:

(i) SEQUENCE CHARACTERISTICS:
        (A) LENGTH:         17 base pairs
        (B) TYPE:            nucleic acid
        (C) STRANDEDNESS:    single
        (D) TOPOLOGY:        linear (xi) SEQUENCE DESCRIPTION: SEQ ID NO: 137:

GCCGCCAUCC CGCAGCU                                                17

(2) INFORMATION FOR SEQ ID NO: 138:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 138:

GGGCCGGUUC GCCUUCU                                                17

(2) INFORMATION FOR SEQ ID NO: 139:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 139:

CCGCAGCUCA UGGAGAU                                                17

(2) INFORMATION FOR SEQ ID NO: 140:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 140:

GGCCGGUUCG CCUUCUC                                                17

(2) INFORMATION FOR SEQ ID NO: 141:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 141:

GUGCAGAUCG UUCUGCU                                                17

(2) INFORMATION FOR SEQ ID NO: 142:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 142:

GUUCGCCUUC UCCGACU                                                17

(2) INFORMATION FOR SEQ ID NO: 143:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 143:

```
CAGAUCGUUC UGCUGGG                                                      17
```

(2) INFORMATION FOR SEQ ID NO: 144:

(i) SEQUENCE CHARACTERISTICS:
        (A) LENGTH:         17 base pairs
        (B) TYPE:           nucleic acid
        (C) STRANDEDNESS:  single
        (D) TOPOLOGY:     linear (xi) SEQUENCE DESCRIPTION: SEQ ID NO: 144:

```
UUCGCCUUCU CCGACUA                                                      17
```

(2) INFORMATION FOR SEQ ID NO: 145:

(i) SEQUENCE CHARACTERISTICS:
        (A) LENGTH:         17 base pairs
        (B) TYPE:           nucleic acid
        (C) STRANDEDNESS:  single
        (D) TOPOLOGY:     linear (xi) SEQUENCE DESCRIPTION: SEQ ID NO: 145:

```
AGAUCGUUCU GCUGGGC                                                      17
```

(2) INFORMATION FOR SEQ ID NO: 146:

(i) SEQUENCE CHARACTERISTICS:
        (A) LENGTH:         17 base pairs
        (B) TYPE:           nucleic acid
        (C) STRANDEDNESS:  single
        (D) TOPOLOGY:     linear (xi) SEQUENCE DESCRIPTION: SEQ ID NO: 146:

```
CGCCUUCUCC GACUACC                                                      17
```

(2) INFORMATION FOR SEQ ID NO: 147:

(i) SEQUENCE CHARACTERISTICS:
        (A) LENGTH:         17 base pairs
        (B) TYPE:           nucleic acid
        (C) STRANDEDNESS:  single
        (D) TOPOLOGY:     linear (xi) SEQUENCE DESCRIPTION: SEQ ID NO: 147:

```
GAAGAAGUUC GAGCGCA                                                      17
```

(2) INFORMATION FOR SEQ ID NO: 148:

(i) SEQUENCE CHARACTERISTICS:
        (A) LENGTH:         17 base pairs
        (B) TYPE:           nucleic acid
        (C) STRANDEDNESS:  single
        (D) TOPOLOGY:     linear (xi) SEQUENCE DESCRIPTION: SEQ ID NO: 148:

```
CUCCGACUAC CCGGAGC                                                      17
```

(2) INFORMATION FOR SEQ ID NO: 149:

(i) SEQUENCE CHARACTERISTICS:
        (A) LENGTH:         17 base pairs
        (B) TYPE:           nucleic acid
        (C) STRANDEDNESS:  single
        (D) TOPOLOGY:     linear (xi) SEQUENCE DESCRIPTION: SEQ ID NO: 149:

```
AAGAAGUUCG AGCGCAU                                                      17
```

(2) INFORMATION FOR SEQ ID NO: 150:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 150:

CUGAACCUCC CGGAGAG                                              17

(2) INFORMATION FOR SEQ ID NO: 151:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 151:

CGCAUGCUCA UGAGCGC                                              17

(2) INFORMATION FOR SEQ ID NO: 152:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 152:

GGAGAGAUUC AAGUCGU                                              17

(2) INFORMATION FOR SEQ ID NO: 153:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 153:

GGAGAAGUUC CCAGGCA                                              17

(2) INFORMATION FOR SEQ ID NO: 154:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 154:

GAGAGAUUCA AGUCGUC                                              17

(2) INFORMATION FOR SEQ ID NO: 155:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 155:

GAGAAGUUCC CAGGCAA                                              17

(2) INFORMATION FOR SEQ ID NO: 156:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 156:

AUUCAAGUCG UCCUUCG                                     17

(2) INFORMATION FOR SEQ ID NO: 157:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 157:

GCCGUGGUCA AGUUCAA                                     17

(2) INFORMATION FOR SEQ ID NO: 158:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 158:

CAAGUCGUCC UUCGAUU                                     17

(2) INFORMATION FOR SEQ ID NO: 159:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 159:

GGUCAAGUUC AACGCGG                                     17

(2) INFORMATION FOR SEQ ID NO: 160:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 160:

GUCGUCCUUC GAUUUCA                                     17

(2) INFORMATION FOR SEQ ID NO: 161:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 161:

GUCAAGUUCA ACGCGGC                                     17

(2) INFORMATION FOR SEQ ID NO: 162:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 162:

UCGUCCUUCG AUUUCAU                                     17

(2) INFORMATION FOR SEQ ID NO: 163:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 163:

CACCACAUCA UGGCCGG                                     17

(2) INFORMATION FOR SEQ ID NO: 164:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 164:

CCUUCGAUUU CAUCGAC                                     17

(2) INFORMATION FOR SEQ ID NO: 165:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 165:

GACGUGCUCG CCGUCAC                                     17

(2) INFORMATION FOR SEQ ID NO: 166:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 166:

CUUCGAUUUC AUCGACG                                     17

(2) INFORMATION FOR SEQ ID NO: 167:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 167:

CUCGCCGUCA CCAGCCG                                     17

(2) INFORMATION FOR SEQ ID NO: 168:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 168:

UUCGAUUUCA UCGACGG                                                          17

(2) INFORMATION FOR SEQ ID NO: 169:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 169:

CAGCCGCUUC GAGCCCU                                                          17

(2) INFORMATION FOR SEQ ID NO: 170:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 170:

GAUUUCAUCG ACGGCUA                                                          17

(2) INFORMATION FOR SEQ ID NO: 171:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 171:

AGCCGCUUCG AGCCCUG                                                          17

(2) INFORMATION FOR SEQ ID NO: 172:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 172:

CGACGGCUAC GAGAAGC                                                          17

(2) INFORMATION FOR SEQ ID NO: 173:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 173:

UGCGGCCUCA UCCAGCU                                                          17

(2) INFORMATION FOR SEQ ID NO: 174:

```
       (i) SEQUENCE CHARACTERISTICS:
             (A) LENGTH:            17 base pairs
             (B) TYPE:              nucleic acid
             (C) STRANDEDNESS:      single
             (D) TOPOLOGY:          linear (xi) SEQUENCE DESCRIPTION: SEQ ID NO: 174:

CGGAAGAUCA ACUGGAU                                              17

(2) INFORMATION FOR SEQ ID NO: 175:

(i) SEQUENCE CHARACTERISTICS:
             (A) LENGTH:            17 base pairs
             (B) TYPE:              nucleic acid
             (C) STRANDEDNESS:      single
             (D) TOPOLOGY:          linear (xi) SEQUENCE DESCRIPTION: SEQ ID NO: 175:

GGCCUCAUCC AGCUGCA                                              17

(2) INFORMATION FOR SEQ ID NO: 176:

(i) SEQUENCE CHARACTERISTICS:
             (A) LENGTH:            17 base pairs
             (B) TYPE:              nucleic acid
             (C) STRANDEDNESS:      single
             (D) TOPOLOGY:          linear (xi) SEQUENCE DESCRIPTION: SEQ ID NO: 176:

GCCGGGAUCC UCGAGGC                                              17

(2) INFORMATION FOR SEQ ID NO: 177:

(i) SEQUENCE CHARACTERISTICS:
             (A) LENGTH:            17 base pairs
             (B) TYPE:              nucleic acid
             (C) STRANDEDNESS:      single
             (D) TOPOLOGY:          linear (xi) SEQUENCE DESCRIPTION: SEQ ID NO: 177:

GAUGCGAUAC GGAACGC                                              17

(2) INFORMATION FOR SEQ ID NO: 178:

(i) SEQUENCE CHARACTERISTICS:
             (A) LENGTH:            17 base pairs
             (B) TYPE:              nucleic acid
             (C) STRANDEDNESS:      single
             (D) TOPOLOGY:          linear (xi) SEQUENCE DESCRIPTION: SEQ ID NO: 178:

GGGAUCCUCG AGGCCGA                                              17

(2) INFORMATION FOR SEQ ID NO: 179:

(i) SEQUENCE CHARACTERISTICS:
             (A) LENGTH:            17 base pairs
             (B) TYPE:              nucleic acid
             (C) STRANDEDNESS:      single
             (D) TOPOLOGY:          linear (xi) SEQUENCE DESCRIPTION: SEQ ID NO: 179:

CUGCGCGUCC ACCGGUG                                              17

(2) INFORMATION FOR SEQ ID NO: 180:

(i) SEQUENCE CHARACTERISTICS:
```

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 180:

GACAGGGUCC UCACCGU                                                          17

(2) INFORMATION FOR SEQ ID NO: 181:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 181:

GGUGGACUCG UCGACAC                                                          17

(2) INFORMATION FOR SEQ ID NO: 182:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 182:

AGGGUCCUCA CCGUCAG                                                          17

(2) INFORMATION FOR SEQ ID NO: 183:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 183:

GGACUCGUCG ACACCAU                                                          17

(2) INFORMATION FOR SEQ ID NO: 184:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 184:

CUCACCGUCA GCCCCUA                                                          17

(2) INFORMATION FOR SEQ ID NO: 185:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 185:

GACACCAUCA UCGAAGG                                                          17

(2) INFORMATION FOR SEQ ID NO: 186:

(i) SEQUENCE CHARACTERISTICS:
            (A) LENGTH:           17 base pairs

```
            (B) TYPE:              nucleic acid
            (C) STRANDEDNESS:      single
            (D) TOPOLOGY:          linear (xi) SEQUENCE DESCRIPTION: SEQ ID NO: 186:

CAGCCCCUAC UACGCCG                                              17

(2) INFORMATION FOR SEQ ID NO: 187:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 187:

ACCAUCAUCG AAGGCAA                                              17

(2) INFORMATION FOR SEQ ID NO: 188:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 188:

CCCCUACUAC GCCGAGG                                              17

(2) INFORMATION FOR SEQ ID NO: 189:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 189:

GACCGGGUUC CACAUGG                                              17

(2) INFORMATION FOR SEQ ID NO: 190:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 190:

GAGGAGCUCA UCUCCGG                                              17

(2) INFORMATION FOR SEQ ID NO: 191:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 191:

ACCGGGUUCC ACAUGGG                                              17

(2) INFORMATION FOR SEQ ID NO: 192:

(i) SEQUENCE CHARACTERISTICS:
            (A) LENGTH:            17 base pairs
            (B) TYPE:              nucleic acid
```

```
            (C) STRANDEDNESS:        single
            (D) TOPOLOGY:            linear (xi) SEQUENCE DESCRIPTION: SEQ ID NO: 192:

GAGCUCAUCU CCGGCAU                                                          17

(2) INFORMATION FOR SEQ ID NO: 193:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 193:

GGCCGCCUCA GCGUCGA                                                          17

(2) INFORMATION FOR SEQ ID NO: 194:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 194:

GCUCAUCUCC GGCAUCG                                                          17

(2) INFORMATION FOR SEQ ID NO: 195:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 195:

CUCAGCGUCG ACUGCAA                                                          17

(2) INFORMATION FOR SEQ ID NO: 196:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 196:

UCCGGCAUCG CCAGGGG                                                          17

(2) INFORMATION FOR SEQ ID NO: 197:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 197:

UGCAACGUCG UGGAGCC                                                          17

(2) INFORMATION FOR SEQ ID NO: 198:

(i) SEQUENCE CHARACTERISTICS:
            (A) LENGTH:              17 base pairs
            (B) TYPE:                nucleic acid
            (C) STRANDEDNESS:        single
```

(D) TOPOLOGY:           linear (xi) SEQUENCE DESCRIPTION: SEQ ID NO: 198:

UGCGAGCUCG ACAACAU                                                        17

(2) INFORMATION FOR SEQ ID NO: 199:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 199:

GCGGACGUCA AGAAGGU                                                        17

(2) INFORMATION FOR SEQ ID NO: 200:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 200:

GACAACAUCA UGCGCCU                                                        17

(2) INFORMATION FOR SEQ ID NO: 201:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 201:

CACCACCUUG CAGCGCG                                                        17

(2) INFORMATION FOR SEQ ID NO: 202:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 202:

AUGCGCCUCA CCGGCAU                                                        17

(2) INFORMATION FOR SEQ ID NO: 203:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 203:

CGCGCCAUCA AGGUGGU                                                        17

(2) INFORMATION FOR SEQ ID NO: 204:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 204:

ACCGGCAUCA CCGGCAU                                              17

(2) INFORMATION FOR SEQ ID NO: 205:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 205:

AAGGUGGUCG GCACGCC                                              17

(2) INFORMATION FOR SEQ ID NO: 206:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 206:

ACCGGCAUCG UCAACGG                                              17

(2) INFORMATION FOR SEQ ID NO: 207:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 207:

GCCGGCGUAC GAGGAGA                                              17

(2) INFORMATION FOR SEQ ID NO: 208:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 208:

GGCAUCGUCA ACGGCAU                                              17

(2) INFORMATION FOR SEQ ID NO: 209:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 209:

UGCAUGAUCC AGGAUCU                                              17

(2) INFORMATION FOR SEQ ID NO: 210:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 210:

UCCAGGAUCU CUCCUGG                                                    17

(2) INFORMATION FOR SEQ ID NO: 211:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 211:

CGGUAAUUUU AUAUUGC                                                    17

(2) INFORMATION FOR SEQ ID NO: 212:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 212:

CAGGAUCUCU CCUGGAA                                                    17

(2) INFORMATION FOR SEQ ID NO: 213:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 213:

GGUAAUUUUA UAUUGCG                                                    17

(2) INFORMATION FOR SEQ ID NO: 214:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 214:

GGAUCUCUCC UGGAAGG                                                    17

(2) INFORMATION FOR SEQ ID NO: 215:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 215:

GUAAUUUUAU AUUGCGA                                                    17

(2) INFORMATION FOR SEQ ID NO: 216:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 216:

GUGCUGCUCA GCCUCGG        17

(2) INFORMATION FOR SEQ ID NO: 217:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 217:

AAUUUUAUAU UGCGAGU        17

(2) INFORMATION FOR SEQ ID NO: 218:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 218:

CUCAGCCUCG GGGUCGC        17

(2) INFORMATION FOR SEQ ID NO: 219:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 219:

UUUUAUAUUG CGAGUAA        17

(2) INFORMATION FOR SEQ ID NO: 220:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 220:

CUCGGGGUCG CCGGCGG        17

(2) INFORMATION FOR SEQ ID NO: 221:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 221:

UUGCGAGUAA AUAAAUG        17

(2) INFORMATION FOR SEQ ID NO: 222:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 222:

CCAGGGGUCG AAGGCGA                                                      17

(2) INFORMATION FOR SEQ ID NO: 223:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 223:

GAGUAAAUAA AUGGACC                                                      17

(2) INFORMATION FOR SEQ ID NO: 224:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 224:

GAGGAGAUCG CGCCGCU                                                      17

(2) INFORMATION FOR SEQ ID NO: 225:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 225:

GGACCUGUAG UGGUGGA                                                      17

(2) INFORMATION FOR SEQ ID NO: 226:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 226:

GCGCCGCUCG CCAAGGA                                                      17

(2) INFORMATION FOR SEQ ID NO: 227:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 227:

UGAAGAGUUC GGCCUGC                                                      17

(2) INFORMATION FOR SEQ ID NO: 228:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 228:

GAAGAGUUCG GCCUGCA                                                      17

(2) INFORMATION FOR SEQ ID NO: 229:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 229:

CCCCUGAUCU CGCGCGU                                       17

(2) INFORMATION FOR SEQ ID NO: 230:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 230:

CCUGAUCUCG CGCGUGG                                       17

(2) INFORMATION FOR SEQ ID NO: 231:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 231:

AAACAUGUUG GGACAUC                                       17

(2) INFORMATION FOR SEQ ID NO: 232:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 232:

UGGGACAUCU UCUUAUA                                     17

(2) INFORMATION FOR SEQ ID NO: 233:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 233:

GGACAUCUUC UUAUAUA                                     17

(2) INFORMATION FOR SEQ ID NO: 234:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 234:

GACAUCUUCU UAUAUAU                                     17

(2) INFORMATION FOR SEQ ID NO: 235:

(i) SEQUENCE CHARACTERISTICS:
        (A) LENGTH:         17 base pairs
        (B) TYPE:           nucleic acid
        (C) STRANDEDNESS:   single
        (D) TOPOLOGY:      linear (xi) SEQUENCE DESCRIPTION: SEQ ID NO: 235:

CAUCUUCUUA UAUAUGC                               17

(2) INFORMATION FOR SEQ ID NO: 236:

(i) SEQUENCE CHARACTERISTICS:
        (A) LENGTH:         17 base pairs
        (B) TYPE:           nucleic acid
        (C) STRANDEDNESS:   single
        (D) TOPOLOGY:      linear (xi) SEQUENCE DESCRIPTION: SEQ ID NO: 236:

AUCUUCUUAU AUAUGCU                               17

(2) INFORMATION FOR SEQ ID NO: 237:

(i) SEQUENCE CHARACTERISTICS:
        (A) LENGTH:         17 base pairs
        (B) TYPE:           nucleic acid
        (C) STRANDEDNESS:   single
        (D) TOPOLOGY:      linear (xi) SEQUENCE DESCRIPTION: SEQ ID NO: 237:

CUUCUUAUAU AUGCUGU                               17

(2) INFORMATION FOR SEQ ID NO: 238:

(i) SEQUENCE CHARACTERISTICS:
        (A) LENGTH:         17 base pairs
        (B) TYPE:           nucleic acid
        (C) STRANDEDNESS:   single
        (D) TOPOLOGY:      linear (xi) SEQUENCE DESCRIPTION: SEQ ID NO: 238:

UCUUAUAUAU GCUGUUU                               17

(2) INFORMATION FOR SEQ ID NO: 239:

(i) SEQUENCE CHARACTERISTICS:
        (A) LENGTH:         17 base pairs
        (B) TYPE:           nucleic acid
        (C) STRANDEDNESS:   single
        (D) TOPOLOGY:      linear (xi) SEQUENCE DESCRIPTION: SEQ ID NO: 239:

UAUGCUGUUU CGUUUAU                               17

(2) INFORMATION FOR SEQ ID NO: 240:

(i) SEQUENCE CHARACTERISTICS:
        (A) LENGTH:         17 base pairs
        (B) TYPE:           nucleic acid
        (C) STRANDEDNESS:   single
        (D) TOPOLOGY:      linear (xi) SEQUENCE DESCRIPTION: SEQ ID NO: 240:

AUGCUGUUUC GUUUAUG                               17

```
(2) INFORMATION FOR SEQ ID NO: 241:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 241:

UGCUGUUUCG UUUAUGU                                                   17

(2) INFORMATION FOR SEQ ID NO: 242:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 242:

UGUUUCGUUU AUGUGAU                                                   17

(2) INFORMATION FOR SEQ ID NO: 243:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 243:

GUUUCGUUUA UGUGAUA                                                   17

(2) INFORMATION FOR SEQ ID NO: 244:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 244:

UUUCGUUUAU GUGAUAU                                                   17

(2) INFORMATION FOR SEQ ID NO: 245:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 245:

UAUGUGAUAU GGACAAG                                                   17

(2) INFORMATION FOR SEQ ID NO: 246:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 246:

GGACAAGUAU GUGUAGC                                                   17

(2) INFORMATION FOR SEQ ID NO: 247:
```

```
    (i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 247:

GUAUGUGUAG CUGCUUG                                                        17

(2) INFORMATION FOR SEQ ID NO: 248:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 248:

UAGCUGCUUG CUUGUGC                                                        17

(2) INFORMATION FOR SEQ ID NO: 249:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 249:

UGCUUGCUUG UGCUAGU                                                        17

(2) INFORMATION FOR SEQ ID NO: 250:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 250:

CUUGUGCUAG UGUAAUA                                                        17

(2) INFORMATION FOR SEQ ID NO: 251:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 251:

GCUAGUGUAA UAUAGUG                                                        17

(2) INFORMATION FOR SEQ ID NO: 252:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 252:

AGUGUAAUAU AGUGUAG                                                        17

(2) INFORMATION FOR SEQ ID NO: 253:
```

```
    (i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 253:

UGUAAUAUAG UGUAGUG                                                17

(2) INFORMATION FOR SEQ ID NO: 254:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 254:

UAUAGUGUAG UGGUGGC                                                17

(2) INFORMATION FOR SEQ ID NO: 255:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 255:

CACAACCUAA UAAGCGC                                                17

(2) INFORMATION FOR SEQ ID NO: 256:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 256:

AACCUAAUAA GCGCAUG                                                17

(2) INFORMATION FOR SEQ ID NO: 257:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 257:

CAUGAACUAA UUGCUUG                                                17

(2) INFORMATION FOR SEQ ID NO: 258:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 258:

GAACUAAUUG CUUGCGU                                                17

(2) INFORMATION FOR SEQ ID NO: 259:

(i) SEQUENCE CHARACTERISTICS:
```

```
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 259:

UAAUUGCUUG CGUGUGU                                                    17

(2) INFORMATION FOR SEQ ID NO: 260:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 260:

GCGUGUGUAG UUAAGUA                                                    17

(2) INFORMATION FOR SEQ ID NO: 261:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 261:

UGUGUAGUUA AGUACCG                                                    17

(2) INFORMATION FOR SEQ ID NO: 262:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 262:

GUGUAGUUAA GUACCGA                                                    17

(2) INFORMATION FOR SEQ ID NO: 263:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 263:

AGUUAAGUAC CGAUCGG                                                    17

(2) INFORMATION FOR SEQ ID NO: 264:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 264:

GUACCGAUCG GUAAUUU                                                    17

(2) INFORMATION FOR SEQ ID NO: 265:

(i) SEQUENCE CHARACTERISTICS:
        (A) LENGTH:            17 base pairs
```

```
        (B) TYPE:            nucleic acid
        (C) STRANDEDNESS:    single
        (D) TOPOLOGY:        linear (xi) SEQUENCE DESCRIPTION: SEQ ID NO: 265:

CGAUCGGUAA UUUUAUA                                                  17

(2) INFORMATION FOR SEQ ID NO: 266:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 266:

UCGGUAAUUU UAUAUUG                                                  17

(2) INFORMATION FOR SEQ ID NO:267:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:267:

UGGCUGUGGC CUGAUGANGA AAUCGAUCGG U                                  31

(2) INFORMATION FOR SEQ ID NO:268:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:268:

GCAGUGAGUU CUGAUGANGA AAUUCCUUCC U                                  31

(2) INFORMATION FOR SEQ ID NO:269:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:269:

GGCUGGCAGU CUGAUGANGA AAGUUUAUUC C                                  31

(2) INFORMATION FOR SEQ ID NO:270:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
```

(D) OTHER INFORMATION:   The letter "N" stands for any base.

(xi) SEQUENCE DESCRIPTION: SEQ ID NO:270:

GACGGAGCAG CUGAUGANGA AACACUUCUC C                                    31

(2) INFORMATION FOR SEQ ID NO:271:

(i) SEQUENCE CHARACTERISTICS:
                (A) LENGTH:          31 base pairs
                (B) TYPE:            nucleic acid
                (C) STRANDEDNESS:    single
                (D) TOPOLOGY:        linear (ix) FEATURE:
                (D) OTHER INFORMATION:   The letter "N" stands for any base.

(xi) SEQUENCE DESCRIPTION: SEQ ID NO:271:

CUGGUGGACG CUGAUGANGA AAGCAGUACA C                                    31

(2) INFORMATION FOR SEQ ID NO:272:

(i) SEQUENCE CHARACTERISTICS:
                (A) LENGTH:          31 base pairs
                (B) TYPE:            nucleic acid
                (C) STRANDEDNESS:    single
                (D) TOPOLOGY:        linear (ix) FEATURE:
                (D) OTHER INFORMATION:   The letter "N" stands for any base.

(xi) SEQUENCE DESCRIPTION: SEQ ID NO:272:

CGCACUGGUG CUGAUGANGA AACGGAGCAG U                                    31

(2) INFORMATION FOR SEQ ID NO:273:

(i) SEQUENCE CHARACTERISTICS:
                (A) LENGTH:          31 base pairs
                (B) TYPE:            nucleic acid
                (C) STRANDEDNESS:    single
                (D) TOPOLOGY:        linear (ix) FEATURE:
                (D) OTHER INFORMATION:   The letter "N" stands for any base.

(xi) SEQUENCE DESCRIPTION: SEQ ID NO:273:

UCGACGAGAU CUGAUGANGA AAGCAGCCCU G                                    31

(2) INFORMATION FOR SEQ ID NO:274:

(i) SEQUENCE CHARACTERISTICS:
                (A) LENGTH:          31 base pairs
                (B) TYPE:            nucleic acid
                (C) STRANDEDNESS:    single
                (D) TOPOLOGY:        linear (ix) FEATURE:
                (D) OTHER INFORMATION:   The letter "N" stands for any base.

(xi) SEQUENCE DESCRIPTION: SEQ ID NO:274:

UCGUCGACGA CUGAUGANGA AAUGAGCAGC C                                    31

(2) INFORMATION FOR SEQ ID NO:275:

(i) SEQUENCE CHARACTERISTICS:
                (A) LENGTH:          31 base pairs
                (B) TYPE:            nucleic acid
                (C) STRANDEDNESS:    single
                (D) TOPOLOGY:        linear (ix) FEATURE:
            (D) OTHER INFORMATION:    The letter "N" stands for any base.

(xi) SEQUENCE DESCRIPTION: SEQ ID NO:275:

GGUCGUCGAC CUGAUGANGA AAGAUGAGCA G                                              31

(2) INFORMATION FOR SEQ ID NO:276:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:276:

ACUGGUCGUC CUGAUGANGA AACGAGAUGA G                                              31

(2) INFORMATION FOR SEQ ID NO:277:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:277:

CAUGCCGAUU CUGAUGANGA AAUCCACUGG U                                              31

(2) INFORMATION FOR SEQ ID NO:278:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:278:

CCAUGCCGAU CUGAUGANGA AAAUCCACUG G                                              31

(2) INFORMATION FOR SEQ ID NO:279:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:279:

CCGCCAUGCC CUGAUGANGA AAUUAAUCCA C                                              31

(2) INFORMATION FOR SEQ ID NO:280:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:280:

GACGUGGCUA CUGAUGANGA AAGCCGCCAU G                                                 31

(2) INFORMATION FOR SEQ ID NO:281:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:281:

GCGACGUGGC CUGAUGANGA AAGAGCCGCC A                                                 31

(2) INFORMATION FOR SEQ ID NO:282:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:282:

GACGAGCUGC CUGAUGANGA AACGUGGCUA G                                                 31

(2) INFORMATION FOR SEQ ID NO:283:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:283:

GCGUUGCGAC CUGAUGANGA AAGCUGCGAC G                                                 31

(2) INFORMATION FOR SEQ ID NO:284:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:284:

CGCGCGUUGC CUGAUGANGA AACGAGCUGC G                                                 31

(2) INFORMATION FOR SEQ ID NO:285:

(i) SEQUENCE CHARACTERISTICS:
            (A) LENGTH:               31 base pairs
            (B) TYPE:                 nucleic acid
            (C) STRANDEDNESS:         single -continued

```
            (D) TOPOLOGY:           linear (ix) FEATURE:
            (D) OTHER INFORMATION:  The letter "N" stands for any base.

(xi) SEQUENCE DESCRIPTION: SEQ ID NO:285:

ACGCGUCCGG CUGAUGANGA AACGCCCAGG C                                            31

(2) INFORMATION FOR SEQ ID NO:286:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:286:

GCGGAACGUG CUGAUGANGA AACGCGUCCG G                                            31

(2) INFORMATION FOR SEQ ID NO:287:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:287:

GCCGCGGCGG CUGAUGANGA AACGUGGACG C                                            31

(2) INFORMATION FOR SEQ ID NO:288:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:288:

CGCCGCGGCG CUGAUGANGA AAACGUGGAC G                                            31

(2) INFORMATION FOR SEQ ID NO:289:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:289:

GUCCGCCGCC CUGAUGANGA AACGCCGUCC G                                            31

(2) INFORMATION FOR SEQ ID NO:290:

(i) SEQUENCE CHARACTERISTICS:
            (A) LENGTH:             31 base pairs
            (B) TYPE:               nucleic acid
```

(C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:290:

UCCGAAUGCU CUGAUGANGA AAGCGUGUCC G                                31

(2) INFORMATION FOR SEQ ID NO:291:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:291:

CGCUGGUCCG CUGAUGANGA AAUGCUGAGC G                                31

(2) INFORMATION FOR SEQ ID NO:292:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:292:

GCGCUGGUCC CUGAUGANGA AAAUGCUGAG C                                31

(2) INFORMATION FOR SEQ ID NO:293:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:293:

GCUGGUGCUG CUGAUGANGA AAGCCUGGGC G                                31

(2) INFORMATION FOR SEQ ID NO:294:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:294:

GAGCGACGGG CUGAUGANGA AACCUGGCCC C                                31

(2) INFORMATION FOR SEQ ID NO:295:

(i) SEQUENCE CHARACTERISTICS:
            (A) LENGTH:              31 base pairs

```
            (B) TYPE:              nucleic acid
            (C) STRANDEDNESS:      single
            (D) TOPOLOGY:          linear (ix) FEATURE:
            (D) OTHER INFORMATION:  The letter "N" stands for any base.

(xi) SEQUENCE DESCRIPTION: SEQ ID NO:295:

CGAGCGACGG CUGAUGANGA AAACCUGGCC C                                      31

(2) INFORMATION FOR SEQ ID NO:296:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:  The letter "N" stands for any base.

(xi) SEQUENCE DESCRIPTION: SEQ ID NO:296:

CACGACGAGC CUGAUGANGA AACGGGAACC U                                      31

(2) INFORMATION FOR SEQ ID NO:297:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:  The letter "N" stands for any base.

(xi) SEQUENCE DESCRIPTION: SEQ ID NO:297:

CGCACACGAC CUGAUGANGA AAGCGACGGG A                                      31

(2) INFORMATION FOR SEQ ID NO:298:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:  The letter "N" stands for any base.

(xi) SEQUENCE DESCRIPTION: SEQ ID NO:298:

UGGCGCACAC CUGAUGANGA AACGAGCGAC G                                      31

(2) INFORMATION FOR SEQ ID NO:299:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:  The letter "N" stands for any base.

(xi) SEQUENCE DESCRIPTION: SEQ ID NO:299:

CGACGAAGAC CUGAUGANGA AACGUUCAUG C                                      31

(2) INFORMATION FOR SEQ ID NO:300:

(i) SEQUENCE CHARACTERISTICS:
```

```
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:300:

CGCCGACGAA CUGAUGANGA AACGACGUUC A                              31

(2) INFORMATION FOR SEQ ID NO:301:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:301:

GGCGCCGACG CUGAUGANGA AAGACGACGU U                              31

(2) INFORMATION FOR SEQ ID NO:302:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:302:

CGGCGCCGAC CUGAUGANGA AAAGACGACG U                              31

(2) INFORMATION FOR SEQ ID NO:303:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:303:

UCUCGGCGCC CUGAUGANGA AACGAAGACG A                              31

(2) INFORMATION FOR SEQ ID NO:304:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:304:

GGACGUCGCC CUGAUGANGA AAGGCCGCCG G                              31

(2) INFORMATION FOR SEQ ID NO:305:
```

```
        (i) SEQUENCE CHARACTERISTICS:
            (A) LENGTH:          31 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any base.

(xi) SEQUENCE DESCRIPTION: SEQ ID NO:305:

GGCCGCCGAG CUGAUGANGA AACGUCGCCG A                                       31

(2) INFORMATION FOR SEQ ID NO:306:

(i) SEQUENCE CHARACTERISTICS:
            (A) LENGTH:          31 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any base.

(xi) SEQUENCE DESCRIPTION: SEQ ID NO:306:

GCAGGCCGCC CUGAUGANGA AAGGACGUCG C                                       31

(2) INFORMATION FOR SEQ ID NO:307:

(i) SEQUENCE CHARACTERISTICS:
            (A) LENGTH:          31 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any base.

(xi) SEQUENCE DESCRIPTION: SEQ ID NO:307:

AGACGACCAU CUGAUGANGA AACACGGUGC C                                       31

(2) INFORMATION FOR SEQ ID NO:308:

(i) SEQUENCE CHARACTERISTICS:
            (A) LENGTH:          31 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any base.

(xi) SEQUENCE DESCRIPTION: SEQ ID NO:308:

GGGGAGAGAC CUGAUGANGA AACCAUGACA C                                       31

(2) INFORMATION FOR SEQ ID NO:309:

(i) SEQUENCE CHARACTERISTICS:
            (A) LENGTH:          31 base pairs
            (B) TYPE:            nucleic acid
            (C) STRANDEDNESS:    single
            (D) TOPOLOGY:        linear (ix) FEATURE:
            (D) OTHER INFORMATION:   The letter "N" stands for any base.

(xi) SEQUENCE DESCRIPTION: SEQ ID NO:309:

AGCGGGGAGA CUGAUGANGA AACGACCAUG A                                       31

(2) INFORMATION FOR SEQ ID NO:310:
```

(i) SEQUENCE CHARACTERISTICS:
              (A) LENGTH:           31 base pairs
              (B) TYPE:             nucleic acid
              (C) STRANDEDNESS:     single
              (D) TOPOLOGY:         linear (ix) FEATURE:
              (D) OTHER INFORMATION:   The letter "N" stands for any base.

(xi) SEQUENCE DESCRIPTION: SEQ ID NO:310:

GUAGCGGGGA CUGAUGANGA AAGACGACCA U                                31

(2) INFORMATION FOR SEQ ID NO:311:

(i) SEQUENCE CHARACTERISTICS:
              (A) LENGTH:           31 base pairs
              (B) TYPE:             nucleic acid
              (C) STRANDEDNESS:     single
              (D) TOPOLOGY:         linear (ix) FEATURE:
              (D) OTHER INFORMATION:   The letter "N" stands for any base.

(xi) SEQUENCE DESCRIPTION: SEQ ID NO:311:

UCGUAGCGGG CUGAUGANGA AAGAGACGAC C                                31

(2) INFORMATION FOR SEQ ID NO:312:

(i) SEQUENCE CHARACTERISTICS:
              (A) LENGTH:           31 base pairs
              (B) TYPE:             nucleic acid
              (C) STRANDEDNESS:     single
              (D) TOPOLOGY:         linear (ix) FEATURE:
              (D) OTHER INFORMATION:   The letter "N" stands for any base.

(xi) SEQUENCE DESCRIPTION: SEQ ID NO:312:

GUACUGGUCG CUGAUGANGA AAGCGGGGAG A                                31

(2) INFORMATION FOR SEQ ID NO:313:

(i) SEQUENCE CHARACTERISTICS:
              (A) LENGTH:           31 base pairs
              (B) TYPE:             nucleic acid
              (C) STRANDEDNESS:     single
              (D) TOPOLOGY:         linear (ix) FEATURE:
              (D) OTHER INFORMATION:   The letter "N" stands for any base.

(xi) SEQUENCE DESCRIPTION: SEQ ID NO:313:

GGCGUCCUUG CUGAUGANGA AACUGGUCGU A                                31

(2) INFORMATION FOR SEQ ID NO:314:

(i) SEQUENCE CHARACTERISTICS:
              (A) LENGTH:           31 base pairs
              (B) TYPE:             nucleic acid
              (C) STRANDEDNESS:     single
              (D) TOPOLOGY:         linear (ix) FEATURE:
              (D) OTHER INFORMATION:   The letter "N" stands for any base.

(xi) SEQUENCE DESCRIPTION: SEQ ID NO:314:

UCUCGGACAC CUGAUGANGA AACGCUGGUG U                                31

(2) INFORMATION FOR SEQ ID NO:315:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:315:

CUUGAUCUCG CUGAUGANGA AACACGACGC U                              31

(2) INFORMATION FOR SEQ ID NO:316:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:316:

CUCCCAUCUU CUGAUGANGA AAUCUCGGAC A                              31

(2) INFORMATION FOR SEQ ID NO:317:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:317:

GACCGUCUCG CUGAUGANGA AACCUGUCUC C                              31

(2) INFORMATION FOR SEQ ID NO:318:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:318:

GGAAGAACCU CUGAUGANGA AACCGUCUCG U                              31

(2) INFORMATION FOR SEQ ID NO:319:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:319:

GCAGUGGAAG CUGAUGANGA AACCUGACCG U                              31

(2) INFORMATION FOR SEQ ID NO:320:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:320:

AGCAGUGGAA CUGAUGANGA AAACCUGACC G                                  31

(2) INFORMATION FOR SEQ ID NO:321:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:321:

GUAGCAGUGG CUGAUGANGA AAGAACCUGA C                                  31

(2) INFORMATION FOR SEQ ID NO:322:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:322:

UGUAGCAGUG CUGAUGANGA AAAGAACCUG A                                  31

(2) INFORMATION FOR SEQ ID NO:323:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:323:

UCCGCGCUUG CUGAUGANGA AAGCAGUGGA A                                  31

(2) INFORMATION FOR SEQ ID NO:324:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:324:

GUGGUCAACG CUGAUGANGA AACACGCGGU C                                  31

(2) INFORMATION FOR SEQ ID NO:325:

(i) SEQUENCE CHARACTERISTICS:
        (A) LENGTH:           31 base pairs
        (B) TYPE:             nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:325:

GGUGGUCAAC CUGAUGANGA AAACACGCGG U                                    31

(2) INFORMATION FOR SEQ ID NO:326:

(i) SEQUENCE CHARACTERISTICS:
        (A) LENGTH:           31 base pairs
        (B) TYPE:             nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:326:

GUGGGUGGUC CUGAUGANGA AACGAACACG C                                    31

(2) INFORMATION FOR SEQ ID NO:327:

(i) SEQUENCE CHARACTERISTICS:
        (A) LENGTH:           31 base pairs
        (B) TYPE:             nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:327:

CCUCUCCAGG CUGAUGANGA AACAGUGGGU G                                    31

(2) INFORMATION FOR SEQ ID NO:328:

(i) SEQUENCE CHARACTERISTICS:
        (A) LENGTH:           31 base pairs
        (B) TYPE:             nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:328:

CCCUCUCCAG CUGAUGANGA AAACAGUGGG U                                    31

(2) INFORMATION FOR SEQ ID NO:329:

(i) SEQUENCE CHARACTERISTICS:
        (A) LENGTH:           31 base pairs
        (B) TYPE:             nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:329:

UCUUUCCCCA CUGAUGANGA AACCCUCUCC A                              31

(2) INFORMATION FOR SEQ ID NO:330:

(i) SEQUENCE CHARACTERISTICS:
        (A) LENGTH:        31 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:330:

GUCUUCCCC CUGAUGANGA AAACCCUCUC C                               31

(2) INFORMATION FOR SEQ ID NO:331:

(i) SEQUENCE CHARACTERISTICS:
        (A) LENGTH:        31 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:331:

CAGGCCCGUA CUGAUGANGA AAUCUUCUCC U                              31

(2) INFORMATION FOR SEQ ID NO:332:

(i) SEQUENCE CHARACTERISTICS:
        (A) LENGTH:        31 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:332:

GUCAGGCCCG CUGAUGANGA AAGAUCUUCU C                              31

(2) INFORMATION FOR SEQ ID NO:333:

(i) SEQUENCE CHARACTERISTICS:
        (A) LENGTH:        31 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:333:

GUUGUCCCUG CUGAUGANGA AAGUCCGUUC C                              31

(2) INFORMATION FOR SEQ ID NO:334:

(i) SEQUENCE CHARACTERISTICS:
        (A) LENGTH:        31 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:334:

UAGCAGGCUG CUGAUGANGA AACCGCAGCU G                                      31

(2) INFORMATION FOR SEQ ID NO:335:

(i) SEQUENCE CHARACTERISTICS:
        (A) LENGTH:        31 base pairs
        (B) TYPE:          nucleic acid
        (C) STRANDEDNESS:  single
        (D) TOPOLOGY:     linear (ix) FEATURE:
        (D) OTHER INFORMATION:    The letter "N" stands for any base.

(xi) SEQUENCE DESCRIPTION: SEQ ID NO:335:

AUAGCAGGCU CUGAUGANGA AAACCGCAGC U                                      31

(2) INFORMATION FOR SEQ ID NO:336:

(i) SEQUENCE CHARACTERISTICS:
        (A) LENGTH:        31 base pairs
        (B) TYPE:          nucleic acid
        (C) STRANDEDNESS:  single
        (D) TOPOLOGY:     linear (ix) FEATURE:
        (D) OTHER INFORMATION:    The letter "N" stands for any base.

(xi) SEQUENCE DESCRIPTION: SEQ ID NO:336:

CUGCCUGGCA CUGAUGANGA AAGCAGGCUG A                                      31

(2) INFORMATION FOR SEQ ID NO:337:

(i) SEQUENCE CHARACTERISTICS:
        (A) LENGTH:        31 base pairs
        (B) TYPE:          nucleic acid
        (C) STRANDEDNESS:  single
        (D) TOPOLOGY:     linear (ix) FEATURE:
        (D) OTHER INFORMATION:    The letter "N" stands for any base.

(xi) SEQUENCE DESCRIPTION: SEQ ID NO:337:

UUGGAGCUUC CUGAUGANGA AAGUGCUGCC U                                      31

(2) INFORMATION FOR SEQ ID NO:338:

(i) SEQUENCE CHARACTERISTICS:
        (A) LENGTH:        31 base pairs
        (B) TYPE:          nucleic acid
        (C) STRANDEDNESS:  single
        (D) TOPOLOGY:     linear (ix) FEATURE:
        (D) OTHER INFORMATION:    The letter "N" stands for any base.

(xi) SEQUENCE DESCRIPTION: SEQ ID NO:338:

AGGAUCCUUG CUGAUGANGA AAGCUUCAAG U                                      31

(2) INFORMATION FOR SEQ ID NO:339:

(i) SEQUENCE CHARACTERISTICS:
        (A) LENGTH:        31 base pairs
        (B) TYPE:          nucleic acid
        (C) STRANDEDNESS:  single
        (D) TOPOLOGY:     linear (ix) FEATURE:
        (D) OTHER INFORMATION:    The letter "N" stands for any base.

-continued (xi) SEQUENCE DESCRIPTION: SEQ ID NO:339:

UGAGGCUCAG CUGAUGANGA AAUCCUUGGA G                                    31

(2) INFORMATION FOR SEQ ID NO:340:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:340:

GGUUGUUGUU CUGAUGANGA AAGGCUCAGG A                                    31

(2) INFORMATION FOR SEQ ID NO:341:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:341:

UCCGGAGAAG CUGAUGANGA AAUGGGUUGU U                                    31

(2) INFORMATION FOR SEQ ID NO:342:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:342:

UGGUCCGGAG CUGAUGANGA AAGUAUGGGU U                                    31

(2) INFORMATION FOR SEQ ID NO:343:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:343:

AUGGUCCGGA CUGAUGANGA AAAGUAUGGG U                                    31

(2) INFORMATION FOR SEQ ID NO:344:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:344:

GUAUGGUCCG CUGAUGANGA AAGAAGUAUG G                                31

(2) INFORMATION FOR SEQ ID NO:345:

(i) SEQUENCE CHARACTERISTICS:
              (A) LENGTH:              31 base pairs
              (B) TYPE:                nucleic acid
              (C) STRANDEDNESS:        single
              (D) TOPOLOGY:            linear (ix) FEATURE:
              (D) OTHER INFORMATION:   The letter "N" stands for any base.

(xi) SEQUENCE DESCRIPTION: SEQ ID NO:345:

GUCCUCCCCG CUGAUGANGA AAUGGUCCGG A                                31

(2) INFORMATION FOR SEQ ID NO:346:

(i) SEQUENCE CHARACTERISTICS:
              (A) LENGTH:              31 base pairs
              (B) TYPE:                nucleic acid
              (C) STRANDEDNESS:        single
              (D) TOPOLOGY:            linear (ix) FEATURE:
              (D) OTHER INFORMATION:   The letter "N" stands for any base.

(xi) SEQUENCE DESCRIPTION: SEQ ID NO:346:

AGACGAACAC CUGAUGANGA AACGUCCUCC C                                31

(2) INFORMATION FOR SEQ ID NO:347:

(i) SEQUENCE CHARACTERISTICS:
              (A) LENGTH:              31 base pairs
              (B) TYPE:                nucleic acid
              (C) STRANDEDNESS:        single
              (D) TOPOLOGY:            linear (ix) FEATURE:
              (D) OTHER INFORMATION:   The letter "N" stands for any base.

(xi) SEQUENCE DESCRIPTION: SEQ ID NO:347:

GUUGCAGACG CUGAUGANGA AACACGACGU C                                31

(2) INFORMATION FOR SEQ ID NO:348:

(i) SEQUENCE CHARACTERISTICS:
              (A) LENGTH:              31 base pairs
              (B) TYPE:                nucleic acid
              (C) STRANDEDNESS:        single
              (D) TOPOLOGY:            linear (ix) FEATURE:
              (D) OTHER INFORMATION:   The letter "N" stands for any base.

(xi) SEQUENCE DESCRIPTION: SEQ ID NO:348:

CGUUGCAGAC CUGAUGANGA AAACACGACG U                                31

(2) INFORMATION FOR SEQ ID NO:349:

(i) SEQUENCE CHARACTERISTICS:
              (A) LENGTH:              31 base pairs
              (B) TYPE:                nucleic acid
              (C) STRANDEDNESS:        single
              (D) TOPOLOGY:            linear (ix) FEATURE:

(D) OTHER INFORMATION: The letter "N" stands for any base.

(xi) SEQUENCE DESCRIPTION: SEQ ID NO:349:

AGUCGUUGCA CUGAUGANGA AACGAACACG A                                    31

(2) INFORMATION FOR SEQ ID NO:350:

(i) SEQUENCE CHARACTERISTICS:
      (A) LENGTH:        31 base pairs
      (B) TYPE:          nucleic acid
      (C) STRANDEDNESS:  single
      (D) TOPOLOGY:      linear (ix) FEATURE:
      (D) OTHER INFORMATION: The letter "N" stands for any base.

(xi) SEQUENCE DESCRIPTION: SEQ ID NO:350:

UAGCACGAGA CUGAUGANGA AAGGGCCGGU G                                    31

(2) INFORMATION FOR SEQ ID NO:351:

(i) SEQUENCE CHARACTERISTICS:
      (A) LENGTH:        31 base pairs
      (B) TYPE:          nucleic acid
      (C) STRANDEDNESS:  single
      (D) TOPOLOGY:      linear (ix) FEATURE:
      (D) OTHER INFORMATION: The letter "N" stands for any base.

(xi) SEQUENCE DESCRIPTION: SEQ ID NO:351:

GGUAGCACGA CUGAUGANGA AAGAGGGCCG G                                    31

(2) INFORMATION FOR SEQ ID NO:352:

(i) SEQUENCE CHARACTERISTICS:
      (A) LENGTH:        31 base pairs
      (B) TYPE:          nucleic acid
      (C) STRANDEDNESS:  single
      (D) TOPOLOGY:      linear (ix) FEATURE:
      (D) OTHER INFORMATION: The letter "N" stands for any base.

(xi) SEQUENCE DESCRIPTION: SEQ ID NO:352:

GAGGUAGCAC CUGAUGANGA AAGAGAGGGC C                                    31

(2) INFORMATION FOR SEQ ID NO:353:

(i) SEQUENCE CHARACTERISTICS:
      (A) LENGTH:        31 base pairs
      (B) TYPE:          nucleic acid
      (C) STRANDEDNESS:  single
      (D) TOPOLOGY:      linear (ix) FEATURE:
      (D) OTHER INFORMATION: The letter "N" stands for any base.

(xi) SEQUENCE DESCRIPTION: SEQ ID NO:353:

GCUCUUGAGG CUGAUGANGA AAGCACGAGA G                                    31

(2) INFORMATION FOR SEQ ID NO:354:

(i) SEQUENCE CHARACTERISTICS:
      (A) LENGTH:        31 base pairs
      (B) TYPE:          nucleic acid
      (C) STRANDEDNESS:  single
      (D) TOPOLOGY:      linear (ix) FEATURE:
              (D) OTHER INFORMATION:    The letter "N" stands for any base.

(xi) SEQUENCE DESCRIPTION: SEQ ID NO:354:

AGUUGCUCUU CUGAUGANGA AAGGUAGCAC G                                31

(2) INFORMATION FOR SEQ ID NO:355:

(i) SEQUENCE CHARACTERISTICS:
              (A) LENGTH:               31 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:355:

GUGGGACUGG CUGAUGANGA AAGUUGCUCU U                                31

(2) INFORMATION FOR SEQ ID NO:356:

(i) SEQUENCE CHARACTERISTICS:
              (A) LENGTH:               31 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:356:

GAUGCCGUGG CUGAUGANGA AACUGGUAGU U                                31

(2) INFORMATION FOR SEQ ID NO:357:

(i) SEQUENCE CHARACTERISTICS:
              (A) LENGTH:               31 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:357:

CGUCCCUGUA CUGAUGANGA AAUGCCGUGG G                                31

(2) INFORMATION FOR SEQ ID NO:358:

(i) SEQUENCE CHARACTERISTICS:
              (A) LENGTH:               31 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:358:

UGCGUCCCUG CUGAUGANGA AAGAUGCCGU G                                31

(2) INFORMATION FOR SEQ ID NO:359:

(i) SEQUENCE CHARACTERISTICS:
              (A) LENGTH:               31 base pairs
              (B) TYPE:                 nucleic acid
              (C) STRANDEDNESS:         single
              (D) TOPOLOGY:             linear (ix) FEATURE:
    (D) OTHER INFORMATION:    The letter "N" stands for any base.

(xi) SEQUENCE DESCRIPTION: SEQ ID NO:359:

UGGAUGCAGA CUGAUGANGA AAGCGGUCUU U                              31

(2) INFORMATION FOR SEQ ID NO:360:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:360:

GUGGAUGCAG CUGAUGANGA AAAGCGGUCU U                              31

(2) INFORMATION FOR SEQ ID NO:361:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:361:

UGUGGAUGCA CUGAUGANGA AAAAGCGGUC U                              31

(2) INFORMATION FOR SEQ ID NO:362:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:362:

AGAUGUUGUG CUGAUGANGA AAUGCAGAAA G                              31

(2) INFORMATION FOR SEQ ID NO:363:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:363:

CCUGGUAGGA CUGAUGANGA AAUGUUGUGG A                              31

(2) INFORMATION FOR SEQ ID NO:364:

(i) SEQUENCE CHARACTERISTICS:
        (A) LENGTH:           31 base pairs
        (B) TYPE:             nucleic acid
        (C) STRANDEDNESS:     single (D) TOPOLOGY:           linear (ix) FEATURE:
            (D) OTHER INFORMATION:  The letter "N" stands for any base.

(xi) SEQUENCE DESCRIPTION: SEQ ID NO:364:

GCCCUGGUAG CUGAUGANGA AAGAUGUUGU G                               31

(2) INFORMATION FOR SEQ ID NO:365:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:365:

CCGGCCCUGG CUGAUGANGA AAGGAGAUGU U                               31

(2) INFORMATION FOR SEQ ID NO:366:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:366:

GGAGAAGGCG CUGAUGANGA AACCGGCCCU G                               31

(2) INFORMATION FOR SEQ ID NO:367:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:367:

CGGAGAAGGC CUGAUGANGA AAACCGGCCC U                               31

(2) INFORMATION FOR SEQ ID NO:368:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:368:

GUAGUCGGAG CUGAUGANGA AAGGCGAACC G                               31

(2) INFORMATION FOR SEQ ID NO:369:

(i) SEQUENCE CHARACTERISTICS:
            (A) LENGTH:             31 base pairs
            (B) TYPE:               nucleic acid

```
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:369:

GGUAGUCGGA CUGAUGANGA AAAGGCGAAC C                              31

(2) INFORMATION FOR SEQ ID NO:370:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:370:

CGGGUAGUCG CUGAUGANGA AAGAAGGCGA A                              31

(2) INFORMATION FOR SEQ ID NO:371:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:371:

CAGCUCCGGG CUGAUGANGA AAGUCGGAGA A                              31

(2) INFORMATION FOR SEQ ID NO:372:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:372:

AUCUCUCCGG CUGAUGANGA AAGGUUCAGC U                              31

(2) INFORMATION FOR SEQ ID NO:373:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:373:

GGACGACUUG CUGAUGANGA AAUCUCUCCG G                              31

(2) INFORMATION FOR SEQ ID NO:374:

(i) SEQUENCE CHARACTERISTICS:
            (A) LENGTH:              31 base pairs
```

(B) TYPE:               nucleic acid
                    (C) STRANDEDNESS:       single
                    (D) TOPOLOGY:           linear (ix) FEATURE:
                    (D) OTHER INFORMATION:  The letter "N" stands for any base.

(xi) SEQUENCE DESCRIPTION: SEQ ID NO:374:

AGGACGACUU CUGAUGANGA AAAUCUCUCC G                                       31

(2) INFORMATION FOR SEQ ID NO:375:

(i) SEQUENCE CHARACTERISTICS:
                    (A) LENGTH:             31 base pairs
                    (B) TYPE:               nucleic acid
                    (C) STRANDEDNESS:       single
                    (D) TOPOLOGY:           linear (ix) FEATURE:
                    (D) OTHER INFORMATION:  The letter "N" stands for any base.

(xi) SEQUENCE DESCRIPTION: SEQ ID NO:375:

AUCGAAGGAC CUGAUGANGA AACUUGAAUC U                                       31

(2) INFORMATION FOR SEQ ID NO:376:

(i) SEQUENCE CHARACTERISTICS:
                    (A) LENGTH:             31 base pairs
                    (B) TYPE:               nucleic acid
                    (C) STRANDEDNESS:       single
                    (D) TOPOLOGY:           linear (ix) FEATURE:
                    (D) OTHER INFORMATION:  The letter "N" stands for any base.

(xi) SEQUENCE DESCRIPTION: SEQ ID NO:376:

GAAAUCGAAG CUGAUGANGA AACGACUUGA A                                       31

(2) INFORMATION FOR SEQ ID NO:377:

(i) SEQUENCE CHARACTERISTICS:
                    (A) LENGTH:             31 base pairs
                    (B) TYPE:               nucleic acid
                    (C) STRANDEDNESS:       single
                    (D) TOPOLOGY:           linear (ix) FEATURE:
                    (D) OTHER INFORMATION:  The letter "N" stands for any base.

(xi) SEQUENCE DESCRIPTION: SEQ ID NO:377:

GAUGAAAUCG CUGAUGANGA AAGGACGACU U                                       31

(2) INFORMATION FOR SEQ ID NO:378:

(i) SEQUENCE CHARACTERISTICS:
                    (A) LENGTH:             31 base pairs
                    (B) TYPE:               nucleic acid
                    (C) STRANDEDNESS:       single
                    (D) TOPOLOGY:           linear (ix) FEATURE:
                    (D) OTHER INFORMATION:  The letter "N" stands for any base.

(xi) SEQUENCE DESCRIPTION: SEQ ID NO:378:

CGAUGAAAUC CUGAUGANGA AAAGGACGAC U                                       31

(2) INFORMATION FOR SEQ ID NO:379:

(i) SEQUENCE CHARACTERISTICS:

```
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION: The letter "N" stands for any base.

(xi) SEQUENCE DESCRIPTION: SEQ ID NO:379:

CCGUCGAUGA CUGAUGANGA AAUCGAAGGA C                                   31

(2) INFORMATION FOR SEQ ID NO:380:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION: The letter "N" stands for any base.

(xi) SEQUENCE DESCRIPTION: SEQ ID NO:380:

GCCGUCGAUG CUGAUGANGA AAAUCGAAGG A                                   31

(2) INFORMATION FOR SEQ ID NO:381:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION: The letter "N" stands for any base.

(xi) SEQUENCE DESCRIPTION: SEQ ID NO:381:

AGCCGUCGAU CUGAUGANGA AAAAUCGAAG G                                   31

(2) INFORMATION FOR SEQ ID NO:382:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION: The letter "N" stands for any base.

(xi) SEQUENCE DESCRIPTION: SEQ ID NO:382:

CGUAGCCGUC CUGAUGANGA AAUGAAAUCG A                                   31

(2) INFORMATION FOR SEQ ID NO:383:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION: The letter "N" stands for any base.

(xi) SEQUENCE DESCRIPTION: SEQ ID NO:383:

GGGCUUCUCG CUGAUGANGA AAGCCGUCGA U                                   31

(2) INFORMATION FOR SEQ ID NO:384:
```

```
        (i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:  The letter "N" stands for any base.

(xi) SEQUENCE DESCRIPTION: SEQ ID NO:384:

UCAUCCAGUU CUGAUGANGA AAUCUUCCGG C                                31

(2) INFORMATION FOR SEQ ID NO:385:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:  The letter "N" stands for any base.

(xi) SEQUENCE DESCRIPTION: SEQ ID NO:385:

CGGCCUCGAG CUGAUGANGA AAUCCCGGCC U                                31

(2) INFORMATION FOR SEQ ID NO:386:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:  The letter "N" stands for any base.

(xi) SEQUENCE DESCRIPTION: SEQ ID NO:386:

UGUCGGCCUC CUGAUGANGA AAGGAUCCCG G                                31

(2) INFORMATION FOR SEQ ID NO:387:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:  The letter "N" stands for any base.

(xi) SEQUENCE DESCRIPTION: SEQ ID NO:387:

UGACGGUGAG CUGAUGANGA AACCCUGUCG G                                31

(2) INFORMATION FOR SEQ ID NO:388:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:  The letter "N" stands for any base.

(xi) SEQUENCE DESCRIPTION: SEQ ID NO:388:

GGCUGACGGU CUGAUGANGA AAGGACCCUG U                                31

(2) INFORMATION FOR SEQ ID NO:389:
```

```
      (i) SEQUENCE CHARACTERISTICS:
          (A) LENGTH:            31 base pairs
          (B) TYPE:              nucleic acid
          (C) STRANDEDNESS:      single
          (D) TOPOLOGY:          linear (ix) FEATURE:
          (D) OTHER INFORMATION:   The letter "N" stands for any base.

(xi) SEQUENCE DESCRIPTION: SEQ ID NO:389:

AGUAGGGGCU CUGAUGANGA AACGGUGAGG A                               31

(2) INFORMATION FOR SEQ ID NO:390:

(i) SEQUENCE CHARACTERISTICS:
          (A) LENGTH:            31 base pairs
          (B) TYPE:              nucleic acid
          (C) STRANDEDNESS:      single
          (D) TOPOLOGY:          linear (ix) FEATURE:
          (D) OTHER INFORMATION:   The letter "N" stands for any base.

(xi) SEQUENCE DESCRIPTION: SEQ ID NO:390:

CUCGGCGUAG CUGAUGANGA AAGGGGCUGA C                               31

(2) INFORMATION FOR SEQ ID NO:391:

(i) SEQUENCE CHARACTERISTICS:
          (A) LENGTH:            31 base pairs
          (B) TYPE:              nucleic acid
          (C) STRANDEDNESS:      single
          (D) TOPOLOGY:          linear (ix) FEATURE:
          (D) OTHER INFORMATION:   The letter "N" stands for any base.

(xi) SEQUENCE DESCRIPTION: SEQ ID NO:391:

CUCCUCGGCG CUGAUGANGA AAGUAGGGGC U                               31

(2) INFORMATION FOR SEQ ID NO:392:

(i) SEQUENCE CHARACTERISTICS:
          (A) LENGTH:            31 base pairs
          (B) TYPE:              nucleic acid
          (C) STRANDEDNESS:      single
          (D) TOPOLOGY:          linear (ix) FEATURE:
          (D) OTHER INFORMATION:   The letter "N" stands for any base.

(xi) SEQUENCE DESCRIPTION: SEQ ID NO:392:

UGCCGGAGAU CUGAUGANGA AAGCUCCUCG G                               31

(2) INFORMATION FOR SEQ ID NO:393:

(i) SEQUENCE CHARACTERISTICS:
          (A) LENGTH:            31 base pairs
          (B) TYPE:              nucleic acid
          (C) STRANDEDNESS:      single
          (D) TOPOLOGY:          linear (ix) FEATURE:
          (D) OTHER INFORMATION:   The letter "N" stands for any base.

(xi) SEQUENCE DESCRIPTION: SEQ ID NO:393:

CGAUGCCGGA CUGAUGANGA AAUGAGCUCC U                               31
```

```
(2) INFORMATION FOR SEQ ID NO:394:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:394:

GGCGAUGCCG CUGAUGANGA AAGAUGAGCU C                                          31

(2) INFORMATION FOR SEQ ID NO:395:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:395:

AGCCCCUGGC CUGAUGANGA AAUGCCGGAG A                                          31

(2) INFORMATION FOR SEQ ID NO:396:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:396:

UGAUGUUGUC CUGAUGANGA AAGCUCGCAG C                                          31

(2) INFORMATION FOR SEQ ID NO:397:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:397:

UGAGGCGCAU CUGAUGANGA AAUGUUGUCG A                                          31

(2) INFORMATION FOR SEQ ID NO:398:

(i) SEQUENCE CHARACTERISTICS:
            (A) LENGTH:             31 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:398:

UGAUGCCGGU CUGAUGANGA AAGGCGCAUG A                                          31
```

(2) INFORMATION FOR SEQ ID NO:399:

(i) SEQUENCE CHARACTERISTICS:
  (A) LENGTH:     31 base pairs
  (B) TYPE:      nucleic acid
  (C) STRANDEDNESS:  single
  (D) TOPOLOGY:    linear (ix) FEATURE:
  (D) OTHER INFORMATION:  The letter "N" stands for any base.

(xi) SEQUENCE DESCRIPTION: SEQ ID NO:399:

CGAUGCCGGU CUGAUGANGA AAUGCCGGUG A             31

(2) INFORMATION FOR SEQ ID NO:400:

(i) SEQUENCE CHARACTERISTICS:
  (A) LENGTH:     31 base pairs
  (B) TYPE:      nucleic acid
  (C) STRANDEDNESS:  single
  (D) TOPOLOGY:    linear (ix) FEATURE:
  (D) OTHER INFORMATION:  The letter "N" stands for any base.

(xi) SEQUENCE DESCRIPTION: SEQ ID NO:400:

UGCCGUUGAC CUGAUGANGA AAUGCCGGUG A             31

(2) INFORMATION FOR SEQ ID NO:401:

(i) SEQUENCE CHARACTERISTICS:
  (A) LENGTH:     31 base pairs
  (B) TYPE:      nucleic acid
  (C) STRANDEDNESS:  single
  (D) TOPOLOGY:    linear (ix) FEATURE:
  (D) OTHER INFORMATION:  The letter "N" stands for any base.

(xi) SEQUENCE DESCRIPTION: SEQ ID NO:401:

CCAUGCCGUU CUGAUGANGA AACGAUGCCG G             31

(2) INFORMATION FOR SEQ ID NO:402:

(i) SEQUENCE CHARACTERISTICS:
  (A) LENGTH:     31 base pairs
  (B) TYPE:      nucleic acid
  (C) STRANDEDNESS:  single
  (D) TOPOLOGY:    linear (ix) FEATURE:
  (D) OTHER INFORMATION:  The letter "N" stands for any base.

(xi) SEQUENCE DESCRIPTION: SEQ ID NO:402:

CCCACUCGCU CUGAUGANGA AACGUCCAUG C             31

(2) INFORMATION FOR SEQ ID NO:403:

(i) SEQUENCE CHARACTERISTICS:
  (A) LENGTH:     31 base pairs
  (B) TYPE:      nucleic acid
  (C) STRANDEDNESS:  single
  (D) TOPOLOGY:    linear (ix) FEATURE:
  (D) OTHER INFORMATION:  The letter "N" stands for any base.

(xi) SEQUENCE DESCRIPTION: SEQ ID NO:403:

CACGGCGAUG CUGAUGANGA AACUUGUCCC U             31

(2) INFORMATION FOR SEQ ID NO:404:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:404:

ACUUCACGGC CUGAUGANGA AAUGUACUUG U                            31

(2) INFORMATION FOR SEQ ID NO:405:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:405:

CGACACGUCG CUGAUGANGA AACUUCACGG C                            31

(2) INFORMATION FOR SEQ ID NO:406:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:406:

CACGGCCGUC CUGAUGANGA AACACGUCGU A                            31

(2) INFORMATION FOR SEQ ID NO:407:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:407:

CCGGGAGCCC CUGAUGANGA AACCUCCGCC U                            31

(2) INFORMATION FOR SEQ ID NO:408:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:408:

```
GGUCCACCGG CUGAUGANGA AAGCCCGACC U                                31
```

(2) INFORMATION FOR SEQ ID NO:409:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:409:

```
CCACCAGCGG CUGAUGANGA AAUGUUCCGG U                                31
```

(2) INFORMATION FOR SEQ ID NO:410:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:410:

```
CCUGCCGAUG CUGAUGANGA AACGCCACCA G                                31
```

(2) INFORMATION FOR SEQ ID NO:411:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:411:

```
GCCUGCCGAU CUGAUGANGA AAACGCCACC A                                31
```

(2) INFORMATION FOR SEQ ID NO:412:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:412:

```
CCAGCCUGCC CUGAUGANGA AAUGAACGCC A                                31
```

(2) INFORMATION FOR SEQ ID NO:413:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:413:

CGGCCGCCAU CUGAUGANGA AACGUCGGGU C                                31

(2) INFORMATION FOR SEQ ID NO:414:

(i) SEQUENCE CHARACTERISTICS:
        (A) LENGTH:            31 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:414:

UGAGCUGCGG CUGAUGANGA AAUGGCGGCC G                                31

(2) INFORMATION FOR SEQ ID NO:415:

(i) SEQUENCE CHARACTERISTICS:
        (A) LENGTH:            31 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:415:

CCAUCUCCAU CUGAUGANGA AAGCUGCGGG A                                31

(2) INFORMATION FOR SEQ ID NO:416:

(i) SEQUENCE CHARACTERISTICS:
        (A) LENGTH:            31 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:416:

CCAGCAGAAC CUGAUGANGA AAUCUGCACG U                                31

(2) INFORMATION FOR SEQ ID NO:417:

(i) SEQUENCE CHARACTERISTICS:
        (A) LENGTH:            31 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:417:

UGCCCAGCAG CUGAUGANGA AACGAUCUGC A                                31

(2) INFORMATION FOR SEQ ID NO:418:

(i) SEQUENCE CHARACTERISTICS:
        (A) LENGTH:            31 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

```
      (xi) SEQUENCE DESCRIPTION: SEQ ID NO:418:

GUGCCCAGCA CUGAUGANGA AAACGAUCUG C                                31

(2) INFORMATION FOR SEQ ID NO:419:

(i) SEQUENCE CHARACTERISTICS:
           (A) LENGTH:          31 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for any base.

(xi) SEQUENCE DESCRIPTION: SEQ ID NO:419:

CAUGCGCUCG CUGAUGANGA AACUUCUUCU U                                31

(2) INFORMATION FOR SEQ ID NO:420:

(i) SEQUENCE CHARACTERISTICS:
           (A) LENGTH:          31 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for any base.

(xi) SEQUENCE DESCRIPTION: SEQ ID NO:420:

GCAUGCGCUC CUGAUGANGA AAACUUCUUC U                                31

(2) INFORMATION FOR SEQ ID NO:421:

(i) SEQUENCE CHARACTERISTICS:
           (A) LENGTH:          31 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for any base.

(xi) SEQUENCE DESCRIPTION: SEQ ID NO:421:

CGGCGCUCAU CUGAUGANGA AAGCAUGCGC U                                31

(2) INFORMATION FOR SEQ ID NO:422:

(i) SEQUENCE CHARACTERISTICS:
           (A) LENGTH:          31 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for any base.

(xi) SEQUENCE DESCRIPTION: SEQ ID NO:422:

CUUGCCUGGG CUGAUGANGA AACUUCUCCU C                                31

(2) INFORMATION FOR SEQ ID NO:423:

(i) SEQUENCE CHARACTERISTICS:
           (A) LENGTH:          31 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for any base.
```

(xi) SEQUENCE DESCRIPTION: SEQ ID NO:423:

CCUUGCCUGG CUGAUGANGA AAACUUCUCC U                                      31

(2) INFORMATION FOR SEQ ID NO:424:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:424:

CGUUGAACUU CUGAUGANGA AACCACGGCG C                                      31

(2) INFORMATION FOR SEQ ID NO:425:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:425:

CGCCGCGUUG CUGAUGANGA AACUUGACCA C                                      31

(2) INFORMATION FOR SEQ ID NO:426:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:426:

GCGCCGCGUU CUGAUGANGA AAACUUGACC A                                      31

(2) INFORMATION FOR SEQ ID NO:427:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:427:

CGCCGGCCAU CUGAUGANGA AAUGUGGUGC G                                      31

(2) INFORMATION FOR SEQ ID NO:428:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:

(D) OTHER INFORMATION:    The letter "N" stands for any base.

(xi) SEQUENCE DESCRIPTION: SEQ ID NO:428:

UGGUGACGGC CUGAUGANGA AAGCACGUCG G        31

(2) INFORMATION FOR SEQ ID NO:429:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:429:

AGCGGCUGGU CUGAUGANGA AACGGCGAGC A        31

(2) INFORMATION FOR SEQ ID NO:430:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:430:

GCAGGGCUCG CUGAUGANGA AAGCGGCUGG U        31

(2) INFORMATION FOR SEQ ID NO:431:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:431:

CGCAGGGCUC CUGAUGANGA AAAGCGGCUG G        31

(2) INFORMATION FOR SEQ ID NO:432:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:432:

GCAGCUGGAU CUGAUGANGA AAGGCCGCAG G        31

(2) INFORMATION FOR SEQ ID NO:433:

(i) SEQUENCE CHARACTERISTICS:
            (A) LENGTH:            31 base pairs
            (B) TYPE:              nucleic acid
            (C) STRANDEDNESS:      single
            (D) TOPOLOGY:          linear (ix) FEATURE:
              (D) OTHER INFORMATION:     The letter "N" stands for any base.

(xi) SEQUENCE DESCRIPTION: SEQ ID NO:433:

CCUGCAGCUG CUGAUGANGA AAUGAGGCCG C                                    31

(2) INFORMATION FOR SEQ ID NO:434:

(i) SEQUENCE CHARACTERISTICS:
              (A) LENGTH:                31 base pairs
              (B) TYPE:                  nucleic acid
              (C) STRANDEDNESS:          single
              (D) TOPOLOGY:              linear (ix) FEATURE:
              (D) OTHER INFORMATION:     The letter "N" stands for any base.

(xi) SEQUENCE DESCRIPTION: SEQ ID NO:434:

GGGCGUUCCG CUGAUGANGA AAUCGCAUCC C                                    31

(2) INFORMATION FOR SEQ ID NO:435:

(i) SEQUENCE CHARACTERISTICS:
              (A) LENGTH:                31 base pairs
              (B) TYPE:                  nucleic acid
              (C) STRANDEDNESS:          single
              (D) TOPOLOGY:              linear (ix) FEATURE:
              (D) OTHER INFORMATION:     The letter "N" stands for any base.

(xi) SEQUENCE DESCRIPTION: SEQ ID NO:435:

UCCACCGGUG CUGAUGANGA AACGCGCAGG C                                    31

(2) INFORMATION FOR SEQ ID NO:436:

(i) SEQUENCE CHARACTERISTICS:
              (A) LENGTH:                31 base pairs
              (B) TYPE:                  nucleic acid
              (C) STRANDEDNESS:          single
              (D) TOPOLOGY:              linear (ix) FEATURE:
              (D) OTHER INFORMATION:     The letter "N" stands for any base.

(xi) SEQUENCE DESCRIPTION: SEQ ID NO:436:

UGGUGUCGAC CUGAUGANGA AAGUCCACCG G                                    31

(2) INFORMATION FOR SEQ ID NO:437:

(i) SEQUENCE CHARACTERISTICS:
              (A) LENGTH:                31 base pairs
              (B) TYPE:                  nucleic acid
              (C) STRANDEDNESS:          single
              (D) TOPOLOGY:              linear (ix) FEATURE:
              (D) OTHER INFORMATION:     The letter "N" stands for any base.

(xi) SEQUENCE DESCRIPTION: SEQ ID NO:437:

UGAUGGUGUC CUGAUGANGA AACGAGUCCA C                                    31

(2) INFORMATION FOR SEQ ID NO:438:

(i) SEQUENCE CHARACTERISTICS:
              (A) LENGTH:                31 base pairs
              (B) TYPE:                  nucleic acid
              (C) STRANDEDNESS:          single
              (D) TOPOLOGY:              linear

```
        (ix) FEATURE:
             (D) OTHER INFORMATION:    The letter "N" stands for any base.

(xi) SEQUENCE DESCRIPTION: SEQ ID NO:438:

UGCCUUCGAU CUGAUGANGA AAUGGUGUCG A                              31

(2) INFORMATION FOR SEQ ID NO:439:

(i) SEQUENCE CHARACTERISTICS:
             (A) LENGTH:               31 base pairs
             (B) TYPE:                 nucleic acid
             (C) STRANDEDNESS:         single
             (D) TOPOLOGY:             linear (ix) FEATURE:
             (D) OTHER INFORMATION:    The letter "N" stands for any base.

(xi) SEQUENCE DESCRIPTION: SEQ ID NO:439:

UCUUGCCUUC CUGAUGANGA AAUGAUGGUG U                              31

(2) INFORMATION FOR SEQ ID NO:440:

(i) SEQUENCE CHARACTERISTICS:
             (A) LENGTH:               31 base pairs
             (B) TYPE:                 nucleic acid
             (C) STRANDEDNESS:         single
             (D) TOPOLOGY:             linear (ix) FEATURE:
             (D) OTHER INFORMATION:    The letter "N" stands for any base.

(xi) SEQUENCE DESCRIPTION: SEQ ID NO:440:

GCCCAUGUGG CUGAUGANGA AACCCGGUCU U                              31

(2) INFORMATION FOR SEQ ID NO:441:

(i) SEQUENCE CHARACTERISTICS:
             (A) LENGTH:               31 base pairs
             (B) TYPE:                 nucleic acid
             (C) STRANDEDNESS:         single
             (D) TOPOLOGY:             linear (ix) FEATURE:
             (D) OTHER INFORMATION:    The letter "N" stands for any base.

(xi) SEQUENCE DESCRIPTION: SEQ ID NO:441:

GGCCCAUGUG CUGAUGANGA AAACCCGGUC U                              31

(2) INFORMATION FOR SEQ ID NO:442:

(i) SEQUENCE CHARACTERISTICS:
             (A) LENGTH:               31 base pairs
             (B) TYPE:                 nucleic acid
             (C) STRANDEDNESS:         single
             (D) TOPOLOGY:             linear (ix) FEATURE:
             (D) OTHER INFORMATION:    The letter "N" stands for any base.

(xi) SEQUENCE DESCRIPTION: SEQ ID NO:442:

AGUCGACGCU CUGAUGANGA AAGGCGGCCC A                              31

(2) INFORMATION FOR SEQ ID NO:443:

(i) SEQUENCE CHARACTERISTICS:
             (A) LENGTH:               31 base pairs
             (B) TYPE:                 nucleic acid
             (C) STRANDEDNESS:         single
```

```
            (D) TOPOLOGY:            linear (ix) FEATURE:
            (D) OTHER INFORMATION:   The letter "N" stands for any base.

(xi) SEQUENCE DESCRIPTION: SEQ ID NO:443:

CGUUGCAGUC CUGAUGANGA AACGCUGAGG C                                        31

(2) INFORMATION FOR SEQ ID NO:444:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:444:

CCGGCUCCAC CUGAUGANGA AACGUUGCAG U                                        31

(2) INFORMATION FOR SEQ ID NO:445:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:445:

CCACCUUCUU CUGAUGANGA AACGUCCGCC G                                        31

(2) INFORMATION FOR SEQ ID NO:446:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:446:

GGCGCGCUGC CUGAUGANGA AAGGUGGUGG C                                        31

(2) INFORMATION FOR SEQ ID NO:447:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:447:

CGACCACCUU CUGAUGANGA AAUGGCGCGC U                                        31

(2) INFORMATION FOR SEQ ID NO:448:

(i) SEQUENCE CHARACTERISTICS:
            (A) LENGTH:              31 base pairs
            (B) TYPE:                nucleic acid
```

```
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:448:

CCGGCGUGCC CUGAUGANGA AACCACCUUG A                                31

(2) INFORMATION FOR SEQ ID NO:449:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:449:

CAUCUCCUCG CUGAUGANGA AACGCCGGCG U                                31

(2) INFORMATION FOR SEQ ID NO:450:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:450:

AGAGAUCCUG CUGAUGANGA AAUCAUGCAG U                                31

(2) INFORMATION FOR SEQ ID NO:451:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:451:

UUCCAGGAGA CUGAUGANGA AAUCCUGGAU C                                31

(2) INFORMATION FOR SEQ ID NO:452:

(i) SEQUENCE CHARACTERISTICS:
            (A) LENGTH:              31 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:452:

CCUUCCAGGA CUGAUGANGA AAGAUCCUGG A                                31

(2) INFORMATION FOR SEQ ID NO:453:

(i) SEQUENCE CHARACTERISTICS:
            (A) LENGTH:              31 base pairs
```

```
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:453:

GCCCUUCCAG CUGAUGANGA AAGAGAUCCU G                                      31

(2) INFORMATION FOR SEQ ID NO:454:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:454:

CCCCGAGGCU CUGAUGANGA AAGCAGCACG U                                      31

(2) INFORMATION FOR SEQ ID NO:455:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:455:

CGGCGACCCC CUGAUGANGA AAGGCUGAGC A                                      31

(2) INFORMATION FOR SEQ ID NO:456:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:456:

CGCCGCCGGC CUGAUGANGA AACCCCGAGG C                                      31

(2) INFORMATION FOR SEQ ID NO:457:

(i) SEQUENCE CHARACTERISTICS:
            (A) LENGTH:               31 base pairs
            (B) TYPE:                 nucleic acid
            (C) STRANDEDNESS:         single
            (D) TOPOLOGY:             linear (ix) FEATURE:
            (D) OTHER INFORMATION:    The letter "N" stands for any base.

(xi) SEQUENCE DESCRIPTION: SEQ ID NO:457:

CCUCGCCUUC CUGAUGANGA AACCCCUGGC U                                      31

(2) INFORMATION FOR SEQ ID NO:458:

(i) SEQUENCE CHARACTERISTICS:
```

```
         (A) LENGTH:            31 base pairs
         (B) TYPE:              nucleic acid
         (C) STRANDEDNESS:      single
         (D) TOPOLOGY:          linear (ix) FEATURE:
         (D) OTHER INFORMATION: The letter "N" stands for any base.

(xi) SEQUENCE DESCRIPTION: SEQ ID NO:458:

CGAGCGGCGC CUGAUGANGA AAUCUCCUCG C                                31

(2) INFORMATION FOR SEQ ID NO:459:

(i) SEQUENCE CHARACTERISTICS:
         (A) LENGTH:            31 base pairs
         (B) TYPE:              nucleic acid
         (C) STRANDEDNESS:      single
         (D) TOPOLOGY:          linear (ix) FEATURE:
         (D) OTHER INFORMATION: The letter "N" stands for any base.

(xi) SEQUENCE DESCRIPTION: SEQ ID NO:459:

UCUCCUUGGC CUGAUGANGA AAGCGGCGCG A                                31

(2) INFORMATION FOR SEQ ID NO:460:

(i) SEQUENCE CHARACTERISTICS:
         (A) LENGTH:            31 base pairs
         (B) TYPE:              nucleic acid
         (C) STRANDEDNESS:      single
         (D) TOPOLOGY:          linear (ix) FEATURE:
         (D) OTHER INFORMATION: The letter "N" stands for any base.

(xi) SEQUENCE DESCRIPTION: SEQ ID NO:460:

CUGCAGGCCG CUGAUGANGA AACUCUUCAG G                                31

(2) INFORMATION FOR SEQ ID NO:461:

(i) SEQUENCE CHARACTERISTICS:
         (A) LENGTH:            31 base pairs
         (B) TYPE:              nucleic acid
         (C) STRANDEDNESS:      single
         (D) TOPOLOGY:          linear (ix) FEATURE:
         (D) OTHER INFORMATION: The letter "N" stands for any base.

(xi) SEQUENCE DESCRIPTION: SEQ ID NO:461:

CCUGCAGGCC CUGAUGANGA AAACUCUUCA G                                31

(2) INFORMATION FOR SEQ ID NO:462:

(i) SEQUENCE CHARACTERISTICS:
         (A) LENGTH:            31 base pairs
         (B) TYPE:              nucleic acid
         (C) STRANDEDNESS:      single
         (D) TOPOLOGY:          linear (ix) FEATURE:
         (D) OTHER INFORMATION: The letter "N" stands for any base.

(xi) SEQUENCE DESCRIPTION: SEQ ID NO:462:

CCACGCGCGA CUGAUGANGA AAUCAGGGGG C                                31

(2) INFORMATION FOR SEQ ID NO:463:
```

```
        (i) SEQUENCE CHARACTERISTICS:
              (A) LENGTH:          31 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:463:

CACCACGCGC CUGAUGANGA AAGAUCAGGG G                                31

(2) INFORMATION FOR SEQ ID NO:464:

(i) SEQUENCE CHARACTERISTICS:
              (A) LENGTH:          31 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:464:

AAGAUGUCCC CUGAUGANGA AACAUGUUUG C                                31

(2) INFORMATION FOR SEQ ID NO:465:

(i) SEQUENCE CHARACTERISTICS:
              (A) LENGTH:          31 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:465:

UAUAUAAGAA CUGAUGANGA AAUGUCCCAA C                                31

(2) INFORMATION FOR SEQ ID NO:466:

(i) SEQUENCE CHARACTERISTICS:
              (A) LENGTH:          31 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:466:

CAUAUAUAAG CUGAUGANGA AAGAUGUCCC A                                31

(2) INFORMATION FOR SEQ ID NO:467:

(i) SEQUENCE CHARACTERISTICS:
              (A) LENGTH:          31 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:467:

GCAUAUAUAA CUGAUGANGA AAAGAUGUCC C                                31

(2) INFORMATION FOR SEQ ID NO:468:
```

```
        (i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:   The letter "N" stands for any base.

(xi) SEQUENCE DESCRIPTION: SEQ ID NO:468:

CAGCAUAUAU CUGAUGANGA AAGAAGAUGU C                                    31

(2) INFORMATION FOR SEQ ID NO:469:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:   The letter "N" stands for any base.

(xi) SEQUENCE DESCRIPTION: SEQ ID NO:469:

ACAGCAUAUA CUGAUGANGA AAAGAAGAUG U                                    31

(2) INFORMATION FOR SEQ ID NO:470:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:   The letter "N" stands for any base.

(xi) SEQUENCE DESCRIPTION: SEQ ID NO:470:

AAACAGCAUA CUGAUGANGA AAUAAGAAGA U                                    31

(2) INFORMATION FOR SEQ ID NO:471:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:   The letter "N" stands for any base.

(xi) SEQUENCE DESCRIPTION: SEQ ID NO:471:

CGAAACAGCA CUGAUGANGA AAUAUAAGAA G                                    31

(2) INFORMATION FOR SEQ ID NO:472:

(i) SEQUENCE CHARACTERISTICS:
             (A) LENGTH:           31 base pairs
             (B) TYPE:             nucleic acid
             (C) STRANDEDNESS:     single
             (D) TOPOLOGY:         linear (ix) FEATURE:
             (D) OTHER INFORMATION:   The letter "N" stands for any base.

(xi) SEQUENCE DESCRIPTION: SEQ ID NO:472:

ACAUAAACGA CUGAUGANGA AACAGCAUAU A                                    31
```

```
(2) INFORMATION FOR SEQ ID NO:473:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:473:

CACAUAAACG CUGAUGANGA AAACAGCAUA U                              31

(2) INFORMATION FOR SEQ ID NO:474:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:474:

UCACAUAAAC CUGAUGANGA AAAACAGCAU A                              31

(2) INFORMATION FOR SEQ ID NO:475:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:475:

AUAUCACAUA CUGAUGANGA AACGAAACAG C                              31

(2) INFORMATION FOR SEQ ID NO:476:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:476:

CAUAUCACAU CUGAUGANGA AAACGAAACA G                              31

(2) INFORMATION FOR SEQ ID NO:477:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:477:

CCAUAUCACA CUGAUGANGA AAAACGAAAC A                              31
```

(2) INFORMATION FOR SEQ ID NO:478:

(i) SEQUENCE CHARACTERISTICS:
        (A) LENGTH:         31 base pairs
        (B) TYPE:           nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:478:

UACUUGUCCA CUGAUGANGA AAUCACAUAA A                              31

(2) INFORMATION FOR SEQ ID NO:479:

(i) SEQUENCE CHARACTERISTICS:
        (A) LENGTH:         31 base pairs
        (B) TYPE:           nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:479:

CAGCUACACA CUGAUGANGA AACUUGUCCA U                              31

(2) INFORMATION FOR SEQ ID NO:480:

(i) SEQUENCE CHARACTERISTICS:
        (A) LENGTH:         31 base pairs
        (B) TYPE:           nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:480:

AGCAAGCAGC CUGAUGANGA AACACAUACU U                              31

(2) INFORMATION FOR SEQ ID NO:481:

(i) SEQUENCE CHARACTERISTICS:
        (A) LENGTH:         31 base pairs
        (B) TYPE:           nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:481:

UAGCACAAGC CUGAUGANGA AAGCAGCUAC A                              31

(2) INFORMATION FOR SEQ ID NO:482:

(i) SEQUENCE CHARACTERISTICS:
        (A) LENGTH:         31 base pairs
        (B) TYPE:           nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:482:

ACACUAGCAC CUGAUGANGA AAGCAAGCAG C                              31

(2) INFORMATION FOR SEQ ID NO:483:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:483:

UAUAUUACAC CUGAUGANGA AAGCACAAGC A                                        31

(2) INFORMATION FOR SEQ ID NO:484:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:484:

UACACUAUAU CUGAUGANGA AACACUAGCA C                                        31

(2) INFORMATION FOR SEQ ID NO:485:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:485:

CACUACACUA CUGAUGANGA AAUUACACUA G                                        31

(2) INFORMATION FOR SEQ ID NO:486:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:486:

ACCACUACAC CUGAUGANGA AAUAUUACAC U                                        31

(2) INFORMATION FOR SEQ ID NO:487:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:487:

UGGCCACCAC CUGAUGANGA AACACUAUAU U                                31

(2) INFORMATION FOR SEQ ID NO:488:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:488:

AUGCGCUUAU CUGAUGANGA AAGGUUGUGC C                                31

(2) INFORMATION FOR SEQ ID NO:489:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:489:

UUCAUGCGCU CUGAUGANGA AAUUAGGUUG U                                31

(2) INFORMATION FOR SEQ ID NO:490:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:490:

CGCAAGCAAU CUGAUGANGA AAGUUCAUGC G                                31

(2) INFORMATION FOR SEQ ID NO:491:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:491:

ACACGCAAGC CUGAUGANGA AAUUAGUUCA U                                31

(2) INFORMATION FOR SEQ ID NO:492:

(i) SEQUENCE CHARACTERISTICS:
        (A) LENGTH:          31 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:492:

CUACACACGC CUGAUGANGA AAGCAAUUAG U                31

(2) INFORMATION FOR SEQ ID NO:493:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:493:

GGUACUUAAC CUGAUGANGA AACACACGCA A                31

(2) INFORMATION FOR SEQ ID NO:494:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:494:

AUCGGUACUU CUGAUGANGA AACUACACAC G                31

(2) INFORMATION FOR SEQ ID NO:495:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:495:

GAUCGGUACU CUGAUGANGA AAACUACACA C                31

(2) INFORMATION FOR SEQ ID NO:496:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:496:

UACCGAUCGG CUGAUGANGA AACUUAACUA C                31

(2) INFORMATION FOR SEQ ID NO:497:

(i) SEQUENCE CHARACTERISTICS:
        (A) LENGTH:         31 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:497:

UAAAAUUACC CUGAUGANGA AAUCGGUACU U                    31

(2) INFORMATION FOR SEQ ID NO:498:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.

(xi) SEQUENCE DESCRIPTION: SEQ ID NO:498:

AAUAUAAAAU CUGAUGANGA AACCGAUCGG U                    31

(2) INFORMATION FOR SEQ ID NO:499:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.

(xi) SEQUENCE DESCRIPTION: SEQ ID NO:499:

CGCAAUAUAA CUGAUGANGA AAUUACCGAU C                    31

(2) INFORMATION FOR SEQ ID NO:500:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.

(xi) SEQUENCE DESCRIPTION: SEQ ID NO:500:

UCGCAAUAUA CUGAUGANGA AAAUUACCGA U                    31

(2) INFORMATION FOR SEQ ID NO:501:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.

(xi) SEQUENCE DESCRIPTION: SEQ ID NO:501:

CUCGCAAUAU CUGAUGANGA AAAAUUACCG A                    31

(2) INFORMATION FOR SEQ ID NO:502:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.

(xi) SEQUENCE DESCRIPTION: SEQ ID NO:502:

ACUCGCAAUA CUGAUGANGA AAAAAUUACC G                                    31

(2) INFORMATION FOR SEQ ID NO:503:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:503:

UUACUCGCAA CUGAUGANGA AAUAAAAUUA C                                    31

(2) INFORMATION FOR SEQ ID NO:504:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:504:

AUUUACUCGC CUGAUGANGA AAUAUAAAAU U                                    31

(2) INFORMATION FOR SEQ ID NO:505:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:505:

UCCAUUUAUU CUGAUGANGA AACUCGCAAU A                                    31

(2) INFORMATION FOR SEQ ID NO:506:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:506:

CAGGUCCAUU CUGAUGANGA AAUUUACUCG C                                    31

(2) INFORMATION FOR SEQ ID NO:507:

(i) SEQUENCE CHARACTERISTICS:
        (A) LENGTH:           31 base pairs
        (B) TYPE:             nucleic acid
        (C) STRANDEDNESS:     single
        (D) TOPOLOGY:         linear (ix) FEATURE:

(D) OTHER INFORMATION:     The letter "N" stands for any base.

(xi) SEQUENCE DESCRIPTION: SEQ ID NO:507:

UUUCCACCAC CUGAUGANGA AACAGGUCCA U                                 31

(2) INFORMATION FOR SEQ ID NO: 508:

(i) SEQUENCE CHARACTERISTICS:
        (A) LENGTH:            52 base pairs
        (B) TYPE:              nucleic acid
        (C) STRANDEDNESS:      single
        (D) TOPOLOGY:          linear (xi) SEQUENCE DESCRIPTION: SEQ ID NO: 508:

CUCCUGGCAG AAGUCGACCA GAGAAACACA CGUUGUGGUA CAUUACCUGG UA          52

(2) INFORMATION FOR SEQ ID NO: 509:

(i) SEQUENCE CHARACTERISTICS:
        (A) LENGTH:            16 base pairs
        (B) TYPE:              nucleic acid
        (C) STRANDEDNESS:      single
        (D) TOPOLOGY:          linear (xi) SEQUENCE DESCRIPTION: SEQ ID NO: 509:

CGACAGCCGC CAGGAG                                                  16

(2) INFORMATION FOR SEQ ID NO: 510:

(i) SEQUENCE CHARACTERISTICS:
        (A) LENGTH:            52 base pairs
        (B) TYPE:              nucleic acid
        (C) STRANDEDNESS:      single
        (D) TOPOLOGY:          linear (xi) SEQUENCE DESCRIPTION: SEQ ID NO: 510:

CCCUGCCGAG AAGUGCACCA GAGAAACACA CGUUGUGGUA CAUUACCUGG UA          52

(2) INFORMATION FOR SEQ ID NO: 511:

(i) SEQUENCE CHARACTERISTICS:
        (A) LENGTH:            16 base pairs
        (B) TYPE:              nucleic acid
        (C) STRANDEDNESS:      single
        (D) TOPOLOGY:          linear (xi) SEQUENCE DESCRIPTION: SEQ ID NO: 511:

GCACCGCCCG GCAGGG                                                  16

(2) INFORMATION FOR SEQ ID NO: 512:

(i) SEQUENCE CHARACTERISTICS:
        (A) LENGTH:            52 base pairs
        (B) TYPE:              nucleic acid
        (C) STRANDEDNESS:      single
        (D) TOPOLOGY:          linear (xi) SEQUENCE DESCRIPTION: SEQ ID NO: 512:

GUCGCCGAAG AAGCCGACCA GAGAAACACA CGUUGUGGUA CAUUACCUGG UA          52

(2) INFORMATION FOR SEQ ID NO: 513:

(i) SEQUENCE CHARACTERISTICS:
        (A) LENGTH:            16 base pairs
        (B) TYPE:              nucleic acid
        (C) STRANDEDNESS:      single
        (D) TOPOLOGY:          linear (xi) SEQUENCE DESCRIPTION: SEQ ID NO: 513:

CGGCGGCCUC GGCGAC                                                    16

(2) INFORMATION FOR SEQ ID NO: 514:

(i) SEQUENCE CHARACTERISTICS:
        (A) LENGTH:           52 base pairs
        (B) TYPE:             nucleic acid
        (C) STRANDEDNESS:     single
        (D) TOPOLOGY:         linear (xi) SEQUENCE DESCRIPTION: SEQ ID NO: 514:

CGGCGGCAAG AAGCCGACCA GAGAAACACA CGUUGUGGUA CAUUACCUGG UA             52

(2) INFORMATION FOR SEQ ID NO: 515:

(i) SEQUENCE CHARACTERISTICS:
        (A) LENGTH:           16 base pairs
        (B) TYPE:             nucleic acid
        (C) STRANDEDNESS:     single
        (D) TOPOLOGY:         linear (xi) SEQUENCE DESCRIPTION: SEQ ID NO: 515:

CGGCGGCCUG CCGCCG                                                    16

(2) INFORMATION FOR SEQ ID NO: 516:

(i) SEQUENCE CHARACTERISTICS:
        (A) LENGTH:           52 base pairs
        (B) TYPE:             nucleic acid
        (C) STRANDEDNESS:     single
        (D) TOPOLOGY:         linear (xi) SEQUENCE DESCRIPTION: SEQ ID NO: 516:

CCAUGGCCAG AAGCAGACCA GAGAAACACA CGUUGUGGUA CAUUACCUGG UA             52

(2) INFORMATION FOR SEQ ID NO: 517:

(i) SEQUENCE CHARACTERISTICS:
        (A) LENGTH:           16 base pairs
        (B) TYPE:             nucleic acid
        (C) STRANDEDNESS:     single
        (D) TOPOLOGY:         linear (xi) SEQUENCE DESCRIPTION: SEQ ID NO: 517:

CUGCCGCCGG CCAUGG                                                    16

(2) INFORMATION FOR SEQ ID NO: 518:

(i) SEQUENCE CHARACTERISTICS:
        (A) LENGTH:           52 base pairs
        (B) TYPE:             nucleic acid
        (C) STRANDEDNESS:     single
        (D) TOPOLOGY:         linear (xi) SEQUENCE DESCRIPTION: SEQ ID NO: 518:

UCUCCAGGAG AAGUGGACCA GAGAAACACA CGUUGUGGUA CAUUACCUGG UA             52

(2) INFORMATION FOR SEQ ID NO: 519:

(i) SEQUENCE CHARACTERISTICS:
        (A) LENGTH:           16 base pairs
        (B) TYPE:             nucleic acid
        (C) STRANDEDNESS:     single
        (D) TOPOLOGY:         linear (xi) SEQUENCE DESCRIPTION: SEQ ID NO: 519:

CCACUGUUCC UGGAGA                                                    16

(2) INFORMATION FOR SEQ ID NO: 520:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 520:

UCCCUGUAAG AAGUUCACCA GAGAAACACA CGUUGUGGUA CAUUACCUGG UA             52

(2) INFORMATION FOR SEQ ID NO: 521:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 521:

GAACGGACUA CAGGGA                                                    16

(2) INFORMATION FOR SEQ ID NO: 522:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 522:

GCAGGCUGAG AAGCAGACCA GAGAAACACA CGUUGUGGUA CAUUACCUGG UA             52

(2) INFORMATION FOR SEQ ID NO: 523:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 523:

CUGCGGUUCA GCCUGC                                                    16

(2) INFORMATION FOR SEQ ID NO: 524:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 524:

GCCUCCACAG AAGUCGACCA GAGAAACACA CGUUGUGGUA CAUUACCUGG UA             52

(2) INFORMATION FOR SEQ ID NO: 525:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 525:

```
CGACGGCCGU GGAGGC                                                        16
```

(2) INFORMATION FOR SEQ ID NO: 526:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 526:

```
GGGAUGGCAG AAGCCAACCA GAGAAACACA CGUUGUGGUA CAUUACCUGG UA               52
```

(2) INFORMATION FOR SEQ ID NO: 527:

(i) SEQUENCE CHARACTERISTICS:
        (A) LENGTH:        16 base pairs
        (B) TYPE:          nucleic acid
        (C) STRANDEDNESS:  single
        (D) TOPOLOGY:     linear (xi) SEQUENCE DESCRIPTION: SEQ ID NO: 527:

```
UGGCGGCCGC CAUCCC                                                        16
```

(2) INFORMATION FOR SEQ ID NO: 528:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 528:

```
GCGAGCACAG AAGCGCACCA GAGAAACACA CGUUGUGGUA CAUUACCUGG UA               52
```

(2) INFORMATION FOR SEQ ID NO: 529:

(i) SEQUENCE CHARACTERISTICS:
        (A) LENGTH:        16 base pairs
        (B) TYPE:          nucleic acid
        (C) STRANDEDNESS:  single
        (D) TOPOLOGY:     linear (xi) SEQUENCE DESCRIPTION: SEQ ID NO: 529:

```
GCGCCGACGU GCUCGC                                                        16
```

(2) INFORMATION FOR SEQ ID NO: 530:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 530:

```
CUGGAUGAAG AAGCAGACCA GAGAAACACA CGUUGUGGUA CAUUACCUGG UA               52
```

(2) INFORMATION FOR SEQ ID NO: 531:

(i) SEQUENCE CHARACTERISTICS:
        (A) LENGTH:        16 base pairs
        (B) TYPE:          nucleic acid
        (C) STRANDEDNESS:  single
        (D) TOPOLOGY:     linear (xi) SEQUENCE DESCRIPTION: SEQ ID NO: 531:

CUGCGGCCUC AUCCAG                                                           16

(2) INFORMATION FOR SEQ ID NO: 532:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 532:

GACGCUGAAG AAGCCCACCA GAGAAACACA CGUUGUGGUA CAUUACCUGG UA                    52

(2) INFORMATION FOR SEQ ID NO: 533:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 533:

GGGCCGCCUC AGCGUC                                                           16

(2) INFORMATION FOR SEQ ID NO: 534:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 534:

UUCUUGACAG AAGCCGACCA GAGAAACACA CGUUGUGGUA CAUUACCUGG UA                    52

(2) INFORMATION FOR SEQ ID NO: 535:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 535:

CGGCGGACGU CAAGAA                                                           16

(2) INFORMATION FOR SEQ ID NO: 536:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 536:

AUAAACGAAG AAGCAUACCA GAGAAACACA CGUUGUGGUA CAUUACCUGG UA                    52

(2) INFORMATION FOR SEQ ID NO: 537:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 537:

AUGCUGUUUC GUUUAU                                                           16

(2) INFORMATION FOR SEQ ID NO: 538:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 538:

GUCGCCUCAG AAGGUGGUAC CAGAGAAACA CACGUUGUGG UACAUUACCU GGUA        54

(2) INFORMATION FOR SEQ ID NO: 539:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 539:

ACCACCCGCC GAGGCGAC        18

(2) INFORMATION FOR SEQ ID NO: 540:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 540:

CUCCUGGCAG AAGUCGCGAC CAGAGAAACA CACGUUGUGG UACAUUACCU GGUA        54

(2) INFORMATION FOR SEQ ID NO: 541:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 541:

CGCGACAGCC GCCAGGAG        18

(2) INFORMATION FOR SEQ ID NO: 542:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 542:

GUGGACGGAG AAGUACACAC CAGAGAAACA CACGUUGUGG UACAUUACCU GGUA        54

(2) INFORMATION FOR SEQ ID NO: 543:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 543:

GUGUACUGCU CCGUCCAC        18

(2) INFORMATION FOR SEQ ID NO: 544:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 544:

CACUGGUGAG AAGAGCAGAC CAGAGAAACA CACGUUGUGG UACAUUACCU GGUA        54

(2) INFORMATION FOR SEQ ID NO: 545:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 545:

CUGCUCCGUC CACCAGUG        18

(2) INFORMATION FOR SEQ ID NO: 546:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 546:

CCCUGCCGAG AAGUGCGCAC CAGAGAAACA CACGUUGUGG UACAUUACCU GGUA        54

(2) INFORMATION FOR SEQ ID NO: 547:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 547:

GCGCACCGCC CGGCAGGG        18

(2) INFORMATION FOR SEQ ID NO: 548:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 548:

ACGAGAUGAG AAGCCCUGAC CAGAGAAACA CACGUUGUGG UACAUUACCU GGUA        54

(2) INFORMATION FOR SEQ ID NO: 549:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 549:

CAGGGCUGCU CAUCUCGU        18

```
(2) INFORMATION FOR SEQ ID NO: 550:

(i) SEQUENCE CHARACTERISTICS:
        (A) LENGTH:           54 base pairs
        (B) TYPE:             nucleic acid
        (C) STRANDEDNESS:     single
        (D) TOPOLOGY:         linear (xi) SEQUENCE DESCRIPTION: SEQ ID NO: 550:

GUGGCUAGAG AAGCCAUGAC CAGAGAAACA CACGUUGUGG UACAUUACCU GGUA          54

(2) INFORMATION FOR SEQ ID NO: 551:

(i) SEQUENCE CHARACTERISTICS:
        (A) LENGTH:           18 base pairs
        (B) TYPE:             nucleic acid
        (C) STRANDEDNESS:     single
        (D) TOPOLOGY:         linear (xi) SEQUENCE DESCRIPTION: SEQ ID NO: 551:

CAUGGCGGCU CUAGCCAC                                                   18

(2) INFORMATION FOR SEQ ID NO: 552:

(i) SEQUENCE CHARACTERISTICS:
        (A) LENGTH:           54 base pairs
        (B) TYPE:             nucleic acid
        (C) STRANDEDNESS:     single
        (D) TOPOLOGY:         linear (xi) SEQUENCE DESCRIPTION: SEQ ID NO: 552:

UUGCGACGAG AAGCGACGAC CAGAGAAACA CACGUUGUGG UACAUUACCU GGUA          54

(2) INFORMATION FOR SEQ ID NO: 553:

(i) SEQUENCE CHARACTERISTICS:
        (A) LENGTH:           18 base pairs
        (B) TYPE:             nucleic acid
        (C) STRANDEDNESS:     single
        (D) TOPOLOGY:         linear (xi) SEQUENCE DESCRIPTION: SEQ ID NO: 553:

CGUCGCAGCU CGUCGCAA                                                   18

(2) INFORMATION FOR SEQ ID NO: 554:

(i) SEQUENCE CHARACTERISTICS:
        (A) LENGTH:           54 base pairs
        (B) TYPE:             nucleic acid
        (C) STRANDEDNESS:     single
        (D) TOPOLOGY:         linear (xi) SEQUENCE DESCRIPTION: SEQ ID NO: 554:

GACGCCCAAG AAGGCGCGAC CAGAGAAACA CACGUUGUGG UACAUUACCU GGUA          54

(2) INFORMATION FOR SEQ ID NO: 555:

(i) SEQUENCE CHARACTERISTICS:
        (A) LENGTH:           18 base pairs
        (B) TYPE:             nucleic acid
        (C) STRANDEDNESS:     single
        (D) TOPOLOGY:         linear (xi) SEQUENCE DESCRIPTION: SEQ ID NO: 555:

CGCGCCGGCC UGGGCGUC                                                   18

(2) INFORMATION FOR SEQ ID NO: 556:
```

```
        (i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 556:

GUGGACGCAG AAGGGACGAC CAGAGAAACA CACGUUGUGG UACAUUACCU GGUA          54

(2) INFORMATION FOR SEQ ID NO: 557:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 557:

CGUCCCGGAC GCGUCCAC                                                  18

(2) INFORMATION FOR SEQ ID NO: 558:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 558:

GGCGCCGCAG AAGAACGUAC CAGAGAAACA CACGUUGUGG UACAUUACCU GGUA          54

(2) INFORMATION FOR SEQ ID NO: 559:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 559:

ACGUUCCGCC GCGGCGCC                                                  18

(2) INFORMATION FOR SEQ ID NO: 560:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 560:

CCGACGCCAG AAGGCCCCAC CAGAGAAACA CACGUUGUGG UACAUUACCU GGUA          54

(2) INFORMATION FOR SEQ ID NO: 561:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 561:

GGGGCCGGAC GGCGUCGG                                                  18

(2) INFORMATION FOR SEQ ID NO: 562:
```

```
    (i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 562:

GCGCGCUGAG AAGAAUGCAC CAGAGAAACA CACGUUGUGG UACAUUACCU GGUA          54

(2) INFORMATION FOR SEQ ID NO: 563:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 563:

GCAUUCGGAC CAGCGCGC                                                  18

(2) INFORMATION FOR SEQ ID NO: 564:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 564:

CGACGAGCAG AAGGAACCAC CAGAGAAACA CACGUUGUGG UACAUUACCU GGUA          54

(2) INFORMATION FOR SEQ ID NO: 565:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 565:

GGUUCCCGUC GCUCGUCG                                                  18

(2) INFORMATION FOR SEQ ID NO: 566:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 566:

GUCGCCGAAG AAGCCGGUAC CAGAGAAACA CACGUUGUGG UACAUUACCU GGUA          54

(2) INFORMATION FOR SEQ ID NO: 567:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 567:

ACCGGCGGCC UCGGCGAC                                                  18

(2) INFORMATION FOR SEQ ID NO: 568:

(i) SEQUENCE CHARACTERISTICS:
```

```
        (A) LENGTH:            54 base pairs
        (B) TYPE:              nucleic acid
        (C) STRANDEDNESS:      single
        (D) TOPOLOGY:          linear (xi) SEQUENCE DESCRIPTION: SEQ ID NO: 568:

CGGCGGCAAG AAGCCGAGAC CAGAGAAACA CACGUUGUGG UACAUUACCU GGUA          54

(2) INFORMATION FOR SEQ ID NO: 569:

(i) SEQUENCE CHARACTERISTICS:
        (A) LENGTH:            18 base pairs
        (B) TYPE:              nucleic acid
        (C) STRANDEDNESS:      single
        (D) TOPOLOGY:          linear (xi) SEQUENCE DESCRIPTION: SEQ ID NO: 569:

CUCGGCGGCC UGCCGCCG                                                  18

(2) INFORMATION FOR SEQ ID NO: 570:

(i) SEQUENCE CHARACTERISTICS:
        (A) LENGTH:            54 base pairs
        (B) TYPE:              nucleic acid
        (C) STRANDEDNESS:      single
        (D) TOPOLOGY:          linear (xi) SEQUENCE DESCRIPTION: SEQ ID NO: 570:

UGGCCGGCAG AAGGCCGCAC CAGAGAAACA CACGUUGUGG UACAUUACCU GGUA          54

(2) INFORMATION FOR SEQ ID NO: 571:

(i) SEQUENCE CHARACTERISTICS:
        (A) LENGTH:            18 base pairs
        (B) TYPE:              nucleic acid
        (C) STRANDEDNESS:      single
        (D) TOPOLOGY:          linear (xi) SEQUENCE DESCRIPTION: SEQ ID NO: 571:

GCGGCCUGCC GCCGGCCA                                                  18

(2) INFORMATION FOR SEQ ID NO: 572:

(i) SEQUENCE CHARACTERISTICS:
        (A) LENGTH:            54 base pairs
        (B) TYPE:              nucleic acid
        (C) STRANDEDNESS:      single
        (D) TOPOLOGY:          linear (xi) SEQUENCE DESCRIPTION: SEQ ID NO: 572:

CCAUGGCCAG AAGCAGGCAC CAGAGAAACA CACGUUGUGG UACAUUACCU GGUA          54

(2) INFORMATION FOR SEQ ID NO: 573:

(i) SEQUENCE CHARACTERISTICS:
        (A) LENGTH:            18 base pairs
        (B) TYPE:              nucleic acid
        (C) STRANDEDNESS:      single
        (D) TOPOLOGY:          linear (xi) SEQUENCE DESCRIPTION: SEQ ID NO: 573:

GCCUGCCGCC GGCCAUGG                                                  18

(2) INFORMATION FOR SEQ ID NO: 574:

(i) SEQUENCE CHARACTERISTICS:
        (A) LENGTH:            54 base pairs
```

```
          (B) TYPE:             nucleic acid
          (C) STRANDEDNESS:     single
          (D) TOPOLOGY:         linear (xi) SEQUENCE DESCRIPTION: SEQ ID NO: 574:

UCUCCAGGAG AAGUGGGUAC CAGAGAAACA CACGUUGUGG UACAUUACCU GGUA          54

(2) INFORMATION FOR SEQ ID NO: 575:

(i) SEQUENCE CHARACTERISTICS:
          (A) LENGTH:           18 base pairs
          (B) TYPE:             nucleic acid
          (C) STRANDEDNESS:     single
          (D) TOPOLOGY:         linear (xi) SEQUENCE DESCRIPTION: SEQ ID NO: 575:

ACCCACUGUU CCUGGAGA                                                  18

(2) INFORMATION FOR SEQ ID NO: 576:

(i) SEQUENCE CHARACTERISTICS:
          (A) LENGTH:           54 base pairs
          (B) TYPE:             nucleic acid
          (C) STRANDEDNESS:     single
          (D) TOPOLOGY:         linear (xi) SEQUENCE DESCRIPTION: SEQ ID NO: 576:

GUUCCAGCAG AAGGCCCGAC CAGAGAAACA CACGUUGUGG UACAUUACCU GGUA          54

(2) INFORMATION FOR SEQ ID NO: 577:

(i) SEQUENCE CHARACTERISTICS:
          (A) LENGTH:           18 base pairs
          (B) TYPE:             nucleic acid
          (C) STRANDEDNESS:     single
          (D) TOPOLOGY:         linear (xi) SEQUENCE DESCRIPTION: SEQ ID NO: 577:

CGGGCCUGAC GCUGGAAC                                                  18

(2) INFORMATION FOR SEQ ID NO: 578:

(i) SEQUENCE CHARACTERISTICS:
          (A) LENGTH:           54 base pairs
          (B) TYPE:             nucleic acid
          (C) STRANDEDNESS:     single
          (D) TOPOLOGY:         linear (xi) SEQUENCE DESCRIPTION: SEQ ID NO: 578:

UCCCUGUAAG AAGUUCCAAC CAGAGAAACA CACGUUGUGG UACAUUACCU GGUA          54

(2) INFORMATION FOR SEQ ID NO: 579:

(i) SEQUENCE CHARACTERISTICS:
          (A) LENGTH:           18 base pairs
          (B) TYPE:             nucleic acid
          (C) STRANDEDNESS:     single
          (D) TOPOLOGY:         linear (xi) SEQUENCE DESCRIPTION: SEQ ID NO: 579:

UGGAACGGAC UACAGGGA                                                  18

(2) INFORMATION FOR SEQ ID NO: 580:

(i) SEQUENCE CHARACTERISTICS:
          (A) LENGTH:           54 base pairs
          (B) TYPE:             nucleic acid
```

```
            (C) STRANDEDNESS:        single
            (D) TOPOLOGY:            linear (xi) SEQUENCE DESCRIPTION: SEQ ID NO: 580:

UGAACCGCAG AAGGUUGUAC CAGAGAAACA CACGUUGUGG UACAUUACCU GGUA          54

(2) INFORMATION FOR SEQ ID NO: 581:

(i) SEQUENCE CHARACTERISTICS:
            (A) LENGTH:             18 base pairs
            (B) TYPE:               nucleic acid
            (C) STRANDEDNESS:       single
            (D) TOPOLOGY:           linear (xi) SEQUENCE DESCRIPTION: SEQ ID NO: 581:

ACAACCAGCU GCGGUUCA                                                   18

(2) INFORMATION FOR SEQ ID NO: 582:

(i) SEQUENCE CHARACTERISTICS:
            (A) LENGTH:             54 base pairs
            (B) TYPE:               nucleic acid
            (C) STRANDEDNESS:       single
            (D) TOPOLOGY:           linear (xi) SEQUENCE DESCRIPTION: SEQ ID NO: 582:

GCAGGCUGAG AAGCAGCUAC CAGAGAAACA CACGUUGUGG UACAUUACCU GGUA          54

(2) INFORMATION FOR SEQ ID NO: 583:

(i) SEQUENCE CHARACTERISTICS:
            (A) LENGTH:             18 base pairs
            (B) TYPE:               nucleic acid
            (C) STRANDEDNESS:       single
            (D) TOPOLOGY:           linear (xi) SEQUENCE DESCRIPTION: SEQ ID NO: 583:

AGCUGCGGUU CAGCCUGC                                                   18

(2) INFORMATION FOR SEQ ID NO: 584:

(i) SEQUENCE CHARACTERISTICS:
            (A) LENGTH:             54 base pairs
            (B) TYPE:               nucleic acid
            (C) STRANDEDNESS:       single
            (D) TOPOLOGY:           linear (xi) SEQUENCE DESCRIPTION: SEQ ID NO: 584:

GCAUAGCAAG AAGAACCGAC CAGAGAAACA CACGUUGUGG UACAUUACCU GGUA          54

(2) INFORMATION FOR SEQ ID NO: 585:

(i) SEQUENCE CHARACTERISTICS:
            (A) LENGTH:             18 base pairs
            (B) TYPE:               nucleic acid
            (C) STRANDEDNESS:       single
            (D) TOPOLOGY:           linear (xi) SEQUENCE DESCRIPTION: SEQ ID NO: 585:

CGGUUCAGCC UGCUAUGC                                                   18

(2) INFORMATION FOR SEQ ID NO: 586:

(i) SEQUENCE CHARACTERISTICS:
            (A) LENGTH:             54 base pairs
            (B) TYPE:               nucleic acid
            (C) STRANDEDNESS:       single
```

(D) TOPOLOGY:          linear (xi) SEQUENCE DESCRIPTION: SEQ ID NO: 586:

CCCGUAUGAG AAGGAGAAAC CAGAGAAACA CACGUUGUGG UACAUUACCU GGUA      54

(2) INFORMATION FOR SEQ ID NO: 587:

(i) SEQUENCE CHARACTERISTICS:
        (A) LENGTH:            18 base pairs
        (B) TYPE:              nucleic acid
        (C) STRANDEDNESS:      single
        (D) TOPOLOGY:          linear (xi) SEQUENCE DESCRIPTION: SEQ ID NO: 587:

UUCUCCGGAC CAUACGGG      18

(2) INFORMATION FOR SEQ ID NO: 588:

(i) SEQUENCE CHARACTERISTICS:
        (A) LENGTH:            54 base pairs
        (B) TYPE:              nucleic acid
        (C) STRANDEDNESS:      single
        (D) TOPOLOGY:          linear (xi) SEQUENCE DESCRIPTION: SEQ ID NO: 588:

CGAGAGAGAG AAGGUGUGAC CAGAGAAACA CACGUUGUGG UACAUUACCU GGUA      54

(2) INFORMATION FOR SEQ ID NO: 589:

(i) SEQUENCE CHARACTERISTICS:
        (A) LENGTH:            18 base pairs
        (B) TYPE:              nucleic acid
        (C) STRANDEDNESS:      single
        (D) TOPOLOGY:          linear (xi) SEQUENCE DESCRIPTION: SEQ ID NO: 589:

CACACCGGCC CUCUCUCG      18

(2) INFORMATION FOR SEQ ID NO: 590:

(i) SEQUENCE CHARACTERISTICS:
        (A) LENGTH:            54 base pairs
        (B) TYPE:              nucleic acid
        (C) STRANDEDNESS:      single
        (D) TOPOLOGY:          linear (xi) SEQUENCE DESCRIPTION: SEQ ID NO: 590:

UGCCGUGGAG AAGGUAGUAC CAGAGAAACA CACGUUGUGG UACAUUACCU GGUA      54

(2) INFORMATION FOR SEQ ID NO: 591:

(i) SEQUENCE CHARACTERISTICS:
        (A) LENGTH:            18 base pairs
        (B) TYPE:              nucleic acid
        (C) STRANDEDNESS:      single
        (D) TOPOLOGY:          linear (xi) SEQUENCE DESCRIPTION: SEQ ID NO: 591:

ACUACCAGUC CCACGGCA      18

(2) INFORMATION FOR SEQ ID NO: 592:

(i) SEQUENCE CHARACTERISTICS:
        (A) LENGTH:            54 base pairs
        (B) TYPE:              nucleic acid
        (C) STRANDEDNESS:      single
        (D) TOPOLOGY:          linear (xi) SEQUENCE DESCRIPTION: SEQ ID NO: 592:

AUGCAGAAAG AAGUCUUUAC CAGAGAAACA CACGUUGUGG UACAUUACCU GGUA        54

(2) INFORMATION FOR SEQ ID NO: 593:

(i) SEQUENCE CHARACTERISTICS:
        (A) LENGTH:         18 base pairs
        (B) TYPE:           nucleic acid
        (C) STRANDEDNESS:  single
        (D) TOPOLOGY:     linear (xi) SEQUENCE DESCRIPTION: SEQ ID NO: 593:

AAAGACCGCU UUCUGCAU        18

(2) INFORMATION FOR SEQ ID NO: 594:

(i) SEQUENCE CHARACTERISTICS:
        (A) LENGTH:         54 base pairs
        (B) TYPE:           nucleic acid
        (C) STRANDEDNESS:  single
        (D) TOPOLOGY:     linear (xi) SEQUENCE DESCRIPTION: SEQ ID NO: 594:

AGAAGGCGAG AAGGCCCUAC CAGAGAAACA CACGUUGUGG UACAUUACCU GGUA        54

(2) INFORMATION FOR SEQ ID NO: 595:

(i) SEQUENCE CHARACTERISTICS:
        (A) LENGTH:         18 base pairs
        (B) TYPE:           nucleic acid
        (C) STRANDEDNESS:  single
        (D) TOPOLOGY:     linear (xi) SEQUENCE DESCRIPTION: SEQ ID NO: 595:

AGGGCCGGUU CGCCUUCU        18

(2) INFORMATION FOR SEQ ID NO: 596:

(i) SEQUENCE CHARACTERISTICS:
        (A) LENGTH:         54 base pairs
        (B) TYPE:           nucleic acid
        (C) STRANDEDNESS:  single
        (D) TOPOLOGY:     linear (xi) SEQUENCE DESCRIPTION: SEQ ID NO: 596:

UCCGGGUAAG AAGAGAAGAC CAGAGAAACA CACGUUGUGG UACAUUACCU GGUA        54

(2) INFORMATION FOR SEQ ID NO: 597:

(i) SEQUENCE CHARACTERISTICS:
        (A) LENGTH:         18 base pairs
        (B) TYPE:           nucleic acid
        (C) STRANDEDNESS:  single
        (D) TOPOLOGY:     linear (xi) SEQUENCE DESCRIPTION: SEQ ID NO: 597:

CUUCUCCGAC UACCCGGA        18

(2) INFORMATION FOR SEQ ID NO: 598:

(i) SEQUENCE CHARACTERISTICS:
        (A) LENGTH:         54 base pairs
        (B) TYPE:           nucleic acid
        (C) STRANDEDNESS:  single
        (D) TOPOLOGY:     linear (xi) SEQUENCE DESCRIPTION: SEQ ID NO: 598:

GUAGUAGGAG AAGACGGUAC CAGAGAAACA CACGUUGUGG UACAUUACCU GGUA					54

(2) INFORMATION FOR SEQ ID NO: 599:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 599:

ACCGUCAGCC CCUACUAC					18

(2) INFORMATION FOR SEQ ID NO: 600:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 600:

GCCUCCACAG AAGUCGACAC CAGAGAAACA CACGUUGUGG UACAUUACCU GGUA					54

(2) INFORMATION FOR SEQ ID NO: 601:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 601:

GUCGACGGCC GUGGAGGC					18

(2) INFORMATION FOR SEQ ID NO: 602:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 602:

ACGCCACCAG AAGGAUGUAC CAGAGAAACA CACGUUGUGG UACAUUACCU GGUA					54

(2) INFORMATION FOR SEQ ID NO: 603:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 603:

ACAUCCCGCU GGUGGCGU					18

(2) INFORMATION FOR SEQ ID NO: 604:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 604:

GCCAUGACAG AAGGUCCCAC CAGAGAAACA CACGUUGUGG UACAUUACCU GGUA 54

(2) INFORMATION FOR SEQ ID NO: 605:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 605:

GGGACCCGAC GUCAUGGC 18

(2) INFORMATION FOR SEQ ID NO: 606:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 606:

GGGAUGGCAG AAGCCAUGAC CAGAGAAACA CACGUUGUGG UACAUUACCU GGUA 54

(2) INFORMATION FOR SEQ ID NO: 607:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 607:

CAUGGCGGCC GCCAUCCC 18

(2) INFORMATION FOR SEQ ID NO: 608:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 608:

UCUCCAUGAG AAGCGGGAAC CAGAGAAACA CACGUUGUGG UACAUUACCU GGUA 54

(2) INFORMATION FOR SEQ ID NO: 609:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 609:

UCCCGCAGCU CAUGGAGA 18

(2) INFORMATION FOR SEQ ID NO: 610:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 610:

```
GCAGAACGAG AAGCACGUAC CAGAGAAACA CACGUUGUGG UACAUUACCU GGUA      54
```

(2) INFORMATION FOR SEQ ID NO: 611:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO: 611:

```
ACGUGCAGAU CGUUCUGC                                              18
```

(2) INFORMATION FOR SEQ ID NO: 612:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO: 612:

```
CCGUGCCCAG AAGAACGAAC CAGAGAAACA CACGUUGUGG UACAUUACCU GGUA      54
```

(2) INFORMATION FOR SEQ ID NO: 613:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO: 613:

```
UCGUUCUGCU GGGCACGG                                              18
```

(2) INFORMATION FOR SEQ ID NO: 614:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO: 614:

```
GCGAGCACAG AAGCGCCGAC CAGAGAAACA CACGUUGUGG UACAUUACCU GGUA      54
```

(2) INFORMATION FOR SEQ ID NO: 615:

(i) SEQUENCE CHARACTERISTICS:
        (A) LENGTH:       18 base pairs
        (B) TYPE:         nucleic acid
        (C) STRANDEDNESS:  single
        (D) TOPOLOGY:     linear (xi) SEQUENCE DESCRIPTION: SEQ ID NO: 615:

```
CGGCGCCGAC GUGCUCGC                                              18
```

(2) INFORMATION FOR SEQ ID NO: 616:

(i) SEQUENCE CHARACTERISTICS:
        (A) LENGTH:       54 base pairs
        (B) TYPE:         nucleic acid
        (C) STRANDEDNESS:  single
        (D) TOPOLOGY:     linear (xi) SEQUENCE DESCRIPTION: SEQ ID NO: 616:

```
CUCGAAGCAG AAGGUGACAC CAGAGAAACA CACGUUGUGG UACAUUACCU GGUA      54
```

(2) INFORMATION FOR SEQ ID NO: 617:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 617:

GUCACCAGCC GCUUCGAG                                  18

(2) INFORMATION FOR SEQ ID NO: 618:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 618:

GGGCUCGAAG AAGCUGGUAC CAGAGAAACA CACGUUGUGG UACAUUACCU GGUA      54

(2) INFORMATION FOR SEQ ID NO: 619:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 619:

ACCAGCCGCU UCGAGCCC                                  18

(2) INFORMATION FOR SEQ ID NO: 620:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 620:

CUGGAUGAAG AAGCAGGGAC CAGAGAAACA CACGUUGUGG UACAUUACCU GGUA      54

(2) INFORMATION FOR SEQ ID NO: 621:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 621:

CCCUGCGGCC UCAUCCAG                                  18

(2) INFORMATION FOR SEQ ID NO: 622:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 622:

UCCCCUGCAG AAGGAUGAAC CAGAGAAACA CACGUUGUGG UACAUUACCU GGUA      54

(2) INFORMATION FOR SEQ ID NO: 623:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 623:

UCAUCCAGCU GCAGGGGA                                                      18

(2) INFORMATION FOR SEQ ID NO: 624:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 624:

GACGCUGAAG AAGCCCAUAC CAGAGAAACA CACGUUGUGG UACAUUACCU GGUA          54

(2) INFORMATION FOR SEQ ID NO: 625:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 625:

AUGGGCCGCC UCAGCGUC                                                      18

(2) INFORMATION FOR SEQ ID NO: 626:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 626:

UUCUUGACAG AAGCCGGCAC CAGAGAAACA CACGUUGUGG UACAUUACCU GGUA          54

(2) INFORMATION FOR SEQ ID NO: 627:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 627:

GCCGGCGGAC GUCAAGAA                                                      18

(2) INFORMATION FOR SEQ ID NO: 628:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 628:

CGAGGCUGAG AAGCACGUAC CAGAGAAACA CACGUUGUGG UACAUUACCU GGUA          54

(2) INFORMATION FOR SEQ ID NO: 629:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 629:

ACGUGCUGCU CAGCCUCG                                          18

(2) INFORMATION FOR SEQ ID NO: 630:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 630:

GACCCCGAAG AAGAGCAGAC CAGAGAAACA CACGUUGUGG UACAUUACCU GGUA      54

(2) INFORMATION FOR SEQ ID NO: 631:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 631:

CUGCUCAGCC UCGGGGUC                                          18

(2) INFORMATION FOR SEQ ID NO: 632:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 632:

CCUUGGCGAG AAGCGCGAAC CAGAGAAACA CACGUUGUGG UACAUUACCU GGUA      54

(2) INFORMATION FOR SEQ ID NO: 633:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 633:

UCGCGCCGCU CGCCAAGG                                          18

(2) INFORMATION FOR SEQ ID NO: 634:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 634:

GGCCUGCAAG AAGAACUCAC CAGAGAAACA CACGUUGUGG UACAUUACCU GGUA      54

(2) INFORMATION FOR SEQ ID NO: 635:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 635:

GAGUUCGGCC UGCAGGCC                                                        18

(2) INFORMATION FOR SEQ ID NO: 636:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 636:

CGCGCGAGAG AAGGGGCAC CAGAGAAACA CACGUUGUGG UACAUUACCU GGUA                 54

(2) INFORMATION FOR SEQ ID NO: 637:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 637:

GCCCCCUGAU CUCGCGCG                                                        18

(2) INFORMATION FOR SEQ ID NO: 638:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 638:

AUAAACGAAG AAGCAUAUAC CAGAGAAACA CACGUUGUGG UACAUUACCU GGUA                54

(2) INFORMATION FOR SEQ ID NO: 639:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 639:

AUAUGCUGUU UCGUUUAU                                                        18

(2) INFORMATION FOR SEQ ID NO: 640:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 640:

CACAAGCAAG AAGCUACAAC CAGAGAAACA CACGUUGUGG UACAUUACCU GGUA                54

(2) INFORMATION FOR SEQ ID NO: 641:

```
    (i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 641:

UGUAGCUGCU UGCUUGUG                                                  18

(2) INFORMATION FOR SEQ ID NO: 642:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 642:

AAUUACCGAG AAGUACUUAC CAGAGAAACA CACGUUGUGG UACAUUACCU GGUA           54

(2) INFORMATION FOR SEQ ID NO: 643:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 643:

AAGUACCGAU CGGUAAUU                                                  18

(2) INFORMATION FOR SEQ ID NO: 644:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 644:

CGCGCCCUCU GCCGCUU                                                   17

(2) INFORMATION FOR SEQ ID NO: 645:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 645:

GUCCAGGUUA CACAUUC                                                   17

(2) INFORMATION FOR SEQ ID NO: 646:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 646:

CUGCCGCUUG UUCGUUC                                                   17

(2) INFORMATION FOR SEQ ID NO: 647:

(i) SEQUENCE CHARACTERISTICS:
```

```
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 647:

UCCAGGUUAC ACAUUCA                                                    17

(2) INFORMATION FOR SEQ ID NO: 648:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 648:

CCGCUUGUUC GUUCCUC                                                    17

(2) INFORMATION FOR SEQ ID NO: 649:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 649:

UUACACAUUC AAUGCCA                                                    17

(2) INFORMATION FOR SEQ ID NO: 650:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 650:

CGCUUGUUCG UUCCUCG                                                    17

(2) INFORMATION FOR SEQ ID NO: 651:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 651:

UACACAUUCA AUGCCAC                                                    17

(2) INFORMATION FOR SEQ ID NO: 652:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 652:

UUGUUCGUUC CUCGCGC                                                    17

(2) INFORMATION FOR SEQ ID NO: 653:

(i) SEQUENCE CHARACTERISTICS:
            (A) LENGTH:              17 base pairs
```

```
            (B) TYPE:            nucleic acid
            (C) STRANDEDNESS:    single
            (D) TOPOLOGY:        linear (xi) SEQUENCE DESCRIPTION: SEQ ID NO: 653:

UGCCACCUCA CAAGAUU                                              17

(2) INFORMATION FOR SEQ ID NO: 654:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 654:

UGUUCGUUCC UCGCGCU                                              17

(2) INFORMATION FOR SEQ ID NO: 655:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 655:

CACAAGAUUG AAAUUUU                                              17

(2) INFORMATION FOR SEQ ID NO: 656:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 656:

UCGUUCCUCG CGCUCGC                                              17

(2) INFORMATION FOR SEQ ID NO: 657:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 657:

AUUGAAAUUU UCAAGUC                                              17

(2) INFORMATION FOR SEQ ID NO: 658:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 658:

CUCGCGCUCG CCACCAG                                              17

(2) INFORMATION FOR SEQ ID NO: 659:

(i) SEQUENCE CHARACTERISTICS:
            (A) LENGTH:          17 base pairs
            (B) TYPE:            nucleic acid
```

```
              (C) STRANDEDNESS:      single
              (D) TOPOLOGY:          linear (xi) SEQUENCE DESCRIPTION: SEQ ID NO: 659:

UUGAAAUUUU CAAGUCG                                                      17

(2) INFORMATION FOR SEQ ID NO: 660:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 660:

ACACACAUCC CAAUCUC                                                      17

(2) INFORMATION FOR SEQ ID NO: 661:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 661:

UGAAAUUUUC AAGUCGC                                                      17

(2) INFORMATION FOR SEQ ID NO: 662:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 662:

AUCCCAAUCU CGCGAGG                                                      17

(2) INFORMATION FOR SEQ ID NO: 663:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 663:

GAAAUUUUCA AGUCGCU                                                      17

(2) INFORMATION FOR SEQ ID NO: 664:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 664:

CCCAAUCUCG CGAGGGC                                                      17

(2) INFORMATION FOR SEQ ID NO: 665:

(i) SEQUENCE CHARACTERISTICS:
              (A) LENGTH:            17 base pairs
              (B) TYPE:              nucleic acid
              (C) STRANDEDNESS:      single
```

(D) TOPOLOGY:          linear (xi) SEQUENCE DESCRIPTION: SEQ ID NO: 665:

UUUCAAGUCG CUUGAUG                                              17

(2) INFORMATION FOR SEQ ID NO: 666:

(i) SEQUENCE CHARACTERISTICS:
           (A) LENGTH:            17 base pairs
           (B) TYPE:              nucleic acid
           (C) STRANDEDNESS:      single
           (D) TOPOLOGY:          linear (xi) SEQUENCE DESCRIPTION: SEQ ID NO: 666:

AGCAGGGUCU GCGGCGG                                              17

(2) INFORMATION FOR SEQ ID NO: 667:

(i) SEQUENCE CHARACTERISTICS:
           (A) LENGTH:            17 base pairs
           (B) TYPE:              nucleic acid
           (C) STRANDEDNESS:      single
           (D) TOPOLOGY:          linear (xi) SEQUENCE DESCRIPTION: SEQ ID NO: 667:

AAGUCGCUUG AUGAUUG                                              17

(2) INFORMATION FOR SEQ ID NO: 668:

(i) SEQUENCE CHARACTERISTICS:
           (A) LENGTH:            17 base pairs
           (B) TYPE:              nucleic acid
           (C) STRANDEDNESS:      single
           (D) TOPOLOGY:          linear (xi) SEQUENCE DESCRIPTION: SEQ ID NO: 668:

GCCGCGCUUC CGGCUCC                                              17

(2) INFORMATION FOR SEQ ID NO: 669:

(i) SEQUENCE CHARACTERISTICS:
           (A) LENGTH:            17 base pairs
           (B) TYPE:              nucleic acid
           (C) STRANDEDNESS:      single
           (D) TOPOLOGY:          linear (xi) SEQUENCE DESCRIPTION: SEQ ID NO: 669:

UUGAUGAUUG GGCUAGA                                              17

(2) INFORMATION FOR SEQ ID NO: 670:

(i) SEQUENCE CHARACTERISTICS:
           (A) LENGTH:            17 base pairs
           (B) TYPE:              nucleic acid
           (C) STRANDEDNESS:      single
           (D) TOPOLOGY:          linear (xi) SEQUENCE DESCRIPTION: SEQ ID NO: 670:

CCGCGCUUCC GGCUCCC                                              17

(2) INFORMATION FOR SEQ ID NO: 671:

(i) SEQUENCE CHARACTERISTICS:
           (A) LENGTH:            17 base pairs
           (B) TYPE:              nucleic acid
           (C) STRANDEDNESS:      single
           (D) TOPOLOGY:          linear (xi) SEQUENCE DESCRIPTION: SEQ ID NO: 671:

AUUGGGCUAG AGAUAAU                                                         17

(2) INFORMATION FOR SEQ ID NO: 672:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 672:

UUCCGGCUCC CCUUCCC                                                         17

(2) INFORMATION FOR SEQ ID NO: 673:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 673:

CUAGAGAUAA UAUCUUG                                                         17

(2) INFORMATION FOR SEQ ID NO: 674:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 674:

GCUCCCCUUC CCAUUGG                                                         17

(2) INFORMATION FOR SEQ ID NO: 675:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 675:

GAGAUAAUAU CUUGACG                                                         17

(2) INFORMATION FOR SEQ ID NO: 676:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 676:

CUCCCCUUCC CAUUGGC                                                         17

(2) INFORMATION FOR SEQ ID NO: 677:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 677:

GAUAAUAUCU UGACGCA                    17

(2) INFORMATION FOR SEQ ID NO: 678:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 678:

CUUCCCAUUG GCCUCCA                    17

(2) INFORMATION FOR SEQ ID NO: 679:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 679:

UAAUAUCUUG ACGCAUC                    17

(2) INFORMATION FOR SEQ ID NO: 680:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 680:

AUUGGCCUCC ACGAUGG                    17

(2) INFORMATION FOR SEQ ID NO: 681:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 681:

UGACGCAUCU CAAGCCA                    17

(2) INFORMATION FOR SEQ ID NO: 682:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 682:

AUGGCGCUCC GCCUCAA                    17

(2) INFORMATION FOR SEQ ID NO: 683:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 683:

ACGCAUCUCA AGCCAGU                                                    17

(2) INFORMATION FOR SEQ ID NO: 684:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 684:

CUCCGCCUCA ACGACGU                                                    17

(2) INFORMATION FOR SEQ ID NO: 685:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 685:

AAGCCAGUCG AGAAGUG                                                    17

(2) INFORMATION FOR SEQ ID NO: 686:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 686:

AACGACGUCG CGCUCUG                                                    17

(2) INFORMATION FOR SEQ ID NO: 687:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 687:

AGAAGUGUUG GCAGCCA                                                    17

(2) INFORMATION FOR SEQ ID NO: 688:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 688:

GUCGCGCUCU GCCUCUC                                                    17

(2) INFORMATION FOR SEQ ID NO: 689:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 689:

```
CACAGGAUUU CCUCCCG                                                   17

(2) INFORMATION FOR SEQ ID NO: 690:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 690:

CUCUGCCUCU CCCCGCC                                                   17

(2) INFORMATION FOR SEQ ID NO: 691:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 691:

ACAGGAUUUC CUCCCGG                                                   17

(2) INFORMATION FOR SEQ ID NO: 692:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 692:

CUGCCUCUCC CCGCCGC                                                   17

(2) INFORMATION FOR SEQ ID NO: 693:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 693:

CAGGAUUCC UCCCGGA                                                    17

(2) INFORMATION FOR SEQ ID NO: 694:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 694:

CCGCCGCUCG CCGCCCG                                                   17

(2) INFORMATION FOR SEQ ID NO: 695:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 695:

GAUUCCUCC CGGACCC                                                    17
```

(2) INFORMATION FOR SEQ ID NO: 696:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 696:

CGGCAGGUUC GUCGCCG                                   17

(2) INFORMATION FOR SEQ ID NO: 697:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 697:

CCCAGCAUCU GAAGGAU                                   17

(2) INFORMATION FOR SEQ ID NO: 698:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 698:

GGCAGGUUCG UCGCCGU                                   17

(2) INFORMATION FOR SEQ ID NO: 699:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 699:

UGAAGGAUUU CAUGAUG                                   17

(2) INFORMATION FOR SEQ ID NO: 700:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 700:

AGGUUCGUCG CCGUCGC                                   17

(2) INFORMATION FOR SEQ ID NO: 701:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 701:

GAAGGAUUUC AUGAUGA                                   17

(2) INFORMATION FOR SEQ ID NO: 702:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 702:

GUCGCCGUCG CCUCCAU                                                  17

(2) INFORMATION FOR SEQ ID NO: 703:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 703:

AAGGAUUUCA UGAUGAA                                                  17

(2) INFORMATION FOR SEQ ID NO: 704:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 704:

CGUCGCCUCC AUGACGU                                                  17

(2) INFORMATION FOR SEQ ID NO: 705:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 705:

GAUGAAGUUA AGGAGCU                                                  17

(2) INFORMATION FOR SEQ ID NO: 706:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 706:

CAUGACGUCC GCCGUCU                                                  17

(2) INFORMATION FOR SEQ ID NO: 707:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 707:

AUGAAGUUAA GGAGCUC                                                  17

(2) INFORMATION FOR SEQ ID NO: 708:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 708:

UCCGCCGUCU CCACCAA                                                  17

(2) INFORMATION FOR SEQ ID NO: 709:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 709:

AAGGAGCUCA GAGAACG                                                  17

(2) INFORMATION FOR SEQ ID NO: 710:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 710:

CGCCGUCUCC ACCAAGG                                                  17

(2) INFORMATION FOR SEQ ID NO: 711:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 711:

AAGGAAAUCC CUGAUGA                                                  17

(2) INFORMATION FOR SEQ ID NO: 712:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 712:

ACCAAGGUCG AGAAUAA                                                  17

(2) INFORMATION FOR SEQ ID NO: 713:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 713:

CUGAUGAUUA UUUUGUU                                                  17

(2) INFORMATION FOR SEQ ID NO: 714:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 714:

UCGAGAAUAA GAAGCCA                                                    17

(2) INFORMATION FOR SEQ ID NO: 715:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 715:

UGAUGAUUAU UUUGUUU                                                    17

(2) INFORMATION FOR SEQ ID NO: 716:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 716:

GAAGCCAUUU GCUCCUC                                                    17

(2) INFORMATION FOR SEQ ID NO: 717:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 717:

AUGAUUAUUU UGUUUGU                                                    17

(2) INFORMATION FOR SEQ ID NO: 718:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 718:

AAGCCAUUUG CUCCUCC                                                    17

(2) INFORMATION FOR SEQ ID NO: 719:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 719:

UGAUUAUUUU GUUUGUU                                                    17

(2) INFORMATION FOR SEQ ID NO: 720:

```
   (i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 720:

CAUUUGCUCC UCCAAGG                                                  17

(2) INFORMATION FOR SEQ ID NO: 721:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 721:

GAUUAUUUUG UUUGUUU                                                  17

(2) INFORMATION FOR SEQ ID NO: 722:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 722:

UUGCUCCUCC AAGGGAG                                                  17

(2) INFORMATION FOR SEQ ID NO: 723:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 723:

UAUUUUGUUU GUUUGGU                                                  17

(2) INFORMATION FOR SEQ ID NO: 724:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 724:

AGGGAGGUAC AUGUCCA                                                  17

(2) INFORMATION FOR SEQ ID NO: 725:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 725:

AUUUUGUUUG UUUGGUG                                                  17

(2) INFORMATION FOR SEQ ID NO: 726:

(i) SEQUENCE CHARACTERISTICS:
```

```
            (A) LENGTH:               17 base pairs
            (B) TYPE:                 nucleic acid
            (C) STRANDEDNESS:         single
            (D) TOPOLOGY:             linear (xi) SEQUENCE DESCRIPTION: SEQ ID NO: 726:

GUACAUGUCC AGGUUAC                                              17

(2) INFORMATION FOR SEQ ID NO: 727:

(i) SEQUENCE CHARACTERISTICS:
            (A) LENGTH:               17 base pairs
            (B) TYPE:                 nucleic acid
            (C) STRANDEDNESS:         single
            (D) TOPOLOGY:             linear (xi) SEQUENCE DESCRIPTION: SEQ ID NO: 727:

UUGUUUGUUU GGUGGGA                                              17

(2) INFORMATION FOR SEQ ID NO: 728:

(i) SEQUENCE CHARACTERISTICS:
            (A) LENGTH:               17 base pairs
            (B) TYPE:                 nucleic acid
            (C) STRANDEDNESS:         single
            (D) TOPOLOGY:             linear (xi) SEQUENCE DESCRIPTION: SEQ ID NO: 728:

UGUUUGUUUG GUGGGAG                                              17

(2) INFORMATION FOR SEQ ID NO: 729:

(i) SEQUENCE CHARACTERISTICS:
            (A) LENGTH:               17 base pairs
            (B) TYPE:                 nucleic acid
            (C) STRANDEDNESS:         single
            (D) TOPOLOGY:             linear (xi) SEQUENCE DESCRIPTION: SEQ ID NO: 729:

ACACUGCUCG UCACGCC                                              17

(2) INFORMATION FOR SEQ ID NO: 730:

(i) SEQUENCE CHARACTERISTICS:
            (A) LENGTH:               17 base pairs
            (B) TYPE:                 nucleic acid
            (C) STRANDEDNESS:         single
            (D) TOPOLOGY:             linear (xi) SEQUENCE DESCRIPTION: SEQ ID NO: 730:

GACAUGAUUA CCGAGGA                                              17

(2) INFORMATION FOR SEQ ID NO: 731:

(i) SEQUENCE CHARACTERISTICS:
            (A) LENGTH:               17 base pairs
            (B) TYPE:                 nucleic acid
            (C) STRANDEDNESS:         single
            (D) TOPOLOGY:             linear (xi) SEQUENCE DESCRIPTION: SEQ ID NO: 731:

CUGCUCGUCA CGCCAAG                                              17

(2) INFORMATION FOR SEQ ID NO: 732:

(i) SEQUENCE CHARACTERISTICS:
            (A) LENGTH:               17 base pairs
```

```
            (B) TYPE:             nucleic acid
            (C) STRANDEDNESS:     single
            (D) TOPOLOGY:         linear (xi) SEQUENCE DESCRIPTION: SEQ ID NO: 732:

ACAUGAUUAC CGAGGAA                                                  17

(2) INFORMATION FOR SEQ ID NO: 733:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 733:

CAAGGACUUU GGCGACU                                                  17

(2) INFORMATION FOR SEQ ID NO: 734:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 734:

AGGAAGCUCU ACCAACA                                                  17

(2) INFORMATION FOR SEQ ID NO: 735:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 735:

AAGGACUUUG GCGACUU                                                  17

(2) INFORMATION FOR SEQ ID NO: 736:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 736:

GAAGCUCUAC CAACAUA                                                  17

(2) INFORMATION FOR SEQ ID NO: 737:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 737:

UGGCGACUUA AAGCUUG                                                  17

(2) INFORMATION FOR SEQ ID NO: 738:

(i) SEQUENCE CHARACTERISTICS:
            (A) LENGTH:           17 base pairs
            (B) TYPE:             nucleic acid
```

```
            (C) STRANDEDNESS:       single
            (D) TOPOLOGY:           linear (xi) SEQUENCE DESCRIPTION: SEQ ID NO: 738:

ACCAACAUAC CAGACUA                                                      17

(2) INFORMATION FOR SEQ ID NO: 739:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 739:

GGCGACUUAA AGCUUGC                                                      17

(2) INFORMATION FOR SEQ ID NO: 740:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 740:

ACCAGACUAU GCUUAAC                                                      17

(2) INFORMATION FOR SEQ ID NO: 741:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 741:

UUAAAGCUUG CACAAAU                                                      17

(2) INFORMATION FOR SEQ ID NO: 742:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 742:

ACUAUGCUUA ACACCCU                                                      17

(2) INFORMATION FOR SEQ ID NO: 743:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 743:

GCACAAAUCU GCGGCAU                                                      17

(2) INFORMATION FOR SEQ ID NO: 744:

(i) SEQUENCE CHARACTERISTICS:
            (A) LENGTH:             17 base pairs
            (B) TYPE:               nucleic acid
            (C) STRANDEDNESS:       single
```

```
            (D) TOPOLOGY:            linear (xi) SEQUENCE DESCRIPTION: SEQ ID NO: 744:

CUAUGCUUAA CACCCUC                                              17

(2) INFORMATION FOR SEQ ID NO: 745:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 745:

UGCGGCAUCA UCGCCUC                                              17

(2) INFORMATION FOR SEQ ID NO: 746:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 746:

AACACCCUCG ACGGUGU                                              17

(2) INFORMATION FOR SEQ ID NO: 747:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 747:

GGCAUCAUCG CCUCAGA                                              17

(2) INFORMATION FOR SEQ ID NO: 748:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 748:

GACGGUGUCA GAGAUGA                                              17

(2) INFORMATION FOR SEQ ID NO: 749:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 749:

CAUCGCCUCA GAUGAGA                                              17

(2) INFORMATION FOR SEQ ID NO: 750:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear
```

(xi) SEQUENCE DESCRIPTION: SEQ ID NO: 750:

UGGGCUGUUU GGACGAG                                                17

(2) INFORMATION FOR SEQ ID NO: 751:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 751:

AACUGCGUAC ACCAAGA                                                17

(2) INFORMATION FOR SEQ ID NO: 752:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 752:

GGGCUGUUUG GACGAGG                                                17

(2) INFORMATION FOR SEQ ID NO: 753:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 753:

ACCAAGAUCG UGGAGAA                                                17

(2) INFORMATION FOR SEQ ID NO: 754:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 754:

AUGGUGAUCU GCUCAAC                                                17

(2) INFORMATION FOR SEQ ID NO: 755:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 755:

GAAGCUGUUU GAGAUCG                                                17

(2) INFORMATION FOR SEQ ID NO: 756:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear

```
        (xi) SEQUENCE DESCRIPTION: SEQ ID NO:  756:

GAUCUGCUCA ACAAGUA                                                    17

(2) INFORMATION FOR SEQ ID NO:  757:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO:  757:

AAGCUGUUUG AGAUCGA                                                    17

(2) INFORMATION FOR SEQ ID NO:  758:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO:  758:

CAACAAGUAU AUGUACC                                                    17

(2) INFORMATION FOR SEQ ID NO:  759:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO:  759:

UUUGAGAUCG ACCCUGA                                                    17

(2) INFORMATION FOR SEQ ID NO:  760:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO:  760:

ACAAGUAUAU GUACCUC                                                    17

(2) INFORMATION FOR SEQ ID NO:  761:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO:  761:

CUGAUGGUAC CGUGGUC                                                    17

(2) INFORMATION FOR SEQ ID NO:  762:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO:  762:
```

GUAUAUGUAC CUCACUG 17

(2) INFORMATION FOR SEQ ID NO: 763:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 763:

ACCGUGGUCG CUCUGGC 17

(2) INFORMATION FOR SEQ ID NO: 764:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 764:

AUGUACCUCA CUGGGAG 17

(2) INFORMATION FOR SEQ ID NO: 765:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 765:

UGGUCGCUCU GGCUGAC 17

(2) INFORMATION FOR SEQ ID NO: 766:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 766:

GGGUGGAUAU GAGGCAG 17

(2) INFORMATION FOR SEQ ID NO: 767:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 767:

AAGAAGAUCU CAAUGCC 17

(2) INFORMATION FOR SEQ ID NO: 768:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 768:

AGGCAGAUUG AGAAGAC                                                    17

(2) INFORMATION FOR SEQ ID NO: 769:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 769:

GAAGAUCUCA AUGCCUG                                                    17

(2) INFORMATION FOR SEQ ID NO: 770:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 770:

AAGACAAUUC AGUAUCU                                                    17

(2) INFORMATION FOR SEQ ID NO: 771:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 771:

CCUGAUGUUU GACGGGC                                                    17

(2) INFORMATION FOR SEQ ID NO: 772:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 772:

AGACAAUUCA GUAUCUU                                                    17

(2) INFORMATION FOR SEQ ID NO: 773:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 773:

CUGAUGUUUG ACGGGCA                                                    17

(2) INFORMATION FOR SEQ ID NO: 774:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 774:

AAUUCAGUAU CUUAUUG                                                    17

(2) INFORMATION FOR SEQ ID NO: 775:

(i) SEQUENCE CHARACTERISTICS:
       (A) LENGTH:         17 base pairs
       (B) TYPE:           nucleic acid
       (C) STRANDEDNESS:   single
       (D) TOPOLOGY:       linear (xi) SEQUENCE DESCRIPTION: SEQ ID NO: 775:

CAAGCUGUUC GAGCACU                                              17

(2) INFORMATION FOR SEQ ID NO: 776:

(i) SEQUENCE CHARACTERISTICS:
       (A) LENGTH:         17 base pairs
       (B) TYPE:           nucleic acid
       (C) STRANDEDNESS:   single
       (D) TOPOLOGY:       linear (xi) SEQUENCE DESCRIPTION: SEQ ID NO: 776:

UUCAGUAUCU UAUUGGC                                              17

(2) INFORMATION FOR SEQ ID NO: 777:

(i) SEQUENCE CHARACTERISTICS:
       (A) LENGTH:         17 base pairs
       (B) TYPE:           nucleic acid
       (C) STRANDEDNESS:   single
       (D) TOPOLOGY:       linear (xi) SEQUENCE DESCRIPTION: SEQ ID NO: 777:

AAGCUGUUCG AGCACUU                                              17

(2) INFORMATION FOR SEQ ID NO: 778:

(i) SEQUENCE CHARACTERISTICS:
       (A) LENGTH:         17 base pairs
       (B) TYPE:           nucleic acid
       (C) STRANDEDNESS:   single
       (D) TOPOLOGY:       linear (xi) SEQUENCE DESCRIPTION: SEQ ID NO: 778:

CAGUAUCUUA UUGGCUC                                              17

(2) INFORMATION FOR SEQ ID NO: 779:

(i) SEQUENCE CHARACTERISTICS:
       (A) LENGTH:         17 base pairs
       (B) TYPE:           nucleic acid
       (C) STRANDEDNESS:   single
       (D) TOPOLOGY:       linear (xi) SEQUENCE DESCRIPTION: SEQ ID NO: 779:

CGAGCACUUC UCCAUGG                                              17

(2) INFORMATION FOR SEQ ID NO: 780:

(i) SEQUENCE CHARACTERISTICS:
       (A) LENGTH:         17 base pairs
       (B) TYPE:           nucleic acid
       (C) STRANDEDNESS:   single
       (D) TOPOLOGY:       linear (xi) SEQUENCE DESCRIPTION: SEQ ID NO: 780:

AGUAUCUUAU UGGCUCU                                              17

(2) INFORMATION FOR SEQ ID NO: 781:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 781:

GAGCACUUCU CCAUGGU                                          17

(2) INFORMATION FOR SEQ ID NO: 782:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 782:

UAUCUUAUUG GCUCUGG                                          17

(2) INFORMATION FOR SEQ ID NO: 783:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 783:

GCACUUCUCC AUGGUCG                                          17

(2) INFORMATION FOR SEQ ID NO: 784:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 784:

UAUUGGCUCU GGAAUGG                                          17

(2) INFORMATION FOR SEQ ID NO: 785:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 785:

UCCAUGGUCG CGCAGAG                                          17

(2) INFORMATION FOR SEQ ID NO: 786:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 786:

GAAUGGAUCC UAGGACU                                          17

(2) INFORMATION FOR SEQ ID NO: 787:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 787:

CAGAGGCUUG GCGUUUA                                                    17

(2) INFORMATION FOR SEQ ID NO: 788:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 788:

UGGAUCCUAG GACUGAG                                                    17

(2) INFORMATION FOR SEQ ID NO: 789:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 789:

CUUGGCGUUU ACACCGC                                                    17

(2) INFORMATION FOR SEQ ID NO: 790:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 790:

CUGAGAAUAA UCCUUAU                                                    17

(2) INFORMATION FOR SEQ ID NO: 791:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 791:

UUGGCGUUUA CACCGCC                                                    17

(2) INFORMATION FOR SEQ ID NO: 792:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 792:

AGAAUAAUCC UUAUCUU                                                    17

(2) INFORMATION FOR SEQ ID NO: 793:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 793:

UGGCGUUUAC ACCGCCA                                                   17

(2) INFORMATION FOR SEQ ID NO: 794:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 794:

AUAAUCCUUA UCUUGGU                                                   17

(2) INFORMATION FOR SEQ ID NO: 795:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 795:

CAGGGACUAC GCCGACA                                                   17

(2) INFORMATION FOR SEQ ID NO: 796:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 796:

UAAUCCUUAU CUUGGUU                                                   17

(2) INFORMATION FOR SEQ ID NO: 797:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 797:

GCCGACAUCC UCGAGUU                                                   17

(2) INFORMATION FOR SEQ ID NO: 798:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 798:

AUCCUUAUCU UGGUUUC                                                   17

(2) INFORMATION FOR SEQ ID NO: 799:

```
        (i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 799:

GACAUCCUCG AGUUCCU                                                        17

(2) INFORMATION FOR SEQ ID NO: 800:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 800:

CCUUAUCUUG GUUUCAU                                                        17

(2) INFORMATION FOR SEQ ID NO: 801:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 801:

CCUCGAGUUC CUCGUCG                                                        17

(2) INFORMATION FOR SEQ ID NO: 802:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 802:

AUCUUGGUUU CAUCUAC                                                        17

(2) INFORMATION FOR SEQ ID NO: 803:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 803:

CUCGAGUUCC UCGUCGA                                                        17

(2) INFORMATION FOR SEQ ID NO: 804:

(i) SEQUENCE CHARACTERISTICS:
            (A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 804:

UCUUGGUUUC AUCUACA                                                        17

(2) INFORMATION FOR SEQ ID NO: 805:

(i) SEQUENCE CHARACTERISTICS:
```

```
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 805:

GAGUUCCUCG UCGACAG                                                   17

(2) INFORMATION FOR SEQ ID NO: 806:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 806:

CUUGGUUUCA UCUACAC                                                   17

(2) INFORMATION FOR SEQ ID NO: 807:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 807:

UUCCUCGUCG ACAGGUG                                                   17

(2) INFORMATION FOR SEQ ID NO: 808:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 808:

GGUUUCAUCU ACACCUC                                                   17

(2) INFORMATION FOR SEQ ID NO: 809:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 809:

UGACUGGUCU GUCGGGU                                                   17

(2) INFORMATION FOR SEQ ID NO: 810:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 810:

UUUCAUCUAC ACCUCCU                                                   17

(2) INFORMATION FOR SEQ ID NO: 811:

(i) SEQUENCE CHARACTERISTICS:
        (A) LENGTH:           17 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 811:

UGGUCUGUCG GGUGAAG                                              17

(2) INFORMATION FOR SEQ ID NO: 812:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 812:

CUACACCUCC UUCCAAG                                              17

(2) INFORMATION FOR SEQ ID NO: 813:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 813:

GCAGGACUAC CUUUGCA                                              17

(2) INFORMATION FOR SEQ ID NO: 814:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 814:

CACCUCCUUC CAAGAGC                                              17

(2) INFORMATION FOR SEQ ID NO: 815:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 815:

GACUACCUUU GCACCCU                                              17

(2) INFORMATION FOR SEQ ID NO: 816:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 816:

ACCUCCUUCC AAGAGCG                                              17

(2) INFORMATION FOR SEQ ID NO: 817:

(i) SEQUENCE CHARACTERISTICS:
            (A) LENGTH:            17 base pairs
            (B) TYPE:              nucleic acid
```

```
            (C) STRANDEDNESS:        single
            (D) TOPOLOGY:            linear (xi) SEQUENCE DESCRIPTION: SEQ ID NO: 817:

ACUACCUUUG CACCCUU                                                      17

(2) INFORMATION FOR SEQ ID NO: 818:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 818:

GGCGACCUUC AUCUCAC                                                      17

(2) INFORMATION FOR SEQ ID NO: 819:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 819:

UGCACCCUUG CUUCAAG                                                      17

(2) INFORMATION FOR SEQ ID NO: 820:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 820:

GCGACCUUCA UCUCACA                                                      17

(2) INFORMATION FOR SEQ ID NO: 821:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 821:

CCCUUGCUUC AAGAAUC                                                      17

(2) INFORMATION FOR SEQ ID NO: 822:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 822:

ACCUUCAUCU CACACGG                                                      17

(2) INFORMATION FOR SEQ ID NO: 823:

(i) SEQUENCE CHARACTERISTICS:
            (A) LENGTH:              17 base pairs
            (B) TYPE:                nucleic acid
            (C) STRANDEDNESS:        single
```

(D) TOPOLOGY:          linear (xi) SEQUENCE DESCRIPTION: SEQ ID NO: 823:

CCUUGCUUCA AGAAUCA                                                17

(2) INFORMATION FOR SEQ ID NO: 824:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 824:

CUUCAUCUCA CACGGGA                                                17

(2) INFORMATION FOR SEQ ID NO: 825:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 825:

UCAAGAAUCA GGAGGCU                                                17

(2) INFORMATION FOR SEQ ID NO: 826:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 826:

CGCUGCCUUU CAGCUGG                                                17

(2) INFORMATION FOR SEQ ID NO: 827:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 827:

UUUGAUGUAC AACCUGU                                                17

(2) INFORMATION FOR SEQ ID NO: 828:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 828:

GCUGCCUUUC AGCUGGG                                                17

(2) INFORMATION FOR SEQ ID NO: 829:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 829:

CAUGCCGUAC UUUGUCU                                                17

(2) INFORMATION FOR SEQ ID NO: 830:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 830:

CUGCCUUUCA GCUGGGU                                                17

(2) INFORMATION FOR SEQ ID NO: 831:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 831:

GCCGUACUUU GUCUGUC                                                17

(2) INFORMATION FOR SEQ ID NO: 832:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 832:

AGCUGGGUAU ACGGUAG                                                17

(2) INFORMATION FOR SEQ ID NO: 833:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 833:

CCGUACUUUG UCUGUCG                                                17

(2) INFORMATION FOR SEQ ID NO: 834:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 834:

CUGGGUAUAC GGUAGGG                                                17

(2) INFORMATION FOR SEQ ID NO: 835:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 835:

UACUUUGUCU GUCGCUG                                                17

(2) INFORMATION FOR SEQ ID NO: 836:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 836:

UAUACGGUAG GGACGUC                                                17

(2) INFORMATION FOR SEQ ID NO: 837:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 837:

UUGUCUGUCG CUGGCGG                                                17

(2) INFORMATION FOR SEQ ID NO: 838:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 838:

AGGGACGUCC AACUGUG                                                17

(2) INFORMATION FOR SEQ ID NO: 839:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 839:

CGGUGUGUUU CGGUAUG                                                17

(2) INFORMATION FOR SEQ ID NO: 840:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 840:

UGUGAGAUCG GAAACCU                                                17

(2) INFORMATION FOR SEQ ID NO: 841:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 841:

GGUGUGUUUC GGUAUGU                                                    17

(2) INFORMATION FOR SEQ ID NO: 842:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 842:

GCUGCGGUCU GCUUAGA                                                    17

(2) INFORMATION FOR SEQ ID NO: 843:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 843:

GUGUGUUUCG GUAUGUU                                                    17

(2) INFORMATION FOR SEQ ID NO: 844:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 844:

GGUCUGCUUA GACAAGA                                                    17

(2) INFORMATION FOR SEQ ID NO: 845:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 845:

GUUUCGGUAU GUUAUUU                                                    17

(2) INFORMATION FOR SEQ ID NO: 846:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 846:

GUCUGCUUAG ACAAGAC                                                    17

(2) INFORMATION FOR SEQ ID NO: 847:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 847:

```
CGGUAUGUUA UUUGAGU                                                    17

(2) INFORMATION FOR SEQ ID NO: 848:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 848:

UGCUGUGUCU GCGUUAC                                                    17

(2) INFORMATION FOR SEQ ID NO: 849:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 849:

GGUAUGUUAU UUGAGUU                                                    17

(2) INFORMATION FOR SEQ ID NO: 850:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 850:

GUCUGCGUUA CAUAGGU                                                    17

(2) INFORMATION FOR SEQ ID NO: 851:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 851:

UAUGUUAUUU GAGUUGC                                                    17

(2) INFORMATION FOR SEQ ID NO: 852:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 852:

UCUGCGUUAC AUAGGUC                                                    17

(2) INFORMATION FOR SEQ ID NO: 853:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 853:

AUGUUAUUUG AGUUGCU                                                    17
```

(2) INFORMATION FOR SEQ ID NO: 854:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 854:

CGUUACAUAG GUCUCCA                                17

(2) INFORMATION FOR SEQ ID NO: 855:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 855:

AUUUGAGUUG CUCAGAU                                17

(2) INFORMATION FOR SEQ ID NO: 856:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 856:

ACAUAGGUCU CCAGGUU                                17

(2) INFORMATION FOR SEQ ID NO: 857:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 857:

GAGUUGCUCA GAUCUGU                                17

(2) INFORMATION FOR SEQ ID NO: 858:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 858:

AUAGGUCUCC AGGUUUU                                17

(2) INFORMATION FOR SEQ ID NO: 859:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 859:

GCUCAGAUCU GUUAAAA                                17

(2) INFORMATION FOR SEQ ID NO: 860:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 860:

CUCCAGGUUU UGAUCAA                                                    17

(2) INFORMATION FOR SEQ ID NO: 861:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 861:

AGAUCUGUUA AAAAAAA                                                    17

(2) INFORMATION FOR SEQ ID NO: 862:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 862:

UCCAGGUUUU GAUCAAA                                                    17

(2) INFORMATION FOR SEQ ID NO: 863:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 863:

GAUCUGUUAA AAAAAAA                                                    17

(2) INFORMATION FOR SEQ ID NO: 864:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 864:

CCAGGUUUUG AUCAAAU                                                    17

(2) INFORMATION FOR SEQ ID NO: 865:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 865:

GUUUUGAUCA AAUGGUC                                                    17

(2) INFORMATION FOR SEQ ID NO: 866:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 866:

CAAAUGGUCC CGUGUCG                                              17

(2) INFORMATION FOR SEQ ID NO: 867:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 867:

UCCCGUGUCG UCUUAUA                                              17

(2) INFORMATION FOR SEQ ID NO: 868:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 868:

CGUGUCGUCU UAUAGAG                                              17

(2) INFORMATION FOR SEQ ID NO: 869:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 869:

UGUCGUCUUA UAGAGCG                                              17

(2) INFORMATION FOR SEQ ID NO: 870:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 870:

GUCGUCUUAU AGAGCGA                                              17

(2) INFORMATION FOR SEQ ID NO: 871:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 871:

CGUCUUAUAG AGCGAUA                                              17

(2) INFORMATION FOR SEQ ID NO: 872:

```
     (i) SEQUENCE CHARACTERISTICS:
           (A) LENGTH:           17 base pairs
           (B) TYPE:             nucleic acid
           (C) STRANDEDNESS:     single
           (D) TOPOLOGY:         linear (xi) SEQUENCE DESCRIPTION: SEQ ID NO: 872:

AGAGCGAUAG GAGAACG                                                    17

(2) INFORMATION FOR SEQ ID NO: 873:

(i) SEQUENCE CHARACTERISTICS:
           (A) LENGTH:           17 base pairs
           (B) TYPE:             nucleic acid
           (C) STRANDEDNESS:     single
           (D) TOPOLOGY:         linear (xi) SEQUENCE DESCRIPTION: SEQ ID NO: 873:

GAACGUGUUG GUCUGUG                                                    17

(2) INFORMATION FOR SEQ ID NO: 874:

(i) SEQUENCE CHARACTERISTICS:
           (A) LENGTH:           17 base pairs
           (B) TYPE:             nucleic acid
           (C) STRANDEDNESS:     single
           (D) TOPOLOGY:         linear (xi) SEQUENCE DESCRIPTION: SEQ ID NO: 874:

GUGUUGGUCU GUGGUGU                                                    17

(2) INFORMATION FOR SEQ ID NO: 875:

(i) SEQUENCE CHARACTERISTICS:
           (A) LENGTH:           17 base pairs
           (B) TYPE:             nucleic acid
           (C) STRANDEDNESS:     single
           (D) TOPOLOGY:         linear (xi) SEQUENCE DESCRIPTION: SEQ ID NO: 875:

UGUGGUGUAG CUUUGUU                                                    17

(2) INFORMATION FOR SEQ ID NO: 876:

(i) SEQUENCE CHARACTERISTICS:
           (A) LENGTH:           17 base pairs
           (B) TYPE:             nucleic acid
           (C) STRANDEDNESS:     single
           (D) TOPOLOGY:         linear (xi) SEQUENCE DESCRIPTION: SEQ ID NO: 876:

GUGUAGCUUU GUUUUUA                                                    17

(2) INFORMATION FOR SEQ ID NO: 877:

(i) SEQUENCE CHARACTERISTICS:
           (A) LENGTH:           17 base pairs
           (B) TYPE:             nucleic acid
           (C) STRANDEDNESS:     single
           (D) TOPOLOGY:         linear (xi) SEQUENCE DESCRIPTION: SEQ ID NO: 877:

UGUAGCUUUG UUUUUAU                                                    17

(2) INFORMATION FOR SEQ ID NO: 878:
```

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 878:

AGCUUUGUUU UUAUUUU                                              17

(2) INFORMATION FOR SEQ ID NO: 879:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 879:

GCUUUGUUUU UAUUUUG                                              17

(2) INFORMATION FOR SEQ ID NO: 880:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 880:

CUUUGUUUUU AUUUUGU                                              17

(2) INFORMATION FOR SEQ ID NO: 881:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 881:

UUUGUUUUUA UUUUGUA                                              17

(2) INFORMATION FOR SEQ ID NO: 882:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 882:

UUGUUUUUAU UUUGUAU                                              17

(2) INFORMATION FOR SEQ ID NO: 883:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 883:

GUUUUUAUUU UGUAUUU                                              17

(2) INFORMATION FOR SEQ ID NO: 884:

(i) SEQUENCE CHARACTERISTICS:

```
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 884:

UUUUUAUUUU GUAUUUU                                                  17

(2) INFORMATION FOR SEQ ID NO: 885:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 885:

UUUUAUUUUG UAUUUUU                                                  17

(2) INFORMATION FOR SEQ ID NO: 886:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 886:

UAUUUUGUAU UUUUCUG                                                  17

(2) INFORMATION FOR SEQ ID NO: 887:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 887:

UUUUGUAUUU UUCUGCU                                                  17

(2) INFORMATION FOR SEQ ID NO: 888:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 888:

UUUGUAUUUU UCUGCUU                                                  17

(2) INFORMATION FOR SEQ ID NO: 889:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 889:

UUGUAUUUUU CUGCUUU                                                  17

(2) INFORMATION FOR SEQ ID NO: 890:

(i) SEQUENCE CHARACTERISTICS:
        (A) LENGTH:          17 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 890:

UGUAUUUUUC UGCUUUG                                                          17

(2) INFORMATION FOR SEQ ID NO: 891:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 891:

GUAUUUUUCU GCUUUGA                                                          17

(2) INFORMATION FOR SEQ ID NO: 892:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 892:

UUUCUGCUUU GAUGUAC                                                          17

(2) INFORMATION FOR SEQ ID NO: 893:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 893:

UUCUGCUUUG AUGUACA                                                          17

(2) INFORMATION FOR SEQ ID NO:894:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION: The letter "N" stands for any base.

(xi) SEQUENCE DESCRIPTION: SEQ ID NO:894:

AAGCGGCACU GAUGANGAAA GGGCGCG                                               27

(2) INFORMATION FOR SEQ ID NO:895:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION: The letter "N" stands for any base.

(xi) SEQUENCE DESCRIPTION: SEQ ID NO:895:

GAACGAACCU GAUGANGAAA GCGGCAG                                               27
```

(2) INFORMATION FOR SEQ ID NO:896:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:896:

GAGGAACGCU GAUGANGAAA CAAGCGG                          27

(2) INFORMATION FOR SEQ ID NO:897:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:897:

CGAGGAACCU GAUGANGAAA ACAAGCG                          27

(2) INFORMATION FOR SEQ ID NO:898:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:898:

GCGCGAGGCU GAUGANGAAA CGAACAA                          27

(2) INFORMATION FOR SEQ ID NO:899:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:899:

AGCGCGAGCU GAUGANGAAA ACGAACA                          27

(2) INFORMATION FOR SEQ ID NO:900:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:900:

GCGAGCGCCU GAUGANGAAA GGAACGA                          27

(2) INFORMATION FOR SEQ ID NO:901:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:901:

CUGGUGGCCU GAUGANGAAA GCGCGAG                                  27

(2) INFORMATION FOR SEQ ID NO:902:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:902:

GAGAUUGGCU GAUGANGAAA UGUGUGU                                  27

(2) INFORMATION FOR SEQ ID NO:903:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:903:

CCUCGCGACU GAUGANGAAA UUGGGAU                                  27

(2) INFORMATION FOR SEQ ID NO:904:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:904:

GCCCUCGCCU GAUGANGAAA GAUUGGG                                  27

(2) INFORMATION FOR SEQ ID NO:905:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:905:

CCGCCGCACU GAUGANGAAA CCCUGCU                                                27

(2) INFORMATION FOR SEQ ID NO:906:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.

(xi) SEQUENCE DESCRIPTION: SEQ ID NO:906:

GGAGCCGGCU GAUGANGAAA GCGCGGC                                                27

(2) INFORMATION FOR SEQ ID NO:907:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.

(xi) SEQUENCE DESCRIPTION: SEQ ID NO:907:

GGGAGCCGCU GAUGANGAAA AGCGCGG                                                27

(2) INFORMATION FOR SEQ ID NO:908:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.

(xi) SEQUENCE DESCRIPTION: SEQ ID NO:908:

GGGAAGGGCU GAUGANGAAA GCCGGAA                                                27

(2) INFORMATION FOR SEQ ID NO:909:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.

(xi) SEQUENCE DESCRIPTION: SEQ ID NO:909:

CCAAUGGGCU GAUGANGAAA GGGGAGC                                                27

(2) INFORMATION FOR SEQ ID NO:910:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.

(xi) SEQUENCE DESCRIPTION: SEQ ID NO:910:

```
GCCAAUGGCU GAUGANGAAA AGGGGAG                                         27
```

(2) INFORMATION FOR SEQ ID NO:911:

(i) SEQUENCE CHARACTERISTICS:
        (A) LENGTH:          27 base pairs
        (B) TYPE:            nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:911:

```
UGGAGGCCCU GAUGANGAAA UGGGAAG                                         27
```

(2) INFORMATION FOR SEQ ID NO:912:

(i) SEQUENCE CHARACTERISTICS:
        (A) LENGTH:          27 base pairs
        (B) TYPE:            nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:912:

```
CCAUCGUGCU GAUGANGAAA GGCCAAU                                         27
```

(2) INFORMATION FOR SEQ ID NO:913:

(i) SEQUENCE CHARACTERISTICS:
        (A) LENGTH:          27 base pairs
        (B) TYPE:            nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:913:

```
UUGAGGCGCU GAUGANGAAA GCGCCAU                                         27
```

(2) INFORMATION FOR SEQ ID NO:914:

(i) SEQUENCE CHARACTERISTICS:
        (A) LENGTH:          27 base pairs
        (B) TYPE:            nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:914:

```
ACGUCGUUCU GAUGANGAAA GGCGGAG                                         27
```

(2) INFORMATION FOR SEQ ID NO:915:

(i) SEQUENCE CHARACTERISTICS:
        (A) LENGTH:          27 base pairs
        (B) TYPE:            nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:915:

CAGAGCGCCU GAUGANGAAA CGUCGUU                    27

(2) INFORMATION FOR SEQ ID NO:916:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:916:

GAGAGGCACU GAUGANGAAA GCGCGAC                    27

(2) INFORMATION FOR SEQ ID NO:917:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:917:

GGCGGGGACU GAUGANGAAA GGCAGAG                    27

(2) INFORMATION FOR SEQ ID NO:918:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:918:

GCGGCGGGCU GAUGANGAAA GAGGCAG                    27

(2) INFORMATION FOR SEQ ID NO:919:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:919:

CGGGCGGCCU GAUGANGAAA GCGGCGG                    27

(2) INFORMATION FOR SEQ ID NO:920:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:920:

CGGCGACGCU GAUGANGAAA CCUGCCG                                                27

(2) INFORMATION FOR SEQ ID NO:921:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:921:

ACGGCGACCU GAUGANGAAA ACCUGCC                                                27

(2) INFORMATION FOR SEQ ID NO:922:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:922:

GCGACGGCCU GAUGANGAAA CGAACCU                                                27

(2) INFORMATION FOR SEQ ID NO:923:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:923:

AUGGAGGCCU GAUGANGAAA CGGCGAC                                                27

(2) INFORMATION FOR SEQ ID NO:924:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:    The letter "N" stands for any base.

(xi) SEQUENCE DESCRIPTION: SEQ ID NO:924:

ACGUCAUGCU GAUGANGAAA GGCGACG                                                27

(2) INFORMATION FOR SEQ ID NO:925:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:    The letter "N" stands for any base.

(xi) SEQUENCE DESCRIPTION: SEQ ID NO:925:

AGACGGCGCU GAUGANGAAA CGUCAUG                                         27

(2) INFORMATION FOR SEQ ID NO:926:

(i) SEQUENCE CHARACTERISTICS:
                (A) LENGTH:           27 base pairs
                (B) TYPE:             nucleic acid
                (C) STRANDEDNESS:     single
                (D) TOPOLOGY:         linear (ix) FEATURE:
                (D) OTHER INFORMATION:    The letter "N" stands for any base.

(xi) SEQUENCE DESCRIPTION: SEQ ID NO:926:

UUGGUGGACU GAUGANGAAA CGGCGGA                                         27

(2) INFORMATION FOR SEQ ID NO:927:

(i) SEQUENCE CHARACTERISTICS:
                (A) LENGTH:           27 base pairs
                (B) TYPE:             nucleic acid
                (C) STRANDEDNESS:     single
                (D) TOPOLOGY:         linear (ix) FEATURE:
                (D) OTHER INFORMATION:    The letter "N" stands for any base.

(xi) SEQUENCE DESCRIPTION: SEQ ID NO:927:

CCUUGGUGCU GAUGANGAAA GACGGCG                                         27

(2) INFORMATION FOR SEQ ID NO:928:

(i) SEQUENCE CHARACTERISTICS:
                (A) LENGTH:           27 base pairs
                (B) TYPE:             nucleic acid
                (C) STRANDEDNESS:     single
                (D) TOPOLOGY:         linear (ix) FEATURE:
                (D) OTHER INFORMATION:    The letter "N" stands for any base.

(xi) SEQUENCE DESCRIPTION: SEQ ID NO:928:

UUAUUCUCCU GAUGANGAAA CCUUGGU                                         27

(2) INFORMATION FOR SEQ ID NO:929:

(i) SEQUENCE CHARACTERISTICS:
                (A) LENGTH:           27 base pairs
                (B) TYPE:             nucleic acid
                (C) STRANDEDNESS:     single
                (D) TOPOLOGY:         linear (ix) FEATURE:
                (D) OTHER INFORMATION:    The letter "N" stands for any base.

(xi) SEQUENCE DESCRIPTION: SEQ ID NO:929:

UGGCUUCUCU GAUGANGAAA UUCUCGA                                         27

(2) INFORMATION FOR SEQ ID NO:930:

(i) SEQUENCE CHARACTERISTICS:
                (A) LENGTH:           27 base pairs
                (B) TYPE:             nucleic acid
                (C) STRANDEDNESS:     single
                (D) TOPOLOGY:         linear (ix) FEATURE:
              (D) OTHER INFORMATION:    The letter "N" stands for any base.

(xi) SEQUENCE DESCRIPTION: SEQ ID NO:930:

GAGGAGCACU GAUGANGAAA UGGCUUC                                          27

(2) INFORMATION FOR SEQ ID NO:931:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:931:

GGAGGAGCCU GAUGANGAAA AUGGCUU                                          27

(2) INFORMATION FOR SEQ ID NO:932:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:932:

CCUUGGAGCU GAUGANGAAA GCAAAUG                                          27

(2) INFORMATION FOR SEQ ID NO:933:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:933:

CUCCCUUGCU GAUGANGAAA GGAGCAA                                          27

(2) INFORMATION FOR SEQ ID NO:934:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:934:

UGGACAUGCU GAUGANGAAA CCUCCCU                                          27

(2) INFORMATION FOR SEQ ID NO:935:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear

```
    (ix) FEATURE:
        (D) OTHER INFORMATION:    The letter "N" stands for any base.

(xi) SEQUENCE DESCRIPTION: SEQ ID NO:935:

GUAACCUGCU GAUGANGAAA CAUGUAC                                          27

(2) INFORMATION FOR SEQ ID NO:936:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
        (D) OTHER INFORMATION:    The letter "N" stands for any base.

(xi) SEQUENCE DESCRIPTION: SEQ ID NO:936:

GAAUGUGUCU GAUGANGAAA CCUGGAC                                          27

(2) INFORMATION FOR SEQ ID NO:937:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
        (D) OTHER INFORMATION:    The letter "N" stands for any base.

(xi) SEQUENCE DESCRIPTION: SEQ ID NO:937:

UGAAUGUGCU GAUGANGAAA ACCUGGA                                          27

(2) INFORMATION FOR SEQ ID NO:938:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
        (D) OTHER INFORMATION:    The letter "N" stands for any base.

(xi) SEQUENCE DESCRIPTION: SEQ ID NO:938:

UGGCAUUGCU GAUGANGAAA UGUGUAA                                          27

(2) INFORMATION FOR SEQ ID NO:939:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
        (D) OTHER INFORMATION:    The letter "N" stands for any base.

(xi) SEQUENCE DESCRIPTION: SEQ ID NO:939:

GUGGCAUUCU GAUGANGAAA AUGUGUA                                          27

(2) INFORMATION FOR SEQ ID NO:940:

(i) SEQUENCE CHARACTERISTICS:
        (A) LENGTH:               27 base pairs
        (B) TYPE:                 nucleic acid
        (C) STRANDEDNESS:         single
```

```
            (D) TOPOLOGY:           linear (ix) FEATURE:
        (D) OTHER INFORMATION:     The letter "N" stands for any base.

(xi) SEQUENCE DESCRIPTION: SEQ ID NO:940:

AAUCUUGUCU GAUGANGAAA GGUGGCA                                              27

(2) INFORMATION FOR SEQ ID NO:941:

(i) SEQUENCE CHARACTERISTICS:
        (A) LENGTH:                27 base pairs
        (B) TYPE:                  nucleic acid
        (C) STRANDEDNESS:          single
        (D) TOPOLOGY:              linear (ix) FEATURE:
        (D) OTHER INFORMATION:     The letter "N" stands for any base.

(xi) SEQUENCE DESCRIPTION: SEQ ID NO:941:

AAAAUUUCCU GAUGANGAAA UCUUGUG                                              27

(2) INFORMATION FOR SEQ ID NO:942:

(i) SEQUENCE CHARACTERISTICS:
        (A) LENGTH:                27 base pairs
        (B) TYPE:                  nucleic acid
        (C) STRANDEDNESS:          single
        (D) TOPOLOGY:              linear (ix) FEATURE:
        (D) OTHER INFORMATION:     The letter "N" stands for any base.

(xi) SEQUENCE DESCRIPTION: SEQ ID NO:942:

GACUUGAACU GAUGANGAAA UUUCAAU                                              27

(2) INFORMATION FOR SEQ ID NO:943:

(i) SEQUENCE CHARACTERISTICS:
        (A) LENGTH:                27 base pairs
        (B) TYPE:                  nucleic acid
        (C) STRANDEDNESS:          single
        (D) TOPOLOGY:              linear (ix) FEATURE:
        (D) OTHER INFORMATION:     The letter "N" stands for any base.

(xi) SEQUENCE DESCRIPTION: SEQ ID NO:943:

CGACUUGACU GAUGANGAAA AUUUCAA                                              27

(2) INFORMATION FOR SEQ ID NO:944:

(i) SEQUENCE CHARACTERISTICS:
        (A) LENGTH:                27 base pairs
        (B) TYPE:                  nucleic acid
        (C) STRANDEDNESS:          single
        (D) TOPOLOGY:              linear (ix) FEATURE:
        (D) OTHER INFORMATION:     The letter "N" stands for any base.

(xi) SEQUENCE DESCRIPTION: SEQ ID NO:944:

GCGACUUGCU GAUGANGAAA AAUUUCA                                              27

(2) INFORMATION FOR SEQ ID NO:945:

(i) SEQUENCE CHARACTERISTICS:
        (A) LENGTH:                27 base pairs
        (B) TYPE:                  nucleic acid
```

```
                (C) STRANDEDNESS:       single
                (D) TOPOLOGY:           linear (ix) FEATURE:
                (D) OTHER INFORMATION:  The letter "N" stands for any base.

(xi) SEQUENCE DESCRIPTION: SEQ ID NO:945:

AGCGACUUCU GAUGANGAAA AAAUUUC                                             27

(2) INFORMATION FOR SEQ ID NO:946:

(i) SEQUENCE CHARACTERISTICS:
                (A) LENGTH:             27 base pairs
                (B) TYPE:               nucleic acid
                (C) STRANDEDNESS:       single
                (D) TOPOLOGY:           linear (ix) FEATURE:
                (D) OTHER INFORMATION:  The letter "N" stands for any base.

(xi) SEQUENCE DESCRIPTION: SEQ ID NO:946:

CAUCAAGCCU GAUGANGAAA CUUGAAA                                             27

(2) INFORMATION FOR SEQ ID NO:947:

(i) SEQUENCE CHARACTERISTICS:
                (A) LENGTH:             27 base pairs
                (B) TYPE:               nucleic acid
                (C) STRANDEDNESS:       single
                (D) TOPOLOGY:           linear (ix) FEATURE:
                (D) OTHER INFORMATION:  The letter "N" stands for any base.

(xi) SEQUENCE DESCRIPTION: SEQ ID NO:947:

CAAUCAUCCU GAUGANGAAA GCGACUU                                             27

(2) INFORMATION FOR SEQ ID NO:948:

(i) SEQUENCE CHARACTERISTICS:
                (A) LENGTH:             27 base pairs
                (B) TYPE:               nucleic acid
                (C) STRANDEDNESS:       single
                (D) TOPOLOGY:           linear (ix) FEATURE:
                (D) OTHER INFORMATION:  The letter "N" stands for any base.

(xi) SEQUENCE DESCRIPTION: SEQ ID NO:948:

UCUAGCCCCU GAUGANGAAA UCAUCAA                                             27

(2) INFORMATION FOR SEQ ID NO:949:

(i) SEQUENCE CHARACTERISTICS:
                (A) LENGTH:             27 base pairs
                (B) TYPE:               nucleic acid
                (C) STRANDEDNESS:       single
                (D) TOPOLOGY:           linear (ix) FEATURE:
                (D) OTHER INFORMATION:  The letter "N" stands for any base.

(xi) SEQUENCE DESCRIPTION: SEQ ID NO:949:

AUUAUCUCCU GAUGANGAAA GCCCAAU                                             27

(2) INFORMATION FOR SEQ ID NO:950:

(i) SEQUENCE CHARACTERISTICS:
                (A) LENGTH:             27 base pairs
```

```
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:950:

CAAGAUAUCU GAUGANGAAA UCUCUAG                                              27

(2) INFORMATION FOR SEQ ID NO:951:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:951:

CGUCAAGACU GAUGANGAAA UUAUCUC                                              27

(2) INFORMATION FOR SEQ ID NO:952:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:952:

UGCGUCAACU GAUGANGAAA UAUUAUC                                              27

(2) INFORMATION FOR SEQ ID NO:953:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:953:

GAUGCGUCCU GAUGANGAAA GAUAUUA                                              27

(2) INFORMATION FOR SEQ ID NO:954:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:954:

UGGCUUGACU GAUGANGAAA UGCGUCA                                              27

(2) INFORMATION FOR SEQ ID NO:955:

(i) SEQUENCE CHARACTERISTICS:
```

```
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:955:

ACUGGCUUCU GAUGANGAAA GAUGCGU                                           27

(2) INFORMATION FOR SEQ ID NO:956:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:956:

CACUUCUCCU GAUGANGAAA CUGGCUU                                           27

(2) INFORMATION FOR SEQ ID NO:957:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:957:

UGGCUGCCCU GAUGANGAAA CACUUCU                                           27

(2) INFORMATION FOR SEQ ID NO:958:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:958:

CGGGAGGACU GAUGANGAAA UCCUGUG                                           27

(2) INFORMATION FOR SEQ ID NO:959:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:959:

CCGGGAGGCU GAUGANGAAA AUCCUGU                                           27

(2) INFORMATION FOR SEQ ID NO:960:
```

```
    (i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:960:

UCCGGGAGCU GAUGANGAAA AAUCCUG                                        27

(2) INFORMATION FOR SEQ ID NO:961:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:961:

GGGUCCGGCU GAUGANGAAA GGAAAUC                                        27

(2) INFORMATION FOR SEQ ID NO:962:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:962:

AUCCUUCACU GAUGANGAAA UGCUGGG                                        27

(2) INFORMATION FOR SEQ ID NO:963:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:963:

CAUCAUGACU GAUGANGAAA UCCUUCA                                        27

(2) INFORMATION FOR SEQ ID NO:964:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:964:

UCAUCAUGCU GAUGANGAAA AUCCUUC                                        27

(2) INFORMATION FOR SEQ ID NO:965:
```

(i) SEQUENCE CHARACTERISTICS:
    (A) LENGTH:        27 base pairs
    (B) TYPE:          nucleic acid
    (C) STRANDEDNESS:  single
    (D) TOPOLOGY:      linear (ix) FEATURE:
    (D) OTHER INFORMATION:  The letter "N" stands for any base.

(xi) SEQUENCE DESCRIPTION: SEQ ID NO:965:

UUCAUCAUCU GAUGANGAAA AAUCCUU                                27

(2) INFORMATION FOR SEQ ID NO:966:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:  The letter "N" stands for any base.

(xi) SEQUENCE DESCRIPTION: SEQ ID NO:966:

AGCUCCUUCU GAUGANGAAA CUUCAUC                                27

(2) INFORMATION FOR SEQ ID NO:967:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:  The letter "N" stands for any base.

(xi) SEQUENCE DESCRIPTION: SEQ ID NO:967:

GAGCUCCUCU GAUGANGAAA ACUUCAU                                27

(2) INFORMATION FOR SEQ ID NO:968:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:  The letter "N" stands for any base.

(xi) SEQUENCE DESCRIPTION: SEQ ID NO:968:

CGUUCUCUCU GAUGANGAAA GCUCCUU                                27

(2) INFORMATION FOR SEQ ID NO:969:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:  The letter "N" stands for any base.

(xi) SEQUENCE DESCRIPTION: SEQ ID NO:969:

UCAUCAGGCU GAUGANGAAA UUUCCUU                                27

(2) INFORMATION FOR SEQ ID NO:970:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:970:

AACAAAAUCU GAUGANGAAA UCAUCAG                                      27

(2) INFORMATION FOR SEQ ID NO:971:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:971:

AAACAAAACU GAUGANGAAA AUCAUCA                                      27

(2) INFORMATION FOR SEQ ID NO:972:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:972:

ACAAACAACU GAUGANGAAA UAAUCAU                                      27

(2) INFORMATION FOR SEQ ID NO:973:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:973:

AACAAACACU GAUGANGAAA AUAAUCA                                      27

(2) INFORMATION FOR SEQ ID NO:974:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:974:

AAACAAACCU GAUGANGAAA AAUAAUC                                      27

(2) INFORMATION FOR SEQ ID NO:975:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:975:

ACCAAACACU GAUGANGAAA CAAAAUA     27

(2) INFORMATION FOR SEQ ID NO:976:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:976:

CACCAAACCU GAUGANGAAA ACAAAAU     27

(2) INFORMATION FOR SEQ ID NO:977:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:977:

UCCCACCACU GAUGANGAAA CAAACAA     27

(2) INFORMATION FOR SEQ ID NO:978:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:978:

CUCCCACCCU GAUGANGAAA ACAAACA     27

(2) INFORMATION FOR SEQ ID NO:979:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:979:

UCCUCGGUCU GAUGANGAAA UCAUGUC     27

(2) INFORMATION FOR SEQ ID NO:980:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:980:

UUCCUCGGCU GAUGANGAAA AUCAUGU                                27

(2) INFORMATION FOR SEQ ID NO:981:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:981:

UGUUGGUACU GAUGANGAAA GCUUCCU                                27

(2) INFORMATION FOR SEQ ID NO:982:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:982:

UAUGUUGGCU GAUGANGAAA GAGCUUC                                27

(2) INFORMATION FOR SEQ ID NO:983:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:983:

UAGUCUGGCU GAUGANGAAA UGUUGGU                                27

(2) INFORMATION FOR SEQ ID NO:984:

(i) SEQUENCE CHARACTERISTICS:
        (A) LENGTH:        27 base pairs
        (B) TYPE:          nucleic acid
        (C) STRANDEDNESS:  single
        (D) TOPOLOGY:      linear (ix) FEATURE:
        (D) OTHER INFORMATION:    The letter "N" stands for any base.

(xi) SEQUENCE DESCRIPTION: SEQ ID NO:984:

```
GUUAAGCACU GAUGANGAAA GUCUGGU                                               27

(2) INFORMATION FOR SEQ ID NO:985:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:985:

AGGGUGUUCU GAUGANGAAA GCAUAGU                                               27

(2) INFORMATION FOR SEQ ID NO:986:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:986:

GAGGGUGUCU GAUGANGAAA AGCAUAG                                               27

(2) INFORMATION FOR SEQ ID NO:987:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:987:

ACACCGUCCU GAUGANGAAA GGGUGUU                                               27

(2) INFORMATION FOR SEQ ID NO:988:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:988:

UCAUCUCUCU GAUGANGAAA CACCGUC                                               27

(2) INFORMATION FOR SEQ ID NO:989:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO:989:
```

CUCGUCCACU GAUGANGAAA CAGCCCA                                                27

(2) INFORMATION FOR SEQ ID NO:990:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:990:

CCUCGUCCCU GAUGANGAAA ACAGCCC                                                27

(2) INFORMATION FOR SEQ ID NO:991:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:991:

GUUGAGCACU GAUGANGAAA UCACCAU                                                27

(2) INFORMATION FOR SEQ ID NO:992:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:992:

UACUUGUUCU GAUGANGAAA GCAGAUC                                                27

(2) INFORMATION FOR SEQ ID NO:993:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:993:

GGUACAUACU GAUGANGAAA CUUGUUG                                                27

(2) INFORMATION FOR SEQ ID NO:994:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:994:

GAGGUACACU GAUGANGAAA UACUUGU                                    27

(2) INFORMATION FOR SEQ ID NO:995:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
         (D) OTHER INFORMATION:   The letter "N" stands for any base.

(xi) SEQUENCE DESCRIPTION: SEQ ID NO:995:

CAGUGAGGCU GAUGANGAAA CAUAUAC                                    27

(2) INFORMATION FOR SEQ ID NO:996:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
         (D) OTHER INFORMATION:   The letter "N" stands for any base.

(xi) SEQUENCE DESCRIPTION: SEQ ID NO:996:

CUCCCAGUCU GAUGANGAAA GGUACAU                                    27

(2) INFORMATION FOR SEQ ID NO:997:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
         (D) OTHER INFORMATION:   The letter "N" stands for any base.

(xi) SEQUENCE DESCRIPTION: SEQ ID NO:997:

CUGCCUCACU GAUGANGAAA UCCACCC                                    27

(2) INFORMATION FOR SEQ ID NO:998:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
         (D) OTHER INFORMATION:   The letter "N" stands for any base.

(xi) SEQUENCE DESCRIPTION: SEQ ID NO:998:

GUCUUCUCCU GAUGANGAAA UCUGCCU                                    27

(2) INFORMATION FOR SEQ ID NO:999:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
         (D) OTHER INFORMATION:   The letter "N" stands for any base.

(xi) SEQUENCE DESCRIPTION: SEQ ID NO:999:

AGAUACUGCU GAUGANGAAA UUGUCUU                                27

(2) INFORMATION FOR SEQ ID NO:1000:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1000:

AAGAUACUCU GAUGANGAAA AUUGUCU                                27

(2) INFORMATION FOR SEQ ID NO:1001:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1001:

CAAUAAGACU GAUGANGAAA CUGAAUU                                27

(2) INFORMATION FOR SEQ ID NO:1002:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1002:

GCCAAUAACU GAUGANGAAA UACUGAA                                27

(2) INFORMATION FOR SEQ ID NO:1003:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1003:

GAGCCAAUCU GAUGANGAAA GAUACUG                                27

(2) INFORMATION FOR SEQ ID NO:1004:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:    The letter "N" stands for any base.

(xi) SEQUENCE DESCRIPTION: SEQ ID NO:1004:

AGAGCCAACU GAUGANGAAA AGAUACU                                              27

(2) INFORMATION FOR SEQ ID NO:1005:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:    The letter "N" stands for any base.

(xi) SEQUENCE DESCRIPTION: SEQ ID NO:1005:

CCAGAGCCCU GAUGANGAAA UAAGAUA                                              27

(2) INFORMATION FOR SEQ ID NO:1006:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:    The letter "N" stands for any base.

(xi) SEQUENCE DESCRIPTION: SEQ ID NO:1006:

CCAUUCCACU GAUGANGAAA GCCAAUA                                              27

(2) INFORMATION FOR SEQ ID NO:1007:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:    The letter "N" stands for any base.

(xi) SEQUENCE DESCRIPTION: SEQ ID NO:1007:

AGUCCUAGCU GAUGANGAAA UCCAUUC                                              27

(2) INFORMATION FOR SEQ ID NO:1008:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:    The letter "N" stands for any base.

(xi) SEQUENCE DESCRIPTION: SEQ ID NO:1008:

CUCAGUCCCU GAUGANGAAA GGAUCCA                                              27

(2) INFORMATION FOR SEQ ID NO:1009:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
              (D) OTHER INFORMATION:    The letter "N" stands for any base.

(xi) SEQUENCE DESCRIPTION: SEQ ID NO:1009:

AUAAGGAUCU GAUGANGAAA UUCUCAG                                              27

(2) INFORMATION FOR SEQ ID NO:1010:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:1010:

AAGAUAAGCU GAUGANGAAA UUAUUCU                                              27

(2) INFORMATION FOR SEQ ID NO:1011:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:1011:

ACCAAGAUCU GAUGANGAAA GGAUUAU                                              27

(2) INFORMATION FOR SEQ ID NO:1012:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:1012:

AACCAAGACU GAUGANGAAA AGGAUUA                                              27

(2) INFORMATION FOR SEQ ID NO:1013:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear (ix) FEATURE:
              (D) OTHER INFORMATION:    The letter "N" stands for any base.

(xi) SEQUENCE DESCRIPTION: SEQ ID NO:1013:

GAAACCAACU GAUGANGAAA UAAGGAU                                              27

(2) INFORMATION FOR SEQ ID NO:1014:

(i) SEQUENCE CHARACTERISTICS:
              (A) LENGTH:               27 base pairs
              (B) TYPE:                 nucleic acid
              (C) STRANDEDNESS:         single
              (D) TOPOLOGY:             linear

```
    (ix) FEATURE:
        (D) OTHER INFORMATION:   The letter "N" stands for any base.

(xi) SEQUENCE DESCRIPTION: SEQ ID NO:1014:

AUGAAACCCU GAUGANGAAA GAUAAGG                                          27

(2) INFORMATION FOR SEQ ID NO:1015:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1015:

GUAGAUGACU GAUGANGAAA CCAAGAU                                          27

(2) INFORMATION FOR SEQ ID NO:1016:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1016:

UGUAGAUGCU GAUGANGAAA ACCAAGA                                          27

(2) INFORMATION FOR SEQ ID NO:1017:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1017:

GUGUAGAUCU GAUGANGAAA AACCAAG                                          27

(2) INFORMATION FOR SEQ ID NO:1018:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1018:

GAGGUGUACU GAUGANGAAA UGAAACC                                          27

(2) INFORMATION FOR SEQ ID NO:1019:

(i) SEQUENCE CHARACTERISTICS:
        (A) LENGTH:              27 base pairs
        (B) TYPE:                nucleic acid
        (C) STRANDEDNESS:        single
```

```
            (D) TOPOLOGY:           linear (ix) FEATURE:
            (D) OTHER INFORMATION:  The letter "N" stands for any base.

(xi) SEQUENCE DESCRIPTION: SEQ ID NO:1019:

AGGAGGUGCU GAUGANGAAA GAUGAAA                                              27

(2) INFORMATION FOR SEQ ID NO:1020:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1020:

CUUGGAAGCU GAUGANGAAA GGUGUAG                                              27

(2) INFORMATION FOR SEQ ID NO:1021:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1021:

GCUCUUGGCU GAUGANGAAA GGAGGUG                                              27

(2) INFORMATION FOR SEQ ID NO:1022:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1022:

CGCUCUUGCU GAUGANGAAA AGGAGGU                                              27

(2) INFORMATION FOR SEQ ID NO:1023:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1023:

GUGAGAUGCU GAUGANGAAA GGUCGCC                                              27

(2) INFORMATION FOR SEQ ID NO:1024:

(i) SEQUENCE CHARACTERISTICS:
            (A) LENGTH:             27 base pairs
            (B) TYPE:               nucleic acid
```

```
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1024:

UGUGAGAUCU GAUGANGAAA AGGUCGC                                           27

(2) INFORMATION FOR SEQ ID NO:1025:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1025:

CCGUGUGACU GAUGANGAAA UGAAGGU                                           27

(2) INFORMATION FOR SEQ ID NO:1026:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1026:

UCCCGUGUCU GAUGANGAAA GAUGAAG                                           27

(2) INFORMATION FOR SEQ ID NO:1027:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1027:

GGCGUGACCU GAUGANGAAA GCAGUGU                                           27

(2) INFORMATION FOR SEQ ID NO:1028:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1028:

CUUGGCGUCU GAUGANGAAA CGAGCAG                                           27

(2) INFORMATION FOR SEQ ID NO:1029:

(i) SEQUENCE CHARACTERISTICS:
            (A) LENGTH:              27 base pairs
```

```
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1029:

AGUCGCCACU GAUGANGAAA GUCCUUG                                            27

(2) INFORMATION FOR SEQ ID NO:1030:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1030:

AAGUCGCCCU GAUGANGAAA AGUCCUU                                            27

(2) INFORMATION FOR SEQ ID NO:1031:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1031:

CAAGCUUUCU GAUGANGAAA GUCGCCA                                            27

(2) INFORMATION FOR SEQ ID NO:1032:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1032:

GCAAGCUUCU GAUGANGAAA AGUCGCC                                            27

(2) INFORMATION FOR SEQ ID NO:1033:

(i) SEQUENCE CHARACTERISTICS:
            (A) LENGTH:              27 base pairs
            (B) TYPE:                nucleic acid
            (C) STRANDEDNESS:        single
            (D) TOPOLOGY:            linear (ix) FEATURE:
            (D) OTHER INFORMATION:   The letter "N" stands for any base.

(xi) SEQUENCE DESCRIPTION: SEQ ID NO:1033:

AUUUGUGCCU GAUGANGAAA GCUUUAA                                            27

(2) INFORMATION FOR SEQ ID NO:1034:

(i) SEQUENCE CHARACTERISTICS:
```

(A) LENGTH:            27 base pairs
          (B) TYPE:              nucleic acid
          (C) STRANDEDNESS:      single
          (D) TOPOLOGY:          linear (ix) FEATURE:
          (D) OTHER INFORMATION:    The letter "N" stands for any base.

(xi) SEQUENCE DESCRIPTION: SEQ ID NO:1034:

AUGCCGCACU GAUGANGAAA UUUGUGC                                             27

(2) INFORMATION FOR SEQ ID NO:1035:

(i) SEQUENCE CHARACTERISTICS:
          (A) LENGTH:            27 base pairs
          (B) TYPE:              nucleic acid
          (C) STRANDEDNESS:      single
          (D) TOPOLOGY:          linear (ix) FEATURE:
          (D) OTHER INFORMATION:    The letter "N" stands for any base.

(xi) SEQUENCE DESCRIPTION: SEQ ID NO:1035:

GAGGCGAUCU GAUGANGAAA UGCCGCA                                             27

(2) INFORMATION FOR SEQ ID NO:1036:

(i) SEQUENCE CHARACTERISTICS:
          (A) LENGTH:            27 base pairs
          (B) TYPE:              nucleic acid
          (C) STRANDEDNESS:      single
          (D) TOPOLOGY:          linear (ix) FEATURE:
          (D) OTHER INFORMATION:    The letter "N" stands for any base.

(xi) SEQUENCE DESCRIPTION: SEQ ID NO:1036:

UCUGAGGCCU GAUGANGAAA UGAUGCC                                             27

(2) INFORMATION FOR SEQ ID NO:1037:

(i) SEQUENCE CHARACTERISTICS:
          (A) LENGTH:            27 base pairs
          (B) TYPE:              nucleic acid
          (C) STRANDEDNESS:      single
          (D) TOPOLOGY:          linear (ix) FEATURE:
          (D) OTHER INFORMATION:    The letter "N" stands for any base.

(xi) SEQUENCE DESCRIPTION: SEQ ID NO:1037:

UCUCAUCUCU GAUGANGAAA GGCGAUG                                             27

(2) INFORMATION FOR SEQ ID NO:1038:

(i) SEQUENCE CHARACTERISTICS:
          (A) LENGTH:            27 base pairs
          (B) TYPE:              nucleic acid
          (C) STRANDEDNESS:      single
          (D) TOPOLOGY:          linear (ix) FEATURE:
          (D) OTHER INFORMATION:    The letter "N" stands for any base.

(xi) SEQUENCE DESCRIPTION: SEQ ID NO:1038:

UCUUGGUGCU GAUGANGAAA CGCAGUU                                             27

(2) INFORMATION FOR SEQ ID NO:1039:

```
    (i) SEQUENCE CHARACTERISTICS:
         (A) LENGTH:          27 base pairs
         (B) TYPE:            nucleic acid
         (C) STRANDEDNESS:    single
         (D) TOPOLOGY:        linear (ix) FEATURE:
         (D) OTHER INFORMATION:   The letter "N" stands for any base.

(xi) SEQUENCE DESCRIPTION: SEQ ID NO:1039:

UUCUCCACCU GAUGANGAAA UCUUGGU                                            27

(2) INFORMATION FOR SEQ ID NO:1040:

(i) SEQUENCE CHARACTERISTICS:
         (A) LENGTH:          27 base pairs
         (B) TYPE:            nucleic acid
         (C) STRANDEDNESS:    single
         (D) TOPOLOGY:        linear (ix) FEATURE:
         (D) OTHER INFORMATION:   The letter "N" stands for any base.

(xi) SEQUENCE DESCRIPTION: SEQ ID NO:1040:

CGAUCUCACU GAUGANGAAA CAGCUUC                                            27

(2) INFORMATION FOR SEQ ID NO:1041:

(i) SEQUENCE CHARACTERISTICS:
         (A) LENGTH:          27 base pairs
         (B) TYPE:            nucleic acid
         (C) STRANDEDNESS:    single
         (D) TOPOLOGY:        linear (ix) FEATURE:
         (D) OTHER INFORMATION:   The letter "N" stands for any base.

(xi) SEQUENCE DESCRIPTION: SEQ ID NO:1041:

UCGAUCUCCU GAUGANGAAA ACAGCUU                                            27

(2) INFORMATION FOR SEQ ID NO:1042:

(i) SEQUENCE CHARACTERISTICS:
         (A) LENGTH:          27 base pairs
         (B) TYPE:            nucleic acid
         (C) STRANDEDNESS:    single
         (D) TOPOLOGY:        linear (ix) FEATURE:
         (D) OTHER INFORMATION:   The letter "N" stands for any base.

(xi) SEQUENCE DESCRIPTION: SEQ ID NO:1042:

UCAGGGUCCU GAUGANGAAA UCUCAAA                                            27

(2) INFORMATION FOR SEQ ID NO:1043:

(i) SEQUENCE CHARACTERISTICS:
         (A) LENGTH:          27 base pairs
         (B) TYPE:            nucleic acid
         (C) STRANDEDNESS:    single
         (D) TOPOLOGY:        linear (ix) FEATURE:
         (D) OTHER INFORMATION:   The letter "N" stands for any base.

(xi) SEQUENCE DESCRIPTION: SEQ ID NO:1043:

GACCACGGCU GAUGANGAAA CCAUCAG                                            27

(2) INFORMATION FOR SEQ ID NO:1044:
```

(i) SEQUENCE CHARACTERISTICS:
    (A) LENGTH:         27 base pairs
    (B) TYPE:           nucleic acid
    (C) STRANDEDNESS:   single
    (D) TOPOLOGY:       linear (ix) FEATURE:
    (D) OTHER INFORMATION:   The letter "N" stands for any base.

(xi) SEQUENCE DESCRIPTION: SEQ ID NO:1044:

GCCAGAGCCU GAUGANGAAA CCACGGU                         27

(2) INFORMATION FOR SEQ ID NO:1045:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1045:

GUCAGCCACU GAUGANGAAA GCGACCA                         27

(2) INFORMATION FOR SEQ ID NO:1046:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1046:

GGCAUUGACU GAUGANGAAA UCUUCUU                         27

(2) INFORMATION FOR SEQ ID NO:1047:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1047:

CAGGCAUUCU GAUGANGAAA GAUCUUC                         27

(2) INFORMATION FOR SEQ ID NO:1048:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1048:

GCCCGUCACU GAUGANGAAA CAUCAGG                         27

(2) INFORMATION FOR SEQ ID NO:1049:

(i) SEQUENCE CHARACTERISTICS:
        (A) LENGTH:             27 base pairs
        (B) TYPE:               nucleic acid
        (C) STRANDEDNESS:     single
        (D) TOPOLOGY:          linear (ix) FEATURE:
        (D) OTHER INFORMATION:    The letter "N" stands for any base.

(xi) SEQUENCE DESCRIPTION: SEQ ID NO:1049:

UGCCCGUCCU GAUGANGAAA ACAUCAG                             27

(2) INFORMATION FOR SEQ ID NO:1050:

(i) SEQUENCE CHARACTERISTICS:
        (A) LENGTH:             27 base pairs
        (B) TYPE:               nucleic acid
        (C) STRANDEDNESS:     single
        (D) TOPOLOGY:          linear (ix) FEATURE:
        (D) OTHER INFORMATION:    The letter "N" stands for any base.

(xi) SEQUENCE DESCRIPTION: SEQ ID NO:1050:

AGUGCUCGCU GAUGANGAAA CAGCUUG                             27

(2) INFORMATION FOR SEQ ID NO:1051:

(i) SEQUENCE CHARACTERISTICS:
        (A) LENGTH:             27 base pairs
        (B) TYPE:               nucleic acid
        (C) STRANDEDNESS:     single
        (D) TOPOLOGY:          linear (ix) FEATURE:
        (D) OTHER INFORMATION:    The letter "N" stands for any base.

(xi) SEQUENCE DESCRIPTION: SEQ ID NO:1051:

AAGUGCUCCU GAUGANGAAA ACAGCUU                             27

(2) INFORMATION FOR SEQ ID NO:1052:

(i) SEQUENCE CHARACTERISTICS:
        (A) LENGTH:             27 base pairs
        (B) TYPE:               nucleic acid
        (C) STRANDEDNESS:     single
        (D) TOPOLOGY:          linear (ix) FEATURE:
        (D) OTHER INFORMATION:    The letter "N" stands for any base.

(xi) SEQUENCE DESCRIPTION: SEQ ID NO:1052:

CCAUGGAGCU GAUGANGAAA GUGCUCG                             27

(2) INFORMATION FOR SEQ ID NO:1053:

(i) SEQUENCE CHARACTERISTICS:
        (A) LENGTH:             27 base pairs
        (B) TYPE:               nucleic acid
        (C) STRANDEDNESS:     single
        (D) TOPOLOGY:          linear (ix) FEATURE:
        (D) OTHER INFORMATION:    The letter "N" stands for any base.

(xi) SEQUENCE DESCRIPTION: SEQ ID NO:1053:

ACCAUGGACU GAUGANGAAA AGUGCUC                             27

(2) INFORMATION FOR SEQ ID NO:1054:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:1054:

CGACCAUGCU GAUGANGAAA GAAGUGC                                   27

(2) INFORMATION FOR SEQ ID NO:1055:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:1055:

CUCUGCGCCU GAUGANGAAA CCAUGGA                                   27

(2) INFORMATION FOR SEQ ID NO:1056:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:1056:

UAAACGCCCU GAUGANGAAA GCCUCUG                                   27

(2) INFORMATION FOR SEQ ID NO:1057:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:1057:

GCGGUGUACU GAUGANGAAA CGCCAAG                                   27

(2) INFORMATION FOR SEQ ID NO:1058:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:    The letter "N" stands for any base.

(xi) SEQUENCE DESCRIPTION: SEQ ID NO:1058:

GGCGGUGUCU GAUGANGAAA ACGCCAA                                   27

(2) INFORMATION FOR SEQ ID NO:1059:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:1059:

UGGCGGUGCU GAUGANGAAA AACGCCA     27

(2) INFORMATION FOR SEQ ID NO:1060:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:1060:

UGUCGGCGCU GAUGANGAAA GUCCCUG     27

(2) INFORMATION FOR SEQ ID NO:1061:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:1061:

AACUCGAGCU GAUGANGAAA UGUCGGC     27

(2) INFORMATION FOR SEQ ID NO:1062:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:1062:

AGGAACUCCU GAUGANGAAA GGAUGUC     27

(2) INFORMATION FOR SEQ ID NO:1063:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:1063:

CGACGAGGCU GAUGANGAAA CUCGAGG                                              27

(2) INFORMATION FOR SEQ ID NO:1064:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1064:

UCGACGAGCU GAUGANGAAA ACUCGAG                                              27

(2) INFORMATION FOR SEQ ID NO:1065:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1065:

CUGUCGACCU GAUGANGAAA GGAACUC                                              27

(2) INFORMATION FOR SEQ ID NO:1066:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1066:

CACCUGUCCU GAUGANGAAA CGAGGAA                                              27

(2) INFORMATION FOR SEQ ID NO:1067:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1067:

ACCCGACACU GAUGANGAAA CCAGUCA                                              27

(2) INFORMATION FOR SEQ ID NO:1068:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:   The letter "N" stands for any base.

(xi) SEQUENCE DESCRIPTION: SEQ ID NO:1068:

CUUCACCCCU GAUGANGAAA CAGACCA					27

(2) INFORMATION FOR SEQ ID NO:1069:

(i) SEQUENCE CHARACTERISTICS:
        (A) LENGTH:			27 base pairs
        (B) TYPE:			nucleic acid
        (C) STRANDEDNESS:		single
        (D) TOPOLOGY:			linear (ix) FEATURE:
        (D) OTHER INFORMATION:		The letter "N" stands for any base.

(xi) SEQUENCE DESCRIPTION: SEQ ID NO:1069:

UGCAAAGGCU GAUGANGAAA GUCCUGC					27

(2) INFORMATION FOR SEQ ID NO:1070:

(i) SEQUENCE CHARACTERISTICS:
        (A) LENGTH:			27 base pairs
        (B) TYPE:			nucleic acid
        (C) STRANDEDNESS:		single
        (D) TOPOLOGY:			linear (ix) FEATURE:
        (D) OTHER INFORMATION:		The letter "N" stands for any base.

(xi) SEQUENCE DESCRIPTION: SEQ ID NO:1070:

AGGGUGCACU GAUGANGAAA GGUAGUC					27

(2) INFORMATION FOR SEQ ID NO:1071:

(i) SEQUENCE CHARACTERISTICS:
        (A) LENGTH:			27 base pairs
        (B) TYPE:			nucleic acid
        (C) STRANDEDNESS:		single
        (D) TOPOLOGY:			linear (ix) FEATURE:
        (D) OTHER INFORMATION:		The letter "N" stands for any base.

(xi) SEQUENCE DESCRIPTION: SEQ ID NO:1071:

AAGGGUGCCU GAUGANGAAA AGGUAGU					27

(2) INFORMATION FOR SEQ ID NO:1072:

(i) SEQUENCE CHARACTERISTICS:
        (A) LENGTH:			27 base pairs
        (B) TYPE:			nucleic acid
        (C) STRANDEDNESS:		single
        (D) TOPOLOGY:			linear (ix) FEATURE:
        (D) OTHER INFORMATION:		The letter "N" stands for any base.

(xi) SEQUENCE DESCRIPTION: SEQ ID NO:1072:

CUUGAAGCCU GAUGANGAAA GGGUGCA					27

(2) INFORMATION FOR SEQ ID NO:1073:

(i) SEQUENCE CHARACTERISTICS:
        (A) LENGTH:			27 base pairs
        (B) TYPE:			nucleic acid
        (C) STRANDEDNESS:		single
        (D) TOPOLOGY:			linear (ix) FEATURE:
        (D) OTHER INFORMATION:		The letter "N" stands for any base.

(xi) SEQUENCE DESCRIPTION: SEQ ID NO:1073:

GAUUCUUGCU GAUGANGAAA GCAAGGG                                              27

(2) INFORMATION FOR SEQ ID NO:1074:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:1074:

UGAUUCUUCU GAUGANGAAA AGCAAGG                                              27

(2) INFORMATION FOR SEQ ID NO:1075:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:1075:

AGCCUCCUCU GAUGANGAAA UUCUUGA                                              27

(2) INFORMATION FOR SEQ ID NO:1076:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:1076:

CCAGCUGACU GAUGANGAAA GGCAGCG                                              27

(2) INFORMATION FOR SEQ ID NO:1077:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:1077:

CCCAGCUGCU GAUGANGAAA AGGCAGC                                              27

(2) INFORMATION FOR SEQ ID NO:1078:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (ix) FEATURE:
        (D) OTHER INFORMATION:   The letter "N" stands for any base.

(xi) SEQUENCE DESCRIPTION: SEQ ID NO:1078:

ACCCAGCUCU GAUGANGAAA AAGGCAG                                              27

(2) INFORMATION FOR SEQ ID NO:1079:

(i) SEQUENCE CHARACTERISTICS:
             (A) LENGTH:              27 base pairs
             (B) TYPE:                nucleic acid
             (C) STRANDEDNESS:        single
             (D) TOPOLOGY:            linear (ix) FEATURE:
             (D) OTHER INFORMATION:   The letter "N" stands for any base.

(xi) SEQUENCE DESCRIPTION: SEQ ID NO:1079:

CUACCGUACU GAUGANGAAA CCCAGCU                                              27

(2) INFORMATION FOR SEQ ID NO:1080:

(i) SEQUENCE CHARACTERISTICS:
             (A) LENGTH:              27 base pairs
             (B) TYPE:                nucleic acid
             (C) STRANDEDNESS:        single
             (D) TOPOLOGY:            linear (ix) FEATURE:
             (D) OTHER INFORMATION:   The letter "N" stands for any base.

(xi) SEQUENCE DESCRIPTION: SEQ ID NO:1080:

CCCUACCGCU GAUGANGAAA UACCCAG                                              27

(2) INFORMATION FOR SEQ ID NO:1081:

(i) SEQUENCE CHARACTERISTICS:
             (A) LENGTH:              27 base pairs
             (B) TYPE:                nucleic acid
             (C) STRANDEDNESS:        single
             (D) TOPOLOGY:            linear (ix) FEATURE:
             (D) OTHER INFORMATION:   The letter "N" stands for any base.

(xi) SEQUENCE DESCRIPTION: SEQ ID NO:1081:

GACGUCCCCU GAUGANGAAA CCGUAUA                                              27

(2) INFORMATION FOR SEQ ID NO:1082:

(i) SEQUENCE CHARACTERISTICS:
             (A) LENGTH:              27 base pairs
             (B) TYPE:                nucleic acid
             (C) STRANDEDNESS:        single
             (D) TOPOLOGY:            linear (ix) FEATURE:
             (D) OTHER INFORMATION:   The letter "N" stands for any base.

(xi) SEQUENCE DESCRIPTION: SEQ ID NO:1082:

CACAGUUGCU GAUGANGAAA CGUCCCU                                              27

(2) INFORMATION FOR SEQ ID NO:1083:

(i) SEQUENCE CHARACTERISTICS:
             (A) LENGTH:              27 base pairs
             (B) TYPE:                nucleic acid
             (C) STRANDEDNESS:        single
             (D) TOPOLOGY:            linear (ix) FEATURE:

(D) OTHER INFORMATION:    The letter "N" stands for any base.

(xi) SEQUENCE DESCRIPTION: SEQ ID NO:1083:

AGGUUUCCCU GAUGANGAAA UCUCACA                                            27

(2) INFORMATION FOR SEQ ID NO:1084:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
         (D) OTHER INFORMATION:   The letter "N" stands for any base.

(xi) SEQUENCE DESCRIPTION: SEQ ID NO:1084:

UCUAAGCACU GAUGANGAAA CCGCAGC                                            27

(2) INFORMATION FOR SEQ ID NO:1085:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
         (D) OTHER INFORMATION:   The letter "N" stands for any base.

(xi) SEQUENCE DESCRIPTION: SEQ ID NO:1085:

UCUUGUCUCU GAUGANGAAA GCAGACC                                            27

(2) INFORMATION FOR SEQ ID NO:1086:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
         (D) OTHER INFORMATION:   The letter "N" stands for any base.

(xi) SEQUENCE DESCRIPTION: SEQ ID NO:1086:

GUCUUGUCCU GAUGANGAAA AGCAGAC                                            27

(2) INFORMATION FOR SEQ ID NO:1087:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
         (D) OTHER INFORMATION:   The letter "N" stands for any base.

(xi) SEQUENCE DESCRIPTION: SEQ ID NO:1087:

GUAACGCACU GAUGANGAAA CACAGCA                                            27

(2) INFORMATION FOR SEQ ID NO:1088:

(i) SEQUENCE CHARACTERISTICS:
        (A) LENGTH:               27 base pairs
        (B) TYPE:                 nucleic acid
        (C) STRANDEDNESS:         single
        (D) TOPOLOGY:             linear (ix) FEATURE:
    (D) OTHER INFORMATION:    The letter "N" stands for any base.

(xi) SEQUENCE DESCRIPTION: SEQ ID NO:1088:

ACCUAUGUCU GAUGANGAAA CGCAGAC                                    27

(2) INFORMATION FOR SEQ ID NO:1089:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1089:

GACCUAUGCU GAUGANGAAA ACGCAGA                                    27

(2) INFORMATION FOR SEQ ID NO:1090:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1090:

UGGAGACCCU GAUGANGAAA UGUAACG                                    27

(2) INFORMATION FOR SEQ ID NO:1091:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1091:

AACCUGGACU GAUGANGAAA CCUAUGU                                    27

(2) INFORMATION FOR SEQ ID NO:1092:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1092:

AAAACCUGCU GAUGANGAAA GACCUAU                                    27

(2) INFORMATION FOR SEQ ID NO:1093:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear

```
    (ix) FEATURE:
        (D) OTHER INFORMATION:    The letter "N" stands for any base.

(xi) SEQUENCE DESCRIPTION: SEQ ID NO:1093:

UUGAUCAACU GAUGANGAAA CCUGGAG                                              27

(2) INFORMATION FOR SEQ ID NO:1094:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:    The letter "N" stands for any base.

(xi) SEQUENCE DESCRIPTION: SEQ ID NO:1094:

UUUGAUCACU GAUGANGAAA ACCUGGA                                              27

(2) INFORMATION FOR SEQ ID NO:1095:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:    The letter "N" stands for any base.

(xi) SEQUENCE DESCRIPTION: SEQ ID NO:1095:

AUUUGAUCCU GAUGANGAAA AACCUGG                                              27

(2) INFORMATION FOR SEQ ID NO:1096:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:    The letter "N" stands for any base.

(xi) SEQUENCE DESCRIPTION: SEQ ID NO:1096:

GACCAUUUCU GAUGANGAAA UCAAAAC                                              27

(2) INFORMATION FOR SEQ ID NO:1097:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:    The letter "N" stands for any base.

(xi) SEQUENCE DESCRIPTION: SEQ ID NO:1097:

CGACACGGCU GAUGANGAAA CCAUUUG                                              27

(2) INFORMATION FOR SEQ ID NO:1098:

(i) SEQUENCE CHARACTERISTICS:
        (A) LENGTH:              27 base pairs
        (B) TYPE:                nucleic acid
        (C) STRANDEDNESS:        single
```

```
            (D) TOPOLOGY:           linear (ix) FEATURE:
            (D) OTHER INFORMATION:  The letter "N" stands for any base.

(xi) SEQUENCE DESCRIPTION: SEQ ID NO:1098:

UAUAAGACCU GAUGANGAAA CACGGGA                                           27

(2) INFORMATION FOR SEQ ID NO:1099:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1099:

CUCUAUAACU GAUGANGAAA CGACACG                                           27

(2) INFORMATION FOR SEQ ID NO:1100:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1100:

CGCUCUAUCU GAUGANGAAA GACGACA                                           27

(2) INFORMATION FOR SEQ ID NO:1101:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1101:

UCGCUCUACU GAUGANGAAA AGACGAC                                           27

(2) INFORMATION FOR SEQ ID NO:1102:

(i) SEQUENCE CHARACTERISTICS:
            (A) LENGTH:             27 base pairs
            (B) TYPE:               nucleic acid
            (C) STRANDEDNESS:       single
            (D) TOPOLOGY:           linear (ix) FEATURE:
            (D) OTHER INFORMATION:  The letter "N" stands for any base.

(xi) SEQUENCE DESCRIPTION: SEQ ID NO:1102:

UAUCGCUCCU GAUGANGAAA UAAGACG                                           27

(2) INFORMATION FOR SEQ ID NO:1103:

(i) SEQUENCE CHARACTERISTICS:
            (A) LENGTH:             27 base pairs
            (B) TYPE:               nucleic acid
```

```
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1103:

CGUUCUCCCU GAUGANGAAA UCGCUCU                                              27

(2) INFORMATION FOR SEQ ID NO:1104:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1104:

CACAGACCCU GAUGANGAAA CACGUUC                                              27

(2) INFORMATION FOR SEQ ID NO:1105:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1105:

ACACCACACU GAUGANGAAA CCAACAC                                              27

(2) INFORMATION FOR SEQ ID NO:1106:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1106:

AACAAAGCCU GAUGANGAAA CACCACA                                              27

(2) INFORMATION FOR SEQ ID NO:1107:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1107:

UAAAAACACU GAUGANGAAA GCUACAC                                              27

(2) INFORMATION FOR SEQ ID NO:1108:

(i) SEQUENCE CHARACTERISTICS:
            (A) LENGTH:                27 base pairs
```

```
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1108:

AUAAAAACCU GAUGANGAAA AGCUACA                                              27

(2) INFORMATION FOR SEQ ID NO:1109:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1109:

AAAAUAAACU GAUGANGAAA CAAAGCU                                              27

(2) INFORMATION FOR SEQ ID NO:1110:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1110:

CAAAAUAACU GAUGANGAAA ACAAAGC                                              27

(2) INFORMATION FOR SEQ ID NO:1111:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1111:

ACAAAAUACU GAUGANGAAA AACAAAG                                              27

(2) INFORMATION FOR SEQ ID NO:1112:

(i) SEQUENCE CHARACTERISTICS:
            (A) LENGTH:                27 base pairs
            (B) TYPE:                  nucleic acid
            (C) STRANDEDNESS:          single
            (D) TOPOLOGY:              linear (ix) FEATURE:
            (D) OTHER INFORMATION:     The letter "N" stands for any base.

(xi) SEQUENCE DESCRIPTION: SEQ ID NO:1112:

UACAAAAUCU GAUGANGAAA AAACAAA                                              27

(2) INFORMATION FOR SEQ ID NO:1113:

(i) SEQUENCE CHARACTERISTICS:
```

```
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1113:

AUACAAAACU GAUGANGAAA AAAACAA                                              27

(2) INFORMATION FOR SEQ ID NO:1114:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1114:

AAAUACAACU GAUGANGAAA UAAAAAC                                              27

(2) INFORMATION FOR SEQ ID NO:1115:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1115:

AAAAUACACU GAUGANGAAA AUAAAAA                                              27

(2) INFORMATION FOR SEQ ID NO:1116:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1116:

AAAAAUACCU GAUGANGAAA AAUAAAA                                              27

(2) INFORMATION FOR SEQ ID NO:1117:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1117:

CAGAAAAACU GAUGANGAAA CAAAAUA                                              27

(2) INFORMATION FOR SEQ ID NO:1118:
```

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:   The letter "N" stands for any base.

(xi) SEQUENCE DESCRIPTION: SEQ ID NO:1118:

AGCAGAAACU GAUGANGAAA UACAAAA                                       27

(2) INFORMATION FOR SEQ ID NO:1119:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:   The letter "N" stands for any base.

(xi) SEQUENCE DESCRIPTION: SEQ ID NO:1119:

AAGCAGAACU GAUGANGAAA AUACAAA                                       27

(2) INFORMATION FOR SEQ ID NO:1120:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:   The letter "N" stands for any base.

(xi) SEQUENCE DESCRIPTION: SEQ ID NO:1120:

AAAGCAGACU GAUGANGAAA AAUACAA                                       27

(2) INFORMATION FOR SEQ ID NO:1121:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:   The letter "N" stands for any base.

(xi) SEQUENCE DESCRIPTION: SEQ ID NO:1121:

CAAAGCAGCU GAUGANGAAA AAAUACA                                       27

(2) INFORMATION FOR SEQ ID NO:1122:

(i) SEQUENCE CHARACTERISTICS:
            (A) LENGTH:            27 base pairs
            (B) TYPE:              nucleic acid
            (C) STRANDEDNESS:      single
            (D) TOPOLOGY:          linear (ix) FEATURE:
            (D) OTHER INFORMATION:   The letter "N" stands for any base.

(xi) SEQUENCE DESCRIPTION: SEQ ID NO:1122:

UCAAAGCACU GAUGANGAAA AAAAUAC                                       27

(2) INFORMATION FOR SEQ ID NO:1123:

```
        (i) SEQUENCE CHARACTERISTICS:
              (A) LENGTH:          27 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:1123:

GUACAUCACU GAUGANGAAA GCAGAAA                                              27

(2) INFORMATION FOR SEQ ID NO:1124:

(i) SEQUENCE CHARACTERISTICS:
              (A) LENGTH:          27 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:1124:

UGUACAUCCU GAUGANGAAA AGCAGAA                                              27

(2) INFORMATION FOR SEQ ID NO:1125:

(i) SEQUENCE CHARACTERISTICS:
              (A) LENGTH:          27 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:1125:

ACAGGUUGCU GAUGANGAAA CAUCAAA                                              27

(2) INFORMATION FOR SEQ ID NO:1126:

(i) SEQUENCE CHARACTERISTICS:
              (A) LENGTH:          27 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:1126:

AGACAAAGCU GAUGANGAAA CGGCAUG                                              27

(2) INFORMATION FOR SEQ ID NO:1127:

(i) SEQUENCE CHARACTERISTICS:
              (A) LENGTH:          27 base pairs
              (B) TYPE:            nucleic acid
              (C) STRANDEDNESS:    single
              (D) TOPOLOGY:        linear (ix) FEATURE:
              (D) OTHER INFORMATION:   The letter "N" stands for any base.

(xi) SEQUENCE DESCRIPTION: SEQ ID NO:1127:

GACAGACACU GAUGANGAAA GUACGGC                                              27
```

```
(2) INFORMATION FOR SEQ ID NO:1128:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:1128:

CGACAGACCU GAUGANGAAA AGUACGG                                   27

(2) INFORMATION FOR SEQ ID NO:1129:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:1129:

CAGCGACACU GAUGANGAAA CAAAGUA                                   27

(2) INFORMATION FOR SEQ ID NO:1130:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:1130:

CCGCCAGCCU GAUGANGAAA CAGACAA                                   27

(2) INFORMATION FOR SEQ ID NO:1131:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:1131:

CAUACCGACU GAUGANGAAA CACACCG                                   27

(2) INFORMATION FOR SEQ ID NO:1132:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ix) FEATURE:
        (D) OTHER INFORMATION:    The letter "N" stands for any base.

(xi) SEQUENCE DESCRIPTION: SEQ ID NO:1132:

ACAUACCGCU GAUGANGAAA ACACACC                                   27
```

(2) INFORMATION FOR SEQ ID NO:1133:

(i) SEQUENCE CHARACTERISTICS:
        (A) LENGTH:            27 base pairs
        (B) TYPE:              nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1133:

AACAUACCCU GAUGANGAAA AACACAC                               27

(2) INFORMATION FOR SEQ ID NO:1134:

(i) SEQUENCE CHARACTERISTICS:
        (A) LENGTH:            27 base pairs
        (B) TYPE:              nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1134:

AAAUAACACU GAUGANGAAA CCGAAAC                               27

(2) INFORMATION FOR SEQ ID NO:1135:

(i) SEQUENCE CHARACTERISTICS:
        (A) LENGTH:            27 base pairs
        (B) TYPE:              nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1135:

ACUCAAAUCU GAUGANGAAA CAUACCG                               27

(2) INFORMATION FOR SEQ ID NO:1136:

(i) SEQUENCE CHARACTERISTICS:
        (A) LENGTH:            27 base pairs
        (B) TYPE:              nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1136:

AACUCAAACU GAUGANGAAA ACAUACC                               27

(2) INFORMATION FOR SEQ ID NO:1137:

(i) SEQUENCE CHARACTERISTICS:
        (A) LENGTH:            27 base pairs
        (B) TYPE:              nucleic acid
        (C) STRANDEDNESS:     single
        (D) TOPOLOGY:         linear (ix) FEATURE:
        (D) OTHER INFORMATION:    The letter "N" stands for any base.

(xi) SEQUENCE DESCRIPTION: SEQ ID NO:1137:

GCAACUCACU GAUGANGAAA UAACAUA                               27

(2) INFORMATION FOR SEQ ID NO:1138:

(i) SEQUENCE CHARACTERISTICS:
        (A) LENGTH:           27 base pairs
        (B) TYPE:             nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:1138:

AGCAACUCCU GAUGANGAAA AUAACAU                                   27

(2) INFORMATION FOR SEQ ID NO:1139:

(i) SEQUENCE CHARACTERISTICS:
        (A) LENGTH:           27 base pairs
        (B) TYPE:             nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:1139:

AUCUGAGCCU GAUGANGAAA CUCAAAU                                   27

(2) INFORMATION FOR SEQ ID NO:1140:

(i) SEQUENCE CHARACTERISTICS:
        (A) LENGTH:           27 base pairs
        (B) TYPE:             nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:1140:

ACAGAUCUCU GAUGANGAAA GCAACUC                                   27

(2) INFORMATION FOR SEQ ID NO:1141:

(i) SEQUENCE CHARACTERISTICS:
        (A) LENGTH:           27 base pairs
        (B) TYPE:             nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:1141:

UUUUAACACU GAUGANGAAA UCUGAGC                                   27

(2) INFORMATION FOR SEQ ID NO:1142:

(i) SEQUENCE CHARACTERISTICS:
        (A) LENGTH:           27 base pairs
        (B) TYPE:             nucleic acid
        (C) STRANDEDNESS:   single
        (D) TOPOLOGY:       linear (ix) FEATURE:
        (D) OTHER INFORMATION:     The letter "N" stands for any base.

(xi) SEQUENCE DESCRIPTION: SEQ ID NO:1142:

UUUUUUUUCU GAUGANGAAA CAGAUCU                                                    27

(2) INFORMATION FOR SEQ ID NO:1143:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (ix) FEATURE:
        (D) OTHER INFORMATION:   The letter "N" stands for any base.

(xi) SEQUENCE DESCRIPTION: SEQ ID NO:1143:

UUUUUUUUCU GAUGANGAAA ACAGAUC                                                    27

(2) INFORMATION FOR SEQ ID NO: 1144:

(i) SEQUENCE CHARACTERISTICS:
        (A) LENGTH:              54 base pairs
        (B) TYPE:                nucleic acid
        (C) STRANDEDNESS:        single
        (D) TOPOLOGY:            linear (xi) SEQUENCE DESCRIPTION: SEQ ID NO: 1144:

GAACAAGCAG AAGAGGGCAC CAGAGAAACA CACGUUGUGG UACAUUACCU GGUA                      54

(2) INFORMATION FOR SEQ ID NO: 1145:

(i) SEQUENCE CHARACTERISTICS:
        (A) LENGTH:              18 base pairs
        (B) TYPE:                nucleic acid
        (C) STRANDEDNESS:        single
        (D) TOPOLOGY:            linear (xi) SEQUENCE DESCRIPTION: SEQ ID NO: 1145:

GCCCUCUGCC GCUUGUUC                                                              18

(2) INFORMATION FOR SEQ ID NO: 1146:

(i) SEQUENCE CHARACTERISTICS:
        (A) LENGTH:              54 base pairs
        (B) TYPE:                nucleic acid
        (C) STRANDEDNESS:        single
        (D) TOPOLOGY:            linear (xi) SEQUENCE DESCRIPTION: SEQ ID NO: 1146:

AACGAACAAG AAGCAGAGAC CAGAGAAACA CACGUUGUGG UACAUUACCU GGUA                      54

(2) INFORMATION FOR SEQ ID NO: 1147:

(i) SEQUENCE CHARACTERISTICS:
        (A) LENGTH:              18 base pairs
        (B) TYPE:                nucleic acid
        (C) STRANDEDNESS:        single
        (D) TOPOLOGY:            linear (xi) SEQUENCE DESCRIPTION: SEQ ID NO: 1147:

CUCUGCCGCU UGUUCGUU                                                              18

(2) INFORMATION FOR SEQ ID NO: 1148:

(i) SEQUENCE CHARACTERISTICS:
        (A) LENGTH:              54 base pairs
        (B) TYPE:                nucleic acid
        (C) STRANDEDNESS:        single
        (D) TOPOLOGY:            linear (xi) SEQUENCE DESCRIPTION: SEQ ID NO: 1148:

GGAAGCGCAG AAGCCGCCAC CAGAGAAACA CACGUUGUGG UACAUUACCU GGUA          54

(2) INFORMATION FOR SEQ ID NO: 1149:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 1149:

GGCGGCGGCC GCGCUUCC          18

(2) INFORMATION FOR SEQ ID NO: 1150:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 1150:

GGAAGGGGAG AAGGAAGCAC CAGAGAAACA CACGUUGUGG UACAUUACCU GGUA          54

(2) INFORMATION FOR SEQ ID NO: 1151:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 1151:

GCUUCCGGCU CCCCUUCC          18

(2) INFORMATION FOR SEQ ID NO: 1152:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 1152:

GUCGUUGAAG AAGAGCGCAC CAGAGAAACA CACGUUGUGG UACAUUACCU GGUA          54

(2) INFORMATION FOR SEQ ID NO: 1153:

(i) SEQUENCE CHARACTERISTICS:
        (A) LENGTH:        18 base pairs
        (B) TYPE:          nucleic acid
        (C) STRANDEDNESS:  single
        (D) TOPOLOGY:     linear (xi) SEQUENCE DESCRIPTION: SEQ ID NO: 1153:

GCGCUCCGCC UCAACGAC          18

(2) INFORMATION FOR SEQ ID NO: 1154:

(i) SEQUENCE CHARACTERISTICS:
        (A) LENGTH:        54 base pairs
        (B) TYPE:          nucleic acid
        (C) STRANDEDNESS:  single
        (D) TOPOLOGY:     linear (xi) SEQUENCE DESCRIPTION: SEQ ID NO: 1154:

CGGGGAGAAG AAGAGCGCAC CAGAGAAACA CACGUUGUGG UACAUUACCU GGUA     54

(2) INFORMATION FOR SEQ ID NO: 1155:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 1155:

GCGCUCUGCC UCUCCCCG     18

(2) INFORMATION FOR SEQ ID NO: 1156:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 1156:

CGGCGAGCAG AAGGGAGAAC CAGAGAAACA CACGUUGUGG UACAUUACCU GGUA     54

(2) INFORMATION FOR SEQ ID NO: 1157:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 1157:

UCUCCCCGCC GCUCGCCG     18

(2) INFORMATION FOR SEQ ID NO: 1158:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 1158:

GGGCGGCGAG AAGCGGGGAC CAGAGAAACA CACGUUGUGG UACAUUACCU GGUA     54

(2) INFORMATION FOR SEQ ID NO: 1159:

(i) SEQUENCE CHARACTERISTICS:
        (A) LENGTH:          18 base pairs
        (B) TYPE:            nucleic acid
        (C) STRANDEDNESS:    single
        (D) TOPOLOGY:        linear (xi) SEQUENCE DESCRIPTION: SEQ ID NO: 1159:

CCCCGCCGCU CGCCGCCC     18

(2) INFORMATION FOR SEQ ID NO: 1160:

(i) SEQUENCE CHARACTERISTICS:
        (A) LENGTH:          54 base pairs
        (B) TYPE:            nucleic acid
        (C) STRANDEDNESS:    single
        (D) TOPOLOGY:        linear (xi) SEQUENCE DESCRIPTION: SEQ ID NO: 1160:

```
CGGCGGCGAG AAGCGAGCAC CAGAGAAACA CACGUUGUGG UACAUUACCU GGUA        54
```

(2) INFORMATION FOR SEQ ID NO: 1161:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1161:

```
GCUCGCCGCC CGCCGCCG                                                18
```

(2) INFORMATION FOR SEQ ID NO: 1162:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 1162:

```
GCGGCGGCAG AAGGCGGCAC CAGAGAAACA CACGUUGUGG UACAUUACCU GGUA        54
```

(2) INFORMATION FOR SEQ ID NO: 1163:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1163:

```
GCCGCCCGCC GCCGCCGC                                                18
```

(2) INFORMATION FOR SEQ ID NO: 1164:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 1164:

```
GCGGCGGCAG AAGCGGGCAC CAGAGAAACA CACGUUGUGG UACAUUACCU GGUA        54
```

(2) INFORMATION FOR SEQ ID NO: 1165:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1165:

```
GCCCGCCGCC GCCGCCGC                                                18
```

(2) INFORMATION FOR SEQ ID NO: 1166:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 1166:

```
GCUGCGGCAG AAGCGGCGAC CAGAGAAACA CACGUUGUGG UACAUUACCU GGUA        54
```

(2) INFORMATION FOR SEQ ID NO: 1167:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 1167:

CGCCGCCGCC GCCGCAGC                                            18

(2) INFORMATION FOR SEQ ID NO: 1168:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 1168:

GCUGCUGCAG AAGCGGCGAC CAGAGAAACA CACGUUGUGG UACAUUACCU GGUA       54

(2) INFORMATION FOR SEQ ID NO: 1169:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 1169:

CGCCGCCGCC GCAGCAGC                                            18

(2) INFORMATION FOR SEQ ID NO: 1170:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 1170:

AUGGAGGCAG AAGCGACGAC CAGAGAAACA CACGUUGUGG UACAUUACCU GGUA       54

(2) INFORMATION FOR SEQ ID NO: 1171:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 1171:

CGUCGCCGUC GCCUCCAU                                            18

(2) INFORMATION FOR SEQ ID NO: 1172:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 1172:

GUGGAGACAG AAGACGUCAC CAGAGAAACA CACGUUGUGG UACAUUACCU GGUA       54

(2) INFORMATION FOR SEQ ID NO: 1173:

(i) SEQUENCE CHARACTERISTICS:
        (A) LENGTH:         18 base pairs
        (B) TYPE:           nucleic acid
        (C) STRANDEDNESS:  single
        (D) TOPOLOGY:      linear (xi) SEQUENCE DESCRIPTION: SEQ ID NO: 1173:

GACGUCCGCC GUCUCCAC                                                  18

(2) INFORMATION FOR SEQ ID NO: 1174:

(i) SEQUENCE CHARACTERISTICS:
        (A) LENGTH:         54 base pairs
        (B) TYPE:           nucleic acid
        (C) STRANDEDNESS:  single
        (D) TOPOLOGY:      linear (xi) SEQUENCE DESCRIPTION: SEQ ID NO: 1174:

UUGGUGGAAG AAGCGGACAC CAGAGAAACA CACGUUGUGG UACAUUACCU GGUA        54

(2) INFORMATION FOR SEQ ID NO: 1175:

(i) SEQUENCE CHARACTERISTICS:
        (A) LENGTH:         18 base pairs
        (B) TYPE:           nucleic acid
        (C) STRANDEDNESS:  single
        (D) TOPOLOGY:      linear (xi) SEQUENCE DESCRIPTION: SEQ ID NO: 1175:

GUCCGCCGUC UCCACCAA                                                  18

(2) INFORMATION FOR SEQ ID NO: 1176:

(i) SEQUENCE CHARACTERISTICS:
        (A) LENGTH:         54 base pairs
        (B) TYPE:           nucleic acid
        (C) STRANDEDNESS:  single
        (D) TOPOLOGY:      linear (xi) SEQUENCE DESCRIPTION: SEQ ID NO: 1176:

CACUUCUCAG AAGGCUUGAC CAGAGAAACA CACGUUGUGG UACAUUACCU GGUA        54

(2) INFORMATION FOR SEQ ID NO: 1177:

(i) SEQUENCE CHARACTERISTICS:
        (A) LENGTH:         18 base pairs
        (B) TYPE:           nucleic acid
        (C) STRANDEDNESS:  single
        (D) TOPOLOGY:      linear (xi) SEQUENCE DESCRIPTION: SEQ ID NO: 1177:

CAAGCCAGUC GAGAAGUG                                                18

(2) INFORMATION FOR SEQ ID NO: 1178:

(i) SEQUENCE CHARACTERISTICS:
        (A) LENGTH:         54 base pairs
        (B) TYPE:           nucleic acid
        (C) STRANDEDNESS:  single
        (D) TOPOLOGY:      linear (xi) SEQUENCE DESCRIPTION: SEQ ID NO: 1178:

GAUGCUGGAG AAGGGAGGAC CAGAGAAACA CACGUUGUGG UACAUUACCU GGUA        54

(2) INFORMATION FOR SEQ ID NO: 1179:

(i) SEQUENCE CHARACTERISTICS:
        (A) LENGTH:          18 base pairs
        (B) TYPE:            nucleic acid
        (C) STRANDEDNESS:   single
        (D) TOPOLOGY:       linear (xi) SEQUENCE DESCRIPTION: SEQ ID NO: 1179:

CCUCCCGGAC CCAGCAUC                                                18

(2) INFORMATION FOR SEQ ID NO: 1180:

(i) SEQUENCE CHARACTERISTICS:
        (A) LENGTH:          54 base pairs
        (B) TYPE:            nucleic acid
        (C) STRANDEDNESS:   single
        (D) TOPOLOGY:       linear (xi) SEQUENCE DESCRIPTION: SEQ ID NO: 1180:

AAAUAAUCAG AAGGGAUUAC CAGAGAAACA CACGUUGUGG UACAUUACCU GGUA      54

(2) INFORMATION FOR SEQ ID NO: 1181:

(i) SEQUENCE CHARACTERISTICS:
        (A) LENGTH:          18 base pairs
        (B) TYPE:            nucleic acid
        (C) STRANDEDNESS:   single
        (D) TOPOLOGY:       linear (xi) SEQUENCE DESCRIPTION: SEQ ID NO: 1181:

AAUCCCUGAU GAUUAUUU                                                18

(2) INFORMATION FOR SEQ ID NO: 1182:

(i) SEQUENCE CHARACTERISTICS:
        (A) LENGTH:          54 base pairs
        (B) TYPE:            nucleic acid
        (C) STRANDEDNESS:   single
        (D) TOPOLOGY:       linear (xi) SEQUENCE DESCRIPTION: SEQ ID NO: 1182:

UAAGCAUAAG AAGGUAUGAC CAGAGAAACA CACGUUGUGG UACAUUACCU GGUA      54

(2) INFORMATION FOR SEQ ID NO: 1183:

(i) SEQUENCE CHARACTERISTICS:
        (A) LENGTH:          18 base pairs
        (B) TYPE:            nucleic acid
        (C) STRANDEDNESS:   single
        (D) TOPOLOGY:       linear (xi) SEQUENCE DESCRIPTION: SEQ ID NO: 1183:

CAUACCAGAC UAUGCUUA                                                18

(2) INFORMATION FOR SEQ ID NO: 1184:

(i) SEQUENCE CHARACTERISTICS:
        (A) LENGTH:          54 base pairs
        (B) TYPE:            nucleic acid
        (C) STRANDEDNESS:   single
        (D) TOPOLOGY:       linear (xi) SEQUENCE DESCRIPTION: SEQ ID NO: 1184:

ACAGCCCAAG AAGUGGGGAC CAGAGAAACA CACGUUGUGG UACAUUACCU GGUA      54

(2) INFORMATION FOR SEQ ID NO: 1185:

```
     (i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 1185:

CCCCACUGCC UGGGCUGU                                                    18

(2) INFORMATION FOR SEQ ID NO: 1186:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 1186:

CUCGUCCAAG AAGCCCAGAC CAGAGAAACA CACGUUGUGG UACAUUACCU GGUA            54

(2) INFORMATION FOR SEQ ID NO: 1187:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 1187:

CUGGGCUGUU UGGACGAG                                                    18

(2) INFORMATION FOR SEQ ID NO: 1188:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 1188:

UUCUCCUCAG AAGUCCAUAC CAGAGAAACA CACGUUGUGG UACAUUACCU GGUA            54

(2) INFORMATION FOR SEQ ID NO: 1189:

(i) SEQUENCE CHARACTERISTICS:
            (A) LENGTH:           18 base pairs
            (B) TYPE:             nucleic acid
            (C) STRANDEDNESS:     single
            (D) TOPOLOGY:         linear (xi) SEQUENCE DESCRIPTION: SEQ ID NO: 1189:

AUGGACUGCU GAGGAGAA                                                    18

(2) INFORMATION FOR SEQ ID NO: 1190:

(i) SEQUENCE CHARACTERISTICS:
            (A) LENGTH:           54 base pairs
            (B) TYPE:             nucleic acid
            (C) STRANDEDNESS:     single
            (D) TOPOLOGY:         linear (xi) SEQUENCE DESCRIPTION: SEQ ID NO: 1190:

ACUUGUUGAG AAGAUCACAC CAGAGAAACA CACGUUGUGG UACAUUACCU GGUA            54

(2) INFORMATION FOR SEQ ID NO: 1191:
```

(i) SEQUENCE CHARACTERISTICS:
    (A) LENGTH:        18 base pairs
    (B) TYPE:          nucleic acid
    (C) STRANDEDNESS:  single
    (D) TOPOLOGY:      linear (xi) SEQUENCE DESCRIPTION: SEQ ID NO: 1191:

GUGAUCUGCU CAACAAGU                                                18

(2) INFORMATION FOR SEQ ID NO: 1192:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO: 1192:

UCUUCUCAAG AAGCCUCAAC CAGAGAAACA CACGUUGUGG UACAUUACCU GGUA         54

(2) INFORMATION FOR SEQ ID NO: 1193:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO: 1193:

UGAGGCAGAU UGAGAAGA                                                18

(2) INFORMATION FOR SEQ ID NO: 1194:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO: 1194:

GCGUGACGAG AAGUGUUCAC CAGAGAAACA CACGUUGUGG UACAUUACCU GGUA         54

(2) INFORMATION FOR SEQ ID NO: 1195:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO: 1195:

GAACACUGCU CGUCACGC                                                18

(2) INFORMATION FOR SEQ ID NO: 1196:

(i) SEQUENCE CHARACTERISTICS:
        (A) LENGTH:        54 base pairs
        (B) TYPE:          nucleic acid
        (C) STRANDEDNESS:  single
        (D) TOPOLOGY:      linear (xi) SEQUENCE DESCRIPTION: SEQ ID NO: 1196:

CGCUUCUCAG AAGAGGCGAC CAGAGAAACA CACGUUGUGG UACAUUACCU GGUA         54

(2) INFORMATION FOR SEQ ID NO: 1197:

(i) SEQUENCE CHARACTERISTICS:

```
              (A) LENGTH:            18 base pairs
              (B) TYPE:              nucleic acid
              (C) STRANDEDNESS:      single
              (D) TOPOLOGY:          linear (xi) SEQUENCE DESCRIPTION: SEQ ID NO: 1197:

CGCCUCAGAU GAGAAGCG                                                 18

(2) INFORMATION FOR SEQ ID NO: 1198:

(i) SEQUENCE CHARACTERISTICS:
              (A) LENGTH:            54 base pairs
              (B) TYPE:              nucleic acid
              (C) STRANDEDNESS:      single
              (D) TOPOLOGY:          linear (xi) SEQUENCE DESCRIPTION: SEQ ID NO: 1198:

CGAUCUCAAG AAGCUUCUAC CAGAGAAACA CACGUUGUGG UACAUUACCU GGUA          54

(2) INFORMATION FOR SEQ ID NO: 1199:

(i) SEQUENCE CHARACTERISTICS:
              (A) LENGTH:            18 base pairs
              (B) TYPE:              nucleic acid
              (C) STRANDEDNESS:      single
              (D) TOPOLOGY:          linear (xi) SEQUENCE DESCRIPTION: SEQ ID NO: 1199:

AGAAGCUGUU UGAGAUCG                                                 18

(2) INFORMATION FOR SEQ ID NO: 1200:

(i) SEQUENCE CHARACTERISTICS:
              (A) LENGTH:            54 base pairs
              (B) TYPE:              nucleic acid
              (C) STRANDEDNESS:      single
              (D) TOPOLOGY:          linear (xi) SEQUENCE DESCRIPTION: SEQ ID NO: 1200:

ACGGUACCAG AAGGGUCGAC CAGAGAAACA CACGUUGUGG UACAUUACCU GGUA          54

(2) INFORMATION FOR SEQ ID NO: 1201:

(i) SEQUENCE CHARACTERISTICS:
              (A) LENGTH:            18 base pairs
              (B) TYPE:              nucleic acid
              (C) STRANDEDNESS:      single
              (D) TOPOLOGY:          linear (xi) SEQUENCE DESCRIPTION: SEQ ID NO: 1201:

CGACCCUGAU GGUACCGU                                                 18

(2) INFORMATION FOR SEQ ID NO: 1202:

(i) SEQUENCE CHARACTERISTICS:
              (A) LENGTH:            54 base pairs
              (B) TYPE:              nucleic acid
              (C) STRANDEDNESS:      single
              (D) TOPOLOGY:          linear (xi) SEQUENCE DESCRIPTION: SEQ ID NO: 1202:

AUCAGGUGAG AAGGCAUUAC CAGAGAAACA CACGUUGUGG UACAUUACCU GGUA          54

(2) INFORMATION FOR SEQ ID NO: 1203:

(i) SEQUENCE CHARACTERISTICS:
              (A) LENGTH:            18 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 1203:

AAUGCCUGCC CACCUGAU                                              18

(2) INFORMATION FOR SEQ ID NO: 1204:

(i) SEQUENCE CHARACTERISTICS:
            (A) LENGTH:            54 base pairs
            (B) TYPE:              nucleic acid
            (C) STRANDEDNESS:      single
            (D) TOPOLOGY:          linear (xi) SEQUENCE DESCRIPTION: SEQ ID NO: 1204:

CGUCAAACAG AAGGUGGGAC CAGAGAAACA CACGUUGUGG UACAUUACCU GGUA       54

(2) INFORMATION FOR SEQ ID NO: 1205:

(i) SEQUENCE CHARACTERISTICS:
            (A) LENGTH:            18 base pairs
            (B) TYPE:              nucleic acid
            (C) STRANDEDNESS:      single
            (D) TOPOLOGY:          linear (xi) SEQUENCE DESCRIPTION: SEQ ID NO: 1205:

CCCACCUGAU GUUUGACG                                              18

(2) INFORMATION FOR SEQ ID NO: 1206:

(i) SEQUENCE CHARACTERISTICS:
            (A) LENGTH:            54 base pairs
            (B) TYPE:              nucleic acid
            (C) STRANDEDNESS:      single
            (D) TOPOLOGY:          linear (xi) SEQUENCE DESCRIPTION: SEQ ID NO: 1206:

AGUGCUCGAG AAGCUUGUAC CAGAGAAACA CACGUUGUGG UACAUUACCU GGUA       54

(2) INFORMATION FOR SEQ ID NO: 1207:

(i) SEQUENCE CHARACTERISTICS:
            (A) LENGTH:            18 base pairs
            (B) TYPE:              nucleic acid
            (C) STRANDEDNESS:      single
            (D) TOPOLOGY:          linear (xi) SEQUENCE DESCRIPTION: SEQ ID NO: 1207:

ACAAGCUGUU CGAGCACU                                              18

(2) INFORMATION FOR SEQ ID NO: 1208:

(i) SEQUENCE CHARACTERISTICS:
            (A) LENGTH:            54 base pairs
            (B) TYPE:              nucleic acid
            (C) STRANDEDNESS:      single
            (D) TOPOLOGY:          linear (xi) SEQUENCE DESCRIPTION: SEQ ID NO: 1208:

ACAGACCAAG AAGGCUCGAC CAGAGAAACA CACGUUGUGG UACAUUACCU GGUA       54

(2) INFORMATION FOR SEQ ID NO: 1209:

(i) SEQUENCE CHARACTERISTICS:
            (A) LENGTH:            18 base pairs
            (B) TYPE:              nucleic acid
```

```
            (C) STRANDEDNESS:         single
            (D) TOPOLOGY:             linear (xi) SEQUENCE DESCRIPTION: SEQ ID NO: 1209:

CGAGCCUGAC UGGUCUGU                                                    18

(2) INFORMATION FOR SEQ ID NO: 1210:

(i) SEQUENCE CHARACTERISTICS:
            (A) LENGTH:               54 base pairs
            (B) TYPE:                 nucleic acid
            (C) STRANDEDNESS:         single
            (D) TOPOLOGY:             linear (xi) SEQUENCE DESCRIPTION: SEQ ID NO: 1210:

CUUCACCCAG AAGACCAGAC CAGAGAAACA CACGUUGUGG UACAUUACCU GGUA            54

(2) INFORMATION FOR SEQ ID NO: 1211:

(i) SEQUENCE CHARACTERISTICS:
            (A) LENGTH:               18 base pairs
            (B) TYPE:                 nucleic acid
            (C) STRANDEDNESS:         single
            (D) TOPOLOGY:             linear (xi) SEQUENCE DESCRIPTION: SEQ ID NO: 1211:

CUGGUCUGUC GGGUGAAG                                                    18

(2) INFORMATION FOR SEQ ID NO: 1212:

(i) SEQUENCE CHARACTERISTICS:
            (A) LENGTH:               54 base pairs
            (B) TYPE:                 nucleic acid
            (C) STRANDEDNESS:         single
            (D) TOPOLOGY:             linear (xi) SEQUENCE DESCRIPTION: SEQ ID NO: 1212:

AGCUGAAAAG AAGCGUGCAC CAGAGAAACA CACGUUGUGG UACAUUACCU GGUA            54

(2) INFORMATION FOR SEQ ID NO: 1213:

(i) SEQUENCE CHARACTERISTICS:
            (A) LENGTH:               18 base pairs
            (B) TYPE:                 nucleic acid
            (C) STRANDEDNESS:         single
            (D) TOPOLOGY:             linear (xi) SEQUENCE DESCRIPTION: SEQ ID NO: 1213:

GCACGCUGCC UUUCAGCU                                                    18

(2) INFORMATION FOR SEQ ID NO: 1214:

(i) SEQUENCE CHARACTERISTICS:
            (A) LENGTH:               54 base pairs
            (B) TYPE:                 nucleic acid
            (C) STRANDEDNESS:         single
            (D) TOPOLOGY:             linear (xi) SEQUENCE DESCRIPTION: SEQ ID NO: 1214:

GUAUACCCAG AAGAAAGGAC CAGAGAAACA CACGUUGUGG UACAUUACCU GGUA            54

(2) INFORMATION FOR SEQ ID NO: 1215:

(i) SEQUENCE CHARACTERISTICS:
            (A) LENGTH:               18 base pairs
            (B) TYPE:                 nucleic acid
            (C) STRANDEDNESS:         single
```

(D) TOPOLOGY:           linear (xi) SEQUENCE DESCRIPTION: SEQ ID NO: 1215:

CCUUUCAGCU GGGUAUAC                                             18

(2) INFORMATION FOR SEQ ID NO: 1216:

(i) SEQUENCE CHARACTERISTICS:
        (A) LENGTH:             54 base pairs
        (B) TYPE:               nucleic acid
        (C) STRANDEDNESS:       single
        (D) TOPOLOGY:           linear (xi) SEQUENCE DESCRIPTION: SEQ ID NO: 1216:

CAGACCGCAG AAGGUUUCAC CAGAGAAACA CACGUUGUGG UACAUUACCU GGUA      54

(2) INFORMATION FOR SEQ ID NO: 1217:

(i) SEQUENCE CHARACTERISTICS:
        (A) LENGTH:             18 base pairs
        (B) TYPE:               nucleic acid
        (C) STRANDEDNESS:       single
        (D) TOPOLOGY:           linear (xi) SEQUENCE DESCRIPTION: SEQ ID NO: 1217:

GAAACCUGCU GCGGUCUG                                             18

(2) INFORMATION FOR SEQ ID NO: 1218:

(i) SEQUENCE CHARACTERISTICS:
        (A) LENGTH:             54 base pairs
        (B) TYPE:               nucleic acid
        (C) STRANDEDNESS:       single
        (D) TOPOLOGY:           linear (xi) SEQUENCE DESCRIPTION: SEQ ID NO: 1218:

UCUAAGCAAG AAGCAGCAAC CAGAGAAACA CACGUUGUGG UACAUUACCU GGUA      54

(2) INFORMATION FOR SEQ ID NO: 1219:

(i) SEQUENCE CHARACTERISTICS:
        (A) LENGTH:             18 base pairs
        (B) TYPE:               nucleic acid
        (C) STRANDEDNESS:       single
        (D) TOPOLOGY:           linear (xi) SEQUENCE DESCRIPTION: SEQ ID NO: 1219:

UGCUGCGGUC UGCUUAGA                                             18

(2) INFORMATION FOR SEQ ID NO: 1220:

(i) SEQUENCE CHARACTERISTICS:
        (A) LENGTH:             54 base pairs
        (B) TYPE:               nucleic acid
        (C) STRANDEDNESS:       single
        (D) TOPOLOGY:           linear (xi) SEQUENCE DESCRIPTION: SEQ ID NO: 1220:

CUUGUCUAAG AAGACCGCAC CAGAGAAACA CACGUUGUGG UACAUUACCU GGUA      54

(2) INFORMATION FOR SEQ ID NO: 1221:

(i) SEQUENCE CHARACTERISTICS:
        (A) LENGTH:             18 base pairs
        (B) TYPE:               nucleic acid
        (C) STRANDEDNESS:       single
        (D) TOPOLOGY:           linear (xi) SEQUENCE DESCRIPTION: SEQ ID NO: 1221:

GCGGUCUGCU UAGACAAG                                                           18

(2) INFORMATION FOR SEQ ID NO: 1222:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 1222:

GCAGACACAG AAGGUCUUAC CAGAGAAACA CACGUUGUGG UACAUUACCU GGUA         54

(2) INFORMATION FOR SEQ ID NO: 1223:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 1223:

AAGACCUGCU GUGUCUGC                                                           18

(2) INFORMATION FOR SEQ ID NO: 1224:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 1224:

UACAUCAAAG AAGAAAAAAC CAGAGAAACA CACGUUGUGG UACAUUACCU GGUA         54

(2) INFORMATION FOR SEQ ID NO: 1225:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 1225:

UUUUUCUGCU UUGAUGUA                                                           18

(2) INFORMATION FOR SEQ ID NO: 1226:

(i) SEQUENCE CHARACTERISTICS:
        (A) LENGTH:         54 base pairs
        (B) TYPE:           nucleic acid
        (C) STRANDEDNESS:   single
        (D) TOPOLOGY:       linear (xi) SEQUENCE DESCRIPTION: SEQ ID NO: 1226:

CCGCCAGCAG AAGACAAAAC CAGAGAAACA CACGUUGUGG UACAUUACCU GGUA         54

(2) INFORMATION FOR SEQ ID NO: 1227:

(i) SEQUENCE CHARACTERISTICS:
        (A) LENGTH:         18 base pairs
        (B) TYPE:           nucleic acid
        (C) STRANDEDNESS:   single
        (D) TOPOLOGY:       linear (xi) SEQUENCE DESCRIPTION: SEQ ID NO: 1227:

UUUGUCUGUC GCUGGCGG                                                  18

(2) INFORMATION FOR SEQ ID NO: 1228:

(i) SEQUENCE CHARACTERISTICS:
        (A) LENGTH:            54 base pairs
        (B) TYPE:              nucleic acid
        (C) STRANDEDNESS:      single
        (D) TOPOLOGY:          linear (xi) SEQUENCE DESCRIPTION: SEQ ID NO: 1228:

UUUAACAGAG AAGAGCAAAC CAGAGAAACA CACGUUGUGG UACAUUACCU GGUA          54

(2) INFORMATION FOR SEQ ID NO: 1229:

(i) SEQUENCE CHARACTERISTICS:
        (A) LENGTH:            18 base pairs
        (B) TYPE:              nucleic acid
        (C) STRANDEDNESS:      single
        (D) TOPOLOGY:          linear (xi) SEQUENCE DESCRIPTION: SEQ ID NO: 1229:

UUGCUCAGAU CUGUUAAA                                                  18

(2) INFORMATION FOR SEQ ID NO: 1230:

(i) SEQUENCE CHARACTERISTICS:
        (A) LENGTH:            11 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.
            The letter "H" stands for A, U or C.

(xi) SEQUENCE DESCRIPTION: SEQ ID NO: 1230:

NNNNUHNNNN N                                                         11

(2) INFORMATION FOR SEQ ID NO: 1231:

(i) SEQUENCE CHARACTERISTICS:
        (A) LENGTH:            28 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.

(xi) SEQUENCE DESCRIPTION: SEQ ID NO: 1231:

NNNNNCUGAN GAGNNNNNNC GAAANNNN                                       28

(2) INFORMATION FOR SEQ ID NO: 1232:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (ix) FEATURE:
        (D) OTHER INFORMATION:   The letter "N" stands for any base.
            The leter "Y" stands for U or C. The letter "H" stands for
            A, U or C.

(xi) SEQUENCE DESCRIPTION: SEQ ID NO: 1232:

NNNNNNNYNG HYNNN                                                         15

(2) INFORMATION FOR SEQ ID NO: 1233:

(i) SEQUENCE CHARACTERISTICS:
        (A) LENGTH:            47 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO: 1233:

NNNNGAAGNN NNNNNNNNNA AAHANNNNNN NACAUUACNN NNNNNNN                       47

(2) INFORMATION FOR SEQ ID NO: 1234:

(i) SEQUENCE CHARACTERISTICS:
        (A) LENGTH:            49 base pairs
        (B) TYPE:              nucleic acid
        (C) STRANDEDNESS:      single
        (D) TOPOLOGY:          linear (ix) FEATURE:
        (D) OTHER INFORMATION: The letter "N" stands for any base.

(xi) SEQUENCE DESCRIPTION: SEQ ID NO: 1234:

CUCCACCUCC UCGCGGUNNN NNNNGGGCUA CUUCGGUAGG CUAAGGGAG                     49

(2) INFORMATION FOR SEQ ID NO: 1235:

(i) SEQUENCE CHARACTERISTICS:
        (A) LENGTH:            176 base pairs
        (B) TYPE:              nucleic acid
        (C) STRANDEDNESS:      single
        (D) TOPOLOGY:          linear (xi) SEQUENCE DESCRIPTION: SEQ ID NO: 1235:

GGGAAAGCUU GCGAAGGGCG UCGUCGCCCC GAGCGGUAGU AAGCAGGGAA CUCACCUCCA         60

AUUUCAGUAC UGAAAUUGUC GUAGCAGUUG ACUACUGUUA UGUGAUUGGU AGAGGCUAAG        120

UGACGGUAUU GGCGUAAGUC AGUAUUGCAG CACAGCACAA GCCCGCUUGC GAGAAU           176

(2) INFORMATION FOR SEQ ID NO: 1236:

(i) SEQUENCE CHARACTERISTICS:
        (A) LENGTH:            91 base pairs
        (B) TYPE:              nucleic acid
        (C) STRANDEDNESS:      double
        (D) TOPOLOGY:          linear (xi) SEQUENCE DESCRIPTION: SEQ ID NO: 1236:

AAGCTTGCAT GCCTGCAGGC CGGCCTTAAT TAAGCGGCCG CGTTTAAACG CCCGGGCATT         60

TTCGAACGTA CGGACGTCCG GCCGGAATTA ATTCGCCGGC GCAAATTTGC GGGCCCGTAA

TAAATGGCGC GCCGCGATCG CTTGCAGATC T                                       91

ATTTACCGCG CGGCGCTAGC GAACGTCTAG A (2) INFORMATION FOR SEQ ID NO: 1237:

(i) SEQUENCE CHARACTERISTICS:
        (A) LENGTH:            10 base pairs
        (B) TYPE:              nucleic acid
        (C) STRANDEDNESS:      single
        (D) TOPOLOGY:          linear (xi) SEQUENCE DESCRIPTION: SEQ ID NO: 1237:

GGCGAAAGCC                                                              10

(2) INFORMATION FOR SEQ ID NO: 1238:

(i) SEQUENCE CHARACTERISTICS:
        (A) LENGTH:         109 base pairs
        (B) TYPE:           nucleic acid
        (C) STRANDEDNESS:   single
        (D) TOPOLOGY:       linear (xi) SEQUENCE DESCRIPTION: SEQ ID NO: 1238:

CGCGGATCCT GGTAGGACTG ATGAGGCCGA AAGGCCGAAA TGTTGTGCTG ATGAGGCCGA        60

AAGGCCGAAA TGCAGAAAGC GGTCTTTGCG TCCCTGTAGA TGCCGTGGC                   109

(2) INFORMATION FOR SEQ ID NO: 1239:

(i) SEQUENCE CHARACTERISTICS:
        (A) LENGTH:         106 base pairs
        (B) TYPE:           nucleic acid
        (C) STRANDEDNESS:   single
        (D) TOPOLOGY:       linear (xi) SEQUENCE DESCRIPTION: SEQ ID NO: 1239:

CGCGAGCTCG GCCCTCTCTT TCGGCCTTTC GGCCTCATCA GGTGCTACCT CAAGAGCAAC        60

TACCAGTTTC GGCCTTTCGG CCTCATCAGC CACGGCATCT ACAGGG                      106

(2) INFORMATION FOR SEQ ID NO: 1240:

(i) SEQUENCE CHARACTERISTICS:
        (A) LENGTH:         47 base pairs
        (B) TYPE:           nucleic acid
        (C) STRANDEDNESS:   single
        (D) TOPOLOGY:       linear (xi) SEQUENCE DESCRIPTION: SEQ ID NO: 1240:

GATCCGATGC CGTGGCTGAT GAGGCCGAAA GGCCGAAACT GGTAGTT                     47

(2) INFORMATION FOR SEQ ID NO: 1241:

(i) SEQUENCE CHARACTERISTICS:
        (A) LENGTH:         43 base pairs
        (B) TYPE:           nucleic acid
        (C) STRANDEDNESS:   single
        (D) TOPOLOGY:       linear (xi) SEQUENCE DESCRIPTION: SEQ ID NO: 1241:

AACTACCAGT TTCGGCCTTT CGGCCTCATC AGCCACGGCA TCG                         43

(2) INFORMATION FOR SEQ ID NO: 1242:

(i) SEQUENCE CHARACTERISTICS:
        (A) LENGTH:         88 base pairs
        (B) TYPE:           nucleic acid
        (C) STRANDEDNESS:   single
        (D) TOPOLOGY:       linear (xi) SEQUENCE DESCRIPTION: SEQ ID NO: 1242:

CTGCAGGCCG GCCTTAATTA AGCGGCCGCG TTTAAACGCC CGGGCATTTA AATGGCGCGC        60

CGCGATCGCT TGCAGATCTG CATGGGTG                                          88

(2) INFORMATION FOR SEQ ID NO: 1243:

(i) SEQUENCE CHARACTERISTICS:

```
            (A) LENGTH:            20 base pairs
            (B) TYPE:              nucleic acid
            (C) STRANDEDNESS:      single
            (D) TOPOLOGY:          linear (xi) SEQUENCE DESCRIPTION: SEQ ID NO: 1243:

GGGGACTCTA GAGGATCCAG                                              20

(2) INFORMATION FOR SEQ ID NO: 1244:

(i) SEQUENCE CHARACTERISTICS:
            (A) LENGTH:            10 base pairs
            (B) TYPE:              nucleic acid
            (C) STRANDEDNESS:      single
            (D) TOPOLOGY:          linear (xi) SEQUENCE DESCRIPTION: SEQ ID NO: 1244:

GACGGATCTG                                                         10

(2) INFORMATION FOR SEQ ID NO: 1245:

(i) SEQUENCE CHARACTERISTICS:
            (A) LENGTH:            24 base pairs
            (B) TYPE:              nucleic acid
            (C) STRANDEDNESS:      single
            (D) TOPOLOGY:          linear (xi) SEQUENCE DESCRIPTION: SEQ ID NO: 1245:

TGAGATCTGA GCTCGAATTT CCCC                                         24

(2) INFORMATION FOR SEQ ID NO: 1246:

(i) SEQUENCE CHARACTERISTICS:
            (A) LENGTH:            19 base pairs
            (B) TYPE:              nucleic acid
            (C) STRANDEDNESS:      single
            (D) TOPOLOGY:          linear (xi) SEQUENCE DESCRIPTION: SEQ ID NO: 1246:

CTGCAGATCT GCATGGGTG                                               19

(2) INFORMATION FOR SEQ ID NO: 1247:

(i) SEQUENCE CHARACTERISTICS:
            (A) LENGTH:            13 base pairs
            (B) TYPE:              nucleic acid
            (C) STRANDEDNESS:      single
            (D) TOPOLOGY:          linear (xi) SEQUENCE DESCRIPTION: SEQ ID NO: 1247:

GGGGACTCTA GAG                                                     13

(2) INFORMATION FOR SEQ ID NO: 1248:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 1248:

GACGGATCCG TCGACC                                                  16

(2) INFORMATION FOR SEQ ID NO: 1249:

(i) SEQUENCE CHARACTERISTICS:
            (A) LENGTH:            10 base pairs
```

```
            (B) TYPE:                 nucleic acid
            (C) STRANDEDNESS:         single
            (D) TOPOLOGY:             linear (xi) SEQUENCE DESCRIPTION: SEQ ID NO: 1249:

GAATTTCCCC                                                              10

(2) INFORMATION FOR SEQ ID NO: 1250:

(i) SEQUENCE CHARACTERISTICS:
            (A) LENGTH:               25 base pairs
            (B) TYPE:                 nucleic acid
            (C) STRANDEDNESS:         single
            (D) TOPOLOGY:             linear (xi) SEQUENCE DESCRIPTION: SEQ ID NO: 1250:

GATCCGCCCG GGGCCCGGGC GGTAC                                             25

(2) INFORMATION FOR SEQ ID NO: 1251:

(i) SEQUENCE CHARACTERISTICS:
            (A) LENGTH:               17 base pairs
            (B) TYPE:                 nucleic acid
            (C) STRANDEDNESS:         single
            (D) TOPOLOGY:             linear (xi) SEQUENCE DESCRIPTION: SEQ ID NO: 1251:

CGCCCGGGCC CCGGGCG                                                      17

(2) INFORMATION FOR SEQ ID NO: 1252:

(i) SEQUENCE CHARACTERISTICS:
            (A) LENGTH:               30 base pairs
            (B) TYPE:                 nucleic acid
            (C) STRANDEDNESS:         single
            (D) TOPOLOGY:             linear (xi) SEQUENCE DESCRIPTION: SEQ ID NO: 1252:

GTGCCCACAA TGGCGCTCCG CCTCAACGAC                                        30

(2) INFORMATION FOR SEQ ID NO: 1253:

(i) SEQUENCE CHARACTERISTICS:
            (A) LENGTH:               57 base pairs
            (B) TYPE:                 nucleic acid
            (C) STRANDEDNESS:         single
            (D) TOPOLOGY:             linear (xi) SEQUENCE DESCRIPTION: SEQ ID NO: 1253:

TCATCACAGG TCCTCCTCGC TGATCAGCTT CTCCTCCAGT TGGACCTGCC TACCGTA          57

(2) INFORMATION FOR SEQ ID NO: 1254:

(i) SEQUENCE CHARACTERISTICS:
            (A) LENGTH:               57 base pairs
            (B) TYPE:                 nucleic acid
            (C) STRANDEDNESS:         single
            (D) TOPOLOGY:             linear (xi) SEQUENCE DESCRIPTION: SEQ ID NO: 1254:

TACGGTAGGG ACGTCCAACT GGAGGAGAAG CTGATCAGCG AGGAGGACCT GTGATGA          57

(2) INFORMATION FOR SEQ ID NO: 1255:

(i) SEQUENCE CHARACTERISTICS:
            (A) LENGTH:               18 base pairs
            (B) TYPE:                 nucleic acid
```

```
        (C) STRANDEDNESS:       single
        (D) TOPOLOGY:           linear (xi) SEQUENCE DESCRIPTION: SEQ ID NO: 1255:

CGCAAGACCG GCAACAGG                                                 18

(2) INFORMATION FOR SEQ ID NO: 1256:

(i) SEQUENCE CHARACTERISTICS:
        (A) LENGTH:             22 base pairs
        (B) TYPE:               nucleic acid
        (C) STRANDEDNESS:       single
        (D) TOPOLOGY:           linear (xi) SEQUENCE DESCRIPTION: SEQ ID NO: 1256:

TGGATTGATG TGATATCTCC AC                                            22

(2) INFORMATION FOR SEQ ID NO: 1257:

(i) SEQUENCE CHARACTERISTICS:
        (A) LENGTH:             18 base pairs
        (B) TYPE:               nucleic acid
        (C) STRANDEDNESS:       single
        (D) TOPOLOGY:           linear (xi) SEQUENCE DESCRIPTION: SEQ ID NO: 1257:

CGCAAGACCG GCAACAGG                                                 18

(2) INFORMATION FOR SEQ ID NO: 1258:

(i) SEQUENCE CHARACTERISTICS:
        (A) LENGTH:             31 base pairs
        (B) TYPE:               nucleic acid
        (C) STRANDEDNESS:       single
        (D) TOPOLOGY:           linear (xi) SEQUENCE DESCRIPTION: SEQ ID NO: 1258:

CAGATCAAGT GCAAAGCTGC GGACGGATCT G                                  31

(2) INFORMATION FOR SEQ ID NO: 1259:

(i) SEQUENCE CHARACTERISTICS:
        (A) LENGTH:             20 base pairs
        (B) TYPE:               nucleic acid
        (C) STRANDEDNESS:       single
        (D) TOPOLOGY:           linear (xi) SEQUENCE DESCRIPTION: SEQ ID NO: 1259:

ATCCGATGCC GTGGCTGATG                                               20

(2) INFORMATION FOR SEQ ID NO: 1260:

(i) SEQUENCE CHARACTERISTICS:
        (A) LENGTH:             20 base pairs
        (B) TYPE:               nucleic acid
        (C) STRANDEDNESS:       single
        (D) TOPOLOGY:           linear (xi) SEQUENCE DESCRIPTION: SEQ ID NO: 1260:

GATGAGATCC GGTGGCATTG                                               20

(2) INFORMATION FOR SEQ ID NO: 1261:

(i) SEQUENCE CHARACTERISTICS:
        (A) LENGTH:             20 base pairs
        (B) TYPE:               nucleic acid
        (C) STRANDEDNESS:       single
```

-continued

```
        (D) TOPOLOGY:           linear (xi) SEQUENCE DESCRIPTION: SEQ ID NO: 1261:

ATCCCCTTGG TGGACTGATG                                              20

(2) INFORMATION FOR SEQ ID NO: 1262:

(i) SEQUENCE CHARACTERISTICS:
        (A) LENGTH:             31 base pairs
        (B) TYPE:               nucleic acid
        (C) STRANDEDNESS:       single
        (D) TOPOLOGY:           linear (xi) SEQUENCE DESCRIPTION: SEQ ID NO: 1262:

CAGATCAAGT GCAAAGCTGC GGACGGATCT G                                 31

(2) INFORMATION FOR SEQ ID NO: 1263:

(i) SEQUENCE CHARACTERISTICS:
        (A) LENGTH:             6 amino acids
        (B) TYPE:               amino acid
        (C) STRANDEDNESS:       single
        (D) TOPOLOGY:           linear (ii) MOLECULE TYPE:         peptide (xi) SEQUENCE DESCRIPTION: SEQ ID NO: 1263:

Ala Val Ala Ser Met Thr
 1               5
```